(12) United States Patent
Aissaoui et al.

(10) Patent No.: US 8,188,082 B2
(45) Date of Patent: May 29, 2012

(54) 5,6,7,8-TETRAHYDRO-IMIDAZO[1,5-α] PYRAZINE DERIVATIVES

(75) Inventors: Hamed Aissaoui, Pulversheim (FR); Christoph Boss, Allschwil (CH); Markus Gude, Allschwil (CH); Raif Koberstein, Lorrach (DE); Thierry Sifferien, Wentzwiller (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 248 days.

(21) Appl. No.: 12/520,693

(22) PCT Filed: Dec. 20, 2007

(86) PCT No.: PCT/IB2007/055245
§ 371 (c)(1),
(2), (4) Date: Jun. 22, 2009

(87) PCT Pub. No.: WO2008/078291
PCT Pub. Date: Jul. 3, 2008

(65) Prior Publication Data
US 2010/0093740 A1    Apr. 15, 2010

(30) Foreign Application Priority Data
Dec. 22, 2006 (WO) .................. PCT/IB2006/055019

(51) Int. Cl.
*A61K 31/495* (2006.01)
(52) U.S. Cl. ........................ 514/249; 544/350
(58) Field of Classification Search ................... 514/249; 544/350
See application file for complete search history.

(56) References Cited

U.S. PATENT DOCUMENTS

| | | | |
|---|---|---|---|
| 6,703,392 B2 | 3/2004 | Aissaoui et al. | |
| 7,732,603 B2 | 6/2010 | McKenna et al. | |
| 7,750,161 B2 | 7/2010 | Bur et al. | |
| 2004/0044031 A1 | 3/2004 | Yamada et al. | |
| 2006/0166973 A1 | 7/2006 | McKenna | |
| 2006/0178515 A1 | 8/2006 | Aissaoui et al. | |
| 2010/0029617 A1 | 2/2010 | Aissaoui et al. | |
| 2011/0105514 A1 | 5/2011 | Aissaoui et al. | |

FOREIGN PATENT DOCUMENTS

| | | |
|---|---|---|
| CA | 2 408 343 | 11/2002 |
| WO | WO 01/68609 | 9/2001 |
| WO | WO 02/051838 | 7/2002 |
| WO | WO 2004/004733 | 1/2004 |
| WO | WO 2004/085403 | 10/2004 |
| WO | WO 2005/118548 | 12/2005 |
| WO | WO 2007/105177 | 9/2007 |
| WO | WO 2007/122591 | 11/2007 |
| WO | WO 2008/078291 | 7/2008 |
| WO | WO 2009/047723 | 4/2009 |

OTHER PUBLICATIONS

Jordan, V. C. Nature Reviews: Drug Discovery, 2, 2003, 205.*
Hackam, et al. JAMA, 296(14), 2006, 1731-1732.*
Borgland, S.L., et al., "Orexin A in the VTA Is Critical for the Induction of Synaptic Plasticity and Behavioral Sensitization to Cocaine", Neuron, vol. 49, pp. 589-601, (2006).
Brisbare-Roch, C., et al., "Promotion of sleep by targeting the orexin system in rats, dogs and humans", Nature Medicine, vol. 13, pp. 150-155, (2007).
Gibson, M., "A Practical Guide from Candidate Drug Selection to Commercial Dosage Form, Pharmaceutical Preformulation and Formulation," HIS Health Group, Englewood, CO, USA, 2001.
Hartz, R.A., et al., "Synthesis and Evaluation of Imidazo[1,5-a} pyrazines as Corticotropin Releasing Hormone Receptor Ligands", Bioorganic & Medicinal Chemistry Letters, Oxford, GB, vol. 12, No. 3, pp. 291-294, (2002).
Remington, The Science and Practice of Pharmacy, 21$^{st}$ Edition (2005), Part 5, "Pharmaceutical Manufacturing" [published by Lippincott Williams & Wilkins].
Hartz et al., Synthesis and Evaluation of Imidazo[1,5-a]pyrazines as Corticotropin Releasing Hormone Receptor Ligands, Bioorganic & Medicinal Chemistry Letters, 12 (2002) 291-294.
Chemelli, R.M. et al., Cell. 1999, 98, 437-451.
Gould, P. et al., "Salt Selection for Basic Drugs", Int. J. Pharm. (1986) 33, 201-217.
Kobersteing, R. et al., "Tetrahydroisoquinolines as Orexin Receptor Antagonists: Strategies for Lead Optimization by Solution-Phase Chemistry", Chimia 57. (2003), 270-275.
Sakurai, T., et al., Cell, 1998. 92, 573-585.

* cited by examiner

*Primary Examiner* — James O Wilson
*Assistant Examiner* — Douglas M Willis
(74) *Attorney, Agent, or Firm* — Hoxie & Associates LLC

(57) ABSTRACT

The invention relates to 5,6,7,8-tetrahydro-imidazo[1,5-a] pyrazine derivatives of formula (I), wherein X represents $CH_2$ or O; $R^1$ represents a phenyl group, which group is independently mono-, di-, or tri-substituted wherein the substituents are independently selected from the group consisting of $(C_{1-4})$alkyl, $(C_{1-4})$alkoxy, halogen, cyano, trifluoromethoxy and trifluoromethyl; $R^2$ represents $(C_{1-4})$alkyl, $(C_{1-4})$alkoxy, $(C_{2-4})$alkenyl, halogen, cyano, hydroxymethyl, trifluoromethyl, $C(O)NR^5R^6$ or cyclopropyl; $R^3$ represents $(C_{1-4})$alkyl, $(C_{1-4})$alkoxy-methyl or halogen; $R^4$ represents $(C_{1-4})$alkyl; $R^5$ represents hydrogen or $(C_{1-4})$alkyl; and $R^6$ represents hydrogen or $(C_{1-4})$alkyl. The invention also relates to pharmaceutically acceptable salts of such compounds; and to the use of such compounds as medicaments; especially as orexin receptor antagonists.

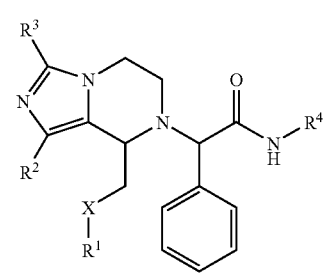

(I)

11 Claims, No Drawings

5,6,7,8-TETRAHYDRO-IMIDAZO[1,5-α] PYRAZINE DERIVATIVES

CROSS-REFERENCE TO RELATED APPLICATIONS

This application is a United States National Stage Application under 35 USC §371 of PCT/IB2007/055245, filed Dec. 20, 2007, which claims the benefit of PCT/IB2006/055019, filed Dec. 22, 2006, the contents of each of which are incorporated herein by reference.

BACKGROUND OF THE INVENTION

The present invention relates to novel 5,6,7,8-tetrahydro-imidazo[1,5-a]pyrazine derivatives of formula (I) and their use as pharmaceuticals. The invention also concerns related aspects including processes for the preparation of the compounds, pharmaceutical compositions containing one or more compounds of formula (I), and especially their use as orexin receptor antagonists.

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to the G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also observed that orexins regulate states of sleep and wakefulness opening potentially novel therapeutic approaches to narcolepsy as well as insomnia and other sleep disorders (Chemelli R. M. et al., Cell, 1999, 98, 437-451).

Orexin receptors are found in the mammalian brain and may have numerous implications in pathologies as known from the literature.

Up to now, some low molecular weight compounds are known having a potential to antagonise either specifically $OX_1$ or $OX_2$, or both receptors at the same time. In WO01/85693, Banyu Pharmaceuticals claimed N-acyltetrahydroisoquinoline derivatives.

Other orexin receptor antagonists such as novel benzazepine derivatives are disclosed in WO02/051838. Pyrazolo-tetrahydropyridine derivatives as orexin receptor antagonists are known from WO07/122,591.

Furthermore, the use of solution-phase chemistry for the lead optimization of 1,2,3,4-tetrahydroisoquinoline derivatives as potential orexin receptor antagonists has been reported (Chimia, 2003, 57, 270-275).

BRIEF SUMMARY OF THE INVENTION

The present invention provides novel substituted 5,6,7,8-tetrahydro-imidazo[1,5-a]pyrazine derivatives, which are non-peptide antagonists of human orexin $OX_1$ and/or $OX_2$ receptors. These compounds are in particular of potential use in the treatment of e.g. eating disorders, drinking disorders, sleep disorders, or cognitive dysfunctions in psychiatric and neurologic disorders.

Various embodiments of the invention are presented hereafter:

i) A first aspect of the invention relates to 5,6,7,8-tetrahydro-imidazo[1,5-a]pyrazine derivatives of formula (I),

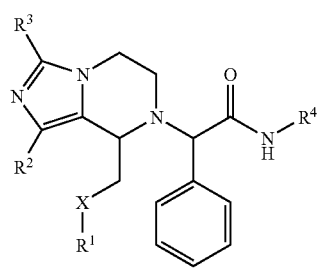

Formula (I)

wherein

X represents $CH_2$ or O;

$R^1$ represents a phenyl group, which group is independently mono-, di-, or tri-substituted wherein the substituents are independently selected from the group consisting of $(C_{1-4})$alkyl, $(C_{1-4})$alkoxy, halogen, cyano, trifluoromethoxy and trifluoromethyl;

$R^2$ represents $(C_{1-4})$alkyl, $(C_{1-4})$alkoxy, $(C_{2-4})$alkenyl, halogen, cyano, hydroxymethyl, trifluoromethyl, $C(O)NR^5R^6$ or cyclopropyl;

$R^3$ represents $(C_{1-4})$alkyl, $(C_{1-4})$alkoxy-methyl or halogen;

$R^4$ represents $(C_{1-4})$alkyl;

$R^5$ represents hydrogen or $(C_{1-4})$alkyl;

$R^6$ represents hydrogen or $(C_{1-4})$alkyl.

In another embodiment of the invention, compounds of formula (I) and (II; see below) also encompass pure enantiomers, mixtures of enantiomers, pure diastereoisomers, mixtures of diastereoisomers, diastereoisomeric racemates, mixtures of diastereoisomeric racemates, pharmaceutically acceptable salts and solvation complexes thereof. In preferred embodiment of the invention, compounds of formula (I) and (II) also encompass pharmaceutically acceptable salts thereof.

As above-mentioned, the present invention encompasses also solvation complexes of compounds of formula (I) and (II). The solvation can be effected in the course of the manufacturing process or can take place separately, e.g. as a consequence of hygroscopic properties of an initially anhydrous compound of formula (I) and (II).

In the present description the term "halogen" means fluorine, chlorine, bromine or iodine.

For the substituent $R^1$, the term "halogen" means fluorine, chlorine, or bromine, and preferably fluorine or chlorine. More preferred the term "halogen" means fluorine.

For the substituent $R^2$, the term "halogen" means fluorine, chlorine, bromine or iodine, and preferably chlorine.

For the substituent $R^3$, the term "halogen" means fluorine, chlorine, bromine or iodine, and preferably chlorine.

The term "$(C_{1-4})$alkyl", alone or in combination, means a straight-chain or branched-chain alkyl group with 1 to 4 carbon atoms. Examples of $(C_{1-4})$alkyl groups are methyl, ethyl, propyl, isopropyl, n-butyl, isobutyl, sec.-butyl or tert.-butyl; the term "$(C_{1-2})$alkyl" means a methyl or ethyl group. Preferred are methyl and ethyl.

For the substituent $R^1$, the term "$(C_{1-4})$alkyl" means preferably methyl or ethyl. More preferred the term "$(C_{1-4})$alkyl" means methyl.

For the substituent $R^2$, the term "$(C_{1-4})$alkyl" means preferably methyl or ethyl.

For the substituent R³, the term "(C₁₋₄)alkyl" means preferably methyl, ethyl, n-propyl or isopropyl. More preferred the term "(C₁₋₄)alkyl" means methyl or ethyl. Most preferred the term "(C₁₋₄)alkyl" means ethyl.

For the substituent R⁴, the term "(C₁₋₄)alkyl" means preferably methyl.

For the substituent R⁵, the term "(C₁₋₄)alkyl" means preferably methyl.

For the substituent R⁶, the term "(C₁₋₄)alkyl" means preferably methyl.

The term "(C₂₋₄)alkenyl", alone or in combination, means a straight-chain or branched-chain alkenyl group with 2 to 4 carbon atoms, preferably vinyl and allyl.

The term "(C₁₋₄)alkoxy", alone or in combination, means a group of the formula (C₁₋₄)alkyl-O— in which the term "(C₁₋₄)alkyl" has the previously given significance, such as methoxy, ethoxy, n-propoxy, isopropoxy, n-butoxy, isobutoxy, sec.-butoxy or tert.-butoxy. Preferred are methoxy and ethoxy.

For the substituent R¹, the term "(C₁₋₄)alkoxy" means preferably methoxy.

For the substituent R², the term "(C₁₋₄)alkoxy" means preferably methoxy.

The term "(C₁₋₄)alkoxy-methyl", alone or in combination, means a group of the formula (C₁₋₄)alkoxy-CH₂— in which the term "(C₁₋₄)alkoxy" has the previously given significance. An example is methoxymethyl.

For the substituent R¹, the term phenyl group is preferably independently mono-, di-, or tri-substituted wherein the substituents are independently selected from the group consisting of (C₁₋₄)alkyl, (C₁₋₄)alkoxy, halogen, cyano, trifluoromethoxy and trifluoromethyl. Examples are trifluoromethyl-phenyl (e.g. 4-trifluoromethyl-phenyl, 3-trifluoromethyl-phenyl), trifluoromethoxy-phenyl (e.g. 4-trifluoromethoxy-phenyl), chloro-phenyl (e.g. 2-chloro-phenyl, 3-chloro-phenyl and 4-chloro-phenyl), methyl-phenyl (e.g. 2-methyl-phenyl, 3-methyl-phenyl, 4-methyl-phenyl), cyano-phenyl (e.g. 4-cyano-phenyl), dimethyl-phenyl (e.g. 2,3-dimethyl-phenyl, 2,4-dimethyl-phenyl, 3,4-dimethyl-phenyl), dimethoxy-phenyl (e.g. 2,5-dimethoxy-phenyl, 2,4-dimethoxy-phenyl), fluoro-methoxy-phenyl (e.g. 3-fluoro-4-methoxy-phenyl), fluoro-trifluoromethyl-phenyl (e.g. 3-fluoro-4-trifluoromethyl-phenyl, 2-fluoro-4-trifluoromethyl-phenyl, 4-fluoro-3-trifluoromethyl-phenyl), dichloro-phenyl (e.g. 2,4-dichloro-phenyl), difluoro-phenyl (e.g. 3,4-difluoro-phenyl), fluoro-methyl-phenyl (e.g. 3-fluoro-4-methyl-phenyl), chloro-trifluoromethyl-phenyl (e.g. 3-chloro-4-trifluoromethyl-phenyl), difluoro-methyl-phenyl (e.g. 3,5-difluoro-4-methyl-phenyl, 2,4-difluoro-3-methyl-phenyl), difluoro-methoxy-phenyl (e.g. 3,5-difluoro-4-methoxy-phenyl, 2,5-difluoro-4-methoxy-phenyl), difluoro-trifluoromethyl-phenyl (e.g. 3,5-difluoro-4-trifluoromethyl-phenyl, 2,5-difluoro-4-trifluoromethyl-phenyl), trifluoro-phenyl (e.g. 2,3,5-trifluoro-phenyl, 3,4,5-trifluoro-phenyl), and chloro-difluoro-phenyl (e.g. 4-chloro-3,5-difluoro-phenyl). Especially examples are trifluoromethyl-phenyl (e.g. 4-trifluoromethyl-phenyl), chloro-phenyl (e.g. 2-chloro-phenyl, 3-chloro-phenyl and 4-chloro-phenyl), methyl-phenyl (e.g. 2-methyl-phenyl, 3-methyl-phenyl, 4-methyl-phenyl), dimethyl-phenyl (e.g. 2,3-dimethyl-phenyl, 2,4-dimethyl-phenyl, 3,4-dimethyl-phenyl), dimethoxy-phenyl (e.g. 2,5-dimethoxy-phenyl, 2,4-dimethoxy-phenyl), fluoro-methoxy-phenyl (e.g. 3-fluoro-4-methoxy-phenyl), dichloro-phenyl (e.g. 2,4-dichloro-phenyl), difluoro-phenyl (e.g. 3,4-difluoro-phenyl), fluoro-methyl-phenyl (e.g. 3-fluoro-4-methyl-phenyl), difluoro-methyl-phenyl (e.g. 3,5-difluoro-4-methyl-phenyl), fluoro-trifluoromethyl-phenyl (e.g. 3-fluoro-4-trifluoromethyl-phenyl) and difluoro-trifluoromethyl-phenyl (e.g. 3,5-difluoro-4-trifluoromethyl-phenyl). In another embodiment examples are trifluoromethyl-phenyl (e.g. 4-trifluoromethyl-phenyl, 3-trifluoromethyl-phenyl), trifluoromethoxy-phenyl (e.g. 4-trifluoromethoxy-phenyl), chloro-phenyl (e.g. 3-chloro-phenyl), methyl-phenyl (e.g. 4-methyl-phenyl), cyano-phenyl (e.g. 4-cyano-phenyl), dimethyl-phenyl (e.g. 2,3-dimethyl-phenyl, 2,4-dimethyl-phenyl, 3,4-dimethyl-phenyl), dimethoxy-phenyl (e.g. 2,4-dimethoxy-phenyl), fluoro-methoxy-phenyl (e.g. 3-fluoro-4-methoxy-phenyl), fluoro-trifluoromethyl-phenyl (e.g. 3-fluoro-4-trifluoromethyl-phenyl, 2-fluoro-4-trifluoromethyl-phenyl, 4-fluoro-3-trifluoromethyl-phenyl), dichloro-phenyl (e.g. 2,4-dichloro-phenyl), difluoro-phenyl (e.g. 3,4-difluoro-phenyl), fluoro-methyl-phenyl (e.g. 3-fluoro-4-methyl-phenyl), chloro-trifluoromethyl-phenyl (e.g. 3-chloro-4-trifluoromethyl-phenyl), difluoro-methyl-phenyl (e.g. 3,5-difluoro-4-methyl-phenyl, 2,4-difluoro-3-methyl-phenyl), difluoro-methoxy-phenyl (e.g. 3,5-difluoro-4-methoxy-phenyl, 2,5-difluoro-4-methoxy-phenyl), difluoro-trifluoromethyl-phenyl (e.g. 3,5-difluoro-4-trifluoromethyl-phenyl, 2,5-difluoro-4-trifluoromethyl-phenyl), trifluoro-phenyl (e.g. 2,3,5-trifluoro-phenyl, 3,4,5-trifluoro-phenyl), and chloro-difluoro-phenyl (e.g. 4-chloro-3,5-difluoro-phenyl).

The term "C(O)NR⁵R⁶" means for example C(O)N(CH₃)₂.

Also part of the invention are compounds of the formula (I) and/or (Ia) and pharmaceutically acceptable salts thereof.

The term "pharmaceutically acceptable salts" refers to non-toxic, inorganic or organic acid and/or base addition salts. Reference can be made to "Salt selection for basic drugs", *Int J. Pharm.* (1986), 33, 201-217.

The compounds of general formula (I) and (II) may contain two or more stereogenic or asymmetric centers, such as two or more asymmetric carbon atoms. Substituents at a double bond or a ring may be present in cis- or trans-form unless indicated otherwise. The compounds of formula (I) and (II) may thus be present as mixtures of stereoisomers or preferably as pure stereoisomers. Mixtures of stereoisomers may be separated in a manner known to a person skilled in the art.

ii) A further embodiment of the invention relates to compounds of formula (I) according to embodiment i), wherein, in case X represents CH₂, the absolute configuration is [(R)-2'; (S)-8] or [(R)-2'; (R)-8]; or, in case X represents O, the absolute configuration is [(R)-2'; (S)-8] or [(R)-2'; (R)-8].

iii) A further embodiment of the invention relates to compounds of formula (I) according to embodiment i) or ii) which are also compounds of formula (II), wherein, in case X represents CH₂, the absolute configuration is [(R)-2'; (S)-8]; or, in case X represents O, the absolute configuration is [(R)-2'; (R)-8]:

iv) A further embodiment of the invention relates to compounds of formula (I) according to any one of embodiments i) to iii), wherein R$^1$ represents a phenyl group, which is independently mono-, di-, or tri-substituted wherein the substituents are independently selected from the group consisting of (C$_{1-4}$)alkyl, (C$_{1-4}$)alkoxy, halogen, trifluoromethoxy and trifluoromethyl;

R$^2$ represents (C$_{1-4}$)alkoxy, halogen, cyano or trifluoromethyl; and

R$^3$ represents (C$_{1-4}$)alkyl or halogen.

v) A further embodiment of the invention relates to compounds of formula (I) according to any one of embodiments i) to iv), wherein R$^1$ represents a phenyl group, which is independently mono-, di-, or tri-substituted wherein the substituents are independently selected from the group consisting of (C$_{1-4}$)alkyl, halogen and trifluoromethyl.

vi) A further embodiment of the invention relates to compounds of formula (I) according to any one of embodiments i) to iv), wherein R$^1$ represents a phenyl group, which is independently di-, or tri-substituted wherein the substituents are independently selected from the group consisting of methyl, methoxy, fluorine, chlorine and trifluoromethyl.

vii) A further embodiment of the invention relates to compounds of formula (I) according to any one of embodiments i) to vi), wherein R$^1$ represents a phenyl group, which is independently di-, or tri-substituted wherein the substituents are independently selected from the group consisting of methyl, fluorine and trifluoromethyl.

viii) A further embodiment of the invention relates to compounds of formula (I) according to any one of embodiments i) to vi), wherein R$^2$ represents (C$_{1-4}$)alkoxy, halogen, cyano or trifluoromethyl.

ix) A further embodiment of the invention relates to compounds of formula (I) according to any one of embodiments i) to viii), wherein R$^2$ represents methoxy, chlorine, cyano or trifluoromethyl.

x) A further embodiment of the invention relates to compounds of formula (I) according to any one of embodiments i) to ix), wherein R$^2$ represents methoxy, chlorine or cyano.

xi) A further embodiment of the invention relates to compounds of formula (I) according to any one of embodiments i) to x), wherein R$^2$ represents chlorine.

xii) A further embodiment of the invention relates to compounds of formula (I) according to any one of embodiments i) to xi), wherein R$^3$ represents (C$_{1-4}$)alkyl or halogen.

xiii) A further embodiment of the invention relates to compounds of formula (I) according to any one of embodiments i) to xii), wherein R$^3$ represents methyl, ethyl, n-propyl, isopropyl or chlorine.

xiv) A further embodiment of the invention relates to compounds of formula (I) according to any one of embodiments i) to xiii), wherein R$^3$ represents methyl or ethyl.

xv) A further embodiment of the invention relates to compounds of formula (I) according to any one of embodiments i) to xiv), wherein R$^3$ represents ethyl.

xvi) A further embodiment of the invention relates to compounds of formula (I) according to any one of embodiments i) to xv), wherein R$^4$ represents methyl.

xvii) A further embodiment of the invention relates to compounds of formula (I) according to any one of embodiments i) to xvi), wherein R$^5$ represents hydrogen or methyl; and R$^6$ represents hydrogen or methyl.

xviii) A further embodiment of the invention relates to compounds of formula (I) according to any one of embodiments i) to xvii), wherein X represents CH$_2$.

xix) A further embodiment of the invention relates to compounds of formula (I) according to any one of embodiments i) to xvii), wherein X represents O.

xx) In another embodiment of the invention compounds of formula (I) according to embodiment i) are selected from the group consisting of:

(R)-2'-{1-chloro-3-ethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-3-ethyl-(S)-8-[2-(3,5-difluoro-4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-(S)-8-[2-(2,4-difluoro-3-methyl-phenyl)-ethyl]-3-ethyl-5,6-dihydro-8H-imidazo[1,5-a]pyrazin-7-yl}-N-methyl-2'-phenyl-acetamide;

(R)-2'-{1-chloro-(S)-8-[2-(3,5-difluoro-4-methyl-phenyl)-ethyl]-3-ethyl-5,6-dihydro-8H-imidazo[1,5-a]pyrazin-7-yl}-N-methyl-2'-phenyl-acetamide;

(R)-2'-{1-chloro-(R)-8-[2-(3,5-difluoro-4-methyl-phenyl)-ethyl]-3-ethyl-5,6-dihydro-8H-imidazo[1,5-a]pyrazin-7-yl}-N-methyl-2'-phenyl-acetamide;

(R)-2'-{1-chloro-3-ethyl-(S)-8-[2-(3-fluoro-4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-8-[2-(3,4-dimethyl-phenyl)-ethyl]-3-ethyl-5,6-dihydro-8H-imidazo[1,5-a]pyrazin-7-yl}-N-methyl-2'-phenyl-acetamide;

(R)-2'-{1-chloro-3-ethyl-(R)-8-[2-(3-fluoro-4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-3-ethyl-8-[2-(3-fluoro-4-methyl-phenyl)-ethyl]-5,6-dihydro-8H-imidazo[1,5-a]pyrazin-7-yl}-N-methyl-2'-phenyl-acetamide;

(R)-2'-{1-chloro-3-ethyl-(R)-8-[2-(3-fluoro-4-methyl-phenyl)-ethyl]-5,6-dihydro-8H-imidazo[1,5-a]pyrazin-7-yl}-N-methyl-2'-phenyl-acetamide;

(R)-2'-{1-chloro-3-ethyl-(S)-8-[2-(2-fluoro-4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-3-ethyl-(R)-8-[2-(2-fluoro-4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-8-[2-(3,4-difluoro-phenyl)-ethyl]-3-ethyl-5,6-dihydro-8H-imidazo[1,5-a]pyrazin-7-yl}-N-methyl-2'-phenyl-acetamide;

(R)-2'-{1-chloro-(S)-8-[2-(3,5-difluoro-4-methyl-phenyl)-ethyl]-3-methyl-5,6-dihydro-8H-imidazo[1,5-a]pyrazin-7-yl}-N-methyl-2'-phenyl-acetamide;

(R)-2'-{1-chloro-(R)-8-[2-(3,5-difluoro-4-methyl-phenyl)-ethyl]-3-methyl-5,6-dihydro-8H-imidazo[1,5-a]pyrazin-7-yl}-N-methyl-2'-phenyl-acetamide;

(R)-2'-{1-chloro-8-[2-(3,4-dimethyl-phenyl)-ethyl]-3-methyl-5,6-dihydro-8H-imidazo[1,5-a]pyrazin-7-yl}-N-methyl-2'-phenyl-acetamide;

(R)-2'-{1-chloro-3-methyl-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{1-chloro-3-isopropyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{1-chloro-3-isopropyl-(R)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{3-isopropyl-1-methoxy-(S)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{(S)-8-[2-(3,4-dimethyl-phenyl)-ethyl]-3-ethyl-1-methoxy-5,6-dihydro-8H-imidazo[1,5-a]pyrazin-7-yl}-N-methyl-2'-phenyl-acetamide;
(R)-2'-{(R)-8-[2-(3,4-dimethyl-phenyl)-ethyl]-3-ethyl-1-methoxy-5,6-dihydro-8H-imidazo[1,5-a]pyrazin-7-yl}-N-methyl-2'-phenyl-acetamide;
(R)-2'-{3-ethyl-1-iodo-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{1,3-dimethyl-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{3-ethyl-1-methyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{8-[2-(3-chloro-phenyl)-ethyl]-1,3-dimethyl-5,6-dihydro-8H-imidazo[1,5-a]pyrazin-7-yl}-N-methyl-2'-phenyl-acetamide;
(R)-2'-[1,3-dimethyl-8-(2-p-tolyl-ethyl)-5,6-dihydro-8H-imidazo[1,5-a]pyrazin-7-yl]-N-methyl-2'-phenyl-acetamide;
(R)-2'-{8-[2-(2,3-dimethyl-phenyl)-ethyl]-1,3-dimethyl-5,6-dihydro-8H-imidazo[1,5-a]pyrazin-7-yl}-N-methyl-2'-phenyl-acetamide;
(R)-2'-{8-[2-(2,4-dimethyl-phenyl)-ethyl]-1,3-dimethyl-5,6-dihydro-8H-imidazo[1,5-a]pyrazin-7-yl}-N-methyl-2'-phenyl-acetamide;
(R)-2'-{8-[2-(2,4-dimethoxy-phenyl)-ethyl]-1,3-dimethyl-5,6-dihydro-8H-imidazo[1,5-a]pyrazin-7-yl}-N-methyl-2'-phenyl-acetamide;
(R)-2'-{8-[2-(3-fluoro-4-methoxy-phenyl)-ethyl]-1,3-dimethyl-5,6-dihydro-8H-imidazo[1,5-a]pyrazin-7-yl}-N-methyl-2'-phenyl-acetamide;
(R)-2'-{8-[2-(2,4-dichloro-phenyl)-ethyl]-1,3-dimethyl-5,6-dihydro-8H-imidazo[1,5-a]pyrazin-7-yl}-N-methyl-2'-phenyl-acetamide;
(R)-2'-{(S)-8-[2-(3,4-difluoro-phenyl)-ethyl]-1,3-dimethyl-5,6-dihydro-8H-imidazo[1,5-a]pyrazin-7-yl}-N-methyl-2'-phenyl-acetamide;
(R)-2'-{3-ethyl-(S)-8-[2-(4-trifluoromethyl-phenyl)-ethyl]-1-vinyl-5,6-dihydro-8H-imidazo[1,5-a]pyrazin-7-yl}-N-methyl-2'-phenyl-acetamide;
(R)-2'-{1-cyano-3-ethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{1-cyano-3-ethyl-(R)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{3-ethyl-1-hydroxymethyl-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{3-ethyl-1-trifluoromethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{3-ethyl-1-trifluoromethyl-(R)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{1-chloro-3-methoxymethyl-8-[2-(4-trifluoromethyl-phenyl)-ethyl]-5,6-dihydro-8H-imidazo[1,5-a]pyrazin-7-yl}-N-methyl-2'-phenyl-acetamide;
3-ethyl-7-(methylcarbamoyl-phenyl-methyl)-8-[2-(4-trifluoromethyl-phenyl)-ethyl]-5,6,7,8-tetrahydro-imidazo[1,5-a]pyrazine-1-carboxylic acid methylamide;
(R)-2'-{1,3-dichloro-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{1-chloro-3-ethyl-(S)-8-[2-(3,4,5-trifluoro-phenyl)-ethyl]-5,6-dihydro-8H-imidazo[1,5-a]pyrazin-7-yl}-N-methyl-2'-phenyl-acetamide;
(R)-2'-{1-chloro-(S)-8-[2-(3-fluoro-4-trifluoromethyl-phenyl)-ethyl]-3-methyl-5,6-dihydro-8H-imidazo[1,5-a]pyrazin-7-yl}-N-methyl-2'-phenyl-acetamide;
(R)-2'-{1-chloro-(S)-8-[2-(3,5-difluoro-4-methoxy-phenyl)-ethyl]-3-ethyl-5,6-dihydro-8H-imidazo[1,5-a]pyrazin-7-yl}-N-methyl-2'-phenyl-acetamide;
(R)-2'-{1-chloro-(S)-8-[2-(4-chloro-3,5-difluoro-phenyl)-ethyl]-3-ethyl-5,6-dihydro-8H-imidazo[1,5-a]pyrazin-7-yl}-N-methyl-2'-phenyl-acetamide;
(R)-2'-{1-chloro-(S)-8-[2-(3-chloro-4-trifluoromethyl-phenyl)-ethyl]-3-ethyl-5,6-dihydro-8H-imidazo[1,5-a]pyrazin-7-yl}-N-methyl-2'-phenyl-acetamide;
(R)-2'-{1-chloro-(S)-8-[2-(2,5-difluoro-4-trifluoromethyl-phenyl)-ethyl]-3-ethyl-5,6-dihydro-8H-imidazo[1,5-a]pyrazin-7-yl}-N-methyl-2'-phenyl-acetamide;
(R)-2'-{1-chloro-3-ethyl-(S)-8-[2-(4-trifluoromethoxy-phenyl)-ethyl]-5,6-dihydro-8H-imidazo[1,5-a]pyrazin-7-yl}-N-methyl-2'-phenyl-acetamide;
(R)-2'-{1-chloro-(S)-8-[2-(4-cyano-phenyl)-ethyl]-3-ethyl-5,6-dihydro-8H-imidazo[1,5-a]pyrazin-7-yl}-N-methyl-2'-phenyl-acetamide;
(R)-2'-{1-cyano-3-ethyl-(S)-8-[2-(3-fluoro-4-trifluoromethyl-phenyl)-ethyl]-5,6-dihydro-8H-imidazo[1,5-a]pyrazin-7-yl}-N-methyl-2'-phenyl-acetamide;
(R)-2'-{1-cyano-(S)-8-[2-(3-fluoro-4-trifluoromethyl-phenyl)-ethyl]-3-methyl-5,6-dihydro-8H-imidazo[1,5-a]pyrazin-7-yl}-N-methyl-2'-phenyl-acetamide;
(R)-2'-{1-chloro-3-propyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{1-chloro-(S)-8-[2-(3-fluoro-4-trifluoromethyl-phenyl)-ethyl]-3-propyl-5,6-dihydro-8H-imidazo[1,5-a]pyrazin-7-yl}-N-methyl-2'-phenyl-acetamide;
(R)-2'-{1-cyclopropyl-3-methyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{1-chloro-3-ethyl-8-[2-(2,3,5-trifluoro-phenyl)-ethyl]-5,6-dihydro-8H-imidazo[1,5-a]pyrazin-7-yl}-N-methyl-2'-phenyl-acetamide;
(R)-2'-{1-chloro-3-ethyl-(S)-8-[2-(3-fluoro-4-methoxy-phenyl)-ethyl]-5,6-dihydro-8H-imidazo[1,5-a]pyrazin-7-yl}-N-methyl-2'-phenyl-acetamide;
(R)-2'-{1-chloro-(S)-8-[2-(2,5-difluoro-4-methoxy-phenyl)-ethyl]-3-ethyl-5,6-dihydro-8H-imidazo[1,5-a]pyrazin-7-yl}-N-methyl-2'-phenyl-acetamide;
(R)-2'-[1-chloro-3-ethyl-(R)-8-(4-fluoro-3-trifluoromethyl-phenoxymethyl)-5,6-dihydro-8H-imidazo[1,5-a]pyrazin-7-yl]-N-methyl-2'-phenyl-acetamide;
(R)-2'-[1-chloro-3-ethyl-(R)-8-(4-trifluoromethyl-phenoxymethyl)-5,6-dihydro-8H-imidazo[1,5-a]pyrazin-7-yl]-N-methyl-2'-phenyl-acetamide;

(R)-2'-[1-chloro-(R)-8-(3,4-dimethyl-phenoxymethyl)-3-ethyl-5,6-dihydro-8H-imidazo[1,5-a]pyrazin-7-yl]-N-methyl-2'-phenyl-acetamide; and (R)-2'-[1-chloro-3-ethyl-(R)-8-(3-trifluoromethyl-phenoxymethyl)-5,6-dihydro-8H-imidazo[1,5-a]pyrazin-7-yl]-N-methyl-2'-phenyl-acetamide;

wherein the first 42 compounds of the above list are especially preferred.

xxi) In another embodiment of the invention compounds of formula (I) according to embodiment i) are selected from the group consisting of:

(R)-2'-{1-chloro-3-ethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-3-ethyl-(S)-8-[2-(3,5-difluoro-4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-(S)-8-[2-(2,4-difluoro-3-methyl-phenyl)-ethyl]-3-ethyl-5,6-dihydro-8H-imidazo[1,5-a]pyrazin-7-yl}-N-methyl-2'-phenyl-acetamide;

(R)-2'-{1-chloro-(S)-8-[2-(3,5-difluoro-4-methyl-phenyl)-ethyl]-3-ethyl-5,6-dihydro-8H-imidazo[1,5-a]pyrazin-7-yl}-N-methyl-2'-phenyl-acetamide;

(R)-2'-{1-chloro-(R)-8-[2-(3,5-difluoro-4-methyl-phenyl)-ethyl]-3-ethyl-5,6-dihydro-8H-imidazo[1,5-a]pyrazin-7-yl}-N-methyl-2'-phenyl-acetamide;

(R)-2'-{1-chloro-3-ethyl-(S)-8-[2-(3-fluoro-4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-8-[2-(3,4-dimethyl-phenyl)-ethyl]-3-ethyl-5,6-dihydro-8H-imidazo[1,5-a]pyrazin-7-yl}-N-methyl-2'-phenyl-acetamide;

(R)-2'-{1-chloro-3-ethyl-8-[2-(3-fluoro-4-methyl-phenyl)-ethyl]-5,6-dihydro-8H-imidazo[1,5-a]pyrazin-7-yl}-N-methyl-2'-phenyl-acetamide;

(R)-2'-{1-chloro-3-ethyl-(R)-8-[2-(3-fluoro-4-methyl-phenyl)-ethyl]-5,6-dihydro-8H-imidazo[1,5-a]pyrazin-7-yl}-N-methyl-2'-phenyl-acetamide;

(R)-2'-{1-chloro-3-ethyl-(S)-8-[2-(2-fluoro-4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-(S)-8-[2-(3,5-difluoro-4-methyl-phenyl)-ethyl]-3-methyl-5,6-dihydro-8H-imidazo[1,5-a]pyrazin-7-yl}-N-methyl-2'-phenyl-acetamide;

(R)-2'-{1-chloro-(R)-8-[2-(3,5-difluoro-4-methyl-phenyl)-ethyl]-3-methyl-5,6-dihydro-8H-imidazo[1,5-a]pyrazin-7-yl}-N-methyl-2'-phenyl-acetamide;

(R)-2'-{1-chloro-8-[2-(3,4-dimethyl-phenyl)-ethyl]-3-methyl-5,6-dihydro-8H-imidazo[1,5-a]pyrazin-7-yl}-N-methyl-2'-phenyl-acetamide;

(R)-2'-{1-chloro-3-methyl-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{3-isopropyl-1-methoxy-(S)-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{(S)-8-[2-(3,4-dimethyl-phenyl)-ethyl]-3-ethyl-1-methoxy-5,6-dihydro-8H-imidazo[1,5-a]pyrazin-7-yl}-N-methyl-2'-phenyl-acetamide;

(R)-2'-{3-ethyl-(S)-8-[2-(4-trifluoromethyl-phenyl)-ethyl]-1-vinyl-5,6-dihydro-8H-imidazo[1,5-a]pyrazin-7-yl}-N-methyl-2'-phenyl-acetamide;

(R)-2'-{1-cyano-3-ethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{3-ethyl-1-trifluoromethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-3-methoxymethyl-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-3-ethyl-(R)-8-[2-(2-fluoro-4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-8-[2-(3,4-difluoro-phenyl)-ethyl]-3-ethyl-5,6-dihydro-8H-imidazo[1,5-a]pyrazin-7-yl}-N-methyl-2'-phenyl-acetamide;

(R)-2'-{1-chloro-3-isopropyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-3-isopropyl-(R)-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{3-ethyl-1-iodo-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{3-ethyl-1-methyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{8-[2-(3-chloro-phenyl)-ethyl]-1,3-dimethyl-5,6-dihydro-8H-imidazo[1,5-a]pyrazin-7-yl}-N-methyl-2'-phenyl-acetamide;

(R)-2'-[1,3-dimethyl-8-(2-p-tolyl-ethyl)-5,6-dihydro-8H-imidazo[1,5-a]pyrazin-7-yl]-N-methyl-2'-phenyl-acetamide;

(R)-2'-{8-[2-(2,4-dimethyl-phenyl)-ethyl]-1,3-dimethyl-5,6-dihydro-8H-imidazo[1,5-a]pyrazin-7-yl}-N-methyl-2'-phenyl-acetamide;

(R)-2'-{8-[2-(3-fluoro-4-methoxy-phenyl)-ethyl]-1,3-dimethyl-5,6-dihydro-8H-imidazo[1,5-a]pyrazin-7-yl}-N-methyl-2'-phenyl-acetamide;

(R)-2'-{(R)-8-[2-(3,4-dimethyl-phenyl)-ethyl]-3-ethyl-1-methoxy-5,6-dihydro-8H-imidazo[1,5-a]pyrazin-7-yl}-N-methyl-2'-phenyl-acetamide;

3-ethyl-7-(methylcarbamoyl-phenyl-methyl)-8-[2-(4-trifluoromethyl-phenyl)-ethyl]-5,6,7,8-tetrahydro-imidazo[1,5-a]pyrazine-1-carboxylic acid methylamide;

(R)-2'-{(S)-8-[2-(3,4-difluoro-phenyl)-ethyl]-1,3-dimethyl-5,6-dihydro-8H-imidazo[1,5-a]pyrazin-7-yl}-N-methyl-2'-phenyl-acetamide;

(R)-2'-{1,3-dichloro-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-3-ethyl-(S)-8-[2-(3,4,5-trifluoro-phenyl)-ethyl]-5,6-dihydro-8H-imidazo[1,5-a]pyrazin-7-yl}-N-methyl-2'-phenyl-acetamide;

(R)-2'-{1-chloro-(S)-8-[2-(3-fluoro-4-trifluoromethyl-phenyl)-ethyl]-3-methyl-5,6-dihydro-8H-imidazo[1,5-a]pyrazin-7-yl}-N-methyl-2'-phenyl-acetamide;

(R)-2'-{1-chloro-(S)-8-[2-(3,5-difluoro-4-methoxy-phenyl)-ethyl]-3-ethyl-5,6-dihydro-8H-imidazo[1,5-a]pyrazin-7-yl}-N-methyl-2'-phenyl-acetamide;

(R)-2'-{1-chloro-(S)-8-[2-(4-chloro-3,5-difluoro-phenyl)-ethyl]-3-ethyl-5,6-dihydro-8H-imidazo[1,5-a]pyrazin-7-yl}-N-methyl-2'-phenyl-acetamide;

(R)-2'-{1-chloro-(S)-8-[2-(3-chloro-4-trifluoromethyl-phenyl)-ethyl]-3-ethyl-5,6-dihydro-8H-imidazo[1,5-a]pyrazin-7-yl}-N-methyl-2'-phenyl-acetamide;

(R)-2'-{1-chloro-(S)-8-[2-(2,5-difluoro-4-trifluoromethyl-phenyl)-ethyl]-3-ethyl-5,6-dihydro-8H-imidazo[1,5-a]pyrazin-7-yl}-N-methyl-2'-phenyl-acetamide;

(R)-2'-{1-chloro-3-ethyl-(S)-8-[2-(4-trifluoromethoxy-phenyl)-ethyl]-5,6-dihydro-8H-imidazo[1,5-a]pyrazin-7-yl}-N-methyl-2'-phenyl-acetamide;

(R)-2'-{1-chloro-(S)-8-[2-(4-cyano-phenyl)-ethyl]-3-ethyl-5,6-dihydro-8H-imidazo[1,5-a]pyrazin-7-yl}-N-methyl-2'-phenyl-acetamide;

(R)-2'-{1-cyano-3-ethyl-(S)-8-[2-(3-fluoro-4-trifluoromethyl-phenyl)-ethyl]-5,6-dihydro-8H-imidazo[1,5-a]pyrazin-7-yl}-N-methyl-2'-phenyl-acetamide;

(R)-2'-{1-cyano-(S)-8-[2-(3-fluoro-4-trifluoromethyl-phenyl)-ethyl]-3-methyl-5,6-dihydro-8H-imidazo[1,5-a]pyrazin-7-yl}-N-methyl-2'-phenyl-acetamide;

(R)-2'-{1-chloro-3-propyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-(S)-8-[2-(3-fluoro-4-trifluoromethyl-phenyl)-ethyl]-3-propyl-5,6-dihydro-8H-imidazo[1,5-a]pyrazin-7-yl}-N-methyl-2'-phenyl-acetamide;

(R)-2'-{1-cyclopropyl-3-methyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-3-ethyl-8-[2-(2,3,5-trifluoro-phenyl)-ethyl]-5,6-dihydro-8H-imidazo[1,5-a]pyrazin-7-yl}-N-methyl-2'-phenyl-acetamide;

(R)-2'-{1-chloro-3-ethyl-(S)-8-[2-(3-fluoro-4-methoxy-phenyl)-ethyl]-5,6-dihydro-8H-imidazo[1,5-a]pyrazin-7-yl}-N-methyl-2'-phenyl-acetamide;

(R)-2'-{1-chloro-(S)-8-[2-(2,5-difluoro-4-methoxy-phenyl)-ethyl]-3-ethyl-5,6-dihydro-8H-imidazo[1,5-a]pyrazin-7-yl}-N-methyl-2'-phenyl-acetamide;

(R)-2'-[1-chloro-3-ethyl-(R)-8-(4-fluoro-3-trifluoromethyl-phenoxymethyl)-5,6-dihydro-8H-imidazo[1,5-a]pyrazin-7-yl]-N-methyl-2'-phenyl-acetamide;

(R)-2'-[1-chloro-3-ethyl-(R)-8-(4-trifluoromethyl-phenoxymethyl)-5,6-dihydro-8H-imidazo[1,5-a]pyrazin-7-yl]-N-methyl-2'-phenyl-acetamide;

(R)-2'-[1-chloro-(R)-8-(3,4-dimethyl-phenoxymethyl)-3-ethyl-5,6-dihydro-8H-imidazo[1,5-a]pyrazin-7-yl]-N-methyl-2'-phenyl-acetamide; and (R)-2'-[1-chloro-3-ethyl-(R)-8-(3-trifluoromethyl-phenoxymethyl)-5,6-dihydro-8H-imidazo[1,5-a]pyrazin-7-yl]-N-methyl-2'-phenyl-acetamide;

wherein the first 34 compounds of the above list are especially preferred.

The compounds of general formula (I) and (II) and their pharmaceutically acceptable salts can be used as medicaments, e.g. in the form of pharmaceutical compositions for enteral or parenteral administration.

A further aspect of the invention is a pharmaceutical composition containing at least one compound according to formula (I) and/or (Ia), or a pharmaceutically acceptable salt thereof, and a pharmaceutically acceptable carrier material.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of Formula (I) and (II) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds of general formula (I) and (II) are useful for the treatment and/or prevention of the diseases mentioned herein.

Where the plural form is used for compounds, salts, pharmaceutical compositions, diseases or the like, this is intended to mean also a single compound, salt, disease or the like.

In one embodiment, the invention relates to a method for the treatment and/or prevention of the diseases mentioned herein, said method comprising administering to a subject a pharmaceutically active amount of a compound of general formula (I) and (II).

The compounds according to general formula (I) and (II) may be used for the preparation of a medicament and are suitable for the prevention or treatment of diseases selected from the group consisting of dysthymic disorders including major depression and cyclothymia, affective neurosis, all types of manic depressive disorders, delirium, psychotic disorders, schizophrenia, catatonic schizophrenia, delusional paranoia, adjustment disorders and all clusters of personality disorders; schizoaffective disorders; anxiety disorders including generalized anxiety, obsessive compulsive disorder, posttraumatic stress disorder, panic attacks, all types of phobic anxiety and avoidance; separation anxiety; all psychoactive substance use, abuse, seeking and reinstatement; all types of psychological or physical addictions, dissociative disorders including multiple personality syndromes and psychogenic amnesias; sexual and reproductive dysfunction; psychosexual dysfunction and addiction; tolerance to narcotics or withdrawal from narcotics; increased anaesthetic risk, anaesthetic responsiveness; hypothalamic-adrenal dysfunctions; disturbed biological and circadian rhythms; sleep disturbances associated with diseases such as neurological disorders including neuropathic pain and restless leg syndrome; sleep apnea; narcolepsy; chronic fatigue syndrome; insomnias related to psychiatric disorders; all types of idiopathic insomnias and parasomnias; sleep-wake schedule disorders including jet-lag; all dementias and cognitive dysfunctions in the healthy population and in psychiatric and neurological disorders; mental dysfunctions of aging; all types of amnesia; severe mental retardation; dyskinesias and muscular diseases; muscle spasticity, tremors, movement disorders; spontaneous and medication-induced dyskinesias; neurodegenerative disorders including Huntington's, Creutzfeld-Jacob's, Alzheimer's diseases and Tourette syndrome; Amyotrophic lateral sclerosis; Parkinson's disease; Cushing's syndrome; traumatic lesions; spinal cord trauma; head trauma; perinatal hypoxia; hearing loss; tinnitus; demyelinating diseases; spinal and cranial nerve diseases; ocular damage; retinopathy; epilepsy; seizure disorders; absence seizures, complex partial and generalized seizures; Lennox-Gastaut syndrome; migraine and headache; pain disorders; anaesthesia and analgesia; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; dental pain; pain related to infection e.g. by HIV; post-chemotherapy pain; post-stroke pain; post-operative pain; neuralgia; osteoarthritis; conditions associated with visceral pain such as irritable bowel syndrome; eating disorders; diabetes; toxic and dysmetabolic disorders including cerebral anoxia, diabetic neuropathies and alcoholism; appetite, taste, eating, or drinking disorders; somatoform disorders including hypochondriasis; vomiting/nausea; emesis; gastric dyskinesia; gastric ulcers; Kallman's syndrome (anosmia); impaired glucose tolerance; intestinal motility dyskinesias; hypothalamic diseases; hypophysis diseases; hyperthermia syndromes, pyrexia, febrile seizures, idiopathic growth deficiency; dwarfism; gigantism; acromegaly; basophil adenoma; prolactinoma; hyperprolactinemia; brain tumors, adenomas; benign prostatic hypertrophy, prostate cancer; endometrial, breast, colon cancer; all types of testicular dysfunctions, fertility control; reproductive hormone abnormalities; hot flashes; hypothalamic hypogonadism, functional or psychogenic amenorrhea; urinary bladder incontinence asthma; allergies; all types of dermatitis, acne and cysts, sebaceous gland dysfunctions; cardiovascular disorders; heart and lung diseases, acute and congestive heart failure; hypotension; hypertension; dyslipidemias, hyperlipidemias, insulin resistance; urinary retention; osteoporosis; angina pectoris; myocardial infarction; arrhythmias, coronary diseases, left ventricular hypertrophy; ischemic or haemorrhagic stroke; all types of cerebrovascular disorders including subarachnoid haemorrhage, ischemic and hemorrhagic stroke and vascular dementia; chronic renal failure and other renal diseases; gout; kidney cancer; urinary incontinence; and other diseases related to general orexin system dysfunctions.

Compounds of general formula (I) and (II) are particularly suitable for the treatment of diseases or disorders selected from the group consisting of all types of sleep disorders, of stress-related syndromes, of psychoactive substance use and abuse, of cognitive dysfunctions in the healthy population and in psychiatric and neurologic disorders, of eating or drinking disorders. Eating disorders may be defined as comprising metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake. Sleep disorders include all types of parasomnias, insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders. Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance; psychoactive substance use, abuse, seeking and reinstatement are defined as all types of psychological or physical addictions and their related tolerance and dependence components. Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

In a further preferred embodiment of the invention compounds of general formula (I) and (II) are particularly suitable for the treatment of diseases or disorders selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders.

In another preferred embodiment of the invention compounds of general formula (I) and (II) are particularly suitable for the treatment of diseases or disorders selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another preferred embodiment of the invention compounds of general formula (I) and (II) are particularly suitable for the treatment of diseases or disorders selected from the group consisting of eating disorders that comprise metabolic dysfunction; dysregulated appetite control; compulsive obesities; emeto-bulimia or anorexia nervosa.

In another preferred embodiment of the invention compounds of general formula (I) and (II) are particularly suitable for the treatment of diseases or disorders selected from the group consisting of psychoactive substance use and abuse that comprise all types of psychological or physical addictions and their related tolerance and dependence components.

DETAILED DESCRIPTION OF THE INVENTION

Compounds of general formula (I) and (II) belonging to this invention could be prepared according to several synthetic routes described below (schemes 1 to 13). All chemical transformations can be performed according to well-known standard methodologies as described in the literature or as described in the procedures below. Starting materials are commercially available or prepared according to procedures known in the literature or as illustrated herein. Some of the examples may be further modified by manipulation of substituents to result in additional examples. These manipulations may include, but are not limited to, reduction, oxidation, alkylation, acylation, and hydrolysis reactions which are commonly known to those skilled in the art. The order of carrying out the foregoing reaction schemes may be varied to facilitate the reaction or to avoid side-products.

An overview of the general synthetic route is presented in scheme 1. Tri-substituted-imidazole derivatives represented key intermediates in this synthesis and therefore their regioselective preparation was envisaged. Thus, the issue of tautomerism associated with imidazoles (and leading to isomeric mixtures) was circumvented in this approach through the use of pseudosymmetric 4,5-diiodoimidazole derivatives. Diiodination ($I_2/Na_2CO_3$) of 2-substituted imidazoles A (from commercial sources or from regioselective syntheses as described in scheme 5) gave the corresponding 4,5-diiodoimidazoles B. Deprotonation of pseudosymmetric B (NaH/DMF) and subsequent N-alkylation with (2-bromoethyl)-carbamic acid tert-butyl ester furnished exclusively the product C. The pivotal step of this synthetic route was the efficient preparation of the corresponding 4-iodoimidazoles D by using a regioselective exchange of the 5-iodo moiety for MgBr (EtMgBr/THF/−40° C.) followed by trapping of the carbanion with water. This process proved to be highly regioselective and only the expected 4-iodoimidazole derivatives D could be detected (as evidenced by $^1$H-NMR). Moreover this approach afforded an operational, convenient and rapid synthesis of these key substrates and could be accomplished on a multigram-scale (see experimental part). Boc-deprotection of D led smoothly to the corresponding primary amines E which were allowed to react with aldehydes $R^1$—X—$CH_2$—CHO in a microwave-assisted Pictet-Spengler like reaction. Subsequent Boc-protection and purification gave the expected 5,6,7,8-tetrahydro-imidazo[1,5-a]pyrazine derivatives F with good to high overall yields. The versatility of the iodo-substituent allowed the access to a variety of derivatives G (see scheme 6 for the introduction of diverse functional groups and substituents). Boc-deprotection of G followed by N-alkylation with electrophiles H (see schemes 4 and 13) furnished the compounds of formula (I) and (II).

The additional building block O was synthesized (scheme 2) in order to prepare some specific compounds of formula (I) and (II) containing either $R^3$ substituents which would be too sensitive and therefore incompatible with the quite harsh reaction conditions of the microwave-assisted Pictet-Spengler like reaction or containing specific $R^2/R^3$ combinations which would not be conveniently incorporated by application of the general synthesis depicted in scheme 1. Iodination of imidazole J ($I_2/Na_2CO_3$) led smoothly to 2,4,5-triiodo-1H-imidazole K which was N-alkylated (NaH/ BrCH$_2$CH$_2$NHBoc) giving compound L. Regioselective one-pot removal of two iodo-substituents with ethylmagnesium bromide (first on position-2, and secondly on position-5) furnished exclusively the expected 4-iodoimidazole derivative M which was Boc-deprotected (HCl in dioxane). The obtained primary amine N was then allowed to react with aldehydes $R^1$—X—CH$_2$—CHO in a microwave-assisted Pictet-Spengler like reaction. Subsequent Boc-protection and purification afforded the 5,6,7,8-tetrahydro-imidazo[1,5-a] pyrazine derivatives O. With this building block O in hand, the planned specific combinations of $R^2/R^3$ substituents could be introduced by iodine/metal exchange and trapping of the resulting carbanion with appropriate electrophiles, by transition metal-catalyzed cross-coupling reactions (mainly Stille cross-coupling reactions), and by aromatic electrophilic substitution reactions performed on the imidazole moiety (scheme 2). This synthetic route was particularly appropriate for the preparation of compounds of formula (I) and (II) with $R^3$ representing halogen.

Scheme 1: General synthetic route allowing the preparartion of compounds of formula (I) and (II).

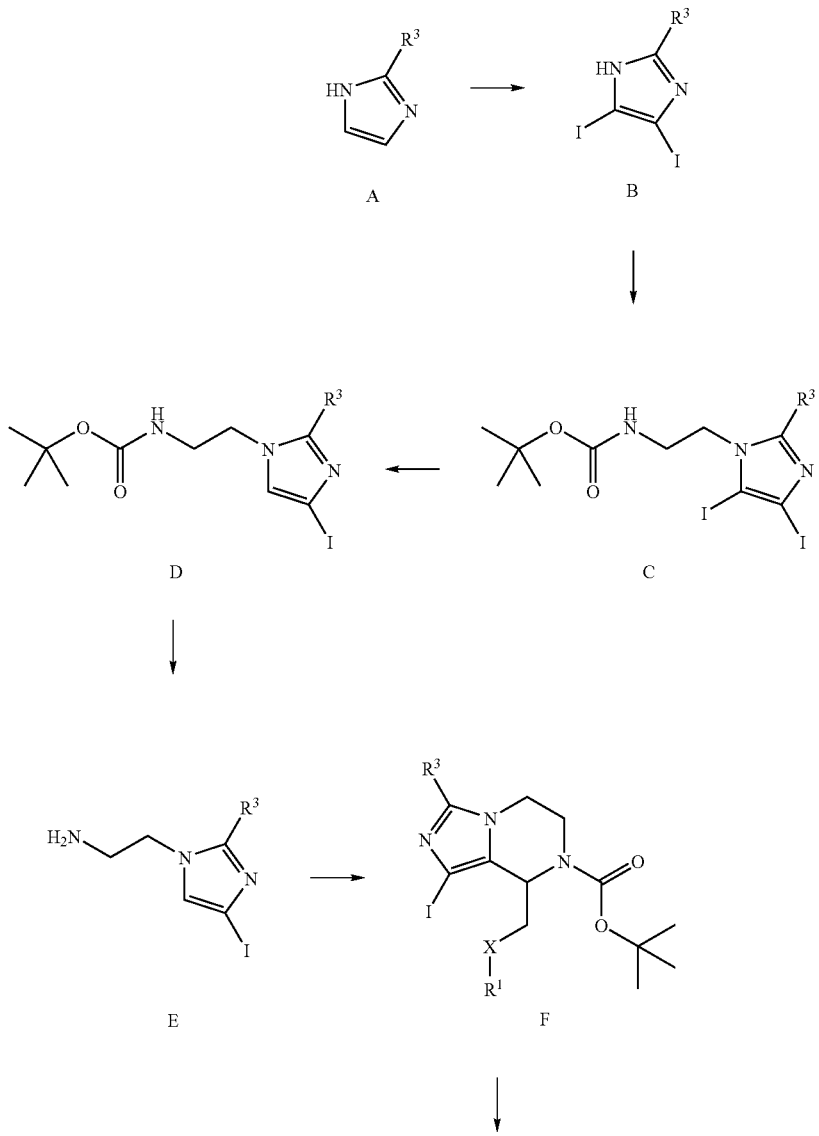

-continued

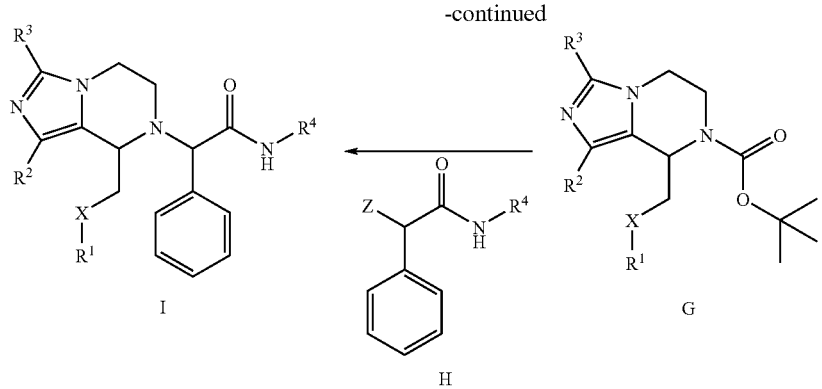

wherein X, R¹, R², R³, R⁴ are described above, and Z is Br or OTs.

Scheme 2: Preparation of building block O allowing introduction of specific R²/R³ substituents.

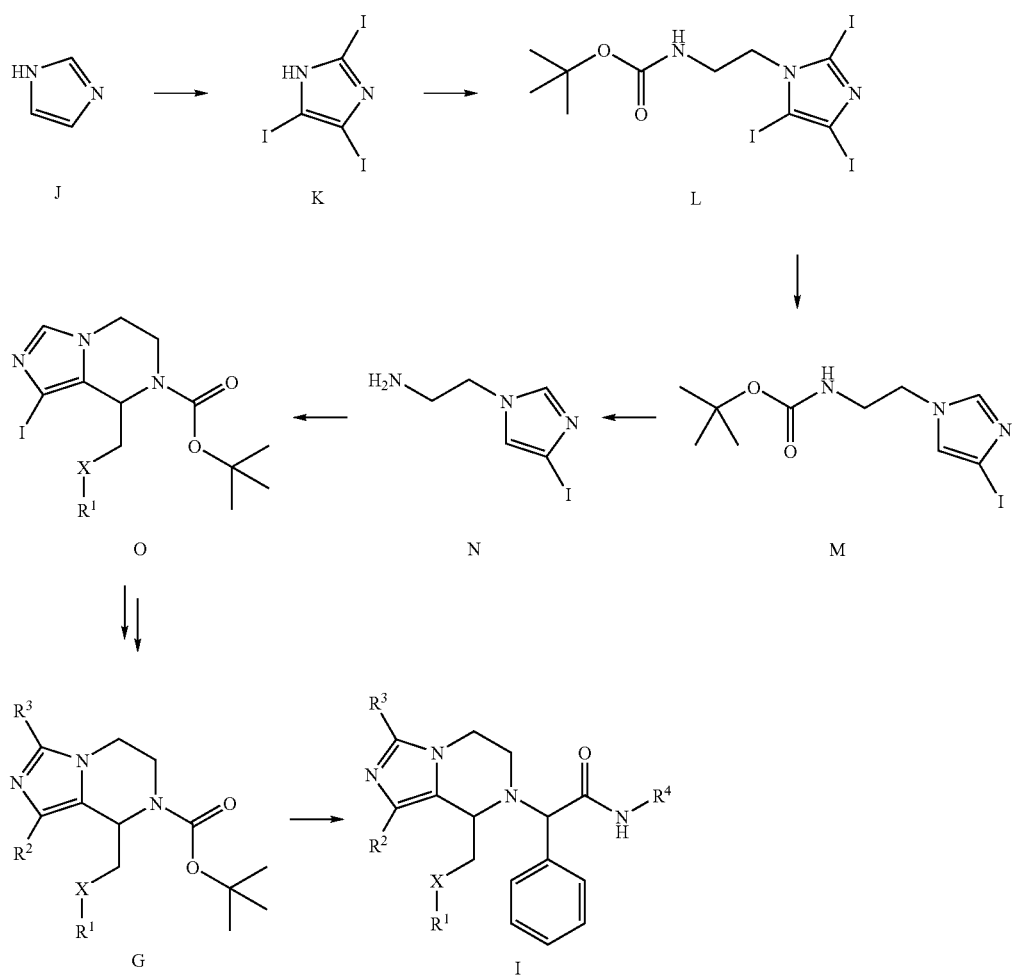

wherein X, R¹, R², R³ and R⁴ are as described above.

As shown in scheme 3, specific R²-substituents could be also advantageously introduced at the earlier stage of imidazole derivative D in order to avoid side-reactions susceptible to occur in the remaining steps (e.g. aromatic nucleophilic substitution reactions with some specifically substituted R¹ residues). Remaining steps affording compounds of general formula (I) and (II) were as previously described in scheme 1.

Scheme 3: Earlier introduction of some specific R²-substituents.

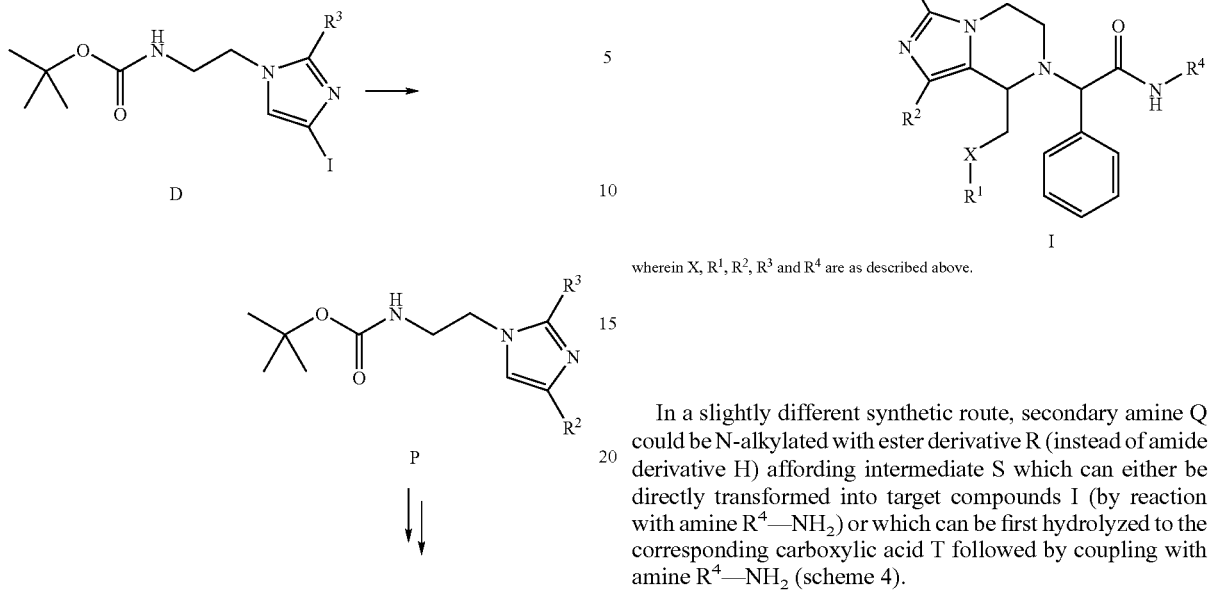

wherein X, R¹, R², R³ and R⁴ are as described above.

In a slightly different synthetic route, secondary amine Q could be N-alkylated with ester derivative R (instead of amide derivative H) affording intermediate S which can either be directly transformed into target compounds I (by reaction with amine R⁴—NH₂) or which can be first hydrolyzed to the corresponding carboxylic acid T followed by coupling with amine R⁴—NH₂ (scheme 4).

Scheme 4: N-alkylation of 5,6,7,8-tetrahydro-imidazo[1,5-a]pyrazines.

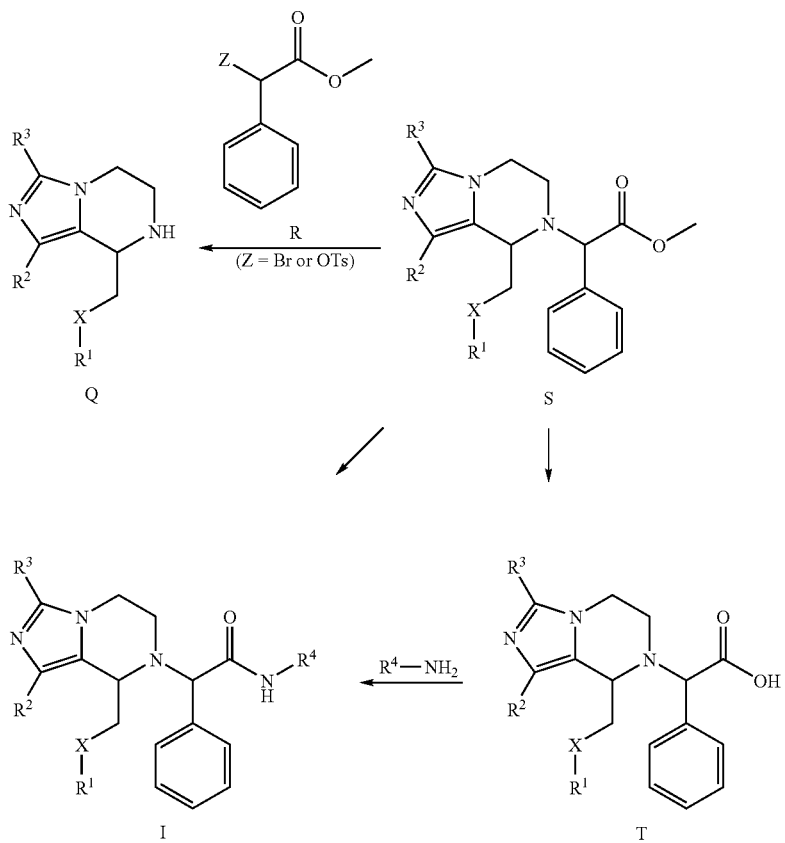

wherein X, R¹, R², R³ and R⁴ are as described above.

A variety of useful 2-substituted imidazoles A were conveniently obtained either from commercial sources or from regioselective synthesis (scheme 5). Treatment of 1-trityl-1H-imidazole with n-butyllithium allowed the abstraction of the most acidic H-2 hydrogen and the generation of the corresponding carbanion. In a next step, this carbanion can react with electrophiles to form 1-trityl-2-E-imidazoles. The triphenylmethyl group could be smoothly removed by acid hydrolysis (AcOH/MeOH) to give the expected 2-substituted imidazoles A. Selected preparations are exemplified in scheme 5 but are not limited to these examples. All the introduced functional groups and substituents could be used for further derivatization (elaboration of $R^3$ substituents). Thus, iodine constituted a useful electrophile for the efficient synthesis of 2-iodoimidazole derivatives. Moreover 2-iodo-1-trityl-1H-imidazole represented a versatile starting material for the preparation of additional 2-substituted imidazoles via palladium-catalyzed cross-coupling reactions (mainly Stille cross-coupling reactions). 1-Trityl-1H-imidazole-2-carbaldehyde could be also obtained regioselectively and efficiently (after trapping with DMF) allowing further functional group interconversions and therefore access to 2-alkoxymethyl-1H-imidazole (after reduction of the aldehyde moiety and subsequent O-alkylation).

The versatility of the iodo-substituent in 5,6,7,8-tetrahydro-imidazo[1,5-a]pyrazines F allowed the access to a variety of derivatives, as exemplified in scheme 6. Thus, treatment of F with n-butyllithium followed by trapping of the resulting carbanion with hexachloroethane afforded the chloro-derivative. Alkoxy-residues could be introduced by copper(I)-catalyzed and microwave-assisted alkoxylation of F (ROH/CuI/1,10-phenanthroline/$Cs_2CO_3$). The carbanion generated after iodine/metal exchange could be smoothly trapped with N,N-dimethylformamide and the introduced formyl-moiety could be additionally manipulated for the preparation of several derivatives (scheme 6a and 6b). Moreover, trapping of the previous carbanion with $CO_2$ allowed the direct preparation of carboxylic acid derivatives which in turn could be converted to amides. The iodo-substituent also allowed the introduction of a trifluoromethyl group via copper(I)-catalyzed trifluoromethylation ($FSO_2CF_2CO_2Me$/CuI). Stille cross-coupling reactions performed with iodo-imidazoles are well documented in the literature, and in our case 5,6,7,8-tetrahydro-imidazo[1,5-a]pyrazines F reacted smoothly in such reactions with a variety of organotin derivatives (e.g. with n-tributyl(vinyl)tin).

Scheme 5: Regioselective preparation of 2-substituted imidazoles.

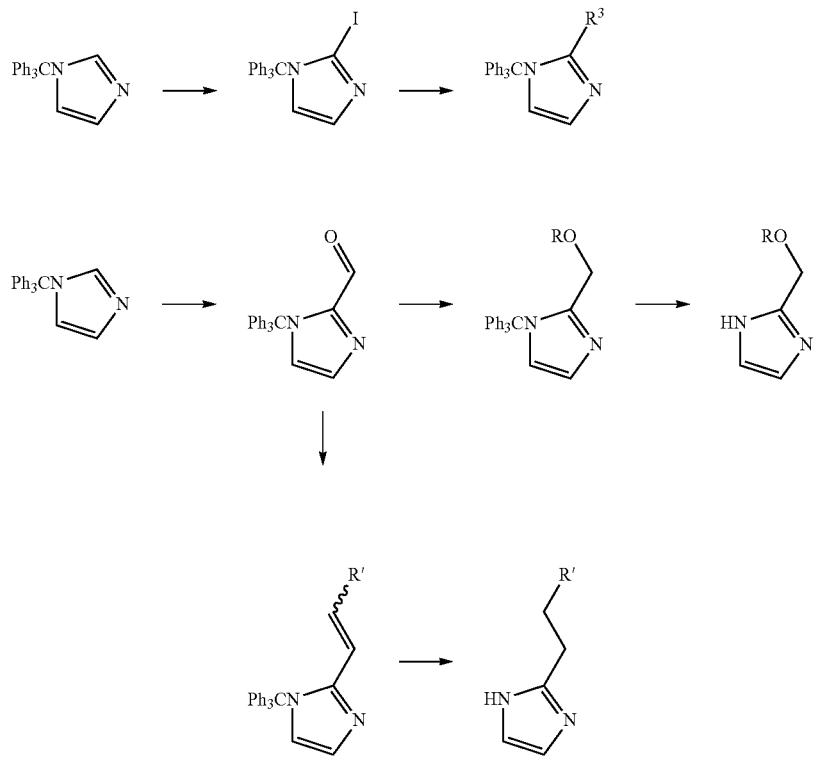

wherein $R^3$ is as described above, R is $C_{(1-4)}$alkyl and R' is $C_{(1-2)}$alkyl.

Scheme 6a: Use of the versatility of the iodo-substituent for the preparation of derivatives.
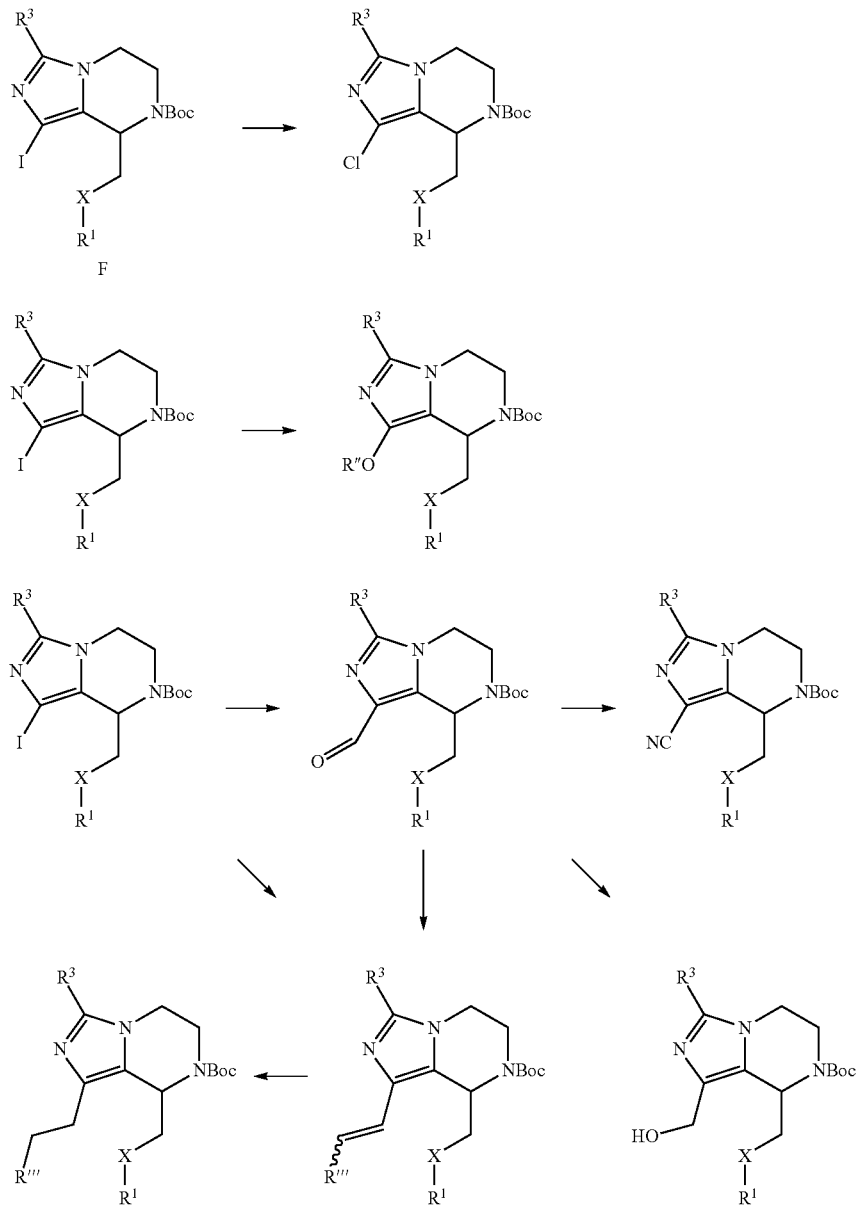
wherein X, $R^1$, $R^3$, $R^5$ and $R^6$ are as described above, R" represents $(C_{1-4})$alkyl and R''' represents $(C_{1-2})$alkyl.
Scheme 6b: Use of the versatility of the iodo-substituent for the preparation of derivatives.
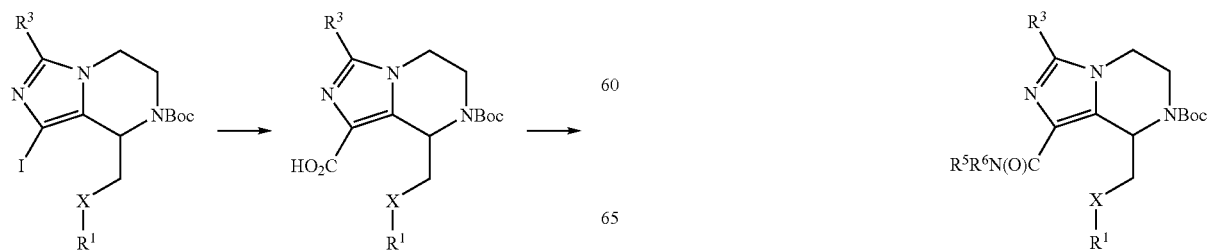

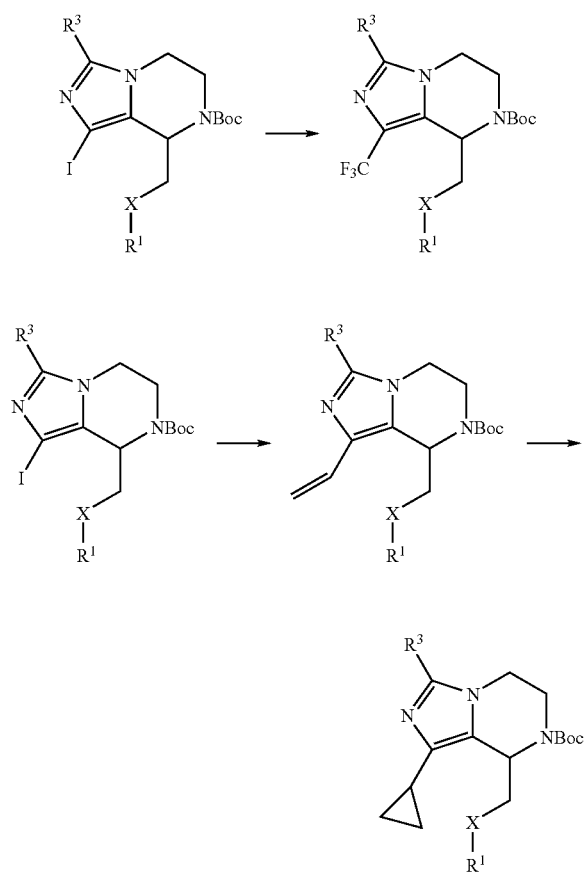

wherein X, $R^1$, $R^3$, $R^5$ and $R^6$ are as described above, R" represents ($C_{1-4}$)alkyl and R'" represents ($C_{1-2}$)alkyl.

The preparation of some compounds of formula (I) and (II) could be directly undertaken starting with appropriately disubstituted imidazoles (commercially available or synthesized; scheme 7). Thus, N-alkylation of 2,4-substituted imidazoles with 2-chloroethylamine hydrochloride (in the presence of powdered NaOH and catalytic amounts of tetrabutylammonium hydrogensulfate) afforded a mixture of isomeric products including the expected compound U. Subsequent microwave-assisted Pictet-Spengler like reaction with aldehydes $R^1$—X—$CH_2$—CHO furnished the expected 5,6,7,8-tetrahydro-imidazo[1,5-a]pyrazine derivatives Q which could be transformed to compounds of formula (I) and (II) according to previously described procedures.

Scheme 7: Preparartion of compounds of formula (I) and (II) starting with 2,4-substituted imidazoles.

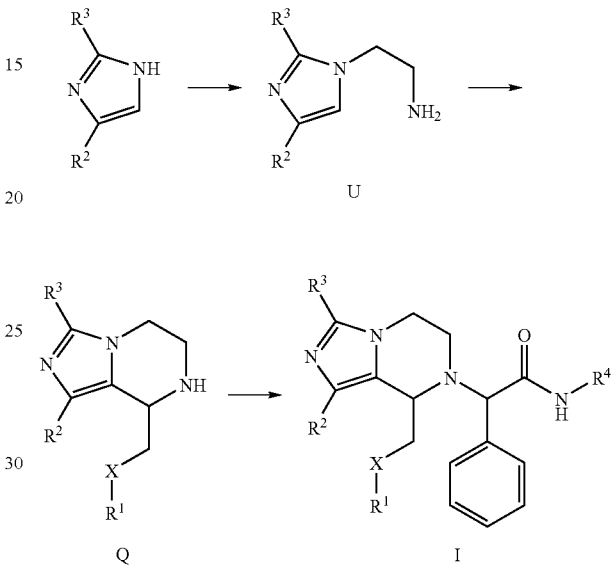

wherein X, $R^1$, $R^2$, $R^3$, $R^4$ are described above.

Aldehydes $R^1$—X—$CH_2$—CHO were pivotal reagents for the preparation of compounds of formula (I) and (II) and several synthetic methods allowed their efficient preparation.

Thus, aldehydes $R^1$—$CH_2$—$CH_2$—CHO (X=$CH_2$) were readily prepared by reduction of the corresponding hydrocinnamic acids ($BH_3$.THF) and subsequent oxidation of the obtained alcohols with PCC (scheme 8). Preliminary hydrogenation of commercially available cinnamic acids allowed a convenient access to unavailable hydrocinnamic acid precursors (scheme 8).

Scheme 8: Synthesis of aldehydes $R^1$—$CH_2$—$CH_2$—CHO from cinnamic or hydrocinnamic acids.

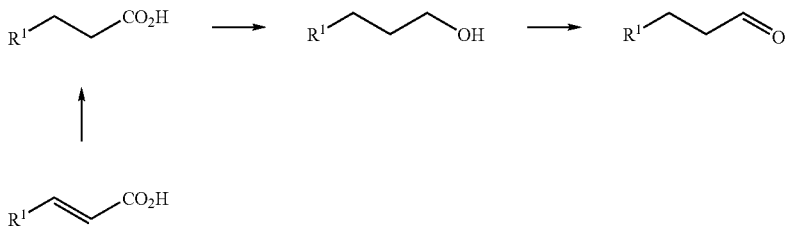

wherein $R^1$ is as described above.

Closely related to this method of preparation, another short and convenient synthesis of diversely substituted propanol derivatives was the reduction of corresponding propionic acid methyl esters (scheme 9).

Scheme 9: Synthesis of aldehydes $R^1$—$CH_2$—$CH_2$—CHO from propionic acid methyl esters.

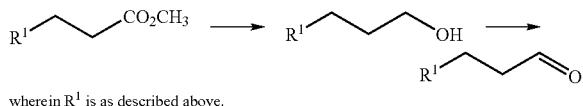

wherein $R^1$ is as described above.

In case neither cinnamic acids nor hydrocinnamic acids were commercially available, additional synthetic routes allowed their successful preparation. Thus, a convenient synthesis was based on a Knoevenagel condensation as depicted in scheme 10. Knoevenagel condensation between aryl aldehydes $R^1$CHO and malonic acid (in pyridine and in the presence of piperidine) gave the expected cinnamic acid derivatives. Catalytic hydrogenation under standard conditions (1 atm $H_2$; 10% Pd(C); MeOH; rt) afforded the corresponding hydrocinnamic acids which were converted to the corresponding aldehydes $R^1$—$CH_2$—$CH_2$—CHO by the previously described reduction/oxidation sequence (scheme 10).

Scheme 10: Preparation of hydrocinnamic acids and aldehydes $R^1$—$CH_2$—$CH_2$—CHO via Knoevenagel condensation.

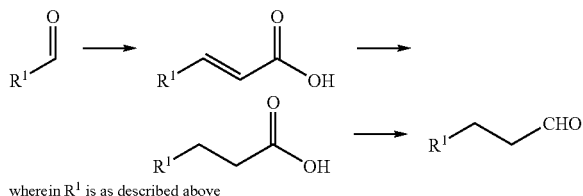

wherein $R^1$ is as described above

An alternative preparation of hydrocinnamic acids was based on a Heck reaction between aryl halides and n-butyl acrylate (with Pd(OAc)$_2$/DABCO as catalytic system; scheme 11). Palladium-catalyzed hydrogenation and subsequent saponification afforded the hydrocinnamic acids which were again converted to the expected aldehydes $R^1$—$CH_2$—$CH_2$—CHO by the previously described reduction/oxidation sequence (scheme 11).

Scheme 11: Preparation of hydrocinnamic acids and aldehydes $R^1$—$CH_2$—$CH_2$—CHO via Heck reaction.

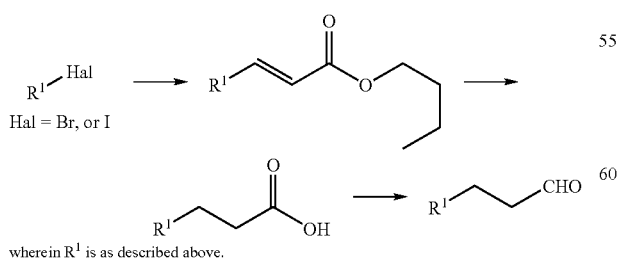

wherein $R^1$ is as described above.

Aldehydes $R^1$—O—$CH_2$—CHO (X=O) were readily prepared according to the synthetic route depicted in scheme 12. Thus, alkylation of phenol derivatives $R^1$OH with methyl bromoacetate, and subsequent reduction afforded the alcohol precursors which could be oxidized under Swern conditions in order to obtain the expected aldehyde derivatives (scheme 12).

Scheme 12: Preparation of aldehydes $R^1$—O—$CH_2$—CHO.

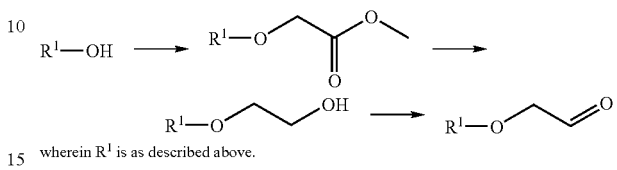

wherein $R^1$ is as described above.

The synthesis of enantiomerically pure toluene-4-sulfonic acid (S)-methylcarbamoyl-phenyl-methyl ester is exemplified in scheme 13. Treatment of methyl (S)-(+)-mandelate with an alcoholic amine solution gave the corresponding amide which could be converted to toluene-4-sulfonic acid (S)-methylcarbamoyl-phenyl-methyl ester after reaction with p-toluenesulfonyl chloride.

Scheme 13: Preparation of toluene-4-sulfonic acid (S)-methylcarbamoyl-phenyl-methyl ester.

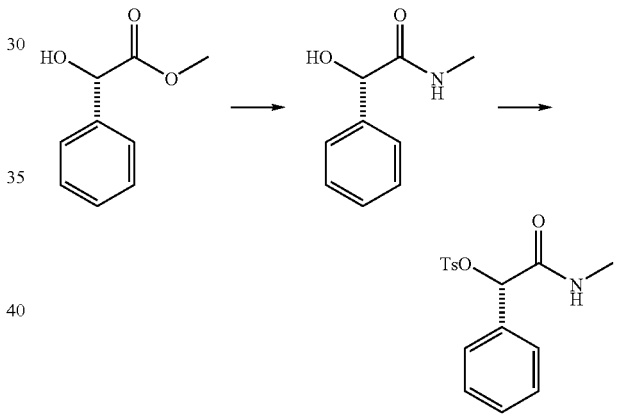

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 µm) column, a Daicel ChiralCel OD-H (5-10 µm) column, or a Daicel ChiralPak IA (10 µm) or AD-H (5 µm) column. Typical conditions of chiral HPLC are an isocratic mixture of eluent A (EtOH, in presence or absence of an amine such as TEA, diethylamine) and eluent B (hexane), at a flow rate of 0.8 to 150 mL/min.

EXPERIMENTAL PART

Abbreviations

As Used Herein and in the Description Above

AcOH acetic acid
anh. anhydrous
aq. aqueous
BH$_3$.THF borane-tetrahydrofuran complex Boc tert-butoxycarbonyl
Boc$_2$O di-tert-butyl dicarbonate
Br(CH$_2$)$_2$NHBoc (2-Bromo-ethyl)-carbamic acid tert-butyl ester
n-BuLi n-butyllithium
DABCO 1,4-diazabicyclo[2.2.2]octane
DCM dichloromethane
DIBAL diisobutylaluminum hydride
DIPEA N-ethyldiisopropylamine
DMF N,N-dimethylformamide
DMSO dimethyl sulfoxide
EA ethyl acetate
ELSD Evaporative Light-Scattering Detection
eq. equivalent
Et ethyl
EtMgBr ethylmagnesium bromide
ether diethylether
EtOH ethanol
FC flash chromatography on silica gel
FLIPR Fluorescent imaging plate reader
FSO$_2$CF$_2$CO$_2$Me methyl 2,2-difluoro-2-(fluorosulfonyl)acetate
h hour(s)
HCl hydrogen chloride
$^1$H-NMR nuclear magnetic resonance of the proton
HPLC High Performance Liquid Chromatography
HV High Vacuum
LC-MS Liquid Chromatography-Mass Spectroscopy
MeCN acetonitrile
MeOH methanol
MsCl methanesulfonyl chloride
min. minute(s)
Ms methanesulfonyl
MS Mass Spectroscopy
PBS phosphate buffered saline
PCC pyridinium chlorochromate
Pd(C) palladium over charcoal
Pd(OAc)$_2$ palladium (II) acetate
Ph phenyl
p-TsOH para-toluenesulfonic acid
rt room temperature
sat. saturated
TBTU O-benzotriazol-1-yl-N,N,N',N'-tetramethyluronium tetrafluoroborate TEA triethylamine
TFA trifluoroacetic acid
THF tetrahydrofuran
TLC Thin Layer Chromatography
t$_R$ retention time
Ts toluenesulfonyl
TsCl p-toluenesulfonyl chloride
UV ultra violet
V is visible
W Watt

I. CHEMISTRY

General Procedures and Examples

The following examples illustrate the preparation of pharmacologically active compounds of the invention but do not at all limit the scope thereof.
All temperatures are stated in ° C.
NMR measurements are done with a Varian Mercury 300 instrument or a Bruker Avance 400 Instrument; chemical shifts are given in ppm relative to the solvent used; multiplicities: s=singlet, d=doublet, t=triplet, m=multiplet, b=broad, coupling constants are given in Hz.

HPLC Conditions:
Analytic: Zorbax 59 SB Aqua column, 4.6×50 mm from Agilent Technologies. Eluents: A: MeCN; B: H$_2$O+0.04% TFA. Gradient: 90% B 5% B→over 2 min. Flow: 4.5 ml/min. Detection: UV/Vis+MS.
Preparative: Waters Xterra RP18 (large), 75×30 mm. Eluent: A: MeCN; B: H$_2$O+0.05% NH$_4$OH (25% aq.). Gradient: 90% B→10% B over 6.5 min. Flow: 75 ml/min. Detection: UV+ELSD.

A. Synthesis of carboxylic acids R$^1$—X—CH$_2$—CO$_2$H, alcohols R$^1$—X—CH$_2$—CH$_2$OH and aldehydes R$^1$—X—CH$_2$—CHO A.1 Synthesis of carboxylic acids R$^1$—CH$_2$—CH$_2$—CO$_2$H A.1.1 Synthesis of carboxylic acids R$^1$—CH$_2$—CH$_2$—CO$_2$H via Knoevenagel condensation 3-(3,4-dimethyl-phenyl)-acrylic acid [general procedure for Knoevenagel condensation (GP1)]

A suspension of 3,4-dimethylbenzaldehyde (15.000 g; 111.793 mmol) and malonic acid (22.103 g; 212.410 mmol) in pyridine (85 ml) was heated to 50° C., under nitrogen. Then piperidine (8.5 ml; 86.079 mmol) was added dropwise (over 5 minutes) and the resulting suspension was heated to 75° C. for 2 h. The reaction mixture was cooled to 0° C., and poured into an ice-cooled solution of concentrated hydrochloric acid (12 N; 96 ml) in water (1200 ml). The precipitated colorless product was filtered off, and washed with water (3×100 ml). Remaining water was evaporated under reduced pressure, then under HV to give the dried product 3-(3,4-dimethyl-phenyl)-acrylic acid as a colorless solid (19.230 g; 98%). LC-MS: t$_R$=0.88 min; [M+H]$^+$: no ionisation.

2,4-difluoro-3-methyl-benzaldehyde

A cooled (−78° C.) solution of 2,4-difluoro-3-methylbromobenzene (2.000 g; 9.661 mmol) in anhydrous THF (36 ml) was treated dropwise (over 10 min.) with a solution of 1.6M n-BuLi in hexanes (6.04 ml; 9.661 mmol) while maintaining the temperature below −70° C. This mixture was further stirred at −78° C. for 2 min. before anhydrous DMF (1.49 ml; 19.326 mmol) was added dropwise (over 10 min.) while maintaining the temperature below −70° C. After completion of the addition, the resulting light brown solution was further stirred at −78° C. for 1 h30. The resulting mixture was then quenched at −78° C. with aq. sat. NH$_4$Cl (10 ml), and was then allowed to warm-up to rt. Ether (50 ml) and water (20 ml) were added, and the organic layer was dried over anh. MgSO$_4$, filtered, and concentrated to dryness under reduced pressure (caution: rotary evaporation bath at 30° C. because the aldehyde is volatile). The crude was purified by FC (DCM) to give the pure product 2,4-difluoro-3-methyl-benzaldehyde as a pale yellow oil (1.250 g; 83%).

3-(2,4-difluoro-3-methyl-phenyl)-acrylic acid

According to the previously described general procedure (GP1), Knoevenagel condensation (75° C.; 3h30) between 2,4-difluoro-3-methyl-benzaldehyde (1.560 g; 9.744 mmol) and malonic acid (1.926 g; 18.515 mmol) gave the product 3-(2,4-difluoro-3-methyl-phenyl)-acrylic acid as a pale yellow solid (1.600 g; 83%). LC-MS: t$_R$=0.86 min; [M+H]$^+$: no ionisation.

3-(2-fluoro-4-trifluoromethyl-phenyl)-acrylic acid

According to the previously described general procedure (GP1), Knoevenagel condensation (75° C.; 3h20) between 2-fluoro-4-(trifluoromethyl)benzaldehyde (5.000 g; 26.027 mmol) and malonic acid (5.145 g; 49.451 mmol) gave the product 3-(2-fluoro-4-trifluoromethyl-phenyl)-acrylic acid as a colorless solid (5.030 g; 82.5%). LC-MS: $t_R$=0.89 min; [M+H]$^+$: no ionisation.

3-(3-fluoro-4-trifluoromethyl-phenyl)-acrylic acid

According to the previously described general procedure (GP1), Knoevenagel condensation (75° C.; 3h20) between 3-fluoro-4-trifluoromethyl-benzaldehyde (9.000 g; 46.848 mmol) and malonic acid (9.262 g; 89.012 mmol) gave the product 3-(3-fluoro-4-trifluoromethyl-phenyl)-acrylic acid as a colorless solid (9.520 g; 87%). LC-MS: $t_R$=0.90 min; [M+H]$^+$: no ionisation.

3-(2,4-dimethyl-phenyl)-acrylic acid

According to the previously described general procedure (GP1), Knoevenagel condensation (75° C.; 3h30) between 2,4-dimethyl-benzaldehyde (10.000 g; 74.528 mmol) and malonic acid (14.735 g; 141.607 mmol) gave the product 3-(2,4-dimethyl-phenyl)-acrylic acid as a colorless solid (9.720 g; 74%). LC-MS: $t_R$=0.86 min; [M+H]$^+$: no ionisation.

3-(3-fluoro-4-methyl-phenyl)-acrylic acid

According to the previously described general procedure (GP1), Knoevenagel condensation (75° C.; 2h30) between 3-fluoro-4-methyl-benzaldehyde (10.519 g; 76.154 mmol) and malonic acid (15.056 g; 144.694 mmol) gave the product 3-(3-fluoro-4-methyl-phenyl)-acrylic acid as a colorless solid (11.860 g; 86%). LC-MS: $t_R$=0.84 min; [M+H]$^+$: no ionisation.

3-(3,4,5-trifluoro-phenyl)-acrylic acid

According to the previously described general procedure (GP1), Knoevenagel condensation (75° C.; 3 h) between 3,4,5-trifluorobenzaldehyde (7.000 g; 43.724 mmol) and malonic acid (8.644 g; 83.076 mmol) gave the product 3-(3,4,5-trifluoro-phenyl)-acrylic acid as a yellow solid (8.600 g; 97%). LC-MS: $t_R$=0.91 min.; [M+H]$^+$: no ionisation.

3-(4-trifluoromethoxy-phenyl)-acrylic acid

According to the previously described general procedure (GP1), Knoevenagel condensation (75° C.; 6 h) between 4-(trifluoromethoxy)benzaldehyde (10.000 g; 52.598 mmol) and malonic acid (10.399 g; 99.937 mmol) gave the product 3-(4-trifluoromethoxy-phenyl)-acrylic acid as a colorless solid (12.080 g; 99%). LC-MS: $t_R$=0.96 min.; [M+H]$^+$: no ionisation.

3-(2,3,5-trifluoro-phenyl)-acrylic acid

According to the previously described general procedure (GP1), Knoevenagel condensation (75° C.; 3h20) between 2,3,5-trifluorobenzaldehyde (9.730 g; 60.777 mmol) and malonic acid (12.016 g; 115.477 mmol) gave the product 3-(2,3,5-trifluoro-phenyl)-acrylic acid as a colorless solid (8.310 g; 68%). LC-MS: $t_R$=0.84 min.; [M+H]$^+$: no ionisation.

3-(3-fluoro-4-methoxy-phenyl)-acrylic acid

According to the previously described general procedure (GP1), Knoevenagel condensation (75° C.; 3 h) between 3-fluoro-4-methoxybenzaldehyde (6.080 g; 39.445 mmol) and malonic acid (7.798 g; 74.946 mmol) gave the product 3-(3-fluoro-4-methoxy-phenyl)-acrylic acid as a colorless solid (7.530 g; 97%). LC-MS: $t_R$=0.86 min.; [M+H]$^+$: no ionisation.

3-(3,4-dimethyl-phenyl)-propionic acid [general procedure for hydrogenation of cinnamic acid derivatives (GP2)]

A mixture of 3-(3,4-dimethyl-phenyl)-acrylic acid (19.269 g; 109.355 mmol) and 10% palladium over activated charcoal (1.920 g) was placed under nitrogen before MeOH (300 ml) was carefully added. The resulting suspension was placed under vacuum, then under hydrogen (1 atm), and the reaction mixture was vigorously stirred at rt for 4 h. The reaction mixture was filtered over a pad of celite, and concentrated under reduced pressure to give the expected product 3-(3,4-dimethyl-phenyl)-propionic acid as a grey solid which was further dried under HV (19.070 g; 98%). LC-MS: $t_R$=0.85 min; [M+H]$^+$: no ionisation.

3-(2,4-difluoro-3-methyl-phenyl)-propionic acid

According to the previously described general procedure (GP2), hydrogenation (1 atm; rt; 3 h) of 3-(2,4-difluoro-3-methyl-phenyl)-acrylic acid (1.568 g; 7.916 mmol) gave the expected product 3-(2,4-difluoro-3-methyl-phenyl)-propionic acid as a grey solid (1.600 g; 100%). LC-MS: $t_R$=0.97 min; [M+H]$^+$: no ionisation.

3-(2-fluoro-4-trifluoromethyl-phenyl)-propionic acid

According to the previously described general procedure (GP2), hydrogenation (1 atm; rt; 4 h) of 3-(2-fluoro-4-trifluoromethyl-phenyl)-acrylic acid (5.937 g; 25.356 mmol) gave the expected product 3-(2-fluoro-4-trifluoromethyl-phenyl)-propionic acid as a grey solid (4.590 g; 77%). LC-MS: $t_R$=0.88 min; [M+H]$^+$: no ionisation.

3-(3-fluoro-4-trifluoromethyl-phenyl)-propionic acid

According to the previously described general procedure (GP2), hydrogenation (1 atm; rt; 3h30) of 3-(3-fluoro-4-trifluoromethyl-phenyl)-acrylic acid (9.510 g; 40.615 mmol) gave the expected product 3-(3-fluoro-4-trifluoromethyl-phenyl)-propionic acid as a grey solid (9.420 g; 98%). LC-MS: $t_R$=0.89 min; [M+H]$^+$: no ionisation.

3-(2,4-dimethyl-phenyl)-propionic acid

According to the previously described general procedure (GP2), hydrogenation (1 atm; rt; 3 h) of 3-(2,4-dimethyl-phenyl)-acrylic acid (9.720 g; 55.160 mmol) gave the expected product 3-(2,4-dimethyl-phenyl)-propionic acid as a grey solid (9.830 g; 100%). LC-MS: $t_R$=0.85 min; [M+H]$^+$: no ionisation.

3-(3-fluoro-4-methyl-phenyl)-propionic acid

According to the previously described general procedure (GP2), hydrogenation (1 atm; rt; 4 h) of 3-(3-fluoro-4-methyl-phenyl)-acrylic acid (11.859 g; 65.824 mmol) gave the expected product 3-(3-fluoro-4-methyl-phenyl)-propionic acid as a grey solid (11.740 g; 98%). LC-MS: $t_R$=0.83 min; [M+H]$^+$: no ionisation.

3-(3,4,5-trifluoro-phenyl)-propionic acid

According to the previously described general procedure (GP2), hydrogenation (1 atm; rt; 5 h) of 3-(3,4,5-trifluoro-phenyl)-acrylic acid (8.600 g; 42.547 mmol) gave the expected product 3-(3,4,5-trifluoro-phenyl)-propionic acid as a colorless solid (8.620 g; 99%). LC-MS: $t_R$=0.90 min.; [M+H]$^+$: no ionisation.

3-(4-trifluoromethoxy-phenyl)-propionic acid

According to the previously described general procedure (GP2), hydrogenation (1 atm; rt; 5h30) of 3-(4-trifluoromethoxy-phenyl)-acrylic acid (14.000 g; 60.304 mmol) gave the expected product 3-(4-trifluoromethoxy-phenyl)-propionic acid as a beige solid (14.120 g; 100%). LC-MS: $t_R$=0.95 min.; [M+H]$^+$: no ionisation.

3-(2,3,5-trifluoro-phenyl)-propionic acid

According to the previously described general procedure (GP2), hydrogenation (1 atm; rt; 3h30) of 3-(2,3,5-trifluoro-phenyl)-acrylic acid (8.310 g; 41.112 mmol) gave the expected product 3-(2,3,5-trifluoro-phenyl)-propionic acid as a grey solid (8.020 g; 96%). LC-MS: $t_R$=0.83 min.; [M+H]$^+$: no ionisation.

3-(3-fluoro-4-methoxy-phenyl)-propionic acid

According to the previously described general procedure (GP2), hydrogenation (1 atm; rt; 2h30) of 3-(3-fluoro-4-methoxy-phenyl)-acrylic acid (3.090 g; 15.751 mmol) gave the expected product 3-(3-fluoro-4-methoxy-phenyl)-propionic acid as a colorless solid (3.080 g; 99%). LC-MS: $t_R$=0.85 min.; [M+H]$^+$: no ionisation.

A.1.2 Synthesis of carboxylic acids R$^1$—CH$_2$—CH$_2$—CO$_2$H via Heck reaction

A.1.2.1 Synthesis of Aryl Bromides

5-bromo-1,3-difluoro-2-methyl-benzene

A solution of methanesulfonyl chloride (4.72 ml; 60.794 mmol) in anhydrous DCM (10 ml) was added dropwise (over 5 min.) to an ice-cooled solution of 4-bromo-2,6-difluorobenzyl alcohol (11.300 g; 50.669 mmol) and TEA (14.1 ml; 101.338 mmol) in DCM (200 ml). The resulting solution was stirred at 0° C., under nitrogen, for 30 min. The reaction mixture was diluted with EA (200 ml), and water (100 ml) was added. The organic layer was successively washed with 1N aq. hydrochloric acid (100 ml), sat. aq. NaHCO$_3$ (100 ml), and finally with brine (100 ml). The organic layer was then dried over magnesium sulfate, filtered, and concentrated to dryness under reduced pressure to give an orange solid which was additionally dried under HV (15.170 g; 99.5%). LC-MS for the mesylate: $t_R$=0.92 min.; [M+H]$^+$: no ionisation.

To an ice-cooled solution of the obtained mesylate derivative (15.170 g; 50.381 mmol) in anhydrous THF (90 ml) was added dropwise a solution of superhydride LiEt$_3$BH (1N in THF; 106 ml; 106 mmol). The resulting mixture was stirred at 0° C. for 5 min., and then at rt for 30 min. The solution was cooled to 0° C. before dropwise addition of water (100 ml), and addition of ether (200 ml). The organic layer was dried over anh. MgSO$_4$, filtered, and carefully concentrated under reduced pressure (CAUTION! product with low boiling point, therefore heating bath of the rotary evaporator at 30° C.!). Purification by FC (DCM) gave the pure product 5-bromo-1,3-difluoro-2-methyl-benzene as a colorless oil (6.910 g; 66%). LC-MS: $t_R$=1.00 min.; [M+H]$^+$: no ionisation.

1-bromo-2,5-difluoro-4-trifluoromethyl-benzene

A slightly yellow solution of 2,5-difluoro-4-(trifluoromethyl)aniline (10.0 ml; 76.708 mmol) in MeCN (90 ml) was treated with copper(II) bromide (17.133 g; 76.708 mmol), and the green heterogeneous mixture was heated to 45° C. A solution of tert-butyl nitrite (10.0 ml; 84.379 mmol) in MeCN (20 ml) was then added dropwise over 30 min., and the resulting mixture was further stirred at 45° C. for 2 h30. The dark-green heterogeneous reaction mixture was allowed to cool to rt, and was directly purified by FC (DCM). After concentration to dryness under reduced pressure, the expected product 1-bromo-2,5-difluoro-4-trifluoromethyl-benzene was obtained as an orange oil (10.290 g; 51%). LC-MS: $t_R$=1.07 min.; [M+H]$^+$: no ionisation.

4-bromo-2-chloro-1-trifluoromethyl-benzene

A solution of 4-amino-2-chlorobenzotrifluoride (9.780 g; 50.007 mmol) in MeCN (65 ml) was treated with copper(II) bromide (11.169 g; 50.007 mmol), and the green heterogeneous mixture was heated to 45° C. A solution of tert-butyl nitrite (6.53 ml; 55.008 mmol) in MeCN (10 ml) was then added dropwise over 30 min., and the resulting mixture was further stirred at 45° C. for 2 h20. The dark heterogeneous reaction mixture was allowed to cool to rt, and was directly purified by FC (DCM). After concentration to dryness under reduced pressure, the expected product 4-bromo-2-chloro-1-trifluoromethyl-benzene was obtained as a yellow oil (12.820 g; 50%). LC-MS: $t_R$=1.10 min.; [M+H]$^+$: no ionisation.

A.1.2.2 Heck Reaction Between Aryl Bromides and Butyl Acrylate

3-(3,5-difluoro-4-methyl-phenyl)-acrylic acid butyl ester [general procedure for Heck reaction (GP3)]

To a solution of 5-bromo-1,3-difluoro-2-methyl-benzene (6.910 g; 33.379 mmol) in anhydrous DMF (200 ml) were added successively butyl acrylate (7.15 ml; 50.062 mmol), DABCO (157 mg; 1.333 mmol), potassium carbonate (4.612 g; 33.379 mmol), and palladium acetate (150 mg; 0.669 mmol). The resulting brown suspension was heated to 120° C. for 1 h. The reaction mixture was allowed to cool to rt before ether (400 ml) was added. This mixture was then washed with water (2×200 ml), and the mixed aq. layers were further extracted with ether (150 ml). The combined organic layers were dried over anh. MgSO$_4$, filtered, and concentrated to dryness under reduced pressure. Purification by FC (DCM/heptane=1/1=>DCM) gave the pure product 3-(3,5-difluoro-4-methyl-phenyl)-acrylic acid butyl ester as a yellow oil which was further dried under HV (4.690 g; 55%). LC-MS: $t_R$=1.10 min.; [M+H]$^+$: no ionisation.

3-(3,5-difluoro-4-trifluoromethyl-phenyl)-acrylic acid butyl ester

According to the previously described general procedure (GP3), 3,5-difluoro-4-(trifluoromethyl)bromobenzene (10.000 g; 38.316 mmol) and butyl acrylate (8.2 ml; 57.474 mmol) gave after Heck reaction (120° C.; 2h30) and purification by FC (DCM/heptane=1/1) the pure product 3-(3,5-difluoro-4-trifluoromethyl-phenyl)-acrylic acid butyl ester as a slightly beige solid (10.120 g; 86%). LC-MS: $t_R$=1.12 min.; [M+H]$^+$: no ionisation.

3-(3,5-difluoro-4-methoxy-phenyl)-acrylic acid butyl ester

According to the previously described general procedure (GP3), 5-bromo-1,3-difluoro-2-methoxy-benzene (10.670 g; 47.849 mmol) and butyl acrylate (10.23 ml; 71.774 mmol) gave after Heck reaction (120° C.; 2 h) and purification by FC (DCM/heptane=1/1) the pure product 3-(3,5-difluoro-4-methoxy-phenyl)-acrylic acid butyl ester as a slightly beige oil (2.410 g; 19%). LC-MS: $t_R$=1.13 min.; [M+H]$^+$: no ionisation.

3-(4-chloro-3,5-difluoro-phenyl)-acrylic acid butyl ester

According to the previously described general procedure (GP3), 5-bromo-2-chloro-1,3-difluoro-benzene (10.000 g; 43.969 mmol) and butyl acrylate (9.40 ml; 65.953 mmol) gave after Heck reaction (120° C.; 2 h) and purification by FC (DCM/heptane=1/1) the pure product 3-(4-chloro-3,5-difluoro-phenyl)-acrylic acid butyl ester as a colorless solid (10.870 g; 90%). LC-MS: $t_R$=1.09 min.; [M+H]$^+$: no ionisation.

3-(3-chloro-4-trifluoromethyl-phenyl)-acrylic acid butyl ester

According to the previously described general procedure (GP3), 4-bromo-2-chloro-1-trifluoromethyl-benzene (12.820 g; 49.412 mmol) and butyl acrylate (10.56 ml; 74.118 mmol) gave after Heck reaction (120° C.; 2h30) and purification by FC (DCM/heptane=1/1) the pure product 3-(3-chloro-4-trifluoromethyl-phenyl)-acrylic acid butyl ester as a yellow solid (7.030 g; 46%). LC-MS: $t_R$=1.19 min.; [M+H]$^+$: no ionisation.

3-(2,5-difluoro-4-trifluoromethyl-phenyl)-acrylic acid butyl ester

According to the previously described general procedure (GP3), 1-bromo-2,5-difluoro-4-trifluoromethyl-benzene (10.290 g; 39.427 mmol) and butyl acrylate (8.43 ml; 59.141 mmol) gave after Heck reaction (120° C.; 15 h) and purification by FC (DCM/heptane=1/1) the pure product 3-(2,5-difluoro-4-trifluoromethyl-phenyl)-acrylic acid butyl ester as a beige solid (6.410 g; 53%). LC-MS: $t_R$=1.18 min.; [M+H]$^+$: no ionisation.

3-(2,5-difluoro-4-methoxy-phenyl)-acrylic acid butyl ester

According to the previously described general procedure (GP3), 1-bromo-2,5-difluoro-4-methoxy-benzene (16.020 g; 71.834 mmol) and butyl acrylate (15.36 ml; 107.750 mmol) gave after Heck reaction (120° C.; 16h30) and purification by FC (DCM/heptane=1/1) the pure product 3-(2,5-difluoro-4-methoxy-phenyl)-acrylic acid butyl ester as a colorless solid (6.183 g; 32%). LC-MS: $t_R$=1.13 min.; [M+H]$^+$: no ionisation.

A.1.2.3 3-(3,5-difluoro-4-methyl-phenyl)-propionic acid butyl ester [general procedure for hydrogenation of cinnamic esters (GP4)]

A mixture of 3-(3,5-difluoro-4-methyl-phenyl)-acrylic acid butyl ester (7.651 g; 30.089 mmol) and 10% palladium over activated charcoal (0.760 g) was placed under nitrogen before MeOH (100 ml) was carefully added. The resulting suspension was placed under vacuum, then under hydrogen (1 atm), and the reaction mixture was vigorously stirred at rt for 2 h45. The reaction mixture was filtered over a pad of celite, and concentrated under reduced pressure to give the expected product 3-(3,5-difluoro-4-methyl-phenyl)-propionic acid butyl ester as a yellow oil which was further dried under HV (6.960 g; 90%). LC-MS: $t_R$=1.10 min; [M+H]$^+$: no ionisation.

3-(3,5-difluoro-4-trifluoromethyl-phenyl)-propionic acid butyl ester

According to the previously described general procedure (GP4), hydrogenation (1 atm; rt; 3h30) of 3-(3,5-difluoro-4-trifluoromethyl-phenyl)-acrylic acid butyl ester (8.849 g; 28.710 mmol) gave the expected product 3-(3,5-difluoro-4-trifluoromethyl-phenyl)-propionic acid butyl ester as a yellow oil (8.622 g; 97%). LC-MS: $t_R$=1.11 min; [M+H]$^+$: no ionisation.

3-(3,5-difluoro-4-methoxy-phenyl)-propionic acid butyl ester

According to the previously described general procedure (GP4), hydrogenation (1 atm; rt; 2 h) of 3-(3,5-difluoro-4-methoxy-phenyl)-acrylic acid butyl ester (2.410 g; 8.917 mmol) gave the expected product 3-(3,5-difluoro-4-methoxy-phenyl)-propionic acid butyl ester as a colorless oil (2.410 g; 99%).

3-(2,5-difluoro-4-trifluoromethyl-phenyl)-propionic acid butyl ester

According to the previously described general procedure (GP4), hydrogenation (1 atm; rt; 4 h) of 3-(2,5-difluoro-4-trifluoromethyl-phenyl)-acrylic acid butyl ester (6.340 g; 20.568 mmol) gave the expected product 3-(2,5-difluoro-4-trifluoromethyl-phenyl)-propionic acid butyl ester as a yellow/green oil (6.160 g; 97%). LC-MS: $t_R$=1.15 min.; [M+H]$^+$: no ionisation.

3-(2,5-difluoro-4-methoxy-phenyl)-propionic acid butyl ester

According to the previously described general procedure (GP4), hydrogenation (1 atm; rt; 3 h) of 3-(2,5-difluoro-4-methoxy-phenyl)-acrylic acid butyl ester (6.180 g; 22.866 mmol) gave the expected product 3-(2,5-difluoro-4-methoxy-phenyl)-propionic acid butyl ester as a colorless oil (5.980 g; 96%). LC-MS: $t_R$=1.10 min.; [M+H]$^+$: no ionisation.

3-(4-chloro-3,5-difluoro-phenyl)-propionic acid butyl ester

A mixture of 3-(4-chloro-3,5-difluoro-phenyl)-acrylic acid butyl ester (5.000 g; 18.202 mmol), zinc bromide (0.819 g; 3.640 mmol), and 10% palladium over activated charcoal (0.320 g) was placed under nitrogen before EA (140 ml) was added. The resulting suspension was placed under vacuum, then under hydrogen (1 atm), and the reaction mixture was vigorously stirred at rt for 22 h. The reaction mixture was filtered over a pad of celite, and concentrated under reduced pressure to give the expected product 3-(4-chloro-3,5-difluoro-phenyl)-propionic acid butyl ester as a slightly yellow oil which was further dried under HV (5.020 g; 98%). LC-MS: $t_R$=1.14 min.; [M+H]$^+$: no ionisation.

3-(3-chloro-4-trifluoromethyl-phenyl)-propionic acid butyl ester

A mixture of 3-(3-chloro-4-trifluoromethyl-phenyl)-acrylic acid butyl ester (7.030 g; 22.921 mmol), zinc bromide (1.031 g; 4.584 mmol), and 10% palladium over activated charcoal (0.403 g) was placed under nitrogen before EA (150 ml) was added. The resulting suspension was placed under vacuum, then under hydrogen (1 atm), and the reaction mixture was vigorously stirred at rt for 9 h. The reaction mixture was filtered over a pad of celite, and concentrated under reduced pressure to give the expected product 3-(3-chloro-4-trifluoromethyl-phenyl)-propionic acid butyl ester as a yellow oil which was further dried under HV (8.430 g; 100%). LC-MS: $t_R$=1.16 min.; [M+H]$^+$: no ionisation.

A.1.2.5 3-(3,5-difluoro-4-methyl-phenyl)-propionic acid [general procedure for saponification of esters (GP5)]

To a solution of 3-(3,5-difluoro-4-methyl-phenyl)-propionic acid butyl ester (6.960 g; 27.157 mmol) in MeOH (150 ml) and water (25 ml) was added at rt aq. 1N NaOH (68 ml; 68 mmol). The resulting solution was further stirred at rt for 1 h. MeOH was then removed under reduced pressure. Water (25 ml) was added, and the mixture was acidified with aq. 1N HCl (68 ml) in order to reach pH=2. DCM (150 ml) was added, and the layers were shaken and separated. The aq. layer was further extracted with DCM (50 ml). The mixed organic layers were dried over anh. MgSO$_4$, filtered, and concentrated to dryness under reduced pressure. The product 3-(3,5-difluoro-4-methyl-phenyl)-propionic acid was obtained as a pale yellow solid which was further dried under HV (5.090 g; 94%). LC-MS: $t_R$=0.86 min.; [M+H]$^+$: no ionisation.

3-(3,5-difluoro-4-trifluoromethyl-phenyl)-propionic acid

According to the previously described general procedure (GP5), saponification (rt; 45 min.) of 3-(3,5-difluoro-4-trifluoromethyl-phenyl)-propionic acid butyl ester (7.658 g; 24.682 mmol) afforded the product 3-(3,5-difluoro-4-trifluoromethyl-phenyl)-propionic acid as a colorless solid (6.216 g; 99%). LC-MS: $t_R$=0.90 min.; [M+H]$^+$: no ionisation.

3-(3-chloro-4-trifluoromethyl-phenyl)-propionic acid

According to the previously described general procedure (GP5), saponification (rt; 1 h) of 3-(3-chloro-4-trifluoromethyl-phenyl)-propionic acid butyl ester (7.070 g; 22.901 mmol) afforded the product 3-(3-chloro-4-trifluoromethyl-phenyl)-propionic acid as a yellow solid (5.670 g; 98%). LC-MS: $t_R$=0.97 min.; [M+H]$^+$: no ionisation.

3-(2,5-difluoro-4-trifluoromethyl-phenyl)-propionic acid

According to the previously described general procedure (GP5), saponification (rt; 1 h30) of 3-(2,5-difluoro-4-trifluoromethyl-phenyl)-propionic acid butyl ester (6.130 g; 19.758 mmol) afforded the product 3-(2,5-difluoro-4-trifluoromethyl-phenyl)-propionic acid as a beige solid (5.011 g; 100%). LC-MS: $t_R$=0.96 min.; [M+H]$^+$: no ionisation.

A.2 Synthesis of alcohols R$^1$—CH$_2$—CH$_2$—CH$_2$OH

A.2.1 Synthesis of alcohols R$^1$—CH$_2$—CH$_2$—CH$_2$OH via reduction of carboxylic acids 3-(4-trifluoromethyl-phenyl)-propan-1-ol [general procedure for reduction of carboxylic acids to alcohols (GP6)]

To an ice-cooled homogeneous solution of 4-(trifluoromethyl)hydrocinnamic acid (9.800 g; 44.918 mmol) in anhydrous THF (250 ml) was added dropwise a solution of 1M BH$_3$.THF (67.4 ml; 67.4 mmol) over 20 min. The resulting homogeneous solution was further stirred at 0° C., under nitrogen, for 1 h, and then at rt for 14 h. The colorless homogeneous reaction mixture was cooled to 0° C., and MeOH (100 ml) was carefully added followed by water (100 ml). MeOH and THF were then removed under vacuum. After extraction with DCM (3×100 ml), the combined organic extracts were washed with brine (100 ml), dried over anh. MgSO$_4$, filtered, and concentrated to dryness under reduced pressure. The crude was purified by FC (DCM/MeOH=9/1) to give the pure product 3-(4-trifluoromethyl-phenyl)-propan-1-ol as a colorless oil which was further dried under HV (9.180 g; 100%). LC-MS: $t_R$=0.89 min.; [M+H]$^+$: no ionisation.

3-(2,4-difluoro-3-methyl-phenyl)-propan-1-ol

According to the previously described general procedure (GP6), reduction of 3-(2,4-difluoro-3-methyl-phenyl)-propionic acid (1.569 g; 7.838 mmol) gave after purification by FC (DCM/MeOH=12/1) the product 3-(2,4-difluoro-3-methyl-phenyl)-propan-1-ol as a pale yellow oil (1.260 g; 86%). LC-MS: $t_R$=0.86 min.; [M+H]$^+$: no ionisation.

3-(2,4-dimethyl-phenyl)-propan-1-ol

According to the previously described general procedure (GP6), reduction of 3-(2,4-dimethyl-phenyl)-propionic acid (9.830 g; 55.153 mmol) gave after purification by FC (DCM/MeOH=12/1) the product 3-(2,4-dimethyl-phenyl)-propan-1-ol as a pale yellow oil (8.280 g; 91%). LC-MS: $t_R$=0.86 min.; [M+H]$^+$: no ionisation.

3-(2-fluoro-4-trifluoromethyl-phenyl)-propan-1-ol

According to the previously described general procedure (GP6), reduction of 3-(2-fluoro-4-trifluoromethyl-phenyl)-propionic acid (9.609 g; 40.692 mmol) gave after purification by FC (DCM/MeOH=9/1) the product 3-(2-fluoro-4-trifluoromethyl-phenyl)-propan-1-ol as a pale yellow oil (7.100 g; 78.5%). LC-MS: $t_R$=0.90 min.; [M+H]$^+$: no ionisation.

3-(3,4-dimethyl-phenyl)-propan-1-ol

According to the previously described general procedure (GP6), reduction of 3-(3,4-dimethyl-phenyl)-propionic acid (12.900 g; 72.378 mmol) gave after purification by FC (DCM/MeOH=9/1) the product 3-(3,4-dimethyl-phenyl)- propan-1-ol as a pale yellow oil (11.660 g; 98%). LC-MS: $t_R$=0.86 min.; [M+H]$^+$: no ionisation.

3-(3-fluoro-4-trifluoromethyl-phenyl)-propan-1-ol

According to the previously described general procedure (GP6), reduction of 3-(3-fluoro-4-trifluoromethyl-phenyl)-propionic acid (9.430 g; 39.930 mmol) gave after purification by FC (DCM/MeOH=9/1) the product 3-(3-fluoro-4-trifluoromethyl-phenyl)-propan-1-ol as a pale yellow oil (8.340 g; 94%). LC-MS: $t_R$=0.90 min.; [M+H]$^+$: no ionisation.

3-(3,4-difluoro-phenyl)-propan-1-ol

According to the previously described general procedure (GP6), reduction of 3-(3,4-difluoro-phenyl)-propionic acid (5.000 g; 26.859 mmol) gave after purification by FC (DCM/MeOH=9/1) the product 3-(3,4-difluoro-phenyl)-propan-1-ol as a colorless oil (4.490 g; 97%). LC-MS: $t_R$=0.82 min.; [M+H]$^+$: no ionisation.

3-p-tolyl-propan-1-ol

According to the previously described general procedure (GP6), reduction of 3-p-tolyl-propionic acid (10.200 g; 62.118 mmol) gave after purification by FC (DCM/MeOH=9/1) the product 3-p-tolyl-propan-1-ol as a pale yellow oil (9.270 g; 99%). LC-MS: $t_R$=0.82 min.; [M+H]$^+$: no ionisation.

3-(3-fluoro-4-methyl-phenyl)-propan-1-ol

According to the previously described general procedure (GP6), reduction of 3-(3-fluoro-4-methyl-phenyl)-propionic acid (12.679 g; 69.596 mmol) gave after purification by FC (DCM/MeOH=9/1) the product 3-(3-fluoro-4-methyl-phenyl)-propan-1-ol as a pale yellow oil (11.010 g; 94%). LC-MS: $t_R$=0.85 min.; [M+H]$^+$: no ionisation.

3-(3-chloro-phenyl)-propan-1-ol prepared by reduction of 3-(3-chloro-phenyl)-propionic acid.
LC-MS: $t_R$=0.84 min.; [M+H]$^+$: no ionisation.

3-(2,4-dichloro-phenyl)-propan-1-ol prepared by reduction of 3-(2,4-dichloro-phenyl)-propionic acid.
$^1$H-NMR (CDCl$_3$; 300 MHz): δ=7.38 (s, 1H), 7.18 (s, 2H), 3.67 (t, 2H), 2.81 (t, 2H), 1.92 (tt, 2H).

3-(3,4,5-trifluoro-phenyl)-propan-1-ol

According to the previously described general procedure (GP6), reduction of 3-(3,4,5-trifluoro-phenyl)-propionic acid (8.620 g; 42.225 mmol) gave after purification by FC (DCM/MeOH=9/1) the product 3-(3,4,5-trifluoro-phenyl)-propan-1-ol as a yellow oil (7.130 g; 89%).

3-(3-chloro-4-trifluoromethyl-phenyl)-propan-1-ol

According to the previously described general procedure (GP6), reduction of 3-(3-chloro-4-trifluoromethyl-phenyl)-propionic acid (3.000 g; 10.498 mmol) gave after purification by FC (DCM/MeOH=9/1) the product 3-(3-chloro-4-trifluoromethyl-phenyl)-propan-1-ol as a colorless oil (2.430 g; 97%). LC-MS: $t_R$=0.98 min.; [M+H]$^+$: no ionisation.

3-(2,5-difluoro-4-trifluoromethyl-phenyl)-propan-1-ol

According to the previously described general procedure (GP6), reduction of 3-(2,5-difluoro-4-trifluoromethyl-phenyl)-propionic acid (2.590 g; 10.191 mmol) gave after purification by FC (DCM/MeOH=9/1) the product 3-(2,5-difluoro-4-trifluoromethyl-phenyl)-propan-1-ol as a slightly yellow oil (2.154 g; 88%). LC-MS: $t_R$=0.97 min.; [M+H]$^+$: no ionisation.

3-(4-trifluoromethoxy-phenyl)-propan-1-ol

According to the previously described general procedure (GP6), reduction of 3-(4-trifluoromethoxy-phenyl)-propionic acid (7.000 g; 29.893 mmol) gave after purification by FC (DCM/MeOH=9/1) the product 3-(4-trifluoromethoxy-phenyl)-propan-1-ol as a colorless oil (5.090 g; 77%). LC-MS: $t_R$=0.96 min.; [M+H]$^+$: no ionisation.

3-(4-bromo-phenyl)-propan-1-ol

According to the previously described general procedure (GP6), reduction of 3-(4-bromo-phenyl)-propionic acid (15.000 g; 64.172 mmol) gave after purification by FC (DCM/MeOH=9/1) the product 3-(4-bromo-phenyl)-propan-1-ol as a colorless oil (13.700 g; 99%). LC-MS: $t_R$=0.81 min.; [M+H]$^+$: no ionisation.

3-(2,3,5-trifluoro-phenyl)-propan-1-ol

According to the previously described general procedure (GP6), reduction of 3-(2,3,5-trifluoro-phenyl)-propionic acid (8.019 g; 39.285 mmol) gave after purification by FC (DCM/MeOH=9/1) the product 3-(2,3,5-trifluoro-phenyl)-propan-1-ol as a pale yellow oil (7.470 g; 100%). LC-MS: $t_R$=0.83 min.; [M+H]$^+$: no ionisation.

3-(3-fluoro-4-methoxy-phenyl)-propan-1-ol

According to the previously described general procedure (GP6), reduction of 3-(3-fluoro-4-methoxy-phenyl)-propionic acid (3.820 g; 19.274 mmol) gave after purification by FC (DCM/MeOH=9/1) the product 3-(3-fluoro-4-methoxy-phenyl)-propan-1-ol as a colorless oil (3.550 g; 100%). LC-MS: $t_R$=0.85 min.; [M+H]$^+$: no ionisation.

A.2.2 Synthesis of alcohols R$^1$—CH$_2$—CH$_2$—CH$_2$OH via reduction of esters

3-(3,5-difluoro-4-methyl-phenyl)-propan-1-ol [general procedure for reduction of esters to alcohols (GP7)]

To an ice-cooled solution of 3-(3,5-difluoro-4-methyl-phenyl)-propionic acid butyl ester (2.200 g; 8.584 mmol) in anhydrous THF (20 ml) was added dropwise a 1N solution of BH$_3$.THF complex in THF (13 ml; 13 mmol). The resulting solution was stirred at 0° C., under nitrogen, for 1 h, and then at rt overnight. The reaction mixture was quenched by dropwise addition of MeOH (5 ml) followed by water (10 ml). The volatiles were removed under vacuum, and the product was extracted with DCM (3×20 ml). The combined organic layers were then washed with brine, dried over anh. MgSO$_4$, filtered, and concentrated to dryness under reduced pressure. The crude was purified by FC (DCM/MeOH=12/1) to give the pure product 3-(3,5-difluoro-4-methyl-phenyl)-propan-1-ol as a pale yellow oil (1.440 g; 90%). LC-MS: $t_R$=0.87 min.; [M+H]$^+$: no ionisation.

3-(3,5-difluoro-4-trifluoromethyl-phenyl)-propan-1-ol

According to the previously described general procedure (GP7), 3-(3,5-difluoro-4-trifluoromethyl-phenyl)-propionic acid butyl ester (4.110 g; 13.247 mmol) was reduced to 3-(3,5-difluoro-4-trifluoromethyl-phenyl)-propan-1-ol (2.716 g; 85%; pale yellow oil). LC-MS: $t_R$=0.91 min.; [M+H]$^+$: no ionisation.

3-(3,5-difluoro-4-methoxy-phenyl)-propan-1-ol

According to the previously described general procedure (GP7), 3-(3,5-difluoro-4-methoxy-phenyl)-propionic acid butyl ester (2.420 g; 8.888 mmol) was reduced to 3-(3,5-difluoro-4-methoxy-phenyl)-propan-1-ol (1.573 g; 88%; colorless oil).

3-(4-chloro-3,5-difluoro-phenyl)-propan-1-ol

According to the previously described general procedure (GP7), 3-(4-chloro-3,5-difluoro-phenyl)-propionic acid butyl ester (5.020 g; 18.142 mmol) was reduced to 3-(4-chloro-3,5-difluoro-phenyl)-propan-1-ol (3.090 g; 82%; yellow oil). LC-MS: $t_R$=0.93 min.; [M+H]$^+$: no ionisation.

3-(2,5-difluoro-4-methoxy-phenyl)-propan-1-ol

According to the previously described general procedure (GP7), 3-(2,5-difluoro-4-methoxy-phenyl)-propionic acid butyl ester (5.980 g; 21.962 mmol) was reduced to 3-(2,5-difluoro-4-methoxy-phenyl)-propan-1-ol (4.440 g; 100%; colorless solid). LC-MS: $t_R$=0.88 min.; [M+H]$^+$: no ionisation.

3-(2,3-dimethyl-phenyl)-propan-1-ol prepared by reduction of 3-(2,3-dimethyl-phenyl)-propionic acid methyl ester.
LC-MS: $t_R$=0.86 min.; [M+H]$^+$: no ionisation.

3-(3-fluoro-4-methoxy-phenyl)-propan-1-ol prepared by reduction of 3-(3-fluoro-4-methoxy-phenyl)-propionic acid methyl ester.
LC-MS: $t_R$=0.80 min.; [M+H]$^+$: no ionisation.

3-(2,4-dimethoxy-phenyl)-propan-1-ol prepared by reduction of 3-(2,4-dimethoxy-phenyl)-propionic acid methyl ester.
LC-MS: $t_R$=0.81 min.; [M+H]$^+$: no ionisation.

A.3 Synthesis of aldehydes R$^1$—CH$_2$—CH$_2$—CHO

3-(4-trifluoromethyl-phenyl)-propionaldehyde
[general procedure for the oxidation of primary alcohols to aldehydes (GP8)]

To an ice-cooled orange suspension of pyridinium chlorochromate (3.659 g; 16.896 mmol) in anhydrous DCM (20 ml) was added dropwise a solution of 3-(4-trifluoromethyl-phenyl)-propan-1-ol (2.300 g; 11.264 mmol) in anhydrous DCM (35 ml). The resulting black suspension was allowed to warm-up to rt and was stirred under nitrogen for 3 h. The reaction mixture was directly filtered over silicagel using DCM. After concentration to dryness under reduced pressure, the product 3-(4-trifluoromethyl-phenyl)-propionaldehyde was isolated as a pale yellow oil (1.970 g; 86.5%). LC-MS: $t_R$=0.95 min.; [M+H]$^+$: no ionisation.

3-(2,4-difluoro-3-methyl-phenyl)-propionaldehyde

According to the previously described general procedure (GP8), the oxidation of 3-(2,4-difluoro-3-methyl-phenyl)-propan-1-ol (0.250 g; 1.342 mmol) gave 3-(2,4-difluoro-3-methyl-phenyl)-propionaldehyde (pale yellow oil; 0.232 g; 94%). LC-MS: $t_R$=0.94 min.; [M+H]$^+$: no ionisation.

3-(3,5-difluoro-4-trifluoromethyl-phenyl)-propionaldehyde

According to the previously described general procedure (GP8), the oxidation of 3-(3,5-difluoro-4-trifluoromethyl-phenyl)-propan-1-ol (1.730 g; 7.203 mmol) gave 3-(3,5-difluoro-4-trifluoromethyl-phenyl)-propionaldehyde (pale yellow oil; 1.180 g; 69%). LC-MS: $t_R$=0.97 min.; [M+H]$^+$: no ionisation.

3-(3,5-difluoro-4-methyl-phenyl)-propionaldehyde

According to the previously described general procedure (GP8), the oxidation of 3-(3,5-difluoro-4-methyl-phenyl)-propan-1-ol (245 mg; 1.315 mmol) gave 3-(3,5-difluoro-4-methyl-phenyl)-propionaldehyde (pale yellow oil; 206.7 mg; 85%). LC-MS: $t_R$=0.94 min.; [M+H]$^+$: no ionisation.

3-(2-fluoro-4-trifluoromethyl-phenyl)-propionaldehyde

According to the previously described general procedure (GP8), the oxidation of 3-(2-fluoro-4-trifluoromethyl-phenyl)-propan-1-ol (330 mg; 1.485 mmol) gave 3-(2-fluoro-4-trifluoromethyl-phenyl)-propionaldehyde (pale yellow oil; 220.2 mg; 67%). LC-MS: $t_R$=0.97 min.; [M+H]$^+$: no ionisation.

3-(3,4-dimethyl-phenyl)-propionaldehyde

According to the previously described general procedure (GP8), the oxidation of 3-(3,4-dimethyl-phenyl)-propan-1-ol (250 mg; 1.522 mmol) gave 3-(3,4-dimethyl-phenyl)-propionaldehyde (pale yellow oil; 211.4 mg; 86%). LC-MS: $t_R$=0.94 min.; [M+H]$^+$: no ionisation.

3-(3,4-difluoro-phenyl)-propionaldehyde

According to the previously described general procedure (GP8), the oxidation of 3-(3,4-difluoro-phenyl)-propan-1-ol (245 mg; 1.422 mmol) gave 3-(3,4-difluoro-phenyl)-propionaldehyde (pale yellow oil; 228.7 mg; 94%). LC-MS: $t_R$=0.87 min.; [M+H]$^+$: no ionisation.

3-(3-fluoro-4-trifluoromethyl-phenyl)-propionaldehyde

According to the previously described general procedure (GP8), the oxidation of 3-(3-fluoro-4-trifluoromethyl-phenyl)-propan-1-ol (330 mg; 1.485 mmol) gave 3-(3-fluoro-4-trifluoromethyl-phenyl)-propionaldehyde (pale yellow oil; 260.4 mg; 80%). LC-MS: $t_R$=0.97 min.; [M+H]$^+$: no ionisation.

3-p-tolyl-propionaldehyde

According to the previously described general procedure (GP8), the oxidation of 3-p-tolyl-propan-1-ol (225.3 mg; 1.500 mmol) gave 3-p-tolyl-propionaldehyde (pale yellow oil; 123 mg; 55%). LC-MS: $t_R$=0.89 min.; [M+H]$^+$: no ionisation.

3-(2,4-dimethyl-phenyl)-propionaldehyde

According to the previously described general procedure (GP8), the oxidation of 3-(2,4-dimethyl-phenyl)-propan-1-ol (492 mg; 3.000 mmol) gave 3-(2,4-dimethyl-phenyl)-propionaldehyde (pale yellow oil; 340 mg; 70%). LC-MS: $t_R$=0.93 min.; [M+H]$^+$: no ionisation.

3-(3-fluoro-4-methyl-phenyl)-propionaldehyde

According to the previously described general procedure (GP8), the oxidation of 3-(3-fluoro-4-methyl-phenyl)-propan-1-ol (250 mg; 1.486 mmol) gave 3-(3-fluoro-4-methyl-phenyl)-propionaldehyde (pale yellow oil; 202 mg; 82%). LC-MS: $t_R$=0.92 min.; [M+H]$^+$: no ionisation.

3-(3-chloro-phenyl)-propionaldehyde prepared by oxidation of 3-(3-chloro-phenyl)-propan-1-ol.
LC-MS: $t_R$=0.84 min.; [M+H]$^+$: no ionisation.

3-(2,3-dimethyl-phenyl)-propionaldehyde prepared by oxidation of 3-(2,3-dimethyl-phenyl)-propan-1-ol.
LC-MS: $t_R$=0.86 min.; [M+H]$^+$: no ionisation.

3-(2,4-dichloro-phenyl)-propionaldehyde prepared by oxidation of 3-(2,4-dichloro-phenyl)-propan-1-ol.
LC-MS: $t_R$=0.91 min.; [M+H]$^+$: no ionisation.

3-(3-fluoro-4-methoxy-phenyl)-propionaldehyde prepared by oxidation of 3-(3-fluoro-4-methoxy-phenyl)-propan-1-ol.
LC-MS: $t_R$=0.79 min.; [M+H]$^+$: no ionisation.

3-(2,4-dimethoxy-phenyl)-propionaldehyde prepared by oxidation of 3-(2,4-dimethoxy-phenyl)-propan-1-ol.
LC-MS: $t_R$=0.80 min.; [M+H]$^+$: no ionisation.

3-(3,4,5-trifluoro-phenyl)-propionaldehyde

According to the previously described general procedure (GP8), the oxidation of 3-(3,4,5-trifluoro-phenyl)-propan-1-ol (2.500 g; 13.147 mmol) gave 3-(3,4,5-trifluoro-phenyl)-propionaldehyde (colorless oil; 1.393 g; 56%).
LC-MS: $t_R$=0.97 min.; [M+H]$^+$: no ionisation.

3-(3,5-difluoro-4-methoxy-phenyl)-propionaldehyde

According to the previously described general procedure (GP8), the oxidation of 3-(3,5-difluoro-4-methoxy-phenyl)-propan-1-ol (1.555 g; 7.693 mmol) gave 3-(3,5-difluoro-4-methoxy-phenyl)-propionaldehyde (yellow oil; 1.034 g; 67%).

3-(4-chloro-3,5-difluoro-phenyl)-propionaldehyde

According to the previously described general procedure (GP8), the oxidation of 3-(4-chloro-3,5-difluoro-phenyl)-propan-1-ol (2.500 g; 12.100 mmol) gave 3-(4-chloro-3,5-difluoro-phenyl)-propionaldehyde (pale yellow oil; 1.030 g; 42%).
LC-MS: $t_R$=1.00 min.; [M+H]$^+$: no ionisation.

3-(3-chloro-4-trifluoromethyl-phenyl)-propionaldehyde

According to the previously described general procedure (GP8), the oxidation of 3-(3-chloro-4-trifluoromethyl-phenyl)-propan-1-ol (2.430 g; 10.183 mmol) gave 3-(3-chloro-4-trifluoromethyl-phenyl)-propionaldehyde (pale yellow oil; 1.060 g; 44%).
LC-MS: $t_R$=1.04 min.; [M+H]$^+$: no ionisation.

3-(2,5-difluoro-4-trifluoromethyl-phenyl)-propionaldehyde

According to the previously described general procedure (GP8), the oxidation of 3-(2,5-difluoro-4-trifluoromethyl-phenyl)-propan-1-ol (2.140 g; 8.910 mmol) gave 3-(2,5-difluoro-4-trifluoromethyl-phenyl)-propionaldehyde (slightly yellow oil; 1.510 g; 71%).

3-(4-trifluoromethoxy-phenyl)-propionaldehyde

According to the previously described general procedure (GP8), the oxidation of 3-(4-trifluoromethoxy-phenyl)-propan-1-ol (5.000 g; 22.708 mmol) gave 3-(4-trifluoromethoxy-phenyl)-propionaldehyde (pale yellow oil; 3.360 g; 68%).

3-(4-bromo-phenyl)-propionaldehyde

According to the previously described general procedure (GP8), the oxidation of 3-(4-bromo-phenyl)-propan-1-ol (7.631 g; 35.480 mmol) gave 3-(4-bromo-phenyl)-propionaldehyde (yellow oil; 6.350 g; 84%).

3-(2,3,5-trifluoro-phenyl)-propionaldehyde

According to the previously described general procedure (GP8), the oxidation of 3-(2,3,5-trifluoro-phenyl)-propan-1-ol (0.633 g; 3.330 mmol) gave 3-(2,3,5-trifluoro-phenyl)-propionaldehyde (pale yellow oil; 0.600 g; 96%).

3-(3-fluoro-4-methoxy-phenyl)-propionaldehyde

According to the previously described general procedure (GP8), the oxidation of 3-(3-fluoro-4-methoxy-phenyl)-propan-1-ol (3.575 g; 19.407 mmol) gave 3-(3-fluoro-4-methoxy-phenyl)-propionaldehyde (colorless oil; 2.516 g; 71%).
LC-MS: $t_R$=0.90 min.; [M+H]$^+$: no ionisation.

3-(2,5-difluoro-4-methoxy-phenyl)-propionaldehyde

According to the previously described general procedure (GP8), the oxidation of 3-(2,5-difluoro-4-methoxy-phenyl)- propan-1-ol (3.000 g; 14.837 mmol) gave 3-(2,5-difluoro-4-methoxy-phenyl)-propionaldehyde (colorless oil; 2.120 g; 71%).

LC-MS: $t_R$=0.95 min.; [M+H]$^+$: no ionisation.

A.4 Synthesis of alcohols R$^1$—O—CH$_2$—CH$_2$OH 2-(3-trifluoromethyl-phenoxy)-ethanol A mixture of 3-trifluoromethyl-phenol (5.000 g; 30.843 mmol), potassium carbonate (5.328 g; 38.554 mmol), and methyl bromoacetate (3.54 ml; 38.554 mmol) in butanone (210 ml) was heated at reflux for 3 h. Filtration, concentration to dryness under reduced pressure, and purification by FC (heptane/EA, 4/1) afforded (3-trifluoromethyl-phenoxy)-acetic acid methyl ester as a pale yellow oil (7.220 g; 99%). LC-MS: $t_R$=0.95 min.; [M+H]$^+$: no ionisation.

A solution of (3-trifluoromethyl-phenoxy)-acetic acid methyl ester (7.220 g; 30.832 mmol) in MeOH (100 ml) was treated with aq. 1N NaOH (46.3 ml; 1.5 eq.), and the resulting mixture was further stirred at rt for 20 min. MeOH was then removed under reduced pressure, water (100 ml) was added followed by aq. 1N HCl (75 ml). Filtration of the precipitated solid, and drying under HV afforded (3-trifluoromethyl-phenoxy)-acetic acid as a colorless solid (6.020 g; 89%). LC-MS: $t_R$=0.85 min.; [M+H]$^+$: no ionisation.

According to the previously described general procedure (GP6), reduction of (3-trifluoromethyl-phenoxy)-acetic acid (6.020 g; 27.346 mmol) gave after purification by FC (DCM/MeOH=9/1) the product 2-(3-trifluoromethyl-phenoxy)-ethanol as a yellow oil (5.270 g; 93%). LC-MS: $t_R$=0.84 min.; [M+H]$^+$: no ionisation.

2-(3,4-dimethyl-phenoxy)-ethanol

A mixture of 3,4-dimethyl-phenol (5.000 g; 40.928 mmol), potassium carbonate (7.070 g; 51.160 mmol), and methyl bromoacetate (4.70 ml; 51.160 mmol) in butanone (280 ml) was heated at reflux for 4 h. Filtration, concentration to dryness under reduced pressure, and purification by FC (heptane/EA, 4/1) afforded (3,4-dimethyl-phenoxy)-acetic acid methyl ester as a pale yellow oil (7.400 g; 93%). LC-MS: $t_R$=0.92 min.; [M+H]$^+$: no ionisation.

A solution of (3,4-dimethyl-phenoxy)-acetic acid methyl ester (7.399 g; 38.099 mmol) in MeOH (100 ml) was treated with aq. 1N NaOH (57 ml; 1.5 eq.), and the resulting mixture was further stirred at rt for 30 min. MeOH was then removed under reduced pressure, water (100 ml) was added followed by aq. 1N HCl (75 ml). Filtration of the precipitated solid, and drying under HV afforded (3,4-dimethyl-phenoxy)-acetic acid as a colorless solid (6.070 g; 88%). LC-MS: $t_R$=0.81 min.; [M+H]$^+$: no ionisation.

According to the previously described general procedure (GP6), reduction of (3,4-dimethyl-phenoxy)-acetic acid (6.770 g; 37.985 mmol) gave after purification by FC (heptane/EA=1/1) the product 2-(3,4-dimethyl-phenoxy)-ethanol as a pale yellow oil (4.510 g; 71%). LC-MS: $t_R$=0.80 min.; [M+H]$^+$: no ionisation.

2-(4-trifluoromethyl-phenoxy)-ethanol

A mixture of 4-trifluoromethyl-phenol (10.000 g; 61.687 mmol), potassium carbonate (9.377 g; 67.856 mmol), and methyl bromoacetate (5.67 ml; 61.687 mmol) in acetone (250 ml) was heated at reflux for 1 h30. Filtration, concentration to dryness under reduced pressure, and purification by FC (DCM) afforded (4-trifluoromethyl-phenoxy)-acetic acid methyl ester as a colorless oil (14.100 g; 98%). LC-MS: $t_R$=0.95 min.; [M+H]$^+$: no ionisation.

To an ice-cooled suspension of lithium aluminum hydride (0.972 g; 25.622 mmol) in anhydrous THF (60 ml) was added dropwise a solution of (4-trifluoromethyl-phenoxy)-acetic acid methyl ester (3.000 g; 12.811 mmol) in anhydrous THF (40 ml). The resulting reaction mixture was further stirred at 0° C. for 20 min. Water (1 ml), 15% aq. NaOH (1 ml), and water (3 ml) were then successively added dropwise. Filtration, concentration to dryness under reduced pressure, and purification by FC (DCM/MeOH, 19/1) afforded 2-(4-trifluoromethyl-phenoxy)-ethanol as a colorless solid (2.370 g; 90%). LC-MS: $t_R$=0.84 min.; [M+H]$^+$: no ionisation.

2-(4-fluoro-3-trifluoromethyl-phenoxy)-ethanol

A mixture of 4-fluoro-3-trifluoromethyl-phenol (10.000 g; 55.525 mmol), potassium carbonate (9.591 g; 69.406 mmol), and methyl bromoacetate (6.38 ml; 69.406 mmol) in butanone (380 ml) was heated at reflux for 1 h30. Filtration, concentration to dryness under reduced pressure, and purification by FC (heptane/EA, 4/1) afforded (4-fluoro-3-trifluoromethyl-phenoxy)-acetic acid methyl ester as a colorless oil (13.300 g; 95%). LC-MS: $t_R$=0.95 min.; [M+H]$^+$: no ionisation.

A solution of (4-fluoro-3-trifluoromethyl-phenoxy)-acetic acid methyl ester (13.300 g; 52.744 mmol) in MeOH (150 ml) was treated with aq. 1N NaOH (79 ml; 1.5 eq.), and the resulting mixture was further stirred at rt for 20 min. MeOH was then removed under reduced pressure, water (150 ml) was added followed by aq. 1N HCl (100 ml). Filtration of the precipitated solid, and drying under HV afforded (4-fluoro-3-trifluoromethyl-phenoxy)-acetic acid as a colorless solid (10.030 g; 80%). LC-MS: $t_R$=0.85 min.; [M+H]$^+$: no ionisation.

According to the previously described general procedure (GP6), reduction of (4-fluoro-3-trifluoromethyl-phenoxy)-acetic acid (10.030 g; 42.119 mmol) gave after purification by FC (DCM/MeOH=9/1) the product 2-(4-fluoro-3-trifluoromethyl-phenoxy)-ethanol as a colorless solid (8.900 g; 94%). LC-MS: $t_R$=0.85 min.; [M+H]$^+$: no ionisation.

A.5 Synthesis of aldehydes R$^1$—O—CH$_2$—CHO (3-trifluoromethyl-phenoxy)-acetaldehyde [general procedure for the oxidation of primary alcohols to aldehydes according to the Swern procedure]

A cooled (−78° C.) solution of oxalyl chloride (0.49 ml; 5.821 mmol) in anhydrous DCM (25 ml) was treated dropwise with a solution of dimethyl sulfoxide (0.91 ml; 11.641 mmol) in anhydrous DCM (4 ml). After 10 min., a solution of 2-(3-trifluoromethyl-phenoxy)-ethanol (0.800 g; 3.880 mmol) in DCM (8 ml) was added dropwise, and the reaction mixture was further stirred at −78° C. for 30 min. TEA (2.70 ml; 19.402 mmol) was then added dropwise, and after 10 min. the resulting mixture was allowed to warm-up to 0° C. before a mixture of water (2.5 ml) and DCM (25 ml) was added. The aq. layer was extracted with DCM (2×25 ml), and the mixed organic layers were then washed with aq. sat. NaHCO$_3$ (20 ml), dried over anh. MgSO$_4$, filtered, and concentrated to dryness under reduced pressure to give (3-trifluoromethyl-phenoxy)-acetaldehyde as a yellow oil (0.792 g; 99%). This aldehyde was used for the next step without additional purification.

(3,4-dimethyl-phenoxy)-acetaldehyde

A cooled (−78° C.) solution of oxalyl chloride (0.76 ml; 9.000 mmol) in anhydrous DCM (40 ml) was treated dropwise with a solution of dimethyl sulfoxide (1.40 ml; 18.000 mmol) in anhydrous DCM (6 ml). After 10 min., a solution of 2-(3,4-dimethyl-phenoxy)-ethanol (0.997 g; 6.000 mmol) in DCM (12 ml) was added dropwise, and the reaction mixture was further stirred at −78° C. for 30 min. TEA (4.17 ml; 30.000 mmol) was then added dropwise, and after 10 min. the resulting mixture was allowed to warm-up to 0° C. before a mixture of water (4 ml) and DCM (40 ml) was added. The aq. layer was extracted with DCM (2×40 ml), and the mixed organic layers were then washed with aq. sat. NaHCO$_3$ (30 ml), dried over anh. MgSO$_4$, filtered, and concentrated to dryness under reduced pressure to give (3,4-dimethyl-phenoxy)-acetaldehyde as a yellow oil (0.985 g; 99%).

(4-trifluoromethyl-phenoxy)-acetaldehyde

According to the general procedure described above for the oxidation of alcohols under Swern conditions, oxidation of 2-(4-trifluoromethyl-phenoxy)-ethanol (0.800 g; 3.880 mmol) afforded the target aldehyde (4-trifluoromethyl-phenoxy)-acetaldehyde (0.792 g; 99%) as a yellow oil which was used for the next step without additional purification.

(4-fluoro-3-trifluoromethyl-phenoxy)-acetaldehyde

According to the general procedure described above for the oxidation of alcohols under Swern conditions, oxidation of 2-(4-fluoro-3-trifluoromethyl-phenoxy)-ethanol (0.450 g; 2.008 mmol) afforded the target aldehyde (4-fluoro-3-trifluoromethyl-phenoxy)-acetaldehyde (0.446 g; 100%) as a yellow oil which was used for the next step without additional purification.

B Synthesis of Substituted Imidazoles

B.1 Synthesis of Imidazoles Based on a Regioselective Deiodination 4,5-diiodo-2-ethyl-1H-imidazole To a slightly yellow homogeneous solution of 2-ethylimidazole (15.000 g; 156.035 mmol) in dioxane (250 ml) and distilled water (250 ml) was added successively, at rt (in one portion), sodium carbonate (49.614 g; 468.104 mmol), and iodine (87.126 g; 343.276 mmol). The resulting brown heterogeneous reaction mixture was further stirred at rt, under nitrogen, for 24 h. EA (500 ml) was then added followed by an aq. solution of sodium thiosulfate (45 g Na$_2$S$_2$O$_3$ in 300 ml of water). The yellow homogeneous organic layer was separated and additionally washed with an aq. solution of sodium thiosulfate (30 g Na$_2$S$_2$O$_3$ in 300 ml of water), and finally with brine (200 ml). The yellow organic layer was then dried over anh. MgSO$_4$, filtered, and concentrated to dryness under reduced pressure to give the pure product 4,5-diiodo-2-ethyl-1H-imidazole as a pale yellow solid which was further dried under HV (49.76 g; 92%). LC-MS: $t_R$=0.55 min.; [M+H]$^+$=349.18 g/mol.

[2-(2-ethyl-4,5-diiodo-imidazol-1-yl)-ethyl]-carbamic acid tert-butyl ester

To a solution of 4,5-diiodo-2-ethyl-1H-imidazole (10.000 g; 28.743 mmol) in anhydrous DMF (140 ml) was added portionwise, at rt, 55-65% sodium hydride moistened with oil (1.379 g; 34.491 mmol). The resulting mixture was further stirred at rt, under nitrogen, for 20 min. The mixture was then heated to 100° C., and a colorless homogeneous solution of 2-(Boc-amino)-ethylbromide (7.085 g; 31.617 mmol) in anhydrous DMF (100 ml) was added dropwise, over 1 h, with an addition funnel. After completion of the addition, the resulting dark-orange homogeneous mixture was further heated at 100° C. for 1 h30. The reaction mixture was cooled to rt, and water (300 ml) was added slowly. This mixture was extracted with ether (7×100 ml). The combined organic layers were washed with brine (3×100 ml), dried over anh. MgSO$_4$, filtered, and concentrated to dryness under reduced pressure to give a yellow oil (13.020 g). The crude was purified by FC (DCM/MeOH=25/1) to give the pure product [2-(2-ethyl-4,5-diiodo-imidazol-1-yl)-ethyl]-carbamic acid tert-butyl ester as a pale yellow solid which was further dried under HV (9.950 g; 70.5%). LC-MS: $t_R$=0.78 min.; [M+H]$^+$=492.33 g/mol.

[2-(2-ethyl-4-iodo-imidazol-1-yl)-ethyl]-carbamic acid tert-butyl ester

A solution of [2-(2-ethyl-4,5-diiodo-imidazol-1-yl)-ethyl] carbamic acid tert-butyl ester (22.990 g; 46.813 mmol) in anhydrous THF (280 ml), under nitrogen, was cooled to −40° C., and a solution of 3M EtMgBr in ether (15.6 ml; 46.8 mmol) was then added dropwise over 15 min. After addition, the resulting solution was stirred between −40° C. and −30° C. for 10 min. (conversion=55% according to LC-MS), and additional 3M EtMgBr in ether (10 ml; 30 mmol) was added until the reaction was finished. The reaction mixture was then treated with water (10 ml) at −40° C., and was allowed to warm-up to rt. Ether (300 ml) was added, and the resulting solution was washed with water (200 ml) and brine (200 ml). The organic layer was dried over anh. MgSO$_4$, filtered, and concentrated to dryness under reduced pressure to give a yellow solid (16.95 g). The crude was purified by FC (DCM/MeOH=20/1) to give the pure product [2-(2-ethyl-4-iodo-imidazol-1-yl)-ethyl]-carbamic acid tert-butyl ester as a yellow solid (15.500 g; 91%). LC-MS: $t_R$=0.65 min.; [M+H]$^+$= 366.39 g/mol.

2-(2-ethyl-4-iodo-imidazol-1-yl)-ethylamine

To an ice-cooled solution of [2-(2-ethyl-4-iodo-imidazol-1-yl)-ethyl]carbamic acid tert-butyl ester (5.720 g; 15.662 mmol) in DCM (125 ml) was added slowly 4N HCl in dioxane (78 ml; 312 mmol). The resulting suspension was stirred at 0° C. for 15 min., then at rt for 1 h. The volatiles were removed under reduced pressure, then under HV. The product 2-(2-ethyl-4-iodo-imidazol-1-yl)-ethylamine was obtained as a pale beige solid (5.96 g; 100%; presence of 3 eq. of HCl). LC-MS: $t_R$=0.14 min.; [M+H]$^+$=266.24 g/mol.

In order to generate the free amine for Pictet-Spengler reaction, the previously dried chlorhydrate salt (5.96 g; with 3 eq. HCl) was suspended in anhydrous ethanol (20 ml) and N-ethyldiisopropylamine (12.1 ml; 70.680 mmol; 4.5 eq.) was added. The resulting homogeneous solution was then appropriate for microwave-assisted Pictet-Spengler reaction.

4,5-diiodo-2-methyl-1H-imidazole

To a slightly yellow homogeneous solution of 2-methylimidazole (15.000 g; 182.680 mmol) in dioxane (305 ml) and distilled water (305 ml) was added successively, at rt (in one portion), sodium carbonate (58.086 g; 548.040 mmol), and iodine (102.005 g; 401.896 mmol). The resulting brown heterogeneous reaction mixture was further stirred at rt, under nitrogen, for 24 h. EA (900 ml) was then added followed by an aq. solution of sodium thiosulfate (54 g Na$_2$S$_2$O$_3$ in 540 ml of water). The yellow homogeneous organic layer was separated and additionally washed with an aq. solution of sodium thiosulfate (36 g Na$_2$S$_2$O$_3$ in 300 ml of water), and finally with brine (300 ml). The yellow organic layer was then dried over anh. MgSO$_4$, filtered, and concentrated to dryness under reduced pressure to give the pure product 4,5-diiodo-2-methyl-1H-imidazole as a yellow solid which was further dried under HV (61.000 g; 100%). LC-MS: $t_R$=0.52 min.; [M+H]$^+$= 335.14 g/mol.

[2-(2-methyl-4,5-diiodo-imidazol-1-yl)-ethyl]-carbamic acid tert-butyl ester

To a yellow solution of 4,5-diiodo-2-methyl-1H-imidazole (5.000 g; 14.975 mmol) in anhydrous DMF (75 ml) was added portionwise, at rt, 55-65% sodium hydride moistened with oil (719 mg; 17.975 mmol). The resulting mixture was further stirred at rt, under nitrogen, for 20 min. The mixture was then heated to 100° C., and a colorless homogeneous solution of 2-(Boc-amino)-ethylbromide (3.691 g; 16.473 mmol) in anhydrous DMF (50 ml) was added dropwise, over 1 h, with an addition funnel. After completion of the addition, the resulting dark-orange homogeneous mixture was further heated at 100° C. for 1 h15. The reaction mixture was cooled to rt, and water (300 ml) was added slowly. This mixture was extracted with ether (4×200 ml). The combined organic layers were washed with brine (100 ml), dried over anh. MgSO$_4$, filtered, and concentrated to dryness under reduced pressure to give an orange oil (6.570 g). The crude was purified by FC (DCM/MeOH=10/1) to give the pure product [2-(2-methyl-4,5-diiodo-imidazol-1-yl)-ethyl]-carbamic acid tert-butyl ester as a yellow solid which was further dried under HV (4.400 g; 62%). LC-MS: $t_R$=0.74 min.; [M+H]$^+$=478.28 g/mol.

[2-(4-iodo-2-methyl-imidazol-1-yl)-ethyl]-carbamic acid tert-butyl ester

A solution of [2-(2-methyl-4,5-diiodo-imidazol-1-yl)-ethyl]-carbamic acid tert-butyl ester (13.300 g; 27.878 mmol) in anhydrous THF (160 ml), under nitrogen, was cooled to −40° C., and a solution of 1M EtMgBr in THF (27.9 ml; 27.9 mmol) was then added dropwise over 20 min. After addition, the resulting solution was stirred between −40° C. and −30° C. for 10 min. (conversion=64% according to LC-MS), and additional 1M EtMgBr in THF (11.15 ml; 11.15 mmol) was added until the reaction was finished. The reaction mixture was then treated with water (8 ml) at −40° C., and was allowed to warm-up to rt. Ether (150 ml) was added, and the resulting solution was washed with water (100 ml) and brine (100 ml). The organic layer was dried over anh. MgSO$_4$, filtered, and concentrated to dryness under reduced pressure to give an orange oil (11.1 g). The crude was purified by FC (DCM/MeOH=15/1) to give the pure product [2-(2-methyl-4-iodo-imidazol-1-yl)-ethyl]-carbamic acid tert-butyl ester as a yellow solid (7.270 g; 74%). LC-MS: $t_R$=0.62 min.; [M+H]$^+$= 352.34 g/mol.

2-(4-iodo-2-methyl-imidazol-1-yl)-ethylamine

To an ice-cooled solution of [2-(4-iodo-2-methyl-imidazol-1-yl)-ethyl]-carbamic acid tert-butyl ester (2.800 g; 7.973 mmol) in DCM (45 ml) was added slowly 4N HCl in dioxane (28.25 ml; 113.000 mmol). The resulting suspension was stirred at 0° C. for 15 min., then at rt for 1 h. The volatiles were removed under reduced pressure, then under HV. The product 2-(4-iodo-2-methyl-imidazol-1-yl)-ethylamine was obtained as a pale beige solid (2.880 g; 100%; presence of 3 eq. of HCl). LC-MS: $t_R$=0.14 min.; [M+H]$^+$=251.92 g/mol.

In order to generate the free amine for Pictet-Spengler reaction, the previously dried chlorhydrate salt (2.880 g; with 3 eq. HCl) was suspended in anhydrous ethanol (9 ml) and N-ethyldiisopropylamine (6.2 ml; 36.216 mmol; 4.5 eq.) was added. The resulting homogeneous solution was then appropriate for microwave-assisted Pictet-Spengler reaction.

4,5-diiodo-2-isopropyl-1H-imidazole

To a slightly yellow homogeneous solution of 2-isopropylimidazole (10.000 g; 90.778 mmol) in dioxane (155 ml) and distilled water (155 ml) was added successively, at rt (in one portion), sodium carbonate (28.865 g; 272.333 mmol), and iodine (50.688 g; 199.711 mmol). The resulting brown heterogeneous reaction mixture was further stirred at rt, under nitrogen, for 24 h. EA (450 ml) was then added followed by an aq. solution of sodium thiosulfate (27 g Na$_2$S$_2$O$_3$ in 270 ml of water). The yellow homogeneous organic layer was separated and additionally washed with an aq. solution of sodium thiosulfate (18 g Na$_2$S$_2$O$_3$ in 180 ml of water), and finally with brine (130 ml). The yellow organic layer was then dried over anh. MgSO$_4$, filtered, and concentrated to dryness under reduced pressure to give the pure product 4,5-diiodo-2-isopropyl-1H-imidazole as a yellow solid which was further dried under HV (31.810 g; 97%). LC-MS: $t_R$=0.62 min.; [M+H]$^+$=363.19 g/mol.

[2-(4,5-diiodo-2-isopropyl-imidazol-1-yl)-ethyl]-carbamic acid tert-butyl ester

To a yellow solution of 4,5-diiodo-2-isopropyl-1H-imidazole (10.000 g; 27.629 mmol) in anhydrous DMF (140 ml) was added portionwise, at rt, 55-65% sodium hydride moistened with oil (1.326 g; 33.154 mmol). The resulting mixture was further stirred at rt, under nitrogen, for 20 min. The mixture was then heated to 100° C., and a colorless homogeneous solution of 2-(Boc-amino)-ethylbromide (6.810 g; 30.391 mmol) in anhydrous DMF (100 ml) was added dropwise, over 1 h, with an addition funnel. After completion of the addition, the resulting mixture was further heated at 100° C. for 1 h30. The reaction mixture was cooled to 0° C., and water (300 ml) was added slowly. This mixture was extracted with ether (5×150 ml). The combined organic layers were washed with brine (100 ml), dried over anh. MgSO$_4$, filtered, and concentrated to dryness under reduced pressure to give an orange oil. The crude was purified by FC (DCM/MeOH=30/1) to give the pure product [2-(4,5-diiodo-2-isopropyl-imidazol-1-yl)-ethyl]-carbamic acid tert-butyl ester as a yellow solid which was further dried under HV (9.720 g; 70%). LC-MS: $t_R$=0.82 min.; [M+H]$^+$=506.32 g/mol.

[2-(4-iodo-2-isopropyl-imidazol-1-yl)-ethyl]-carbamic acid tert-butyl ester

A solution of [2-(4,5-diiodo-2-isopropyl-imidazol-1-yl)-ethyl]-carbamic acid tert-butyl ester (22.930 g; 45.394 mmol) in anhydrous THF (280 ml), under nitrogen, was cooled to −40° C., and a solution of 3M EtMgBr in ether (15.2 ml; 45.600 mmol) was then added dropwise over 10 min. After addition, the resulting solution was stirred between −40° C. and −30° C. for 10 min. (conversion=55% according to LC-MS), and then additional 3M EtMgBr in ether (7.6 ml; 22.800 mmol) was added. Finally in order to complete this reaction, a last addition of 3M EtMgBr in ether (2.9 ml; 8.700 mmol) was performed. The reaction mixture was then treated with water (10 ml) at −40° C., and was allowed to warm-up to rt. Ether (300 ml) was added, and the resulting solution was washed with water (200 ml) and brine (200 ml). The organic layer was dried over anh. MgSO$_4$, filtered, and concentrated to dryness under reduced pressure to give a yellow solid (16.950 g). The crude was purified by FC (DCM/MeOH=20/1) to give the pure product [2-(4-iodo-2-isopropyl-imidazol-1-yl)-ethyl]-carbamic acid tert-butyl ester as a yellow solid (15.800 g; 92%). LC-MS: $t_R$=0.67 min.; [M+H]$^+$=380.39 g/mol.

2-(4-iodo-2-isopropyl-imidazol-1-yl)-ethylamine

To an ice-cooled solution of [2-(4-iodo-2-isopropyl-imidazol-1-yl)-ethyl]-carbamic acid tert-butyl ester (3.011 g; 7.941 mmol) in DCM (75 ml) was added slowly 4N HCl in dioxane (40 ml; 160 mmol). The resulting suspension was stirred at 0° C. for 15 min., then at rt for 2 h45. The volatiles were removed under reduced pressure, then under HV. The product 2-(4-iodo-2-isopropyl-imidazol-1-yl)-ethylamine was obtained as a colorless solid (2.720 g; 100%; presence of 2 eq. of HCl). LC-MS: $t_R$=0.19 min.; [M+H]$^+$=280.17 g/mol.

In order to generate the free amine for Pictet-Spengler reaction, the previously dried chlorhydrate salt (2.720 g; with 2 eq. HCl) was suspended in anhydrous ethanol (8 ml) and N-ethyldiisopropylamine (4.0 ml; 23.300 mmol; 3 eq.) was added. The resulting homogeneous solution was then appropriate for microwave-assisted Pictet-Spengler reaction.

4,5-diiodo-2-propyl-1H-imidazole

To a slightly yellow homogeneous solution of 2-propylimidazole (10.000 g; 86.239 mmol) in dioxane (155 ml) and distilled water (155 ml) was added successively, at rt (in one portion), sodium carbonate (27.559 g; 258.716 mmol), and iodine (48.154 g; 189.725 mmol). The resulting brown heterogeneous reaction mixture was further stirred at rt, under nitrogen, for 24 h. EA (350 ml) was then added followed by an aq. solution of sodium thiosulfate (30 g Na$_2$S$_2$O$_3$ in 200 ml of water). The yellow homogeneous organic layer was separated and additionally washed with an aq. solution of sodium thiosulfate (30 g Na$_2$S$_2$O$_3$ in 200 ml of water), and finally with brine (2×200 ml). The yellow organic layer was then dried over anh. MgSO$_4$, filtered, and concentrated to dryness under reduced pressure to give the pure product 4,5-diiodo-2-propyl-1H-imidazole as a yellow solid which was further dried under HV (30.660 g; 98%). LC-MS: $t_R$=0.68 min.; [M+H]$^+$=362.73 g/mol.

[2-(4,5-diiodo-2-propyl-imidazol-1-yl)-ethyl]-carbamic acid tert-butyl ester

To a solution of 4,5-diiodo-2-propyl-1H-imidazole (15.000 g; 41.443 mmol) in anhydrous DMF (260 ml) was added portionwise, at rt, 55-65% sodium hydride moistened with oil (1.989 g; 49.732 mmol). The resulting mixture was further stirred at rt, under nitrogen, for 20 min. The mixture was then heated to 100° C., and a colorless homogeneous solution of 2-(Boc-amino)-ethylbromide (10.216 g; 45.587 mmol) in anhydrous DMF (100 ml) was added dropwise, over 1 h, with an addition funnel. After completion of the addition, the resulting dark-orange homogeneous mixture was further heated at 100° C. for 1 h30. The reaction mixture was cooled to rt, and water (300 ml) was added slowly. This mixture was extracted with ether (3×200 ml). The combined organic layers were washed with brine (2×100 ml), dried over anh. MgSO$_4$, filtered, and concentrated to dryness under reduced pressure to give a yellow oil. The crude was purified by FC (heptane/EA=1/1) to give the pure product [2-(4,5-diiodo-2-propyl-imidazol-1-yl)-ethyl]-carbamic acid tert-butyl ester as a yellow solid which was further dried under HV (8.690 g; 42%). LC-MS: $t_R$=0.88 min.; [M+H]$^+$=505.77 g/mol.

[2-(4-iodo-2-propyl-imidazol-1-yl)-ethyl]-carbamic acid tert-butyl ester

A solution of [2-(4,5-diiodo-2-propyl-imidazol-1-yl)-ethyl]-carbamic acid tert-butyl ester (8.690 g; 17.204 mmol) in anhydrous THF (100 ml), under nitrogen, was cooled to −40° C., and a solution of 1M EtMgBr in THF (20.5 ml; 20.5 mmol; 1.2 eq.) was then added dropwise over 15 min. After addition, the resulting solution was stirred between −40° C. and −30° C. for 10 min. (conversion=55% according to LC-MS), and additional 1M EtMgBr in THF (13.9 ml; 13.9 mmol; 0.8 eq.) was added in order to complete the reaction. The reaction mixture was then treated with water (5 ml) at −40° C., and was allowed to warm-up to rt. Ether (200 ml) was added, and the resulting solution was washed with brine (2×200 ml). The organic layer was dried over anh. MgSO$_4$, filtered, and concentrated to dryness under reduced pressure. The crude was purified by FC (DCM/MeOH=20/1) to give the pure product [2-(4-iodo-2-propyl-imidazol-1-yl)-ethyl]-carbamic acid tert-butyl ester as a yellow oil (6.110 g; 94%). LC-MS: $t_R$=0.74 min.; [M+H]$^+$=380.00 g/mol.

2-(4-iodo-2-propyl-imidazol-1-yl)-ethylamine

To an ice-cooled solution of [2-(4-iodo-2-propyl-imidazol-1-yl)-ethyl]-carbamic acid tert-butyl ester (6.110 g; 16.111 mmol) in DCM (100 ml) was added slowly 4N HCl in dioxane (80.5 ml; 322 mmol; 20 eq.). The resulting suspension was stirred at 0° C. for 15 min., and then at rt for 2 h. The volatiles were removed under reduced pressure, then under HV. The product 2-(4-iodo-2-propyl-imidazol-1-yl)-ethylamine was obtained as a colorless solid (5.620 g; 100%; presence of 2 eq. of HCl). LC-MS: $t_R$=0.24 min.; [M+H]$^+$=279.96 g/mol.

In order to generate the free amine 2-(4-iodo-2-propyl-imidazol-1-yl)-ethylamine for Pictet-Spengler reaction, the previously dried chlorhydrate salt (5.620 g; with 2 eq. HCl) was suspended in anhydrous ethanol (35 ml) and N-ethyldiisopropylamine (10 ml; 58.413 mmol; 3.6 eq.) was added. The resulting homogeneous solution was then appropriate for microwave-assisted Pictet-Spengler reaction.

1-trityl-1H-imidazole-2-carbaldehyde

A cooled (−78° C.) yellow solution of 1-(triphenylmethyl) imidazole (25.000 g; 80.542 mmol) in anhydrous THF (750 ml) was treated dropwise (in 55 min.) with a 1.6M solution of butyllithium in hexanes (55.35 ml; 88.560 mmol). After addition, the resulting pink homogeneous solution was further stirred at −78° C., under nitrogen, for 30 min. before a solution of anhydrous DMF (6.8 ml; 88.186 mmol) in anhydrous THF (40 ml) was added dropwise (in 40 min.). The resulting mixture was additionally stirred at −78° C., under nitrogen, for 1 h before aq. sat. NH$_4$Cl (50 ml) was added dropwise. Ether (300 ml) and water (400 ml) were successively added, and this mixture was allowed to warm-up to rt. The yellow organic layer was additionally washed with water (300 ml), dried over anh. MgSO$_4$, filtered, and concentrated to dryness under reduced pressure. The crude was purified by FC (DCM/MeOH=30/1) to give the pure product 1-trityl-1H-imidazole- 2-carbaldehyde as a pale yellow solid which was further dried under HV (20.660 g; 76%). LC-MS: $t_R$=1.03 min.; [M+H]$^+$: no ionisation.

(1-trityl-1H-imidazol-2-yl)-MeOH

A heterogeneous mixture of 1-trityl-1H-imidazole-2-carbaldehyde (6.310 g; 18.646 mmol) in anhydrous MeOH (150 ml) was heated to 45° C., and was treated portionwise with sodium borohydride (2.116 g; 55.938 mmol). After completion of the addition, heating at 45° C. was continued for 2 h. The reaction mixture was then allowed to cool to rt, filtered, and the discarded colorless solid was additionally washed with chloroform. The filtrate was concentrated to dryness under reduced pressure affording the expected product (1-trityl-1H-imidazol-2-yl)-MeOH as a colorless solid which was further dried under HV (6.340 g; 99%). This dried product was used for the next step without additional purification. LC-MS: $t_R$=0.80 min.; [M+H]$^+$: no ionisation.

2-methoxymethyl-1-trityl-1H-imidazole

A cooled (0° C.) colorless homogeneous solution of (1-trityl-1H-imidazol-2-yl)-MeOH (6.340 g; 18.624 mmol) in anhydrous THF (100 ml) was treated with sodium hydride (2.234 g; 55.871 mmol; 60% NaH moistened with oil). The resulting mixture was stirred at rt, under nitrogen, for 20 min. and was again cooled (0° C.) before a colorless homogeneous solution of iodomethane (2 ml; 32.055 mmol) in anhydrous THF (18 ml) was added dropwise. The resulting mixture was allowed to warm-up to rt, and was further stirred during 1h30. Water (50 ml) was then added dropwise followed by ether (100 ml). The aq. layer was additionally extracted with ether (2×50 ml), and the mixed organic extracts were dried over anh. MgSO$_4$, filtered, and concentrated to dryness under reduced pressure. Purification by FC (DCM/MeOH=50/1) gave the pure product 2-methoxymethyl-1-trityl-1H-imidazole as a grey solid which was further dried under HV (3.370 g; 51%). LC-MS: $t_R$=0.84 min.; [M+H]$^+$: no ionisation.

2-methoxymethyl-1H-imidazole

A heterogeneous mixture of 2-methoxymethyl-1-trityl-1H-imidazole (3.892 g; 10.980 mmol) in anhydrous MeOH (320 ml) was treated with acetic acid (16 ml), and the resulting mixture was heated at reflux (75° C.) for 2 h. The resulting yellow homogeneous solution was allowed to cool to rt, and was then concentrated to dryness under reduced pressure. DCM (30 ml) was added and this organic layer was extracted with water (3×10 ml). The mixed aq. layers were concentrated to dryness under reduced pressure to give the expected product 2-methoxymethyl-1H-imidazole as a yellow oil which was further dried under high vacuum (1.230 g; 99%). LC-MS: $t_R$=0.15 min.; [M+H]$^+$: no ionisation.

4,5-diiodo-2-methoxymethyl-1H-imidazole

A homogeneous solution of 2-methoxymethyl-1H-imidazole (1.230 g; 10.969 mmol) in dioxane (20 ml) and water (20 ml) was successively treated at rt with sodium carbonate (3.487 g; 32.908 mmol), and iodine (6.125 g; 24.132 mmol). The resulting brown heterogeneous reaction mixture was further stirred at rt, under nitrogen, for 24 h. EA (60 ml) was then added followed by an aq. solution of sodium thiosulfate (3.5 g Na$_2$S$_2$O$_3$ in 35 ml of water). The yellow homogeneous organic layer was separated and additionally washed with an aq. solution of sodium thiosulfate (2.3 g Na$_2$S$_2$O$_3$ in 23 ml of water), and finally with brine (25 ml). The yellow organic layer was then dried over anh. MgSO$_4$, filtered, and concentrated to dryness under reduced pressure to give the pure product 4,5-diiodo-2-methoxymethyl-1H-imidazole as a yellow solid which was further dried under HV (3.006 g; 75%). LC-MS: $t_R$=0.66 min.; [M+H]$^+$=365.09 g/mol.

[2-(4,5-diiodo-2-methoxymethyl-imidazol-1-yl)-ethyl]-carbamic acid tert-butylester To a solution of 4,5-diiodo-2-methoxymethyl-1H-imidazole (3.000 g; 8.244 mmol) in anhydrous DMF (35 ml) was added portionwise, at rt, 55-65% sodium hydride moistened with oil (395 mg; 9.895 mmol). The resulting mixture was further stirred at rt, under nitrogen, for 20 min. The mixture was then heated to 100° C., and a colorless homogeneous solution of 2-(Boc-amino)-ethylbromide (2.032 g; 9.068 mmol) in anhydrous DMF (30 ml) was added dropwise, over 15 min., with an addition funnel. After completion of the addition, the resulting dark-orange homogeneous mixture was further heated at 100° C. for 1 h45. The reaction mixture was cooled to rt, and water (175 ml) was added slowly. This mixture was extracted with ether (4×120 ml). The combined organic layers were dried over anh. MgSO$_4$, filtered, and concentrated to dryness under reduced pressure. The crude was purified by FC (DCM/MeOH=50/1) to give the pure product [2-(4,5-diiodo-2-methoxymethyl-imidazol-1-yl)-ethyl]-carbamic acid tert-butylester as a pale yellow solid which was further dried under HV (3.050 g; 73%). LC-MS: $t_R$=0.87 min.; [M+H]$^+$=508.16 g/mol.

[2-(4-iodo-2-methoxymethyl-imidazol-1-yl)-ethyl]-carbamic acid tert-butyl ester

A solution of [2-(4,5-diiodo-2-methoxymethyl-imidazol-1-yl)-ethyl]-carbamic acid tert-butylester (3.050 g; 6.015 mmol) in anhydrous THF (30 ml), under nitrogen, was cooled to −40° C., and a solution of 1M EtMgBr in THF (6.02 ml; 6.02 mmol) was then added dropwise over 10 min. After addition, the resulting solution was stirred between −40° C. and −30° C. for 10 min. (conversion=53% according to LC-MS), and additional 1M EtMgBr (3 ml; 3 mmol) was added. Stirring at −40° C. was continued for additional 20 min. (reaction completed). The reaction mixture was then treated with water (2 ml) at −40° C., and was allowed to warm-up to rt. Ether (40 ml) was added, and the resulting solution was washed with water (25 ml) and brine (30 ml). The organic layer was dried over anh. MgSO$_4$, filtered, and concentrated to dryness under reduced pressure. The crude was purified by FC (DCM/MeOH=50/1) to give the pure product [2-(4-iodo-2-methoxymethyl-imidazol-1-yl)-ethyl]-carbamic acid tert-butyl ester as a yellow solid (1.645 g; 72%). LC-MS: $t_R$=0.70 min.; [M+H]$^+$=382.29 g/mol.

2-(4-iodo-2-methoxymethyl-imidazol-1-yl)-ethylamine

To an ice-cooled solution of [2-(4-iodo-2-methoxymethyl-imidazol-1-yl)-ethyl]-carbamic acid tert-butyl ester (3.051 g; 8.003 mmol) in DCM (60 ml) was added slowly 4N HCl in dioxane (40 ml; 160 mmol). The resulting suspension was stirred at 0° C. for 15 min., then at rt for 2 h. The volatiles were removed under reduced pressure, then under HV. The product 2-(4-iodo-2-methoxymethyl-imidazol-1-yl)-ethylamine was obtained as a pale beige solid (2.750 g; 100%; presence of 2 eq. of HCl). LC-MS: $t_R$=0.21 min.; [M+H]$^+$=282.24 g/mol.

In order to generate the free amine for Pictet-Spengler reaction, the previously dried chlorhydrate salt (2.750 g; with 2 eq. HCl) was suspended in anhydrous ethanol (9 ml) and N-ethyldiisopropylamine (4.1 ml; 23.949 mmol; 3 eq.) was added. The resulting homogeneous solution was then appropriate for microwave-assisted Pictet-Spengler reaction.

2,4,5-triiodo-1H-imidazole

To a slightly yellow homogeneous solution of imidazole (5.000 g; 73.444 mmol) in dioxane (135 ml) and distilled water (135 ml) was added successively, at rt (in one portion), sodium carbonate (35.029 g; 330.500 mmol), and iodine (61.515 g; 242.366 mmol). The resulting brown heterogeneous reaction mixture was further stirred at rt, under nitrogen, for 24 h. EA (250 ml) was then added followed by an aq. solution of sodium thiosulfate (22.50 g $Na_2S_2O_3$ in 150 ml of water). The yellow homogeneous organic layer was then dried over anh. $MgSO_4$, filtered, and concentrated to dryness under reduced pressure to give the crude product 2,4,5-triiodo-1H-imidazole as a yellow solid which was further dried under HV (32.700 g; 100%). LC-MS: $t_R$=0.78 min.; $[M+H]^+$=447.03 g/mol.

[2-(2,4,5-triiodo-imidazol-1-yl)-ethyl]-carbamic acid tert-butyl ester

To a yellow solution of 2,4,5-triiodo-1H-imidazole (15.295 g; 34.313 mmol) in anhydrous DMF (200 ml) was added portionwise, at rt, 55-65% sodium hydride moistened with oil (2.058 g; 51.469 mmol). The resulting mixture was further stirred at rt, under nitrogen, for 20 min. The mixture was then heated to 100° C., and a colorless homogeneous solution of 2-(Boc-amino)-ethylbromide (11.534 g; 51.469 mmol) in anhydrous DMF (100 ml) was added dropwise, over 1 h, with an addition funnel. After completion of the addition, the resulting mixture was further heated at 100° C. for 1 h. The reaction mixture was cooled to 0° C., and water (200 ml) was added slowly. This mixture was extracted with ether (5×200 ml). The combined organic layers were washed with brine (100 ml), dried over anh. $MgSO_4$, filtered, and concentrated to dryness under reduced pressure to give a yellow oil. The crude was purified by FC (heptane/EA=3/2) to give the pure product [2-(2,4,5-triiodo-imidazol-1-yl)-ethyl]-carbamic acid tert-butyl ester as a colorless solid which was further dried under HV (8.540 g; 42%). LC-MS: $t_R$=0.93 min.; $[M+H]^+$=589.89 g/mol.

[2-(4-iodo-imidazol-1-yl)-ethyl]-carbamic acid tert-butyl ester

A solution of [2-(2,4,5-triiodo-imidazol-1-yl)-ethyl]-carbamic acid tert-butyl ester (8.120 g; 13.787 mmol) in anhydrous THF (100 ml), under nitrogen, was cooled to −40° C., and a solution of 1M EtMgBr in THF (27.6 ml; 27.6 mmol) was then added dropwise over 15 min. After addition, the resulting milky mixture was stirred between −40° C. and −30° C. for 10 min. (reaction completed according to LC-MS). The reaction mixture was then treated with water (5 ml) at −40° C., and was allowed to warm-up to rt. Ether (100 ml) was added, and the resulting solution was washed with water (150 ml) and brine (150 ml). The organic layer was dried over anh. $MgSO_4$, filtered, and concentrated to dryness under reduced pressure to give a purple oil (5.480 g). The crude was purified by FC (DCM/MeOH=20/1) to give the pure product [2-(4-iodo-imidazol-1-yl)-ethyl]-carbamic acid tert-butyl ester as a colorless solid (2.940 g; 63%). LC-MS: $t_R$=0.62 min.; $[M+H]^+$=338.07 g/mol.

2-(4-iodo-imidazol-1-yl)-ethylamine

To an ice-cooled solution of [2-(4-iodo-imidazol-1-yl)-ethyl]-carbamic acid tert-butyl ester (6.154 g; 18.253 mmol) in DCM (200 ml) was added slowly 4N HCl in dioxane (91 ml; 364 mmol). The resulting suspension was stirred at 0° C. for 15 min., then at rt for 1 h. The volatiles were removed under reduced pressure, then under HV. The product 2-(4-iodo-imidazol-1-yl)-ethylamine was obtained as a colorless solid (5.690 g; 100%; presence of 2 eq. of HCl). LC-MS: $t_R$=0.15 min.; $[M+H]^+$=238.14 g/mol.

In order to generate the free amine for Pictet-Spengler reaction, the previously dried chlorhydrate salt (5.690 g; with 2 eq. HCl) was suspended in anhydrous ethanol (80 ml) and N-ethyldiisopropylamine (9.37 ml; 54.759 mmol; 3 eq.) was added. The resulting homogeneous solution was then appropriate for microwave-assisted Pictet-Spengler reaction.

B.2 Synthesis of Imidazoles Starting with Disubstituted Imidazoles

Synthesis of 2-imidazol-1-yl-ethylamine derivatives by N-alkylation of disubstituted imidazoles [general procedure (GP9)]

Sodium hydroxide (180 mmol; powder) and tetrabutylammonium hydrogensulfate (1.80 mmol) were successively added to a solution of the respective imidazole derivative (45.00 mmol) in MeCN (100 ml). After 30 min., 2-chloroethylamine hydrochloride (54.00 mmol) was added and the reaction mixture was stirred for 24 h at reflux. The obtained suspension was filtered and the filtrate was concentrated in vacuo to give a crude oil which was used without further purification.

2-(2,4-dimethyl-imidazol-1-yl)-ethylamine

Prepared by N-alkylation of 2,4-dimethyl-1H-imidazole according to the previously described general procedure (GP9).
$^1$H-NMR (CDCl$_3$; 300 MHz): δ=6.50 (s; 1H), 3.76 (t, J=6.2 Hz, 2H), 2.91 (t, J=6.2 Hz, 2H), 2.28 (s, 3H), 2.09 (s, 3H).

2-(2-ethyl-4-methyl-imidazol-1-yl)-ethylamine

Prepared by N-alkylation of 2-ethyl-4-methyl-1H-imidazole according to the previously described general procedure (GP9).
$^1$H-NMR (CDCl$_3$; 300 MHz): δ=6.43 (s; 1H), 3.70 (t, J=6.2 Hz, 2H), 2.84 (t, J=6.2 Hz, 2H), 2.52 (q, J=7.5 Hz, 2H), 2.04 (s, 3H), 1.17 (t, J=7.5 Hz, 3H).

C Synthesis of 5,6,7,8-tetrahydro-imidazo[1,5-a]pyrazine derivatives

C.1 Synthesis of 5,6,7,8-tetrahydro-imidazo[1,5-a]pyrazine derivatives via microwave-assisted Pictet-Spengler reaction followed by Boc-protection 3-ethyl-1-iodo-8-[2-(4-trifluoromethyl-phenyl)-ethyl]-5,6-dihydro-8H-imidazo[1,5-a]pyrazine-7-carboxylic acid tert-butyl ester [general procedure for microwave-assisted Pictet-Spengler reaction (GP10)]

A homogeneous solution of 2-(2-ethyl-4-iodo-imidazol-1-yl)-ethylamine (518 mg; 1.954 mmol) in anhydrous ethanol (2.5 ml) was treated with a solution of 3-(4-trifluoromethyl-phenyl)-propionaldehyde (395 mg; 1.954 mmol) in anhydrous ethanol (2.5 ml). The mixture was sealed and put in the microwave oven (70 W; 110° C.; 13 bars; 10 min.). This microwave-assisted Pictet-Spengler reaction was repeated three additional times with the same amount of starting material. The resulting crude reaction mixtures were finally mixed and concentrated to dryness under reduced pressure giving the crude 3-ethyl-1-iodo-8-[2-(4-trifluoromethyl-phenyl)-ethyl]-5,6,7,8-tetrahydro-imidazo[1,5-a]pyrazine (brown oil; 5.370 g). LC-MS: $t_R$=0.72 min.; [M+H]$^+$=450.28 g/mol.

The crude 3-ethyl-1-iodo-8-[2-(4-trifluoromethyl-phenyl)-ethyl]-5,6,7,8-tetrahydro-imidazo[1,5-a]pyrazine (theoretical amount: 7.815 mmol) was dissolved in anhydrous DCM (10 ml), and N-ethyldiisopropylamine (2.67 ml; 15.630 mmol) was added. The resulting mixture was then cooled to 0° C., and a solution of di-tert-butyl dicarbonate Boc$_2$O (2.046 g; 9.378 mmol) in anhydrous DCM (5 ml) was added in one portion. After completion of the addition, the reaction mixture was further stirred at 0° C. for 15 min., and at rt overnight. The resulting mixture was then washed with brine (2×100 ml), and the organic layer was dried over anh. MgSO$_4$, filtered, and concentrated to dryness under reduced pressure. The crude was purified by FC (DCM/MeOH=25/1) to give the pure product 3-ethyl-1-iodo-8-[2-(4-trifluoromethyl-phenyl)-ethyl]-5,6-dihydro-8H-imidazo[1,5-a]pyrazine-7-carboxylic acid tert-butyl ester as a yellow solid which was further dried under HV (2.820 g; 66%). LC-MS: $t_R$=0.93 min.; [M+H]$^+$=550.41 g/mol.

8-[2-(3,5-difluoro-4-trifluoromethyl-phenyl)-ethyl]-3-ethyl-1-iodo-5,6-dihydro-8H-imidazo[1,5-a]pyrazine-7-carboxylic acid tert-butyl ester According to the previously described general procedure (GP10), the microwave-assisted Pictet-Spengler reaction affording 8-[2-(3,5-difluoro-4-trifluoromethyl-phenyl)-ethyl]-3-ethyl-1-iodo-5,6,7,8-tetrahydro-imidazo[1,5-a]pyrazine (LC-MS: $t_R$=0.75 min.; [M+H]$^+$=486.38 g/mol) was performed in three experiments (70 W; 110° C.; 11 bars; 10 min.) with the same amount of starting material 2-(2-ethyl-4-iodo-imidazol-1-yl)-ethylamine (439 mg; 1.656 mmol).

After Boc-protection and purification by FC (DCM/MeOH=30/1), pure 8-[2-(3,5-difluoro-4-trifluoromethyl-phenyl)-ethyl]-3-ethyl-1-iodo-5,6-dihydro-8H-imidazo[1,5-a]pyrazine-7-carboxylic acid tert-butyl ester (2.450 g; 84%) was obtained as a yellow solid. LC-MS: $t_R$=0.96 min.; [M+H]$^+$=586.29 g/mol.

8-[2-(3,4-difluoro-phenyl)-ethyl]-3-ethyl-1-iodo-5,6-dihydro-8H-imidazo[1,5-a]pyrazine-7-carboxylic acid tert-butyl ester According to the general procedure (GP10), the microwave-assisted Pictet-Spengler reaction (60 W; 100° C.; 8 bars; 10 min.) between 2-(2-ethyl-4-iodo-imidazol-1-yl)-ethylamine (355.2 mg; 1.340 mmol) and 3-(3,4-difluoro-phenyl)-propionaldehyde (228.7 mg; 1.340 mmol) afforded 8-[2-(3,4-difluoro-phenyl)-ethyl]-3-ethyl-1-iodo-5,6,7,8-tetrahydro-imidazo[1,5-a]pyrazine which was Boc-protected and finally purified by HPLC.

The pure product 8-[2-(3,4-difluoro-phenyl)-ethyl]-3-ethyl-1-iodo-5,6-dihydro-8H-imidazo[1,5-a]pyrazine-7-carboxylic acid tert-butyl ester was isolated as a yellow solid (387.2 mg; 0.748 mmol; 56%). LC-MS: $t_R$=0.92 min.; [M+H]$^+$=518.08 g/mol.

8-[2-(3,5-difluoro-4-methyl-phenyl)-ethyl]-3-ethyl-1-iodo-5,6-dihydro-8H-imidazo[1,5-a]pyrazine-7-carboxylic acid tert-butyl ester According to the general procedure (GP10), the microwave-assisted Pictet-Spengler reaction (60 W; 100° C.; 8 bars; 10 min.) between 2-(2-ethyl-4-iodo-imidazol-1-yl)-ethylamine (296.9 mg; 1.120 mmol) and 3-(3,5-difluoro-4-methyl-phenyl)-propionaldehyde (206.7 mg; 1.120 mmol) afforded 8-[2-(3,5-difluoro-4-methyl-phenyl)-ethyl]-3-ethyl-1-iodo-5,6,7,8-tetrahydro-imidazo[1,5-a]pyrazine which was Boc-protected and finally purified by HPLC.

The pure product 8-[2-(3,5-difluoro-4-methyl-phenyl)-ethyl]-3-ethyl-1-iodo-5,6-dihydro-8H-imidazo[1,5-a]pyrazine-7-carboxylic acid tert-butyl ester was isolated as a yellow solid (349.3 mg; 0.657 mmol; 59%). LC-MS: $t_R$=0.95 min.; [M+H]$^+$=532.10 g/mol.

3-ethyl-8-[2-(2-fluoro-4-trifluoromethyl-phenyl)-ethyl]-1-iodo-5,6-dihydro-8H-imidazo[1,5-a]pyrazine-7-carboxylic acid tert-butyl ester According to the general procedure (GP10), the microwave-assisted Pictet-Spengler reaction (60 W; 100° C.; 8 bars; 10 min.) between 2-(2-ethyl-4-iodo-imidazol-1-yl)-ethylamine (265.1 mg; 1.000 mmol) and 3-(2-fluoro-4-trifluoromethyl-phenyl)-propionaldehyde (220.2 mg; 1.000 mmol) afforded 3-ethyl-8-[2-(2-fluoro-4-trifluoromethyl-phenyl)-ethyl]-1-iodo-5,6,7,8-tetrahydro-imidazo[1,5-a]pyrazine which was Boc-protected and finally purified by HPLC.

The pure product 3-ethyl-8-[2-(2-fluoro-4-trifluoromethyl-phenyl)-ethyl]-1-iodo-5,6-dihydro-8H-imidazo[1,5-a]pyrazine-7-carboxylic acid tert-butyl ester was isolated as a yellow solid (396.3 mg; 0.698 mmol; 70%). LC-MS: $t_R$=0.95 min.; [M+H]$^+$=568.32 g/mol.

3-ethyl-8-[2-(3-fluoro-4-methyl-phenyl)-ethyl]-1-iodo-5,6-dihydro-8H-imidazo[1,5-a]pyrazine-7-carboxylic acid tert-butyl ester According to the general procedure (GP10), the microwave-assisted Pictet-Spengler reaction (60 W; 100° C.; 8 bars; 10 min.) between 2-(2-ethyl-4-iodo-imidazol-1-yl)-ethylamine (320.7 mg; 1.210 mmol) and 3-(3-fluoro-4-methyl-phenyl)-propionaldehyde (202 mg; 1.210 mmol) afforded 3-ethyl-8-[2-(3-fluoro-4-methyl-phenyl)-ethyl]-1-iodo-5,6,7,8-tetrahydro-imidazo[1,5-a]pyrazine which was Boc-protected and finally purified by HPLC.

The pure product 3-ethyl-8-[2-(3-fluoro-4-methyl-phenyl)-ethyl]-1-iodo-5,6-dihydro-8H-imidazo[1,5-a]pyrazine-7-carboxylic acid tert-butyl ester was isolated as a yellow solid (394.8 mg; 0.769 mmol; 64%). LC-MS: $t_R$=0.91 min.; [M+H]$^+$=514.37 g/mol.

8-[2-(3,4-dimethyl-phenyl)-ethyl]-3-ethyl-1-iodo-5,6-dihydro-8H-imidazo[1,5-a]pyrazine-7-carboxylic acid tert-butyl ester According to the general procedure (GP10), the microwave-assisted Pictet-Spengler reaction (60 W; 100° C.; 8 bars; 10 min.) between 2-(2-ethyl-4-iodo-imidazol-1-yl)-ethylamine (344.6 mg; 1.300 mmol) and 3-(3,4-dimethyl-phenyl)-propionaldehyde (211.4 mg; 1.300 mmol) afforded 8-[2-(3,4-dimethyl-phenyl)-ethyl]-3-ethyl-1-iodo-5,6,7,8-tetrahydro-imidazo[1,5-a]pyrazine which was Boc-protected and finally purified by HPLC.

The pure product 8-[2-(3,4-dimethyl-phenyl)-ethyl]-3-ethyl-1-iodo-5,6-dihydro-8H-imidazo[1,5-a]pyrazine-7-carboxylic acid tert-butyl ester was isolated as a yellow solid (393.5 mg; 0.772 mmol; 59%). LC-MS: $t_R$=0.91 min.; [M+H]$^+$=510.39 g/mol.

3-ethyl-8-[2-(3-fluoro-4-trifluoromethyl-phenyl)-ethyl]-1-iodo-5,6-dihydro-8H-imidazo[1,5-a]pyrazine-7-carboxylic acid tert-butyl ester According to the general procedure (GP10), the microwave-assisted Pictet-Spengler reaction (60 W; 100° C.; 8 bars; 10 min.) between 2-(2-ethyl-4-iodo-imidazol-1-yl)-ethylamine (312.8 mg; 1.180 mmol) and 3-(3-fluoro-4-trifluoromethyl-phenyl)-propionaldehyde (260.4 mg; 1.180 mmol) afforded 3-ethyl-8-[2-(3-fluoro-4-trifluoromethyl-phenyl)-ethyl]-1-iodo-5,6,7,8-tetrahydro-imidazo[1,5-a]pyrazine which was Boc-protected and finally purified by HPLC.

The pure product 3-ethyl-8-[2-(3-fluoro-4-trifluoromethyl-phenyl)-ethyl]-1-iodo-5,6-dihydro-8H-imidazo[1,5-a]pyrazine-7-carboxylic acid tert-butyl ester was isolated as a yellow solid (365.3 mg; 0.643 mmol; 54.5%). LC-MS: $t_R$=0.93 min.; [M+H]$^+$=568.32 g/mol.

8-[2-(2,4-difluoro-3-methyl-phenyl)-ethyl]-3-ethyl-1-iodo-5,6-dihydro-8H-imidazo[1,5-a]pyrazine-7-carboxylic acid tert-butyl ester According to the general procedure (GP10), the microwave-assisted Pictet-Spengler reaction (60 W; 100° C.; 8 bars; 10 min.) between 2-(2-ethyl-4-iodo-imidazol-1-yl)-ethylamine (334.0 mg; 1.260 mmol) and 3-(2,4-difluoro-3-methyl-phenyl)-propionaldehyde (232.7 mg; 1.260 mmol) afforded 8-[2-(2,4-difluoro-3-methyl-phenyl)-ethyl]-3-ethyl-1-iodo-5,6,7,8-tetrahydro-imidazo[1,5-a]pyrazine which was Boc-protected and finally purified by HPLC.

The pure product 8-[2-(2,4-difluoro-3-methyl-phenyl)-ethyl]-3-ethyl-1-iodo-5,6-dihydro-8H-imidazo[1,5-a]pyrazine-7-carboxylic acid tert-butyl ester was isolated as a yellow solid (403.8 mg; 0.759 mmol; 60%). LC-MS: $t_R$=0.89 min.; [M+H]$^+$=532.33 g/mol.

1-iodo-3-methyl-8-[2-(4-trifluoromethyl-phenyl)-ethyl]-5,6-dihydro-8H-imidazo[1,5-a]pyrazine-7-carboxylic acid tert-butyl ester According to the general procedure (GP10), the microwave-assisted Pictet-Spengler reaction (60 W; 110° C.; 8 bars; 10 min.) between 2-(4-iodo-2-methyl-imidazol-1-yl)-ethylamine (373.8 mg; 1.489 mmol) and 3-(4-trifluoromethyl-phenyl)-propionaldehyde (301 mg; 1.489 mmol) afforded 1-iodo-3-methyl-8-[2-(4-trifluoromethyl-phenyl)-ethyl]-5,6,7,8-tetrahydro-imidazo[1,5-a]pyrazine which was Boc-protected and finally purified by FC (DCM/MeOH=25/1).

The pure product 1-iodo-3-methyl-8-[2-(4-trifluoromethyl-phenyl)-ethyl]-5,6-dihydro-8H-imidazo[1,5-a]pyrazine-7-carboxylic acid tert-butyl ester was isolated as a yellow solid (389 mg; 0.726 mmol; 49%). LC-MS: $t_R$=0.95 min.; [M+H]$^+$=536.11 g/mol.

8-[2-(3,4-dimethyl-phenyl)-ethyl]-1-iodo-3-methyl-5,6-dihydro-8H-imidazo[1,5-a]pyrazine-7-carboxylic acid tert-butyl ester According to the general procedure (GP10), the microwave-assisted Pictet-Spengler reaction (60 W; 110° C.; 6 bars; 10 min.) between 2-(4-iodo-2-methyl-imidazol-1-yl)-ethylamine (758 mg; 3.020 mmol) and 3-(3,4-dimethyl-phenyl)-propionaldehyde (490 mg; 3.020 mmol) afforded 8-[2-(3,4-dimethyl-phenyl)-ethyl]-1-iodo-3-methyl-5,6,7,8-tetrahydro-imidazo[1,5-a]pyrazine which was Boc-protected and finally purified by FC (DCM/MeOH=25/1).

The pure product 8-[2-(3,4-dimethyl-phenyl)-ethyl]-1-iodo-3-methyl-5,6-dihydro-8H-imidazo[1,5-a]pyrazine-7-carboxylic acid tert-butyl ester was isolated as a yellow solid (1.177 g; 2.375 mmol; 79%). LC-MS: $t_R$=0.94 min.; [M+H]$^+$=496.17 g/mol

8-[2-(3,5-difluoro-4-methyl-phenyl)-ethyl]-1-iodo-3-methyl-5,6-dihydro-8H-imidazo[1,5-a]pyrazine-7-carboxylic acid tert-butyl ester According to the general procedure (GP10), the microwave-assisted Pictet-Spengler reaction (60 W; 110° C.; 5 bars; 10 min.) between 2-(4-iodo-2-methyl-imidazol-1-yl)-ethylamine (696 mg; 2.774 mmol) and 3-(3,5-difluoro-4-methyl-phenyl)-propionaldehyde (510 mg; 2.774 mmol) afforded 8-[2-(3,5-difluoro-4-methyl-phenyl)-ethyl]-1-iodo-3-methyl-5,6,7,8-tetrahydro-imidazo[1,5-a]pyrazine which was Boc-protected and finally purified by FC (DCM/MeOH=25/1).

The pure product 8-[2-(3,5-difluoro-4-methyl-phenyl)-ethyl]-1-iodo-3-methyl-5,6-dihydro-8H-imidazo[1,5-a]pyrazine-7-carboxylic acid tert-butyl ester was isolated as a yellow solid (582 mg; 1.124 mmol; 41%). LC-MS: $t_R$=0.94 min.; [M+H]$^+$=518.12 g/mol.

1-iodo-3-methoxymethyl-8-[2-(4-trifluoromethyl-phenyl)-ethyl]-5,6-dihydro-8H-imidazo[1,5-a]pyrazine-7-carboxylic acid tert-butyl ester According to the general procedure (GP10), the microwave-assisted Pictet-Spengler reaction (60 W; 95° C.; 9 bars; 10 min.) between 2-(4-iodo-2-methoxymethyl-imidazol-1-yl)-ethylamine (596 mg; 2.119 mmol) and 3-(4-trifluoromethyl-phenyl)-propionaldehyde (428 mg; 2.119 mmol) afforded 1-iodo-3-methoxymethyl-8-[2-(4-trifluoromethyl-phenyl)-ethyl]-5,6,7,8-tetrahydro-imidazo[1,5-a]pyrazine which was Boc-protected and finally purified by FC (DCM/MeOH=30/1).

The pure product 1-iodo-3-methoxymethyl-8-[2-(4-trifluoromethyl-phenyl)-ethyl]-5,6-dihydro-8H-imidazo[1,5-a]pyrazine-7-carboxylic acid tert-butyl ester was isolated as a yellow solid (720 mg; 1.273 mmol; 60%). LC-MS: $t_R$=1.03 min.; [M+H]$^+$=566.31 g/mol.

1-Iodo-3-isopropyl-8-[2-(4-trifluoromethyl-phenyl)-ethyl]-5,6-dihydro-8H-imidazo[1,5-a]pyrazine-7-carboxylic acid tert-butyl ester A homogeneous solution of 2-(4-iodo-2-isopropyl-imidazol-1-yl)-ethylamine (541 mg; 1.938 mmol) in anhydrous ethanol (2 ml) was treated with a solution of 3-(4-trifluoromethyl-phenyl)-propionaldehyde (481 mg; 2.379 mmol) in anhydrous ethanol (2.5 ml). The mixture was sealed and put in the microwave oven (60 W; 100° C.; 8 bars; 10 min.). This microwave-assisted Pictet-Spengler reaction was repeated three additional times with the same amount of starting material. The resulting crude reaction mixtures were finally mixed and concentrated to dryness under reduced pressure giving the crude 1-iodo-3-isopropyl-8-[2-(4-trifluoromethyl-phenyl)-ethyl]-5,6,7,8-tetrahydro-imidazo[1,5-a]pyrazine as a brown oil. LC-MS: $t_R$=0.75 min.; [M+H]$^+$=464.27 g/mol.

The crude 1-iodo-3-isopropyl-8-[2-(4-trifluoromethyl-phenyl)-ethyl]-5,6,7,8-tetrahydro-imidazo[1,5-a]pyrazine (theoretical amount: 7.752 mmol) was dissolved in anhydrous DCM (20 ml), and N-ethyldiisopropylamine (2.65 ml; 15.510 mmol) was added. The resulting mixture was then cooled to 0° C., and a solution of di-tert-butyl dicarbonate Boc$_2$O (2.030 g; 9.306 mmol) in anhydrous DCM (10 ml) was added in one portion. After completion of the addition, the reaction mixture was further stirred at 0° C. for 15 min., and at rt overnight. After reaction, the resulting mixture was washed with brine (2×100 ml), the organic layer was dried over anh. MgSO$_4$, filtered, and concentrated to dryness under reduced pressure.

The crude was purified by FC (DCM/MeOH=25/1) to give the pure product 1-iodo-3-isopropyl-8-[2-(4-trifluoromethyl-phenyl)-ethyl]-5,6-dihydro-8H-imidazo[1,5-a]pyrazine-7-carboxylic acid tert-butyl ester as a pale yellow solid which was further dried under HV (3.580 g; 82%). LC-MS: $t_R$=0.95 min.; [M+H]$^+$=564.45 g/mol.

1-iodo-8-[2-(4-trifluoromethyl-phenyl)-ethyl]-5,6-dihydro-8H-imidazo[1,5-a]pyrazine-7-carboxylic acid tert-butyl ester According to the general procedure (GP10), the microwave-assisted Pictet-Spengler reaction (70 W; 130° C.; 10 bars; 10 min.) between 2-(4-iodo-imidazol-1-yl)-ethylamine (4.326 g; 18.253 mmol) and 3-(4-trifluoromethyl-phenyl)-propionaldehyde (3.690 g; 18.253 mmol) afforded 1-iodo-8-[2-(4-trifluoromethyl-phenyl)-ethyl]-5,6,7,8-tetrahydro-imidazo[1,5-a]pyrazine which was Boc-protected and finally purified by FC (DCM/MeOH=25/1).

The pure product 1-iodo-8-[2-(4-trifluoromethyl-phenyl)-ethyl]-5,6-dihydro-8H-imidazo[1,5-a]pyrazine-7-carboxylic acid tert-butyl ester was isolated as a yellow solid (3.720 g; 7.135 mmol; 39%). LC-MS: $t_R$=0.89 min.; [M+H]$^+$=522.15 g/mol.

3-ethyl-1-iodo-8-[2-(3,4,5-trifluoro-phenyl)-ethyl]-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(2-ethyl-4-iodo-imidazol-1-yl)-ethylamine (7.394 mmol) and 3-(3,4,5-trifluoro-phenyl)-propionaldehyde (1.391 g; 7.394 mmol) afforded 3-ethyl-1-iodo-8-[2-(3,4,5-trifluoro-phenyl)-ethyl]-5,6,7,8-tetrahydro-imidazo[1,5-a]pyrazine. LC-MS: $t_R$=0.74 min.; [M+H]$^+$=435.86 g/mol.

Subsequent protection of the secondary amine, and purification by FC (DCM/MeOH=25/1) allowed the isolation of the pure product 3-ethyl-1-iodo-8-[2-(3,4,5-trifluoro-phenyl)-ethyl]-5,6-dihydro-8H-imidazo[1,5-a]pyrazine-7-carboxylic acid tert-butyl ester as a colorless solid (2.010 g; 51%). LC-MS: $t_R$=0.97 min.; [M+H]$^+$=535.87 g/mol.

8-[2-(3-fluoro-4-trifluoromethyl-phenyl)-ethyl]-1-iodo-3-methyl-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(4-iodo-2-methyl-imidazol-1-yl)-ethylamine (51.840 mmol) and 3-(3-fluoro-4-trifluoromethyl-phenyl)-propionaldehyde (13.125 g; 59.616 mmol) afforded 8-[2-(3-fluoro-4-trifluoromethyl-phenyl)-ethyl]-1-iodo-3-methyl-5,6,7,8-tetrahydro-imidazo[1,5-a]pyrazine. LC-MS: $t_R$=0.76 min.; [M+H]$^+$=453.93 g/mol. Subsequent protection of the secondary amine, and purification by FC (DCM/MeOH=20/1) allowed the isolation of the pure product 8-[2-(3-fluoro-4-trifluoromethyl-phenyl)-ethyl]-1-iodo-3-methyl-5,6-dihydro-8H-imidazo[1,5-a]pyrazine-7-carboxylic acid tert-butyl ester as a pale yellow solid (15.450 g; 54%). LC-MS: $t_R$=0.97 min.; [M+H]$^+$=554.84 g/mol.

8-[2-(3,5-difluoro-4-methoxy-phenyl)-ethyl]-3-ethyl-1-iodo-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(2-ethyl-4-iodo-imidazol-1-yl)-ethylamine (5.168 mmol) and 3-(3,5-difluoro-4-methoxy-phenyl)-propionaldehyde (1.034 g; 5.168 mmol) afforded 8-[2-(3,5-difluoro-4-methoxy-phenyl)-ethyl]-3-ethyl-1-iodo-5,6,7,8-tetrahydro-imidazo[1,5-a]pyrazine. LC-MS: $t_R$=0.73 min.; [M+H]$^+$=448.42 g/mol.

Subsequent protection of the secondary amine, and purification by FC (DCM/MeOH=25/1) allowed the isolation of the pure product 8-[2-(3,5-difluoro-4-methoxy-phenyl)-ethyl]-3-ethyl-1-iodo-5,6-dihydro-8H-imidazo[1,5-a]pyrazine-7-carboxylic acid tert-butyl ester as a yellow solid (1.440 g; 62%). LC-MS: $t_R$=0.96 min.; [M+H]$^+$=547.97 g/mol.

8-[2-(4-chloro-3,5-difluoro-phenyl)-ethyl]-3-ethyl-1-iodo-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(2-ethyl-4-iodo-imidazol-1-yl)-ethylamine (4.012 mmol) and 3-(4-chloro-3,5-difluoro-phenyl)-propionaldehyde (1.030 g; 5.034 mmol) afforded 8-[2-(4-chloro-3,5-difluoro-phenyl)-ethyl]-3-ethyl-1-iodo-5,6,7,8-tetrahydro-imidazo[1,5-a]pyrazine. LC-MS: $t_R$=0.78 min.; [M+H]$^+$=451.76 g/mol.

Subsequent protection of the secondary amine, and purification by FC (DCM/MeOH=25/1) allowed the isolation of the pure product 8-[2-(4-chloro-3,5-difluoro-phenyl)-ethyl]-3-ethyl-1-iodo-5,6-dihydro-8H-imidazo[1,5-a]pyrazine-7-carboxylic acid tert-butyl ester as a yellow solid (1.790 g; 81%). LC-MS: $t_R$=0.99 min.; [M+H]$^+$=551.80 g/mol.

8-[2-(3-chloro-4-trifluoromethyl-phenyl)-ethyl]-3-ethyl-1-iodo-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(2-ethyl-4-iodo-imidazol-1-yl)-ethylamine (4.497 mmol) and 3-(3-chloro-4-trifluoromethyl-phenyl)-propionaldehyde (1.064 g; 4.497 mmol) afforded 8-[2-(3-chloro-4-trifluoromethyl-phenyl)-ethyl]-3-ethyl-1-iodo-5,6,7,8-tetrahydro-imidazo[1,5-a]pyrazine. LC-MS: $t_R$=0.81 min.; [M+H]$^+$=483.73 g/mol.

Subsequent protection of the secondary amine, and purification by FC (DCM/MeOH=20/1) allowed the isolation of the pure product 8-[2-(3-chloro-4-trifluoromethyl-phenyl)-ethyl]-3-ethyl-1-iodo-5,6-dihydro-8H-imidazo[1,5-a]pyrazine-7-carboxylic acid tert-butyl ester as a pale yellow solid (2.070 g; 79%). LC-MS: $t_R$=1.00 min.; [M+H]$^+$=583.70 g/mol.

8-[2-(2,5-difluoro-4-trifluoromethyl-phenyl)-ethyl]-3-ethyl-1-iodo-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(2-ethyl-4-iodo-imidazol-1-yl)-ethylamine (6.340 mmol) and 3-(2,5-difluoro-4-trifluoromethyl-phenyl)-propionaldehyde (1.509 g; 6.340 mmol) afforded 8-[2-(2,5-difluoro-4-trifluoromethyl-phenyl)-ethyl]-3-ethyl-1-iodo-5,6,7,8-tetrahydro-imidazo[1,5-a]pyrazine. LC-MS: $t_R$=0.79 min.; [M+H]$^+$=485.87 g/mol. Subsequent protection of the secondary amine, and purification by FC (DCM/MeOH=50/1) allowed the isolation of the pure product 8-[2-(2,5-difluoro-4-trifluoromethyl-phenyl)-ethyl]-3-ethyl-1-iodo-5,6-dihydro-8H-imidazo[1,5-a]pyrazine-7-carboxylic acid tert-butyl ester as a slightly beige solid (1.890 g; 51%). LC-MS: $t_R$=0.99 min.; [M+H]$^+$=585.78 g/mol.

3-ethyl-1-iodo-8-[2-(4-trifluoromethoxy-phenyl)-ethyl]-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(2-ethyl-4-iodo-imidazol-1-yl)-ethylamine (5.621 mmol) and 3-(4-trifluoromethoxy-phenyl)-propionaldehyde (1.206 g; 5.528 mmol) afforded 3-ethyl-1-iodo-8-[2-(4-trifluoromethoxy-phenyl)-ethyl]-5,6,7,8-tetrahydro-imidazo[1,5-a]pyrazine. LC-MS: $t_R$=0.78 min.; [M+H]$^+$=465.87 g/mol.

Subsequent protection of the secondary amine, and purification by FC (DCM/MeOH=40/1) allowed the isolation of the pure product 3-ethyl-1-iodo-8-[2-(4-trifluoromethoxy-phenyl)-ethyl]-5,6-dihydro-8H-imidazo[1,5-a]pyrazine-7-carboxylic acid tert-butyl ester as a yellow oil (1.680 g; 53%). LC-MS: $t_R$=0.97 min.; [M+H]$^+$=565.80 g/mol.

8-[2-(4-bromo-phenyl)-ethyl]-3-ethyl-1-iodo-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(2-ethyl-4-iodo-imidazol-1-yl)-ethylamine (26.610 mmol) and 3-(4-bromo-phenyl)-propionaldehyde (6.350 g; 29.803 mmol) afforded 8-[2-(4-bromo-phenyl)-ethyl]-3-ethyl-1-iodo-5,6,7,8-tetrahydro-imidazo[1,5-a]pyrazine. LC-MS: $t_R$=0.74 min.; [M+H]$^+$=460.01 g/mol.

Subsequent protection of the secondary amine, and purification by FC (DCM/MeOH=15/1) allowed the isolation of the pure product 8-[2-(4-bromo-phenyl)-ethyl]-3-ethyl-1-iodo-5,6-dihydro-8H-imidazo[1,5-a]pyrazine-7-carboxylic acid tert-butyl ester as a slightly beige solid (7.610 g; 51%). LC-MS: $t_R$=0.96 min.; [M+H]$^+$=562.09 g/mol.

1-iodo-3-propyl-8-[2-(4-trifluoromethyl-phenyl)-ethyl]-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(4-iodo-2-propyl-imidazol-1-yl)-ethylamine (9.260 mmol) and 3-(4-trifluoromethyl-phenyl)-propionaldehyde (2.730 g; 13.503 mmol) afforded 1-iodo-3-propyl-8-[2-(4-trifluoromethyl-phenyl)-ethyl]-5,6,7,8-tetrahydro-imidazo[1,5-a]pyrazine. LC-MS: $t_R$=0.80 min.; [M+H]$^+$=463.88 g/mol.

Subsequent protection of the secondary amine, and purification by FC (DCM/MeOH=25/1) allowed the isolation of the pure product 1-iodo-3-propyl-8-[2-(4-trifluoromethyl-phenyl)-ethyl]-5,6-dihydro-8H-imidazo[1,5-a]pyrazine-7-carboxylic acid tert-butyl ester as a yellow solid (4.540 g; 87%). LC-MS: $t_R$=1.00 min.; [M+H]$^+$=563.79 g/mol.

8-[2-(3-fluoro-4-trifluoromethyl-phenyl)-ethyl]-1-iodo-3-propyl-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(4-iodo-2-propyl-imidazol-1-yl)-ethylamine (6.840 mmol) and 3-(3-fluoro-4-trifluoromethyl-phenyl)-propionaldehyde (2.195 g; 9.970 mmol) afforded 8-[2-(3-fluoro-4-trifluoromethyl-phenyl)-ethyl]-1-iodo-3-propyl-5,6,7,8-tetrahydro-imidazo[1,5-a]pyrazine. LC-MS: $t_R$=0.81 min.; [M+H]$^+$=481.75 g/mol.

Subsequent protection of the secondary amine, and purification by FC (DCM/MeOH=25/1) allowed the isolation of the pure product 8-[2-(3-fluoro-4-trifluoromethyl-phenyl)-ethyl]-1-iodo-3-propyl-5,6-dihydro-8H-imidazo[1,5-a]pyrazine-7-carboxylic acid tert-butyl ester as a yellow solid (3.500 g; 88%). LC-MS: $t_R$=1.01 min.; [M+H]$^+$=581.87 g/mol.

3-ethyl-1-iodo-8-[2-(2,3,5-trifluoro-phenyl)-ethyl]-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(2-ethyl-4-iodo-imidazol-1-yl)-ethylamine (2.331 mmol) and 3-(2,3,5-trifluoro-phenyl)-propionaldehyde (0.600 g; 3.189 mmol) afforded 3-ethyl-1-iodo-8-[2-(2,3,5-trifluoro-phenyl)-ethyl]-5,6,7,8-tetrahydro-imidazo[1,5-a]pyrazine. LC-MS: $t_R$=0.69 min.; [M+H]$^+$=436.23 g/mol.

Subsequent protection of the secondary amine, and purification by FC (heptane/EA=2/3) allowed the isolation of the pure product 3-ethyl-1-iodo-8-[2-(2,3,5-trifluoro-phenyl)-ethyl]-5,6-dihydro-8H-imidazo[1,5-a]pyrazine-7-carboxylic acid tert-butyl ester as a colorless solid (0.917 g; 90%). LC-MS: $t_R$=0.92 min.; [M+H]$^+$=536.12 g/mol.

3-ethyl-8-[2-(3-fluoro-4-methoxy-phenyl)-ethyl]-1-iodo-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(2-ethyl-4-iodo-imidazol-1-yl)-ethylamine (11.500 mmol) and 3-(3-fluoro-4-methoxy-phenyl)-propionaldehyde (2.514 g; 13.800 mmol) afforded 3-ethyl-8-[2-(3-fluoro-4-methoxy-phenyl)-ethyl]-1-iodo-5,6,7,8-tetrahydro-imidazo[1,5-a]pyrazine. LC-MS: $t_R$=0.70 min.; [M+H]$^+$=429.88 g/mol.

Subsequent protection of the secondary amine, and purification by FC (DCM/MeOH=25/1) allowed the isolation of the pure product 3-ethyl-8-[2-(3-fluoro-4-methoxy-phenyl)-ethyl]-1-iodo-5,6-dihydro-8H-imidazo[1,5-a]pyrazine-7-carboxylic acid tert-butyl ester as a yellow solid (3.870 g; 64%). LC-MS: $t_R$=0.94 min.; [M+H]$^+$=529.88 g/mol.

8-[2-(2,5-difluoro-4-methoxy-phenyl)-ethyl]-3-ethyl-1-iodo-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(2-ethyl-4-iodo-imidazol-1-yl)-ethylamine (9.700 mmol) and 3-(2,5-difluoro-4-methoxy-phenyl)-propionaldehyde (2.135 g; 10.670 mmol) afforded 8-[2-(2,5-difluoro-4-methoxy-phenyl)-ethyl]-3-ethyl-1-iodo-5,6,7,8-tetrahydro-imidazo[1,5-a]pyrazine. LC-MS: $t_R$=0.72 min.; $[M+H]^+$=447.67 g/mol.

Subsequent protection of the secondary amine, and purification by FC (DCM/MeOH=25/1) allowed the isolation of the pure product 8-[2-(2,5-difluoro-4-methoxy-phenyl)-ethyl]-3-ethyl-1-iodo-5,6-dihydro-8H-imidazo[1,5-a]pyrazine-7-carboxylic acid tert-butyl ester as a yellow solid (3.850 g; 73%). LC-MS: $t_R$=0.95 min.; $[M+H]^+$=547.79 g/mol.

3-ethyl-8-(4-fluoro-3-trifluoromethyl-phenoxymethyl)-1-iodo-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(2-ethyl-4-iodo-imidazol-1-yl)-ethylamine (1.540 mmol) and (4-fluoro-3-trifluoromethyl-phenoxy)-acetaldehyde (0.342 g; 1.540 mmol) afforded 3-ethyl-8-(4-fluoro-3-trifluoromethyl-phenoxymethyl)-1-iodo-5,6,7,8-tetrahydro-imidazo[1,5-a]pyrazine. Subsequent protection of the secondary amine, and purification by FC (DCM/MeOH=60/1) allowed the isolation of the pure product 3-ethyl-8-(4-fluoro-3-trifluoromethyl-phenoxymethyl)-1-iodo-5,6-dihydro-8H-imidazo[1,5-a]pyrazine-7-carboxylic acid tert-butyl ester as a yellow solid (0.412 g; 47%). LC-MS: $t_R$=0.93 min.; $[M+H]^+$=570.37 g/mol.

3-ethyl-1-iodo-8-(4-trifluoromethyl-phenoxymethyl)-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(2-ethyl-4-iodo-imidazol-1-yl)-ethylamine (3.880 mmol) and (4-trifluoromethyl-phenoxy)-acetaldehyde (0.792 g; 3.880 mmol) afforded 3-ethyl-1-iodo-8-(4-trifluoromethyl-phenoxymethyl)-5,6,7,8-tetrahydro-imidazo[1,5-a]pyrazine. LC-MS: $t_R$=0.73 min.; $[M+H]^+$=452.12 g/mol.

Subsequent protection of the secondary amine, and purification by FC (DCM/MeOH=90/1) allowed the isolation of the pure product 3-ethyl-1-iodo-8-(4-trifluoromethyl-phenoxymethyl)-5,6-dihydro-8H-imidazo[1,5-a]pyrazine-7-carboxylic acid tert-butyl ester as a yellow solid (0.890 g; 42%). LC-MS: $t_R$=0.93 min.; $[M+H]^+$=552.13 g/mol.

8-(3,4-dimethyl-phenoxymethyl)-3-ethyl-1-iodo-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(2-ethyl-4-iodo-imidazol-1-yl)-ethylamine (6.000 mmol) and (3,4-dimethyl-phenoxy)-acetaldehyde (0.985 g; 6.000 mmol) afforded 8-(3,4-dimethyl-phenoxymethyl)-3-ethyl-1-iodo-5,6,7,8-tetrahydro-imidazo[1,5-a]pyrazine. LC-MS: $t_R$=0.70 min.; $[M+H]^+$=412.12 g/mol.

Subsequent protection of the secondary amine, and purification by FC (DCM/MeOH=60/1) allowed the isolation of the pure product 8-(3,4-dimethyl-phenoxymethyl)-3-ethyl-1-iodo-5,6-dihydro-8H-imidazo[1,5-a]pyrazine-7-carboxylic acid tert-butyl ester as a yellow solid (0.919 g; 30%). LC-MS: $t_R$=0.90 min.; $[M+H]^+$=512.18 g/mol.

3-ethyl-1-iodo-8-(3-trifluoromethyl-phenoxymethyl)-5,6-dihydro-8H-imidazo[1,5-a]pyrazine-7-carboxylic acid tert-butyl ester According to the general procedure (GP10), microwave-assisted Pictet-Spengler reaction (60 W; 140° C.; 6.5 bars; 10 min.) between 2-(2-ethyl-4-iodo-imidazol-1-yl)-ethylamine (3.880 mmol) and (3-trifluoromethyl-phenoxy)-acetaldehyde (0.792 g; 3.880 mmol) afforded 3-ethyl-1-iodo-8-(3-trifluoromethyl-phenoxymethyl)-5,6,7,8-tetrahydro-imidazo[1,5-a]pyrazine.

Subsequent protection of the secondary amine, and purification by FC (DCM/MeOH=80/1) allowed the isolation of the pure product 3-ethyl-1-iodo-8-(3-trifluoromethyl-phenoxymethyl)-5,6-dihydro-8H-imidazo[1,5-a]pyrazine-7-carboxylic acid tert-butyl ester as an orange solid (1.272 g; 59%). LC-MS: $t_R$=0.92 min.; $[M+H]^+$=552.30 g/mol.

C.2 Synthesis of 5,6,7,8-tetrahydro-imidazo[1,5-a]pyrazine derivatives via Pictet-Spengler reaction with isomeric 2-imidazol-1-yl-ethylamine derivatives [second general procedure for microwave-assisted Pictet-Spengler reaction (GP11)]

A mixture of the respective 2-imidazol-1-yl-ethylamine (2.200 mmol) and the respective aldehyde (2.500 mmol) in toluene (4 ml) was heated in a microwave oven for 7 min. to 120° C. (135-150 W). The solvent was removed in vacuo and the residue was either purified by preparative HPLC or used without further purification.

1,3-dimethyl-8-(2-p-tolyl-ethyl)-5,6,7,8-tetrahydro-imidazo[1,5-a]pyrazine

Prepared according to the previously described general procedure (GP11) by reaction of 2-(2,4-dimethyl-imidazol-1-yl)-ethylamine with 3-p-tolyl-propionaldehyde. LC-MS: $t_R$=0.57 min.; $[M+H]^+$=270 g/mol.

1,3-dimethyl-8-[2-(4-trifluoromethyl-phenyl)-ethyl]-5,6,7,8-tetrahydro-imidazo[1,5-a]pyrazine Prepared according to the previously described general procedure (GP11) by reaction of 2-(2,4-dimethyl-imidazol-1-yl)-ethylamine with 3-(4-trifluoromethyl-phenyl)-propionaldehyde. LC-MS: $t_R$=0.64 min.; $[M+H]^+$=324 g/mol.

8-[2-(3-chloro-phenyl)-ethyl]-1,3-dimethyl-5,6,7,8-tetrahydro-imidazo[1,5-a]pyrazine Prepared according to the previously described general procedure (GP11) by reaction of 2-(2,4-dimethyl-imidazol-1-yl)-ethylamine with 3-(3-chloro-phenyl)-propionaldehyde. LC-MS: $t_R$=0.59 min.; $[M+H]^+$=290 g/mol.

8-[2-(2,3-dimethyl-phenyl)-ethyl]-1,3-dimethyl-5,6,7,8-tetrahydro-imidazo[1,5-a]pyrazine Prepared according to the previously described general procedure (GP11) by reaction of 2-(2,4-dimethyl-imidazol- 1-yl)-ethylamine with 3-(2,3-dimethyl-phenyl)-propionaldehyde. LC-MS: $t_R$=0.61 min.; [M+H]$^+$=284 g/mol.

8-[2-(2,4-dimethyl-phenyl)-ethyl]-1,3-dimethyl-5,6,7,8-tetrahydro-imidazo[1,5-a]pyrazine Prepared according to the previously described general procedure (GP11) by reaction of 2-(2,4-dimethyl-imidazol-1-yl)-ethylamine with 3-(2,4-dimethyl-phenyl)-propionaldehyde. LC-MS: $t_R$=0.62 min.; [M+H]$^+$=284 g/mol.

8-[2-(3,4-difluoro-phenyl)-ethyl]-1,3-dimethyl-5,6,7,8-tetrahydro-imidazo[1,5-a]pyrazine Prepared according to the previously described general procedure (GP11) by reaction of 2-(2,4-dimethyl-imidazol-1-yl)-ethylamine with 3-(3,4-difluoro-phenyl)-propionaldehyde. LC-MS: $t_R$=0.57 min.; [M+H]$^+$=292 g/mol.

8-[2-(2,4-dichloro-phenyl)-ethyl]-1,3-dimethyl-5,6,7,8-tetrahydro-imidazo[1,5-a]pyrazine Prepared according to the previously described general procedure (GP11) by reaction of 2-(2,4-dimethyl-imidazol-1-yl)-ethylamine with 3-(2,4-dichloro-phenyl)-propionaldehyde. LC-MS: $t_R$=0.64 min.; [M+H]$^+$=324 g/mol.

8-[2-(3-fluoro-4-methoxy-phenyl)-ethyl]-1,3-dimethyl-5,6,7,8-tetrahydro-imidazo[1,5-a]pyrazine Prepared according to the previously described general procedure (GP11) by reaction of 2-(2,4-dimethyl-imidazol-1-yl)-ethylamine with 3-(3-fluoro-4-methoxy-phenyl)-propionaldehyde. LC-MS: $t_R$=0.57 min.; [M+H]$^+$=304 g/mol.

8-[2-(2,4-dimethoxy-phenyl)-ethyl]-1,3-dimethyl-5,6,7,8-tetrahydro-imidazo[1,5-a]pyrazine Prepared according to the previously described general procedure (GP11) by reaction of 2-(2,4-dimethyl-imidazol-1-yl)-ethylamine with 3-(2,4-dimethoxy-phenyl)-propionaldehyde. LC-MS: $t_R$=0.59 min.; [M+H]$^+$=316 g/mol.

3-ethyl-1-methyl-8-[2-(4-trifluoromethyl-phenyl)-ethyl]-5,6,7,8-tetrahydro-imidazo[1,5-a]pyrazine Prepared according to the previously described general procedure (GP11) by reaction of 2-(2-ethyl-4-methyl-imidazol-1-yl)-ethylamine with 3-(4-trifluoromethyl-phenyl)-propionaldehyde. LC-MS: $t_R$=0.65 min.; [M+H]$^+$=338 g/mol.

D Functionalization and derivatization of 5,6,7,8-tetrahydro-imidazo[1,5-a]pyrazine derivatives

D.1 Chlorination

1-chloro-3-ethyl-8-[2-(4-trifluoromethyl-phenyl)-ethyl]-5,6-dihydro-8H-imidazo[1,5-a]pyrazine-7-carboxylic acid tert-butyl ester [first general procedure for chlorination of the imidazole ring (GP12)]

A cooled (−78° C.) solution of 3-ethyl-1-iodo-8-[2-(4-trifluoromethyl-phenyl)-ethyl]-5,6-dihydro-8H-imidazo[1,5-a]pyrazine-7-carboxylic acid tert-butyl ester (300 mg; 0.546 mmol) in anhydrous THF (4 ml) was treated dropwise with a solution of 1.6M n-BuLi in hexanes (0.34 ml; 0.546 mmol). The resulting solution was additionally stirred at −78° C. for 10 min., and was then treated dropwise with a solution of hexachloroethane (517 mg; 2.184 mmol; 4 eq.) in anhydrous THF (1 ml). The reaction mixture was further stirred at −78° C. for 1 h. The mixture was then quenched with water (0.2 ml), diluted with ether (30 ml), and was allowed to warm-up to rt. The organic layer was dried over anh. MgSO$_4$, filtered, and concentrated to dryness under reduced pressure. The crude was purified by FC (DCM/MeOH=100/3) to give the pure product 1-chloro-3-ethyl-8-[2-(4-trifluoromethyl-phenyl)-ethyl]-5,6-dihydro-8H-imidazo[1,5-a]pyrazine-7-carboxylic acid tert-butyl ester as a yellow solid (143 mg; 57%). LC-MS: $t_R$=1.02 min.; [M+H]$^+$=458.49 g/mol.

1-chloro-8-[2-(3,5-difluoro-4-trifluoromethyl-phenyl)-ethyl]-3-ethyl-5,6-dihydro-8H-imidazo[1,5-a]pyrazine-7-carboxylic acid tert-butyl ester According to the general procedure (GP12), chlorination of 8-[2-(3,5-difluoro-4-trifluoromethyl-phenyl)-ethyl]-3-ethyl-1-iodo-5,6-dihydro-8H-imidazo[1,5-a]pyrazine-7-carboxylic acid tert-butyl ester (500 mg; 0.854 mmol) and purification by FC (DCM/MeOH=100/3) gave the product 1-chloro-8-[2-(3,5-difluoro-4-trifluoromethyl-phenyl)-ethyl]-3-ethyl-5,6-dihydro-8H-imidazo[1,5-a]pyrazine-7-carboxylic acid tert-butyl ester as a yellow solid (179 mg; 42%). LC-MS: $t_R$=1.05 min.; [M+H]$^+$=494.37 g/mol.

1-chloro-8-[2-(3,4-difluoro-phenyl)-ethyl]-3-ethyl-5,6-dihydro-8H-imidazo[1,5-a]pyrazine-7-carboxylic acid tert-butyl ester According to the general procedure (GP12), chlorination of 8-[2-(3,4-difluoro-phenyl)-ethyl]-3-ethyl-1-iodo-5,6-dihydro-8H-imidazo[1,5-a]pyrazine-7-carboxylic acid tert-butyl ester (387.2 mg; 0.748 mmol) and purification by FC (heptane/EA=2/3) gave the product 1-chloro-8-[2-(3,4-difluoro-phenyl)-ethyl]-3-ethyl-5,6-dihydro-8H-imidazo[1,5-a]pyrazine-7-carboxylic acid tert-butyl ester as a yellow solid (143 mg; 45%). LC-MS: $t_R$=0.99 min.; [M+H]$^+$=426.28 g/mol.

1-chloro-8-[2-(3,5-difluoro-4-methyl-phenyl)-ethyl]-3-ethyl-5,6-dihydro-8H-imidazo[1,5-a]pyrazine-7-carboxylic acid tert-butyl ester According to the general procedure (GP12), chlorination of 8-[2-(3,5-difluoro-4-methyl-phenyl)-ethyl]-3-ethyl-1-iodo-5,6-dihydro-8H-imidazo[1,5-a]pyrazine-7-carboxylic acid tert-butyl ester (349.3 mg; 0.657 mmol) and purification by FC (heptane/EA=2/3) gave the product 1-chloro-8-[2-(3,5-difluoro-4-methyl-phenyl)-ethyl]-3-ethyl-5,6-dihydro-8H-imidazo[1,5-a]pyrazine-7-carboxylic acid tert-butyl ester as a yellow solid (136.8 mg; 47%). LC-MS: $t_R$=1.03 min.; [M+H]$^+$=440.36 g/mol.

1-chloro-3-ethyl-8-[2-(2-fluoro-4-trifluoromethyl-phenyl)-ethyl]-5,6-dihydro-8H-imidazo[1,5-a]pyrazine-7-carboxylic acid tert-butyl ester According to the general procedure (GP12), chlorination of 3-ethyl-8-[2-(2-fluoro-4-trifluoromethyl-phenyl)-ethyl]-1-iodo-5,6-dihydro-8H-imidazo[1,5-a]pyrazine-7-carboxylic acid tert-butyl ester (396.3 mg; 0.698 mmol) and purification by FC (heptane/EA=2/3) gave the product 1-chloro-3-ethyl-8-[2-(2-fluoro-4-trifluoromethyl-phenyl)-ethyl]-5,6-dihydro-8H-imidazo[1,5-a]pyrazine-7-carboxylic acid tert-butyl ester as a yellow solid (153.6 mg; 46%). LC-MS: $t_R$=1.04 min.; [M+H]$^+$=476.32 g/mol.

1-chloro-3-ethyl-8-[2-(3-fluoro-4-methyl-phenyl)-ethyl]-5,6-dihydro-8H-imidazo[1,5-a]pyrazine-7-carboxylic acid tert-butyl ester According to the general procedure (GP12), chlorination of 3-ethyl-8-[2-(3-fluoro-4-methyl-phenyl)-ethyl]-1-iodo-5,6-dihydro-8H-imidazo[1,5-a]pyrazine-7-carboxylic acid tert-butyl ester (394.8 mg; 0.769 mmol) and purification by FC (heptane/EA=2/3) gave the product 1-chloro-3-ethyl-8-[2-(3-fluoro-4-methyl-phenyl)-ethyl]-5,6-dihydro-8H-imidazo[1,5-a]pyrazine-7-carboxylic acid tert-butyl ester as a yellow solid (191.4 mg; 59%). LC-MS: $t_R$=1.01 min.; [M+H]$^+$=422.32 g/mol.

1-chloro-8-[2-(3,4-dimethyl-phenyl)-ethyl]-3-ethyl-5,6-dihydro-8H-imidazo[1,5-a]pyrazine-7-carboxylic acid tert-butyl ester According to the general procedure (GP12), chlorination of 8-[2-(3,4-dimethyl-phenyl)-ethyl]-3-ethyl-1-iodo-5,6-dihydro-8H-imidazo[1,5-a]pyrazine-7-carboxylic acid tert-butyl ester (393.5 mg; 0.772 mmol) and purification by FC (heptane/EA=2/3) gave the product 1-chloro-8-[2-(3,4-dimethyl-phenyl)-ethyl]-3-ethyl-5,6-dihydro-8H-imidazo[1,5-a]pyrazine-7-carboxylic acid tert-butyl ester as a yellow solid (225 mg; 70%). LC-MS: $t_R$=1.02 min.; [M+H]$^+$=418.34 g/mol.

1-chloro-3-ethyl-8-[2-(3-fluoro-4-trifluoromethyl-phenyl)-ethyl]-5,6-dihydro-8H-imidazo[1,5-a]pyrazine-7-carboxylic acid tert-butyl ester According to the general procedure (GP12), chlorination of 3-ethyl-8-[2-(3-fluoro-4-trifluoromethyl-phenyl)-ethyl]-1-iodo-5,6-dihydro-8H-imidazo[1,5-a]pyrazine-7-carboxylic acid tert-butyl ester (365.3 mg; 0.643 mmol) and purification by FC (heptane/EA=2/3) gave the product 1-chloro-3-ethyl-8-[2-(3-fluoro-4-trifluoromethyl-phenyl)-ethyl]-5,6-dihydro-8H-imidazo[1,5-a]pyrazine-7-carboxylic acid tert-butyl ester as a yellow solid (135.3 mg; 44%). LC-MS: $t_R$=1.04 min.; [M+H]$^+$=476.32 g/mol.

1-chloro-8-[2-(2,4-difluoro-3-methyl-phenyl)-ethyl]-3-ethyl-5,6-dihydro-8H-imidazo[1,5-a]pyrazine-7-carboxylic acid tert-butyl ester According to the general procedure (GP12), chlorination of 8-[2-(2,4-difluoro-3-methyl-phenyl)-ethyl]-3-ethyl-1-iodo-5,6-dihydro-8H-imidazo[1,5-a]pyrazine-7-carboxylic acid tert-butyl ester (403.8 mg; 0.759 mmol) and purification by FC (heptane/EA=2/3) gave the product 1-chloro-8-[2-(2,4-difluoro-3-methyl-phenyl)-ethyl]-3-ethyl-5,6-dihydro-8H-imidazo[1,5-a]pyrazine-7-carboxylic acid tert-butyl ester as a yellow solid (213.9 mg; 64%). LC-MS: $t_R$=1.02 min.; [M+H]$^+$=440.35 g/mol.

1-chloro-8-[2-(3,5-difluoro-4-methyl-phenyl)-ethyl]-3-methyl-5,6-dihydro-8H-imidazo[1,5-a]pyrazine-7-carboxylic acid tert-butyl ester According to the general procedure (GP12), chlorination of 8-[2-(3,5-difluoro-4-methyl-phenyl)-ethyl]-1-iodo-3-methyl-5,6-dihydro-8H-imidazo[1,5-a]pyrazine-7-carboxylic acid tert-butyl ester (582 mg; 1.125 mmol) and purification by FC (DCM/MeOH=40/1) gave the product 1-chloro-8-[2-(3,5-difluoro-4-methyl-phenyl)-ethyl]-3-methyl-5,6-dihydro-8H-imidazo[1,5-a]pyrazine-7-carboxylic acid tert-butyl ester as a yellow oil (49 mg; 0.115 mmol). LC-MS: $t_R$=1.02 min.; [M+H]$^+$=426.45 g/mol.

1-chloro-3-methyl-8-[2-(4-trifluoromethyl-phenyl)-ethyl]-5,6-dihydro-8H-imidazo[1,5-a]pyrazine-7-carboxylic acid tert-butyl ester According to the general procedure (GP12), chlorination of 1-iodo-3-methyl-8-[2-(4-trifluoromethyl-phenyl)-ethyl]-5,6-dihydro-8H-imidazo[1,5-a]pyrazine-7-carboxylic acid tert-butyl ester (389 mg; 0.727 mmol) and purification by FC (DCM/MeOH=20/1) gave the product 1-chloro-3-methyl-8-[2-(4-trifluoromethyl-phenyl)-ethyl]-5,6-dihydro-8H-imidazo[1,5-a]pyrazine-7-carboxylic acid tert-butyl ester as an orange oil (33 mg; 0.074 mmol). LC-MS: $t_R$=1.02 min.; [M+H]$^+$=444.44 g/mol.

1-chloro-8-[2-(3,4-dimethyl-phenyl)-ethyl]-3-methyl-5,6-dihydro-8H-imidazo[1,5-a]pyrazine-7-carboxylic acid tert-butyl ester According to the general procedure (GP12), chlorination of 8-[2-(3,4-dimethyl-phenyl)-ethyl]-1-iodo-3-methyl-5,6-dihydro-8H-imidazo[1,5-a]pyrazine-7-carboxylic acid tert-butyl ester (1.061 g; 2.142 mmol) and purification by FC (DCM/MeOH=40/1) gave the product 1-chloro-8-[2-(3,4-dimethyl-phenyl)-ethyl]-3-methyl-5,6-dihydro-8H-imidazo[1,5-a]pyrazine-7-carboxylic acid tert-butyl ester as an orange oil (157 mg; 0.388 mmol). LC-MS: $t_R$=1.01 min.; [M+H]$^+$=404.50 g/mol.

1-chloro-3-methoxymethyl-8-[2-(4-trifluoromethyl-phenyl)-ethyl]-5,6-dihydro-8H-imidazo[1,5-a]pyrazine-7-carboxylic acid tert-butyl ester According to the general procedure (GP12), chlorination of 1-iodo-3-methoxymethyl-8-[2-(4-trifluoromethyl-phenyl)-ethyl]-5,6-dihydro-8H-imidazo[1,5-a]pyrazine-7-carboxylic acid tert-butyl ester (720 mg; 1.274 mmol) and purification by FC (DCM/MeOH=60/1) gave the expected product 1-chloro-3-methoxymethyl-8-[2-(4-trifluoromethyl-phenyl)-ethyl]-5,6-dihydro-8H-imidazo[1,5-a]pyrazine-7-carboxylic acid tert-butyl ester as an orange oil (254 mg; 42%). LC-MS: $t_R$=1.09 min.; [M+H]$^+$=474.42 g/mol.

3-Methoxymethyl-8-[2-(4-trifluoromethyl-phenyl)-ethyl]-5,6-dihydro-8H-imidazo[1,5-a]pyrazine-7-carboxylic acid tert-butyl ester (177 mg) was also isolated after FC in order to be converted into the target product (chlorination with N-chlorosuccinimide).

1-chloro-3-ethyl-8-(4-fluoro-3-trifluoromethyl-phenoxymethyl)-5,6-dihydro-8H-imidazo[1,5-a]pyrazine-7-carboxylic acid tert-butyl ester According to the general procedure (GP12), chlorination of 3-ethyl-8-(4-fluoro-3-trifluoromethyl-phenoxymethyl)-1-iodo-5,6-dihydro-8H-imidazo[1,5-a]pyrazine-7-carboxylic acid tert-butyl ester (844 mg; 1.482 mmol), and purification by FC (DCM/MeOH=60/1) gave the expected product 1-chloro-3-ethyl-8-(4-fluoro-3-trifluoromethyl-phenoxymethyl)-5,6-dihydro-8H-imidazo[1,5-a]pyrazine-7-carboxylic acid tert-butyl ester as an orange solid (186 mg; 26%). LC-MS: $t_R$=1.04 min.; [M+H]$^+$=478.39 g/mol.

1-chloro-3-ethyl-8-(3-trifluoromethyl-phenoxymethyl)-5,6-dihydro-8H-imidazo[1,5-a]pyrazine-7-carboxylic acid tert-butyl ester According to the general procedure (GP12), chlorination of 3-ethyl-1-iodo-8-(3-trifluoromethyl-phenoxymethyl)-5,6-dihydro-8H-imidazo[1,5-a]pyrazine-7-carboxylic acid tert-butyl ester (1.272 g; 2.307 mmol), and purification by FC (DCM/MeOH=60/1) gave the expected product 1-chloro-3-ethyl-8-(3-trifluoromethyl-phenoxymethyl)-5,6-dihydro-8H-imidazo[1,5-a]pyrazine-7-carboxylic acid tert-butyl ester as a yellow oil (0.403 g; 38%). LC-MS: $t_R$=1.03 min.; [M+H]$^+$=460.37 g/mol.

1-chloro-8-[2-(2,5-difluoro-4-trifluoromethyl-phenyl)-ethyl]-3-ethyl-5,6-dihydro-8H-imidazo[1,5-a]pyrazine-7-carboxylic acid tert-butyl ester [second general procedure for chlorination of the imidazole ring (GP12B)]

A mixture of 8-[2-(2,5-difluoro-4-trifluoromethyl-phenyl)-ethyl]-3-ethyl-1-iodo-5,6-dihydro-8H-imidazo[1,5-a]pyrazine-7-carboxylic acid tert-butyl ester (1.890 g; 3.229 mmol), 10% palladium on activated charcoal (567 mg), and anhydrous potassium carbonate (1.115 g; 8.072 mmol; 2.5 eq.) in anhydrous MeOH (75 ml) was stirred at rt, under hydrogen (1 atm), for 3 h15. Filtration over a pad of celite, and subsequent concentration to dryness afforded a crude heterogeneous residue which was dissolved in DCM (100 ml), and water (50 ml). The organic layer was then dried over anh. MgSO$_4$, filtered, and concentrated to dryness under reduced pressure to give 8-[2-(2,5-difluoro-4-trifluoromethyl-phenyl)-ethyl]-3-ethyl-5,6-dihydro-8H-imidazo[1,5-a]pyrazine-7-carboxylic acid tert-butyl ester as a yellow oil (1.400 g; 94%). LC-MS: $t_R$=0.94 min.; [M+H]$^+$=460.04 g/mol.

To a yellow homogeneous solution of 8-[2-(2,5-difluoro-4-trifluoromethyl-phenyl)-ethyl]-3-ethyl-5,6-dihydro-8H-imidazo[1,5-a]pyrazine-7-carboxylic acid tert-butyl ester (1.400 g; 3.047 mmol) in anhydrous MeCN (50 ml) was added dropwise, at rt, a solution of N-chlorosuccinimide (0.407 g; 3.047 mmol; 1 eq.) in anhydrous MeCN (25 ml). The resulting solution was then heated to 70° C., under nitrogen, for 3 h30. Concentration to dryness afforded a yellow oily residue which was dissolved in EA (150 ml), and this organic layer was successively washed with aq. sat. NaHCO$_3$ (2×50 ml), and brine (50 ml), and was then dried over anh. MgSO$_4$, filtered, and concentrated to dryness under reduced pressure. Purification by FC (DCM/MeOH=50/1) gave the expected 1-chloro-8-[2-(2,5-difluoro-4-trifluoromethyl-phenyl)-ethyl]-3-ethyl-5,6-dihydro-8H-imidazo[1,5-a]pyrazine-7-carboxylic acid tert-butyl ester as a yellow solid (0.711 g; 47%). LC-MS: $t_R$=1.10 min.; [M+H]$^+$=493.93 g/mol.

1-chloro-3-ethyl-8-[2-(3,4,5-trifluoro-phenyl)-ethyl]-5,6-dihydro-8H-imidazo[1,5-a]pyrazine-7-carboxylic acid tert-butyl ester According to the previously described general procedure (GP12B), hydrogenation (rt; 1 h) of 3-ethyl-1-iodo-8-[2-(3,4,5-trifluoro-phenyl)-ethyl]-5,6-dihydro-8H-imidazo[1,5-a]pyrazine-7-carboxylic acid tert-butyl ester (2.010 g; 3.755 mmol) afforded 3-ethyl-8-[2-(3,4,5-trifluoro-phenyl)-ethyl]-5,6-dihydro-8H-imidazo[1,5-a]pyrazine-7-carboxylic acid tert-butyl ester as a pale yellow oil (1.530 g; 97%). LC-MS: $t_R$=0.95 min.; [M+H]$^+$=410.14 g/mol.

Subsequent chlorination (70° C.; 3h30) of 3-ethyl-8-[2-(3,4,5-trifluoro-phenyl)-ethyl]-5,6-dihydro-8H-imidazo[1,5-a]pyrazine-7-carboxylic acid tert-butyl ester (2.070 g; 5.056 mmol), and purification by FC (DCM/MeOH=25/1) afforded 1-chloro-3-ethyl-8-[2-(3,4,5-trifluoro-phenyl)-ethyl]-5,6-dihydro-8H-imidazo[1,5-a]pyrazine-7-carboxylic acid tert-butyl ester as a yellow oil (1.220 g; 54%). LC-MS: $t_R$=1.06 min.; [M+H]$^+$=444.00 g/mol.

1-chloro-8-[2-(3-fluoro-4-trifluoromethyl-phenyl)-ethyl]-3-methyl-5,6-dihydro-8H-imidazo[1,5-a]pyrazine-7-carboxylic acid tert-butyl ester According to the previously described general procedure (GP12B), hydrogenation (rt; 1h30) of 8-[2-(3-fluoro-4-trifluoromethyl-phenyl)-ethyl]-1-iodo-3-methyl-5,6-dihydro-8H-imidazo[1,5-a]pyrazine-7-carboxylic acid tert-butyl ester (10.910 g; 19.717 mmol) afforded 8-[2-(3-fluoro-4-trifluoromethyl-phenyl)-ethyl]-3-methyl-5,6-dihydro-8H-imidazo[1,5-a]pyrazine-7-carboxylic acid tert-butyl ester as a yellow solid (8.280 g; 98%). LC-MS: $t_R$=0.93 min.; [M+H]$^+$=428.07 g/mol.

Subsequent chlorination (70° C.; 4h30) of 8-[2-(3-fluoro-4-trifluoromethyl-phenyl)-ethyl]-3-methyl-5,6-dihydro-8H-imidazo[1,5-a]pyrazine-7-carboxylic acid tert-butyl ester (8.080 g; 18.903 mmol), and purification by FC (DCM/MeOH=50/1) afforded 1-chloro-8-[2-(3-fluoro-4-trifluoromethyl-phenyl)-ethyl]-3-methyl-5,6-dihydro-8H-imidazo[1,5-a]pyrazine-7-carboxylic acid tert-butyl ester as a yellow solid (4.730 g; 54%). LC-MS: $t_R$=1.08 min.; [M+H]$^+$=461.98 g/mol.

1-chloro-8-[2-(3,5-difluoro-4-methoxy-phenyl)-ethyl]-3-ethyl-5,6-dihydro-8H-imidazo[1,5-a]pyrazine-7-carboxylic acid tert-butyl ester According to the previously described general procedure (GP12B), hydrogenation (rt; 1 h) of 8-[2-(3,5-difluoro-4-methoxy-phenyl)-ethyl]-3-ethyl-1-iodo-5,6-dihydro-8H-imidazo[1,5-a]pyrazine-7-carboxylic acid tert-butyl ester (1.440 g; 2.631 mmol) afforded 8-[2-(3,5-difluoro-4-methoxy-phenyl)-ethyl]-3-ethyl-5,6-dihydro-8H-imidazo[1,5-a]pyrazine-7-carboxylic acid tert-butyl ester (1.050 g; 95%). LC-MS: $t_R$=0.91 min.; [M+H]$^+$=422.04 g/mol.

Subsequent chlorination (70° C.; 3h30) of 8-[2-(3,5-difluoro-4-methoxy-phenyl)-ethyl]-3-ethyl-5,6-dihydro-8H-imidazo[1,5-a]pyrazine-7-carboxylic acid tert-butyl ester (1.330 g; 3.156 mmol), and purification by FC (DCM/MeOH=25/1) afforded 1-chloro-8-[2-(3,5-difluoro-4-methoxy-phenyl)-ethyl]-3-ethyl-5,6-dihydro-8H-imidazo[1,5-a]pyrazine-7-carboxylic acid tert-butyl ester as a yellow oil (0.730 g; 51%). LC-MS: $t_R$=1.04 min.; [M+H]$^+$=456.05 g/mol.

1-chloro-3-ethyl-8-[2-(4-trifluoromethoxy-phenyl)-ethyl]-5,6-dihydro-8H-imidazo[1,5-a]pyrazine-7-carboxylic acid tert-butyl ester According to the previously described general procedure (GP12B), hydrogenation (rt; 4 h) of 3-ethyl-1-iodo-8-[2-(4-trifluoromethoxy-phenyl)-ethyl]-5,6-dihydro-8H-imidazo[1,5-a]pyrazine-7-carboxylic acid tert-butyl ester (1.680 g; 2.972 mmol) afforded 3-ethyl-8-[2-(4-trifluoromethoxy-phenyl)-ethyl]-5,6-dihydro-8H-imidazo[1,5-a]pyrazine-7-carboxylic acid tert-butyl ester (1.200 g; 92%). LC-MS: $t_R$=0.93 min.; [M+H]$^+$=440.03 g/mol.

Subsequent chlorination (70° C.; 4h30) of 3-ethyl-8-[2-(4-trifluoromethoxy-phenyl)-ethyl]-5,6-dihydro-8H-imidazo[1,5-a]pyrazine-7-carboxylic acid tert-butyl ester (1.200 g; 2.731 mmol), and purification by FC (DCM/MeOH=50/1) afforded 1-chloro-3-ethyl-8-[2-(4-trifluoromethoxy-phenyl)-ethyl]-5,6-dihydro-8H-imidazo[1,5-a]pyrazine-7-carboxylic acid tert-butyl ester as a yellow oil (0.810 g; 63%). LC-MS: $t_R$=1.08 min.; [M+H]$^+$=473.97 g/mol.

1-chloro-3-propyl-8-[2-(4-trifluoromethyl-phenyl)-ethyl]-5,6-dihydro-8H-imidazo[1,5-a]pyrazine-7-carboxylic acid tert-butyl ester According to the previously described general procedure (GP12B), hydrogenation (rt; 1 h) of 1-iodo-3-propyl-8-[2-(4-trifluoromethyl-phenyl)-ethyl]-5,6-dihydro-8H-imidazo[1,5-a]pyrazine-7-carboxylic acid tert-butyl ester (5.450 g; 9.673 mmol) afforded 3-propyl-8-[2-(4-trifluoromethyl-phenyl)-ethyl]-5,6-dihydro-8H-imidazo[1,5-a]pyrazine-7-carboxylic acid tert-butyl ester (2.940 g; 69%). LC-MS: $t_R$=0.96 min.; [M+H]$^+$=438.05 g/mol.

Subsequent chlorination (70° C.; 3h30) of 3-propyl-8-[2-(4-trifluoromethyl-phenyl)-ethyl]-5,6-dihydro-8H-imidazo[1,5-a]pyrazine-7-carboxylic acid tert-butyl ester (2.940 g; 6.720 mmol), and purification by FC (DCM/MeOH=25/1) afforded 1-chloro-3-propyl-8-[2-(4-trifluoromethyl-phenyl)-ethyl]-5,6-dihydro-8H-imidazo[1,5-a]pyrazine-7-carboxylic acid tert-butyl ester as a yellow oil (1.550 g; 49%). LC-MS: $t_R$=1.09 min.; [M+H]$^+$=472.00 g/mol.

1-chloro-8-[2-(3-fluoro-4-trifluoromethyl-phenyl)-ethyl]-3-propyl-5,6-dihydro-8H-imidazo[1,5-a]pyrazine-7-carboxylic acid tert-butyl ester According to the previously described general procedure (GP12B), hydrogenation (rt; 1 h) of 8-[2-(3-fluoro-4-trifluoromethyl-phenyl)-ethyl]-1-iodo-3-propyl-5,6-dihydro-8H-imidazo[1,5-a]pyrazine-7-carboxylic acid tert-butyl ester (3.500 g; 6.020 mmol) afforded 8-[2-(3-fluoro-4-trifluoromethyl-phenyl)-ethyl]-3-propyl-5,6-dihydro-8H-imidazo[1,5-a]pyrazine-7-carboxylic acid tert-butyl ester (2.310 g; 84%). LC-MS: $t_R$=0.97 min.; [M+H]$^+$=456.02 g/mol.

Subsequent chlorination (70° C.; 3h30) of 8-[2-(3-fluoro-4-trifluoromethyl-phenyl)-ethyl]-3-propyl-5,6-dihydro-8H-imidazo[1,5-a]pyrazine-7-carboxylic acid tert-butyl ester (2.310 g; 5.071 mmol), and purification by FC (DCM/MeOH=50/1) afforded 1-chloro-8-[2-(3-fluoro-4-trifluoromethyl-phenyl)-ethyl]-3-propyl-5,6-dihydro-8H-imidazo[1,5-a]pyrazine-7-carboxylic acid tert-butyl ester as a yellow oil (1.130 g; 45%). LC-MS: $t_R$=1.10 min.; [M+H]$^+$=489.94 g/mol.

1-chloro-3-ethyl-8-[2-(2,3,5-trifluoro-phenyl)-ethyl]-5,6-dihydro-8H-imidazo[1,5-a]pyrazine-7-carboxylic acid tert-butyl ester According to the previously described general procedure (GP12B), hydrogenation (rt; 1 h) of 3-ethyl-1-iodo-8-[2-(2,3,5-trifluoro-phenyl)-ethyl]-5,6-dihydro-8H-imidazo[1,5-a]pyrazine-7-carboxylic acid tert-butyl ester (0.917 g; 1.713 mmol) afforded 3-ethyl-8-[2-(2,3,5-trifluoro-phenyl)-ethyl]-5,6-dihydro-8H-imidazo[1,5-a]pyrazine-7-carboxylic acid tert-butyl ester (0.570 g; 81%). LC-MS: $t_R$=0.88 min.; [M+H]$^+$=410.40 g/mol.

Subsequent chlorination (70° C.; 3h30) of 3-ethyl-8-[2-(2,3,5-trifluoro-phenyl)-ethyl]-5,6-dihydro-8H-imidazo[1,5-a]pyrazine-7-carboxylic acid tert-butyl ester (0.570 g; 1.392 mmol), and purification by FC (heptane/EA=2/3) afforded 1-chloro-3-ethyl-8-[2-(2,3,5-trifluoro-phenyl)-ethyl]-5,6-dihydro-8H-imidazo[1,5-a]pyrazine-7-carboxylic acid tert-butyl ester as a pale yellow solid (0.373 g; 60%). LC-MS: $t_R$=1.01 min.; [M+H]$^+$=444.35 g/mol.

1-chloro-3-ethyl-8-[2-(3-fluoro-4-methoxy-phenyl)-ethyl]-5,6-dihydro-8H-imidazo[1,5-a]pyrazine-7-carboxylic acid tert-butyl ester According to the previously described general procedure (GP12B), hydrogenation (rt; 1 h) of 3-ethyl-8-[2-(3-fluoro-4-methoxy-phenyl)-ethyl]-1-iodo-5,6-dihydro-8H-imidazo[1,5-a]pyrazine-7-carboxylic acid tert-butyl ester (3.870 g; 7.310 mmol) afforded 3-ethyl-8-[2-(3-fluoro-4-methoxy-phenyl)-ethyl]-5,6-dihydro-8H-imidazo[1,5-a]pyrazine-7-carboxylic acid tert-butyl ester (2.920 g; 99%). LC-MS: $t_R$=0.89 min.; [M+H]$^+$=404.01 g/mol.

Subsequent chlorination (70° C.; 4h30) of 3-ethyl-8-[2-(3-fluoro-4-methoxy-phenyl)-ethyl]-5,6-dihydro-8H-imidazo[1,5-a]pyrazine-7-carboxylic acid tert-butyl ester (2.920 g; 7.237 mmol), and purification by FC (heptane/EA=2/3) afforded 1-chloro-3-ethyl-8-[2-(3-fluoro-4-methoxy-phenyl)-ethyl]-5,6-dihydro-8H-imidazo[1,5-a]pyrazine-7-carboxylic acid tert-butyl ester as a yellow solid (1.790 g; 56%). LC-MS: $t_R$=1.02 min.; [M+H]$^+$=438.01 g/mol.

1-chloro-8-[2-(2,5-difluoro-4-methoxy-phenyl)-ethyl]-3-ethyl-5,6-dihydro-8H-imidazo[1,5-a]pyrazine-7-carboxylic acid tert-butyl ester According to the previously described general procedure (GP12B), hydrogenation (rt; 1 h) of 8-[2-(2,5-difluoro-4-methoxy-phenyl)-ethyl]-3-ethyl-1-iodo-5,6-dihydro-8H-imidazo[1,5-a]pyrazine-7-carboxylic acid tert-butyl ester (2.470 g; 4.512 mmol) afforded 8-[2-(2,5-difluoro-4-methoxy-phenyl)-ethyl]-3-ethyl-5,6-dihydro-8H-imidazo[1,5-a]pyrazine-7-carboxylic acid tert-butyl ester (1.830 g; 96%). LC-MS: $t_R$=0.90 min.; [M+H]$^+$=422.05 g/mol.

Subsequent chlorination (70° C.; 3h45) of 8-[2-(2,5-difluoro-4-methoxy-phenyl)-ethyl]-3-ethyl-5,6-dihydro-8H-imidazo[1,5-a]pyrazine-7-carboxylic acid tert-butyl ester (2.640 g; 6.264 mmol), and purification by FC (heptane/EA=1/1) afforded 1-chloro-8-[2-(2,5-difluoro-4-methoxy-phenyl)-ethyl]-3-ethyl-5,6-dihydro-8H-imidazo[1,5-a]pyrazine-7-carboxylic acid tert-butyl ester as a yellow solid (1.601 g; 56%). LC-MS: $t_R$=1.04 min.; [M+H]$^+$=456.00 g/mol.

1-chloro-3-ethyl-8-(4-trifluoromethyl-phenoxymethyl)-5,6-dihydro-8H-imidazo[1,5-a]pyrazine-7-carboxylic acid tert-butyl ester According to the previously described general procedure (GP12B), hydrogenation (rt; 14 h) of 3-ethyl-1-iodo-8-(4-trifluoromethyl-phenoxymethyl)-5,6-dihydro-8H-imidazo[1,5-a]pyrazine-7-carboxylic acid tert-butyl ester (0.890 g; 1.614 mmol) afforded 3-ethyl-8-(4-trifluoromethyl-phenoxymethyl)-5,6-dihydro-8H-imidazo[1,5-a]pyrazine-7-carboxylic acid tert-butyl ester (0.664 g; 97%). LC-MS: $t_R$=0.88 min.; [M+H]$^+$=426.24 g/mol.

Subsequent chlorination (70° C.; 3 h) of 3-ethyl-8-(4-trifluoromethyl-phenoxymethyl)-5,6-dihydro-8H-imidazo[1,5-a]pyrazine-7-carboxylic acid tert-butyl ester (0.664 g; 1.561 mmol), and purification by FC (DCM/MeOH=80/1) afforded 1-chloro-3-ethyl-8-(4-trifluoromethyl-phenoxymethyl)-5,6- dihydro-8H-imidazo[1,5-a]pyrazine-7-carboxylic acid tert-butyl ester as a yellow solid (0.381 g; 53%). LC-MS: $t_R$=1.04 min.; [M+H]⁺=460.23 g/mol.

1-chloro-8-(3,4-dimethyl-phenoxymethyl)-3-ethyl-5,6-dihydro-8H-imidazo[1,5-a]pyrazine-7-carboxylic acid tert-butyl ester According to the previously described general procedure (GP12B), hydrogenation (rt; 4 h) of 8-(3,4-dimethyl-phenoxymethyl)-3-ethyl-1-iodo-5,6-dihydro-8H-imidazo[1,5-a]pyrazine-7-carboxylic acid tert-butyl ester (0.919 g; 1.797 mmol) afforded 8-(3,4-dimethyl-phenoxymethyl)-3-ethyl-5,6-dihydro-8H-imidazo[1,5-a]pyrazine-7-carboxylic acid tert-butyl ester (0.600 g; 87%). LC-MS: $t_R$=0.88 min.; [M+H]⁺=386.43 g/mol.

Subsequent chlorination (70° C.; 5 h) of 8-(3,4-dimethyl-phenoxymethyl)-3-ethyl-5,6-dihydro-8H-imidazo[1,5-a]pyrazine-7-carboxylic acid tert-butyl ester (0.600 g; 1.556 mmol), and purification by FC (heptane/EA=2/3) afforded 1-chloro-8-(3,4-dimethyl-phenoxymethyl)-3-ethyl-5,6-dihydro-8H-imidazo[1,5-a]pyrazine-7-carboxylic acid tert-butyl ester as a pale yellow solid (0.328 g; 50%). LC-MS: $t_R$=1.02 min.; [M+H]⁺=420.38 g/mol.

1-chloro-8-[2-(4-chloro-3,5-difluoro-phenyl)-ethyl]-3-ethyl-5,6-dihydro-8H-imidazo[1,5-a]pyrazine-7-carboxylic acid tert-butyl ester [third general procedure for chlorination of the imidazole ring (GP12C)]

A cooled (−30° C.) solution of 8-[2-(4-chloro-3,5-difluoro-phenyl)-ethyl]-3-ethyl-1-iodo-5,6-dihydro-8H-imidazo[1,5-a]pyrazine-7-carboxylic acid tert-butyl ester (1.790 g; 3.244 mmol) in anhydrous THF (90 ml) was treated dropwise with a solution of 1-Methylmagnesium bromide in THF (14.6 ml; 14.6 mmol; 4.5 eq.) until complete removal of the iodine substituent. The mixture was then quenched with water (10 ml), diluted with ether (100 ml), and was allowed to warm-up to rt. This solution was washed with brine (2×150 ml), dried over anh. MgSO₄, filtered, and concentrated to dryness under reduced pressure. The crude was purified by FC (DCM/MeOH=15/1) to give the pure product 8-[2-(4-chloro-3,5-difluoro-phenyl)-ethyl]-3-ethyl-5,6-dihydro-8H-imidazo[1,5-a]pyrazine-7-carboxylic acid tert-butyl ester as a yellow solid (1.150 g; 83%). LC-MS: $t_R$=0.95 min.; [M+H]⁺=426.01 g/mol.

To a yellow homogeneous solution of 8-[2-(4-chloro-3,5-difluoro-phenyl)-ethyl]-3-ethyl-5,6-dihydro-8H-imidazo[1,5-a]pyrazine-7-carboxylic acid tert-butyl ester (1.150 g; 2.700 mmol) in anhydrous MeCN (40 ml) was added dropwise, at rt, a solution of N-chlorosuccinimide (0.367 g; 2.700 mmol; 1 eq.) in anhydrous MeCN (10 ml). The resulting solution was then heated to 70° C., under nitrogen, for 3 h30. Concentration to dryness afforded a yellow oily residue which was dissolved in EA (80 ml), and this organic layer was washed with aq. sat. NaHCO₃ (2×120 ml), was then dried over anh. MgSO₄, filtered, and concentrated to dryness under reduced pressure. Purification by FC (heptane/EA=2/3) gave the expected 1-chloro-8-[2-(4-chloro-3,5-difluoro-phenyl)-ethyl]-3-ethyl-5,6-dihydro-8H-imidazo[1,5-a]pyrazine-7-carboxylic acid tert-butyl ester as a yellow solid (0.724 g; 58%). LC-MS: $t_R$=1.08 min.; [M+H]⁺=461.94 g/mol.

1-chloro-8-[2-(3-chloro-4-trifluoromethyl-phenyl)-ethyl]-3-ethyl-5,6-dihydro-8H-imidazo[1,5-a]pyrazine-7-carboxylic acid tert-butyl ester According to the previously described general procedure (GP12C), treatment of 8-[2-(3-chloro-4-trifluoromethyl-phenyl)-ethyl]-3-ethyl-1-iodo-5,6-dihydro-8H-imidazo[1,5-a]pyrazine-7-carboxylic acid tert-butyl ester (2.070 g; 3.546 mmol) with 1M ethylmagnesium bromide in THF (15.6 ml; 15.6 mmol; 4.4 eq.) afforded 8-[2-(3-chloro-4-trifluoromethyl-phenyl)-ethyl]-3-ethyl-5,6-dihydro-8H-imidazo[1,5-a]pyrazine-7-carboxylic acid tert-butyl ester (1.170 g; 72%) as a pale yellow oil. LC-MS: $t_R$=0.95 min.; [M+H]⁺=457.98 g/mol.

Subsequent chlorination (70° C.; 3h30) of 8-[2-(3-chloro-4-trifluoromethyl-phenyl)-ethyl]-3-ethyl-5,6-dihydro-8H-imidazo[1,5-a]pyrazine-7-carboxylic acid tert-butyl ester (1.170 g; 2.555 mmol), and purification by FC (heptane/EA=1/1) afforded 1-chloro-8-[2-(3-chloro-4-trifluoromethyl-phenyl)-ethyl]-3-ethyl-5,6-dihydro-8H-imidazo[1,5-a]pyrazine-7-carboxylic acid tert-butyl ester as a yellow oil (0.684 g; 54%). LC-MS: $t_R$=1.10 min.; [M+H]⁺=491.95 g/mol.

1-chloro-8-[2-(4-cyano-phenyl)-ethyl]-3-ethyl-5,6-dihydro-8H-imidazo[1,5-a]pyrazine-7-carboxylic acid tert-butyl ester A cooled (−30° C.) solution of 8-[2-(4-bromo-phenyl)-ethyl]-3-ethyl-1-iodo-5,6-dihydro-8H-imidazo[1,5-a]pyrazine-7-carboxylic acid tert-butyl ester (2.200 g; 3.927 mmol) in anhydrous THF (90 ml) was treated dropwise with a solution of 1-Methylmagnesium bromide in THF (10.25 ml; 10.25 mmol; 2.6 eq.) until complete removal of the iodine substituent. The mixture was then quenched with water (5 ml), diluted with ether (100 ml), and was allowed to warm-up to rt. This solution was washed with brine (2×150 ml), dried over anh. MgSO₄, filtered, and concentrated to dryness under reduced pressure. The crude was purified by FC (DCM/MeOH=15/1) to give the pure product 8-[2-(4-bromo-phenyl)-ethyl]-3-ethyl-5,6-dihydro-8H-imidazo[1,5-a]pyrazine-7-carboxylic acid tert-butyl ester as a yellow oil (1.570 g; 92%). LC-MS: $t_R$=0.93 min.; [M+H]⁺=435.98 g/mol.

To a mixture of potassium cyanide (0.482 g; 4.075 mmol), calcium hydroxide (0.207 g; 2.717 mmol), palladium diacetate (91 mg; 0.407 mmol), and triphenylphosphine (0.213 g; 0.815 mmol) was added a solution of 8-[2-(4-bromo-phenyl)-ethyl]-3-ethyl-5,6-dihydro-8H-imidazo[1,5-a]pyrazine-7-carboxylic acid tert-butyl ester (1.180 g; 2.717 mmol) in anhydrous DMF (12 ml). The resulting pale yellow suspension was stirred at 120° C., under nitrogen, for 1 h45. Ether (100 ml) was then added, and this solution was successively washed with aq. sat. NaHCO₃ (100 ml), and with brine (100 ml). The organic layer was dried over anh. MgSO₄, filtered, and concentrated to dryness under reduced pressure.

Purification by FC (DCM/MeOH, 25/1) afforded the pure target compound 8-[2-(4-cyano-phenyl)-ethyl]-3-ethyl-5,6-dihydro-8H-imidazo[1,5-a]pyrazine-7-carboxylic acid tert-butyl ester as a yellow solid (0.700 g; 68%). LC-MS: $t_R$=0.87 min.; [M+H]⁺=381.07 g/mol.

To a solution of 8-[2-(4-cyano-phenyl)-ethyl]-3-ethyl-5,6-dihydro-8H-imidazo[1,5-a]pyrazine-7-carboxylic acid tert-butyl ester (0.700 g; 1.840 mmol) in anhydrous MeCN (20 ml) was added dropwise, at rt, a solution of N-chlorosuccinimide (0.250 g; 1.840 mmol; 1 eq.) in anhydrous MeCN (5 ml). The resulting solution was then heated to 70° C., under nitrogen, for 4 h. Concentration to dryness afforded an oily residue which was dissolved in EA (80 ml), and this organic layer was washed with aq. sat. NaHCO₃ (2×100 ml), was then dried over anh. MgSO₄, filtered, and finally concentrated to dryness under reduced pressure. Purification by FC (heptane/EA=2/3) gave the expected 1-chloro-8-[2-(4-cyano-phenyl)-ethyl]-3-ethyl-5,6-dihydro-8H-imidazo[1,5-a]pyrazine-7- carboxylic acid tert-butyl ester as a yellow solid (0.417 g; 55%). LC-MS: $t_R$=1.00 min.; [M+H]$^+$=414.94 g/mol.

3-isopropyl-8-[2-(4-trifluoromethyl-phenyl)-ethyl]-5,6-dihydro-8H-imidazo[1,5-a]pyrazine-7-carboxylic acid tert-butyl ester A cooled (−78° C.) solution of 1-iodo-3-isopropyl-8-[2-(4-trifluoromethyl-phenyl)-ethyl]-5,6-dihydro-8H-imidazo[1,5-a]pyrazine-7-carboxylic acid tert-butyl ester (379 mg; 0.673 mmol) in anhydrous THF (6 ml) was treated dropwise with a 1.6N butyllithium solution in hexanes (1.05 ml; 1.680 mmol). The resulting mixture was additionally stirred at −78° C., under nitrogen, for 15 min. Water (0.2 ml) was then added and the reaction mixture was allowed to warm-up to rt. The resulting solution was diluted with ether (30 ml), the organic layer was dried over anh. MgSO$_4$, filtered, and concentrated to dryness under reduced pressure. Purification by FC (DCM/MeOH=25/1) gave the pure product 3-isopropyl-8-[2-(4-trifluoromethyl-phenyl)-ethyl]-5,6-dihydro-8H-imidazo[1,5-a]pyrazine-7-carboxylic acid tert-butyl ester as a yellow solid (229 mg; 78%). LC-MS: $t_R$=0.92 min.; [M+H]$^+$=438.43 g/mol.

1-chloro-3-isopropyl-8-[2-(4-trifluoromethyl-phenyl)-ethyl]-5,6-dihydro-8H-imidazo[1,5-a]pyrazine-7-carboxylic acid tert-butyl ester To a solution of N-chlorosuccinimide (87.3 mg; 0.628 mmol) in chloroform (1 ml) was added a solution of 3-isopropyl-8-[2-(4-trifluoromethyl-phenyl)-ethyl]-5,6-dihydro-8H-imidazo[1,5-a]pyrazine-7-carboxylic acid tert-butyl ester (229 mg; 0.523 mmol) in chloroform (2 ml) and the resulting solution was heated to 70° C. for 5 h30. The reaction mixture was allowed to cool to rt, diluted with DCM (20 ml) and washed with water (3×10 ml). The organic layer was dried over anh. MgSO$_4$, filtered, and concentrated to dryness under reduced pressure. Purification by preparative HPLC gave the pure product 1-chloro-3-isopropyl-8-[2-(4-trifluoromethyl-phenyl)-ethyl]-5,6-dihydro-8H-imidazo[1,5-a]pyrazine-7-carboxylic acid tert-butyl ester as a yellow solid (97 mg; 39%). LC-MS: $t_R$=1.04 min.; [M+H]$^+$=472.51 g/mol.

3-chloro-1-iodo-8-[2-(4-trifluoromethyl-phenyl)-ethyl]-5,6-dihydro-8H-imidazo[1,5-a]pyrazine-7-carboxylic acid tert-butyl ester To a solution of 1-iodo-8-[2-(4-trifluoromethyl-phenyl)-ethyl]-5,6-dihydro-8H-imidazo[1,5-a]pyrazine-7-carboxylic acid tert-butyl ester (1.000 g; 1.918 mmol) in chloroform (30 ml) was added N-chlorosuccinimide (307 mg; 2.298 mmol; 1.2 eq.), and the resulting mixture was heated to reflux (70° C.) for 2 h30. Additional N-chlorosuccinimide (120 mg; 0.898 mmol; 0.46 eq.) was then added and the resulting mixture was additionally refluxed for 2 h30. The reaction mixture was allowed to cool to rt, diluted with DCM (50 ml), and washed with brine (80 ml). The organic layer was dried over magnesium sulfate, filtered, and concentrated to dryness under reduced pressure. Purification by FC (heptane/EA=1/1) afforded the expected product 3-chloro-1-iodo-8-[2-(4-trifluoromethyl-phenyl)-ethyl]-5,6-dihydro-8H-imidazo[1,5-a]pyrazine-7-carboxylic acid tert-butyl ester as a yellow solid (475 mg; 45%). LC-MS: $t_R$=1.13 min.; [M+H]$^+$=556.24 g/mol.

1,3-dichloro-8-[2-(4-trifluoromethyl-phenyl)-ethyl]-5,6-dihydro-8H-imidazo[1,5-a]pyrazine-7-carboxylic acid tert-butyl ester According to the general procedure (GP12), chlorination of 3-chloro-1-iodo-8-[2-(4-trifluoromethyl-phenyl)-ethyl]-5,6-dihydro-8H-imidazo[1,5-a]pyrazine-7-carboxylic acid tert-butyl ester (522 mg; 0.939 mmol) and purification by FC (heptane/EA=1/1) gave the expected product 1,3-dichloro-8-[2-(4-trifluoromethyl-phenyl)-ethyl]-5,6-dihydro-8H-imidazo[1,5-a]pyrazine-7-carboxylic acid tert-butyl ester as a yellow oil (185.7 mg; 43%). LC-MS: $t_R$=1.13 min.; [M+H]$^+$=464.22 g/mol.

D.2 Alkoxylation

8-[2-(3,4-dimethyl-phenyl)-ethyl]-3-ethyl-1-methoxy-5,6-dihydro-8H-imidazo[1,5-a]pyrazine-7-carboxylic acid tert-butyl ester A solution of 8-[2-(3,4-dimethyl-phenyl)-ethyl]-3-ethyl-1-iodo-5,6-dihydro-8H-imidazo[1,5-a]pyrazine-7-carboxylic acid tert-butyl ester (1.500 g; 2.944 mmol) in anhydrous MeOH (30 ml) was treated successively with copper(I) iodide (56 mg; 0.294 mmol), 1,10-phenanthroline (116.7 mg; 0.589 mmol), and cesium carbonate (1.535 g; 4.711 mmol). The resulting brown suspension was sealed and put in the microwave oven (150 W; 150° C.; 13 bars; 1h30). The resulting brown suspension was concentrated to dryness under reduced pressure and the crude was purified by FC (EA/heptane: 2/3 to 3/2]. The expected product 8-[2-(3,4-dimethyl-phenyl)-ethyl]-3-ethyl-1-methoxy-5,6-dihydro-8H-imidazo[1,5-a]pyrazine-7-carboxylic acid tert-butyl ester was obtained as a yellow oil (260.6 mg; 21%). LC-MS: $t_R$=0.91 min.; [M+H]$^+$=414.35 g/mol.

3-isopropyl-1-methoxy-8-[2-(4-trifluoromethyl-phenyl)-ethyl]-5,6-dihydro-8H-imidazo[1,5-a]pyrazine-7-carboxylic acid tert-butyl ester A solution of 1-iodo-3-isopropyl-8-[2-(4-trifluoromethyl-phenyl)-ethyl]-5,6-dihydro-8H-imidazo[1,5-a]pyrazine-7-carboxylic acid tert-butyl ester (150 mg; 0.266 mmol) in anhydrous MeOH (3 ml) was treated successively with copper(I) iodide (5 mg; 0.026 mmol), 1,10-phenanthroline (10.5 mg; 0.053 mmol), and cesium carbonate (138.8 mg; 0.426 mmol). The resulting brown suspension was sealed and put in the microwave oven (35 W; 100° C.; 6 bars; 1 h). This microwave-assisted methoxylation was repeated two additional times with the same amount of starting material. The resulting mixed brown suspension was concentrated to dryness under reduced pressure and the crude was purified by preparative HPLC. The expected product 3-isopropyl-1-methoxy-8-[2-(4-trifluoromethyl-phenyl)-ethyl]-5,6-dihydro-8H-imidazo[1,5-a]pyrazine-7-carboxylic acid tert-butyl ester was obtained as a yellow oil (107.5 mg; 29%). LC-MS: $t_R$=0.94 min.; [M+H]$^+$=468.55 g/mol.

D.3 Derivatization Via Stille Cross-Coupling Reactions

3-ethyl-8-[2-(4-trifluoromethyl-phenyl)-ethyl]-1-vinyl-5,6-dihydro-8H-imidazo[1,5-a]pyrazine-7-carboxylic acid tert-butyl ester A slightly yellow homogeneous solution of 3-ethyl-1-iodo-8-[2-(4-trifluoromethyl-phenyl)-ethyl]-5,6-dihydro-8H-imidazo[1,5-a]pyrazine-7-carboxylic acid tert-butyl ester (619.7 mg; 1.128 mmol) in anhydrous DMF (6 ml) was treated successively at rt with tris(dibenzylideneacetone)dipalladium(0) (33 mg; 0.036 mmol), triphenylphosphine (37 mg; 0.141 mmol), and finally with tributyl(vinyl)tin (0.66 ml; 2.256 mmol). The resulting mixture was heated to 90° C., under nitrogen, for 20 h. The reaction mixture was cooled to rt, EA (75 ml) was added, and the resulting solution was washed with water (2×50 ml). The resulting yellow organic layer was dried over anh. MgSO$_4$, filtered, and concentrated to dryness under reduced pressure to give an orange oil (1.230 g). Purification by FC (DCM/MeOH=40/1) gave the pure product 3-ethyl-8-[2-(4-trifluoromethyl-phenyl)-ethyl]-1-vinyl-5,6-dihydro-8H-imidazo[1,5-a]pyrazine-7-carboxylic acid tert-butyl ester as a yellow oil (384 mg; 76%). LC-MS: $t_R$=0.93 min.; [M+H]$^+$=450.22 g/mol.

3-methyl-8-[2-(4-trifluoromethyl-phenyl)-ethyl]-1-vinyl-5,6-dihydro-8H-imidazo[1,5-a]pyrazine-7-carboxylic acid tert-butyl ester A slightly yellow homogeneous solution of 1-iodo-3-methyl-8-[2-(4-trifluoromethyl-phenyl)-ethyl]-5,6-dihydro-8H-imidazo[1,5-a]pyrazine-7-carboxylic acid tert-butyl ester (1.500 g; 2.802 mmol) in anhydrous DMF (15 ml) was treated successively at rt with tris(dibenzylideneacetone)dipalladium(0) (82 mg; 0.090 mmol), triphenylphosphine (91 mg; 0.350 mmol), and finally with tributyl(vinyl)tin (1.63 ml; 5.604 mmol). The resulting mixture was heated to 90° C., under nitrogen, for 20 h. The reaction mixture was cooled to rt, EA (200 ml) was added, and the resulting solution was washed with water (2×125 ml). The resulting yellow organic layer was dried over anh. MgSO$_4$, filtered, and concentrated to dryness under reduced pressure to give an orange oil. Purification by FC (DCM/MeOH=40/1) gave the pure product 3-methyl-8-[2-(4-trifluoromethyl-phenyl)-ethyl]-1-vinyl-5,6-dihydro-8H-imidazo[1,5-a]pyrazine-7-carboxylic acid tert-butyl ester as a yellow solid (0.936 g; 77%). LC-MS: $t_R$=0.88 min.; [M+H]$^+$=436.48 g/mol.

D.4 Trifluoromethylation 3-ethyl-1-trifluoromethyl-8-[2-(4-trifluoromethyl-phenyl)-ethyl]-5,6-dihydro-8H-imidazo[1,5-a]pyrazine-7-carboxylic acid tert-butyl ester A slightly yellow homogeneous solution of 3-ethyl-1-iodo-8-[2-(4-trifluoromethyl-phenyl)-ethyl]-5,6-dihydro-8H-imidazo[1,5-a]pyrazine-7-carboxylic acid tert-butyl ester (500 mg; 0.910 mmol) in anhydrous DMF (25 ml) was treated successively at rt with copper(I) iodide (866.6 mg; 4.551 mmol), hexamethylphosphoramide (1.58 ml; 9.101 mmol), and finally with methyl 2,2-difluoro-2-(fluorosulfonyl)acetate (0.75 ml; 5.916 mmol). The resulting beige heterogeneous mixture was heated to 80° C., under nitrogen, for 6 h30. The reaction mixture was cooled to rt, water (100 ml), and ether (150 ml) were then added. The organic layer was additionally washed with water (3×75 ml), dried over anh. MgSO$_4$, filtered, and concentrated to dryness under reduced pressure to give a yellow oil (438 mg). Purification by FC (DCM/MeOH=40/1) gave the pure product 3-ethyl-1-trifluoromethyl-8-[2-(4-trifluoromethyl-phenyl)-ethyl]-5,6-dihydro-8H-imidazo[1,5-a]pyrazine-7-carboxylic acid tert-butyl ester as a yellow oil (253.6 mg; 57%). LC-MS: $t_R$=1.09 min.; [M+H]$^+$=492.46 g/mol.

D.5 Formylation 3-ethyl-1-formyl-8-[2-(4-trifluoromethyl-phenyl)-ethyl]-5,6-dihydro-8H-imidazo[1,5-a]pyrazine-7-carboxylic acid tert-butyl ester A cooled (−30° C.) solution of 3-ethyl-1-iodo-8-[2-(4-trifluoromethyl-phenyl)-ethyl]-5,6-dihydro-8H-imidazo[1,5-a]pyrazine-7-carboxylic acid tert-butyl ester (1.000 g; 1.820 mmol) in anhydrous THF (10 ml) was treated dropwise with 1-Methylmagnesium bromide in THF (4.0 ml; 4.0 mmol), and the resulting suspension was then allowed to warm-up to rt in 10 min. After cooling to −35° C., a mixture of anhydrous DMF (2.0 ml; 25.831 mmol) and anhydrous THF (2 ml) was added dropwise, and the resulting mixture was then allowed to warm-up to rt (in 30 min.), and was further stirred at rt for 16 h. Water (2 ml) and EA were then successively added, and this mixture was washed with aq. sat. NH$_4$Cl. The organic extract was dried over anh. MgSO$_4$, filtered, and concentrated to dryness under reduced pressure (yellow oil; 950 mg). Purification by FC (EA/heptane=1/9 to 1/1) gave the pure product 3-ethyl-1-formyl-8-[2-(4-trifluoromethyl-phenyl)-ethyl]-5,6-dihydro-8H-imidazo[1,5-a]pyrazine-7-carboxylic acid tert-butyl ester as a colorless oil (640 mg; 78%). LC-MS: $t_R$=1.01 min.; [M+H]$^+$=452.12 g/mol.

D.6 Introduction of Cyano Substituent 1-cyano-3-ethyl-8-[2-(4-trifluoromethyl-phenyl)-ethyl]-5,6-dihydro-8H-imidazo[1,5-a]pyrazine-7-carboxylic acid tert-butyl ester To a solution of 3-ethyl-1-formyl-8-[2-(4-trifluoromethyl-phenyl)-ethyl]-5,6-dihydro-8H-imidazo[1,5-a]pyrazine-7-carboxylic acid tert-butyl ester (6.000 g; 13.289 mmol) in pyridine (100 ml) was added hydroxylamine hydrochloride (1.015 g; 14.618 mmol). The resulting mixture was first stirred at rt (4 h), and was then heated to 60° C. for 1 h before acetic anhydride (1.9 ml; 20.099 mmol; 1.5 eq.) was added at this temperature. After further heating at 60° C. (30 min.), the reaction mixture was then heated at 80° C. for 16 h. A second addition of acetic anhydride (0.3 ml; 3.173 mmol) was performed at 60° C., and the resulting mixture was additionally stirred at 80° C. for 10 h. The resulting yellow solution was then allowed to cool to rt before water was added. Extractions with DCM, washing with aq. 2N HCl, drying of the organic layer over magnesium sulfate, filtration, and concentration to dryness under reduced pressure afforded the crude product (yellow oil; 7.50 g). Purification by FC (EA/heptane=4/1) gave the expected pure product 1-cyano-3-ethyl-8-[2-(4-trifluoromethyl-phenyl)-ethyl]-5,6-dihydro-8H-imidazo[1,5-a]pyrazine-7-carboxylic acid tert-butyl ester as a yellow oil (5.000 g; 84%). LC-MS: $t_R$=1.09 min.; [M+H]$^+$=449.40 g/mol.

1-cyano-3-ethyl-8-[2-(3-fluoro-4-trifluoromethyl-phenyl)-ethyl]-5,6-dihydro-8H-imidazo[1,5-a]pyrazine-7-carboxylic acid tert-butyl ester A cooled (−78° C.) solution of 3-ethyl-8-[2-(3-fluoro-4-trifluoromethyl-phenyl)-ethyl]-1-iodo-5,6-dihydro-8H-imidazo[1,5-a]pyrazine-7-carboxylic acid tert-butyl ester (1.040 g; 1.833 mmol) in anhydrous THF (50 ml) was treated dropwise with 1.6M n-BuLi in hexanes (1.6 ml; 2.560 mmol). The resulting reaction mixture was further stirred at −78° C., under nitrogen, for 3 min., and a solution of para-toluenesulfonyl cyanide (0.576 g; 3.025 mmol) in anhydrous THF (5 ml) was then added dropwise. Stirring at −78° C. was continued for 20 min. before aq. sat. NH$_4$Cl (2 ml) was added. The resulting mixture was allowed to warm-up to rt, and water (50 ml), followed by ether (50 ml) were added. The organic layer was dried over anh. MgSO$_4$, filtered, and concentrated to dryness under reduced pressure. Purification by FC (DCM/MeOH, 25/1) afforded 1-cyano-3-ethyl-8-[2-(3-fluoro-4-trifluoromethyl-phenyl)-ethyl]-5,6-dihydro-8H-imidazo[1,5- a]pyrazine-7-carboxylic acid tert-butyl ester as a pale yellow solid (0.233 g; 27%). LC-MS: $t_R$=1.12 min.; [M+H]$^+$=467.23 g/mol.

1-cyano-8-[2-(3-fluoro-4-trifluoromethyl-phenyl)-ethyl]-3-methyl-5,6-dihydro-8H-imidazo[1,5-a]pyrazine-7-carboxylic acid tert-butyl ester A cooled (−78° C.) solution of 8-[2-(3-fluoro-4-trifluoromethyl-phenyl)-ethyl]-1-iodo-3-methyl-5,6-dihydro-8H-imidazo[1,5-a]pyrazine-7-carboxylic acid tert-butyl ester (0.666 g; 1.204 mmol) in anhydrous THF (20 ml) was treated dropwise with 1.6M n-BuLi in hexanes (0.76 ml; 1.204 mmol). The resulting reaction mixture was further stirred at −78° C., under nitrogen, for 15 min., and a solution of para-toluenesulfonyl cyanide (0.379 g; 1.987 mmol) in anhydrous THF (5 ml) was then added dropwise. Stirring at −78° C. was continued for 20 min. before aq. sat. NH$_4$Cl (2 ml) was added. The resulting mixture was allowed to warm-up to rt, and water (50 ml), followed by ether (50 ml) were added. The organic layer was dried over anh. MgSO$_4$, filtered, and concentrated to dryness under reduced pressure. Purification by FC (DCM/MeOH, 50/1) afforded 1-cyano-8-[2-(3-fluoro-4-trifluoromethyl-phenyl)-ethyl]-3-methyl-5,6-dihydro-8H-imidazo[1,5-a]pyrazine-7-carboxylic acid tert-butyl ester as a pale yellow solid (0.271 g; 50%). LC-MS: $t_R$=0.96 min.; [M+H]$^+$=453.31 g/mol.

D.7 Introduction of Hydroxymethyl Substituent

3-ethyl-1-hydroxymethyl-8-[2-(4-trifluoromethyl-phenyl)-ethyl]-5,6-dihydro-8H-imidazo[1,5-a]pyrazine-7-carboxylic acid tert-butyl ester To a cooled (−78° C.) colorless solution of 3-ethyl-1-formyl-8-[2-(4-trifluoromethyl-phenyl)-ethyl]-5,6-dihydro-8H-imidazo[1,5-a]pyrazine-7-carboxylic acid tert-butyl ester (19.9 mg; 0.044 mmol) in anhydrous toluene (2 ml) was added dropwise 1M DIBAL in THF (88 µl; 2 eq.). The resulting yellow homogeneous solution was further stirred at −78° C. for 10 min., and then at rt for 1 h. The resulting crude mixture was purified by preparative HPLC to give the pure product 3-ethyl-1-hydroxymethyl-8-[2-(4-trifluoromethyl-phenyl)-ethyl]-5,6-dihydro-8H-imidazo[1,5-a]pyrazine-7-carboxylic acid tert-butyl ester (16 mg; 0.035 mmol; 80%). LC-MS: $t_R$=0.91 min.; [M+H]$^+$=454.27 g/mol.

D.8 Introduction of Amide Substituent

3-ethyl-8-[2-(4-trifluoromethyl-phenyl)-ethyl]-5,6-dihydro-8H-imidazo[1,5-a]pyrazine-1,7-dicarboxylic acid 7-tert-butyl ester To a cooled (−30° C.) solution of 3-ethyl-1-iodo-8-[2-(4-trifluoromethyl-phenyl)-ethyl]-5,6-dihydro-8H-imidazo[1,5-a]pyrazine-7-carboxylic acid tert-butyl ester (500 mg; 0.910 mmol) in anhydrous THF (10 ml) was added dropwise 1M ethylmagnesium bromide in THF (2.0 ml; 2 mmol). The resulting colorless suspension was allowed to warm-up to rt in 30 min., and was again cooled to −35° C. before continuous injection of carbon dioxide during 2 h. Water and EA were then added, and the resulting reaction mixture was allowed to warm-up to rt. The organic layer was further washed with aq. sat. NH$_4$Cl, dried over magnesium sulfate, filtered, and concentrated to dryness under reduced pressure to give the expected product 3-ethyl-8-[2-(4-trifluoromethyl-phenyl)-ethyl]-5,6-dihydro-8H-imidazo[1,5-a]pyrazine-1,7-dicarboxylic acid 7-tert-butyl ester as a colorless foam (350 mg; 0.748 mmol; 82%).

3-ethyl-1-methylcarbamoyl-8-[2-(4-trifluoromethyl-phenyl)-ethyl]-5,6-dihydro-8H-imidazo[1,5-a]pyrazine-7-carboxylic acid tert-butyl ester To a solution of 3-ethyl-8-[2-(4-trifluoromethyl-phenyl)-ethyl]-5,6-dihydro-8H-imidazo[1,5-a]pyrazine-1,7-dicarboxylic acid 7-tert-butyl ester (47 mg; 0.100 mmol) in anhydrous DMF (1 ml) was added successively TBTU (35 mg; 0.110 mmol), DIPEA (51 µl; 0.300 mmol), and finally 2M methylamine in THF (0.15 ml; 0.300 mmol). The resulting reaction mixture was further stirred at rt, under nitrogen, for 16 h, and was then purified by preparative HPLC to give the pure product 3-ethyl-1-methylcarbamoyl-8-[2-(4-trifluoromethyl-phenyl)-ethyl]-5,6-dihydro-8H-imidazo[1,5-a]pyrazine-7-carboxylic acid tert-butyl ester (27.8 mg; 0.057 mmol; 58%).

D.9 Cyclopropanation

1-cyclopropyl-3-methyl-8-[2-(4-trifluoromethyl-phenyl)-ethyl]-5,6,7,8-tetrahydro-imidazo[1,5-a]pyrazine To an ice-cooled solution of 1M diethylzinc in hexane (37.0 ml; 37.000 mmol) in anhydrous DCM (40 ml) was added dropwise a solution of TFA (2.82 ml; 36.924 mmol) in anhydrous DCM (20 ml). After 30 min., a solution of methylene iodide (2.97 ml; 36.924 mmol) in anhydrous DCM (20 ml) was added dropwise to the reaction mixture, and stirring at 0° C. was continued for 10 min. A solution of 3-methyl-8-[2-(4-trifluoromethyl-phenyl)-ethyl]-1-vinyl-5,6-dihydro-8H-imidazo[1,5-a]pyrazine-7-carboxylic acid tert-butyl ester (0.536 g; 1.231 mmol) in anhydrous DCM (5 ml) was then added dropwise, and the resulting mixture was further stirred at 0° C. for 1 h, and finally at rt for 6 h. The reaction mixture was then treated dropwise with TEA (7 ml), and with an aq. sat. solution of NaHCO$_3$ (50 ml). The organic layer was dried over anh. MgSO$_4$, filtered, and concentrated to dryness under reduced pressure. Purification by FC (DCM/MeOH/25% aq. NH$_4$OH, 200/10/1) afforded the target compound 1-cyclopropyl-3-methyl-8-[2-(4-trifluoromethyl-phenyl)-ethyl]-5,6,7,8-tetrahydro-imidazo[1,5-a]pyrazine as a yellow solid (0.186 g; 34%). LC-MS: $t_R$=0.68 min.; [M+H]$^+$=350.42 g/mol.

E Boc-deprotection of 5,6,7,8-tetrahydro-imidazo[1,5-a]pyrazines

1-chloro-3-ethyl-8-[2-(4-trifluoromethyl-phenyl)-ethyl]-5,6,7,8-tetrahydro-imidazo[1,5-a]pyrazine [general procedure for Boc-deprotection (GP13)]

To an ice-cooled solution of 1-chloro-3-ethyl-8-[2-(4-trifluoromethyl-phenyl)-ethyl]-5,6-dihydro-8H-imidazo[1,5-a]pyrazine-7-carboxylic acid tert-butyl ester (226 mg; 0.494 mmol) in DCM (5 ml) was added 4N HCl in dioxane (2.5 ml; 10 mmol; 20 eq.). The resulting suspension was further stirred at 0° C. for 10 min., and at rt for 2 h. The volatiles were removed under vacuum and the resulting pale yellow chlorhydrate salt (240 mg) was purified by preparative HPLC in basic conditions leading to the pure product 1-chloro-3-ethyl- 8-[2-(4-trifluoromethyl-phenyl)-ethyl]-5,6,7,8-tetrahydro-imidazo[1,5-a]pyrazine (89.6 mg; 51%). LC-MS: $t_R$=0.77 min.; [M+H]$^+$=358.36 g/mol.

3-ethyl-1-trifluoromethyl-8-[2-(4-trifluoromethyl-phenyl)-ethyl]-5,6,7,8-tetrahydro-imidazo[1,5-a]pyrazine According to the general procedure (GP13), Boc-deprotection (rt; 3h15) of 3-ethyl-1-trifluoromethyl-8-[2-(4-trifluoromethyl-phenyl)-ethyl]-5,6-dihydro-8H-imidazo[1,5-a]pyrazine-7-carboxylic acid tert-butyl ester (250 mg; 0.509 mmol) gave after HPLC-purification the expected product 3-ethyl-1-trifluoromethyl-8-[2-(4-trifluoromethyl-phenyl)-ethyl]-5,6,7,8-tetrahydro-imidazo[1,5-a]pyrazine as a slightly beige solid (138.6 mg; 70%). LC-MS: $t_R$=0.80 min.; [M+H]$^+$=392.39 g/mol.

8-[2-(3,4-dimethyl-phenyl)-ethyl]-3-ethyl-1-methoxy-5,6,7,8-tetrahydro-imidazo[1,5-a]pyrazine According to the general procedure (GP13), Boc-deprotection (0° C., 1h30; rt, 2h30) of 8-[2-(3,4-dimethyl-phenyl)-ethyl]-3-ethyl-1-methoxy-5,6-dihydro-8H-imidazo[1,5-a]pyrazine-7-carboxylic acid tert-butyl ester (260.6 mg; 0.630 mmol) gave after purification by FC (DCM/MeOH/25% aq. NH$_4$OH=150/10/1) the expected product 8-[2-(3,4-dimethyl-phenyl)-ethyl]-3-ethyl-1-methoxy-5,6,7,8-tetrahydro-imidazo[1,5-a]pyrazine as a pale yellow solid (189.2 mg; 96%). LC-MS: $t_R$=0.68 min.; [M+H]$^+$=314.27 g/mol.

3-isopropyl-1-methoxy-8-[2-(4-trifluoromethyl-phenyl)-ethyl]-5,6,7,8-tetrahydro-imidazo[1,5-a]pyrazine According to the general procedure (GP13), Boc-deprotection (rt; 4 h) of 3-isopropyl-1-methoxy-8-[2-(4-trifluoromethyl-phenyl)-ethyl]-5,6-dihydro-8H-imidazo[1,5-a]pyrazine-7-carboxylic acid tert-butyl ester (107.5 mg; 0.230 mmol) gave after HPLC-purification the expected product 3-isopropyl-1-methoxy-8-[2-(4-trifluoromethyl-phenyl)-ethyl]-5,6,7,8-tetrahydro-imidazo[1,5-a]pyrazine as a pale yellow solid (45.6 mg; 54%). LC-MS: $t_R$=0.73 min.; [M+H]$^+$=368.26 g/mol.

1-chloro-3-isopropyl-8-[2-(4-trifluoromethyl-phenyl)-ethyl]-5,6,7,8-tetrahydro-imidazo[1,5-a]pyrazine According to the general procedure (GP13), Boc-deprotection (rt; 4 h) of 1-chloro-3-isopropyl-8-[2-(4-trifluoromethyl-phenyl)-ethyl]-5,6-dihydro-8H-imidazo[1,5-a]pyrazine-7-carboxylic acid tert-butyl ester (97.1 mg; 0.206 mmol) gave after HPLC-purification the expected product 1-chloro-3-isopropyl-8-[2-(4-trifluoromethyl-phenyl)-ethyl]-5,6,7,8-tetrahydro-imidazo[1,5-a]pyrazine as a pale yellow oil (39.6 mg; 0.106 mmol; 52%). LC-MS: $t_R$=0.79 min.; [M+H]$^+$=372.20 g/mol.

1-chloro-8-[2-(3,4-difluoro-phenyl)-ethyl]-3-ethyl-5,6,7,8-tetrahydro-imidazo[1,5-a]pyrazine According to the general procedure (GP13), Boc-deprotection (rt; 2 h) of 1-chloro-8-[2-(3,4-difluoro-phenyl)-ethyl]-3-ethyl-5,6-dihydro-8H-imidazo[1,5-a]pyrazine-7-carboxylic acid tert-butyl ester (143 mg; 0.335 mmol) gave after HPLC-purification the expected product 1-chloro-8-[2-(3,4-difluoro-phenyl)-ethyl]-3-ethyl-5,6,7,8-tetrahydro-imidazo[1,5-a]pyrazine as a yellow oil (44 mg; 0.135 mmol; 40%). LC-MS: $t_R$=0.72 min.; [M+H]$^+$=326.24 g/mol.

1-chloro-8-[2-(3,5-difluoro-4-methyl-phenyl)-ethyl]-3-ethyl-5,6,7,8-tetrahydro-imidazo[1,5-a]pyrazine According to the general procedure (GP13), Boc-deprotection (rt; 2 h) of 1-chloro-8-[2-(3,5-difluoro-4-methyl-phenyl)-ethyl]-3-ethyl-5,6-dihydro-8H-imidazo[1,5-a]pyrazine-7-carboxylic acid tert-butyl ester (136.8 mg; 0.310 mmol) gave after HPLC-purification the expected product 1-chloro-8-[2-(3,5-difluoro-4-methyl-phenyl)-ethyl]-3-ethyl-5,6,7,8-tetrahydro-imidazo[1,5-a]pyrazine as a yellow oil (45.9 mg; 0.135 mmol; 44%). LC-MS: $t_R$=0.76 min.; [M+H]$^+$=340.27 g/mol.

1-chloro-8-[2-(3,5-difluoro-4-trifluoromethyl-phenyl)-ethyl]-3-ethyl-5,6,7,8-tetrahydro-imidazo[1,5-a]pyrazine According to the general procedure (GP13), Boc-deprotection (rt; 4 h) of 1-chloro-8-[2-(3,5-difluoro-4-trifluoromethyl-phenyl)-ethyl]-3-ethyl-5,6-dihydro-8H-imidazo[1,5-a]pyrazine-7-carboxylic acid tert-butyl ester (179.7 mg; 0.364 mmol) gave after HPLC-purification the expected product 1-chloro-8-[2-(3,5-difluoro-4-trifluoromethyl-phenyl)-ethyl]-3-ethyl-5,6,7,8-tetrahydro-imidazo[1,5-a]pyrazine as a pale yellow solid (70 mg; 0.177 mmol; 49%). LC-MS: $t_R$=0.77 min.; [M+H]$^+$=394.27 g/mol.

1-chloro-3-ethyl-8-[2-(2-fluoro-4-trifluoromethyl-phenyl)-ethyl]-5,6,7,8-tetrahydro-imidazo[1,5-a]pyrazine According to the general procedure (GP13), Boc-deprotection (rt; 2 h) of 1-chloro-3-ethyl-8-[2-(2-fluoro-4-trifluoromethyl-phenyl)-ethyl]-5,6-dihydro-8H-imidazo[1,5-a]pyrazine-7-carboxylic acid tert-butyl ester (153.6 mg; 0.322 mmol) gave after HPLC-purification the expected product 1-chloro-3-ethyl-8-[2-(2-fluoro-4-trifluoromethyl-phenyl)-ethyl]-5,6,7,8-tetrahydro-imidazo[1,5-a]pyrazine as a yellow oil (77.8 mg; 0.207 mmol; 64%). LC-MS: $t_R$=0.78 min.; [M+H]$^+$=376.29 g/mol.

1-chloro-3-ethyl-8-[2-(3-fluoro-4-methyl-phenyl)-ethyl]-5,6,7,8-tetrahydro-imidazo[1,5-a]pyrazine According to the general procedure (GP13), Boc-deprotection (rt; 2 h) of 1-chloro-3-ethyl-8-[2-(3-fluoro-4-methyl-phenyl)-ethyl]-5,6-dihydro-8H-imidazo[1,5-a]pyrazine-7-carboxylic acid tert-butyl ester (191.4 mg; 0.453 mmol) gave after HPLC-purification the expected product 1-chloro-3-ethyl-8-[2-(3-fluoro-4-methyl-phenyl)-ethyl]-5,6,7,8-tetrahydro-imidazo[1,5-a]pyrazine as a yellow oil (68.2 mg; 0.211 mmol; 47%). LC-MS: $t_R$=0.75 min.; [M+H]$^+$=322.25 g/mol.

1-chloro-8-[2-(3,4-dimethyl-phenyl)-ethyl]-3-ethyl-5,6,7,8-tetrahydro-imidazo[1,5-a]pyrazine According to the general procedure (GP13), Boc-deprotection (rt; 2 h) of 1-chloro-8-[2-(3,4-dimethyl-phenyl)-ethyl]-5,6-dihydro-8H-imidazo[1,5-a]pyrazine-7-carboxylic acid tert-butyl ester (225 mg; 0.538 mmol) gave after HPLC-purification the expected product 1-chloro-8-[2-(3,4-dimethyl-phenyl)-ethyl]-3-ethyl-5,6,7,8-tetrahydro-

1-chloro-3-ethyl-8-[2-(3-fluoro-4-trifluoromethyl-phenyl)-ethyl]-5,6,7,8-tetrahydro-imidazo[1,5-a]pyrazine According to the general procedure (GP13), Boc-deprotection (rt; 2 h) of 1-chloro-3-ethyl-8-[2-(3-fluoro-4-trifluoromethyl-phenyl)-ethyl]-5,6-dihydro-8H-imidazo[1,5-a]pyrazine-7-carboxylic acid tert-butyl ester (135.3 mg; 0.284 mmol) gave after HPLC-purification the expected product 1-chloro-3-ethyl-8-[2-(3-fluoro-4-trifluoromethyl-phenyl)-ethyl]-5,6,7,8-tetrahydro-imidazo[1,5-a]pyrazine as a colorless solid (71.1 mg; 0.189 mmol; 67%). LC-MS: $t_R$=0.78 min.; [M+H]$^+$=376.20 g/mol.

1-chloro-8-[2-(2,4-difluoro-3-methyl-phenyl)-ethyl]-3-ethyl-5,6,7,8-tetrahydro-imidazo[1,5-a]pyrazine According to the general procedure (GP13), Boc-deprotection (rt; 2 h) of 1-chloro-8-[2-(2,4-difluoro-3-methyl-phenyl)-ethyl]-3-ethyl-5,6-dihydro-8H-imidazo[1,5-a]pyrazine-7-carboxylic acid tert-butyl ester (213.9 mg; 0.486 mmol) gave after HPLC-purification the expected product 1-chloro-8-[2-(2,4-difluoro-3-methyl-phenyl)-ethyl]-3-ethyl-5,6,7,8-tetrahydro-imidazo[1,5-a]pyrazine as a colorless solid (90.1 mg; 0.265 mmol; 55%). LC-MS: $t_R$=0.75 min.; [M+H]$^+$=340.21 g/mol.

1-chloro-8-[2-(3,4-dimethyl-phenyl)-ethyl]-3-methyl-5,6,7,8-tetrahydro-imidazo[1,5-a]pyrazine According to the general procedure (GP13), Boc-deprotection (rt; 4 h) of 1-chloro-8-[2-(3,4-dimethyl-phenyl)-ethyl]-3-methyl-5,6-dihydro-8H-imidazo[1,5-a]pyrazine-7-carboxylic acid tert-butyl ester (259 mg; 0.641 mmol) gave after HPLC-purification the expected product 1-chloro-8-[2-(3,4-dimethyl-phenyl)-ethyl]-3-methyl-5,6,7,8-tetrahydro-imidazo[1,5-a]pyrazine as a pale yellow oil (61 mg; 0.200 mmol; 31%). LC-MS: $t_R$=0.74 min.; [M+H]$^+$=304.38 g/mol.

1-chloro-8-[2-(3,5-difluoro-4-methyl-phenyl)-ethyl]-3-methyl-5,6,7,8-tetrahydro-imidazo[1,5-a]pyrazine According to the general procedure (GP13), Boc-deprotection (rt; 4 h) of 1-chloro-8-[2-(3,5-difluoro-4-methyl-phenyl)-ethyl]-3-methyl-5,6-dihydro-8H-imidazo[1,5-a]pyrazine-7-carboxylic acid tert-butyl ester (191 mg; 0.448 mmol) gave after HPLC-purification the expected product 1-chloro-8-[2-(3,5-difluoro-4-methyl-phenyl)-ethyl]-3-methyl-5,6,7,8-tetrahydro-imidazo[1,5-a]pyrazine as a pale yellow oil (68.3 mg; 0.209 mmol; 47%). LC-MS: $t_R$=0.74 min.; [M+H]$^+$=326.38 g/mol.

1-chloro-3-methyl-8-[2-(4-trifluoromethyl-phenyl)-ethyl]-5,6,7,8-tetrahydro-imidazo[1,5-a]pyrazine According to the general procedure (GP13), Boc-deprotection (rt; 4 h) of 1-chloro-3-methyl-8-[2-(4-trifluoromethyl-phenyl)-ethyl]-5,6-dihydro-8H-imidazo[1,5-a]pyrazine-7-carboxylic acid tert-butyl ester (52 mg; 0.117 mmol) gave after HPLC-purification the expected product 1-chloro-3-methyl-8-[2-(4-trifluoromethyl-phenyl)-ethyl]-5,6,7,8-tetrahydro-imidazo[1,5-a]pyrazine as a pale yellow oil (15.4 mg; 0.044 mmol; 38%). LC-MS: $t_R$=0.75 min.; [M+H]$^+$=344.40 g/mol.

3-ethyl-8-[2-(4-trifluoromethyl-phenyl)-ethyl]-1-vinyl-5,6,7,8-tetrahydro-imidazo[1,5-a]pyrazine According to the general procedure (GP13), Boc-deprotection of 3-ethyl-8-[2-(4-trifluoromethyl-phenyl)-ethyl]-1-vinyl-5,6-dihydro-8H-imidazo[1,5-a]pyrazine-7-carboxylic acid tert-butyl ester gave the expected product 3-ethyl-8-[2-(4-trifluoromethyl-phenyl)-ethyl]-1-vinyl-5,6,7,8-tetrahydro-imidazo[1,5-a]pyrazine (15 mg; 0.042 mmol). LC-MS: $t_R$=0.66 min.; [M+H]$^+$=350.32 g/mol.

3-ethyl-8-[2-(4-trifluoromethyl-phenyl)-ethyl]-5,6,7,8-tetrahydro-imidazo[1,5-a]pyrazine-1-carbonitrile According to the general procedure (GP13), Boc-deprotection of 1-cyano-3-ethyl-8-[2-(4-trifluoromethyl-phenyl)-ethyl]-5,6-dihydro-8H-imidazo[1,5-a]pyrazine-7-carboxylic acid tert-butyl ester (5.000 g; 11.148 mmol) gave the expected product 3-ethyl-8-[2-(4-trifluoromethyl-phenyl)-ethyl]-5,6,7,8-tetrahydro-imidazo[1,5-a]pyrazine-1-carbonitrile as a yellow solid (3.300 g; 9.472 mmol; 85%). LC-MS: $t_R$=0.75 min.; [M+H]$^+$=349.2 g/mol.

1-chloro-3-methoxymethyl-8-[2-(4-trifluoromethyl-phenyl)-ethyl]-5,6,7,8-tetrahydro-imidazo[1,5-a]pyrazine According to the general procedure (GP13), Boc-deprotection (rt; 4 h) of 1-chloro-3-methoxymethyl-8-[2-(4-trifluoromethyl-phenyl)-ethyl]-5,6-dihydro-8H-imidazo[1,5-a]pyrazine-7-carboxylic acid tert-butyl ester (350 mg; 0.739 mmol) gave after purification by FC (DCM/MeOH/25% aq. NH$_4$OH=200/10/1] the expected product 1-chloro-3-methoxymethyl-8-[2-(4-trifluoromethyl-phenyl)-ethyl]-5,6,7,8-tetrahydro-imidazo[1,5-a]pyrazine as an orange oil (190 mg; 0.508 mmol; 69%). LC-MS: $t_R$=0.76 min.; [M+H]$^+$=374.34 g/mol.

{3-ethyl-8-[2-(4-trifluoromethyl-phenyl)-ethyl]-5,6,7,8-tetrahydro-imidazo[1,5-a]pyrazin-1-yl}-MeOH According to the general procedure (GP13), Boc-deprotection of 3-ethyl-1-hydroxymethyl-8-[2-(4-trifluoromethyl-phenyl)-ethyl]-5,6-dihydro-8H-imidazo[1,5-a]pyrazine-7-carboxylic acid tert-butyl ester (16 mg; 0.035 mmol) gave the expected product {3-ethyl-8-[2-(4-trifluoromethyl-phenyl)-ethyl]-5,6,7,8-tetrahydro-imidazo[1,5-a]pyrazin-1-yl}-MeOH as a yellow oil (12 mg; 0.033 mmol; 96%). LC-MS: $t_R$=0.61 min.; [M+H]$^+$=354.32 g/mol.

3-ethyl-8-[2-(4-trifluoromethyl-phenyl)-ethyl]-5,6,7,8-tetrahydro-imidazo[1,5-a]pyrazine-1-carboxylic acid methylamide According to the general procedure (GP13), Boc-deprotection of 3-ethyl-1-methylcarbamoyl-8-[2-(4-trifluoromethyl-phenyl)-ethyl]-5,6-dihydro-8H-imidazo[1,5-a]pyrazine-7-carboxylic acid tert-butyl ester (27.8 mg; 0.057 mmol) gave the expected product 3-ethyl-8-[2-(4-trifluoromethyl-phenyl)-ethyl]-5,6,7,8-tetrahydro-imidazo[1,5-a]pyrazine-1-carboxylic acid methylamide as a yellow oil (22 mg; 0.057 mmol). LC-MS: $t_R$=0.74 min.; [M+H]$^+$=381.3 g/mol.

1,3-dichloro-8-[2-(4-trifluoromethyl-phenyl)-ethyl]-5,6,7,8-tetrahydro-imidazo[1,5-a]pyrazine According to the general procedure (GP13), Boc-deprotection of 1,3-dichloro-8-[2-(4-trifluoromethyl-phenyl)- ethyl]-5,6-dihydro-8H-imidazo[1,5-a]pyrazine-7-carboxylic acid tert-butyl ester (185.7 mg; 0.400 mmol) and purification by FC (DCM/MeOH/25% aq. NH$_4$OH=150/10/1) gave the expected product 1,3-dichloro-8-[2-(4-trifluoromethyl-phenyl)-ethyl]-5,6,7,8-tetrahydro-imidazo[1,5-a]pyrazine as a yellow oil (121 mg; 0.332 mmol; 83%). LC-MS: t$_R$=0.79 min.; [M+H]$^+$=364.11 g/mol.

1-chloro-3-ethyl-8-[2-(3,4,5-trifluoro-phenyl)-ethyl]-5,6,7,8-tetrahydro-imidazo[1,5-a]pyrazine According to the general procedure (GP13), Boc-deprotection (0° C., 10 min.; rt, 1h30) of 1-chloro-3-ethyl-8-[2-(3,4,5-trifluoro-phenyl)-ethyl]-5,6-dihydro-8H-imidazo[1,5-a]pyrazine-7-carboxylic acid tert-butyl ester (1.283 g; 2.891 mmol) gave after purification by FC (DCM/MeOH/25% aq. NH$_4$OH=150/10/1) the expected product 1-chloro-3-ethyl-8-[2-(3,4,5-trifluoro-phenyl)-ethyl]-5,6,7,8-tetrahydro-imidazo[1,5-a]pyrazine as a yellow oil (0.939 g; 94%). LC-MS: t$_R$=0.79 min.; [M+H]$^+$=344.03 g/mol.

1-chloro-8-[2-(3-fluoro-4-trifluoromethyl-phenyl)-ethyl]-3-methyl-5,6,7,8-tetrahydro-imidazo[1,5-a]pyrazine According to the general procedure (GP13), Boc-deprotection (0° C., 10 min.; rt, 1h30) of 1-chloro-8-[2-(3-fluoro-4-trifluoromethyl-phenyl)-ethyl]-3-methyl-5,6-dihydro-8H-imidazo[1,5-a]pyrazine-7-carboxylic acid tert-butyl ester (6.980 g; 15.112 mmol) gave after purification by FC (DCM/MeOH/25% aq. NH$_4$OH=150/10/1) the expected product 1-chloro-8-[2-(3-fluoro-4-trifluoromethyl-phenyl)-ethyl]-3-methyl-5,6,7,8-tetrahydro-imidazo[1,5-a]pyrazine as a yellow oil (5.450 g; 100%). LC-MS: t$_R$=0.79 min.; [M+H]$^+$=361.99 g/mol.

1-chloro-8-[2-(3,5-difluoro-4-methoxy-phenyl)-ethyl]-3-ethyl-5,6,7,8-tetrahydro-imidazo[1,5-a]pyrazine According to the general procedure (GP13), Boc-deprotection (0° C., 10 min.; rt, 1h30) of 1-chloro-8-[2-(3,5-difluoro-4-methoxy-phenyl)-ethyl]-3-ethyl-5,6-dihydro-8H-imidazo[1,5-a]pyrazine-7-carboxylic acid tert-butyl ester (0.730 g; 1.601 mmol) gave after purification by FC (DCM/MeOH/25% aq. NH$_4$OH=150/10/1) the expected product 1-chloro-8-[2-(3,5-difluoro-4-methoxy-phenyl)-ethyl]-3-ethyl-5,6,7,8-tetrahydro-imidazo[1,5-a]pyrazine as a yellow oil (0.569 g; 100%). LC-MS: t$_R$=0.77 min.; [M+H]$^+$=355.94 g/mol.

1-chloro-8-[2-(4-chloro-3,5-difluoro-phenyl)-ethyl]-3-ethyl-5,6,7,8-tetrahydro-imidazo[1,5-a]pyrazine According to the general procedure (GP13), Boc-deprotection (0° C., 10 min.; rt, 1h30) of 1-chloro-8-[2-(4-chloro-3,5-difluoro-phenyl)-ethyl]-3-ethyl-5,6-dihydro-8H-imidazo[1,5-a]pyrazine-7-carboxylic acid tert-butyl ester (0.724 g; 1.574 mmol) gave after purification by FC (DCM/MeOH/25% aq. NH$_4$OH=150/10/1) the expected product 1-chloro-8-[2-(4-chloro-3,5-difluoro-phenyl)-ethyl]-3-ethyl-5,6,7,8-tetrahydro-imidazo[1,5-a]pyrazine as a yellow oil (0.567 g; 100%). LC-MS: t$_R$=0.81 min.; [M+H]$^+$=359.96 g/mol.

1-chloro-8-[2-(3-chloro-4-trifluoromethyl-phenyl)-ethyl]-3-ethyl-5,6,7,8-tetrahydro-imidazo[1,5-a]pyrazine According to the general procedure (GP13), Boc-deprotection (0° C., 10 min.; rt, 2 h) of 1-chloro-8-[2-(3-chloro-4-trifluoromethyl-phenyl)-ethyl]-3-ethyl-5,6-dihydro-8H-imidazo[1,5-a]pyrazine-7-carboxylic acid tert-butyl ester (0.684 g; 1.390 mmol) gave after purification by FC (DCM/MeOH/25% aq. NH$_4$OH=150/10/1) the expected product 1-chloro-8-[2-(3-chloro-4-trifluoromethyl-phenyl)-ethyl]-3-ethyl-5,6,7,8-tetrahydro-imidazo[1,5-a]pyrazine as a yellow oil (0.508 g; 93%). LC-MS: t$_R$=0.84 min.; [M+H]$^+$=391.90 g/mol.

1-chloro-8-[2-(2,5-difluoro-4-trifluoromethyl-phenyl)-ethyl]-3-ethyl-5,6,7,8-tetrahydro-imidazo[1,5-a]pyrazine According to the general procedure (GP13), Boc-deprotection (0° C., 5 min.; rt, 3h15) of 1-chloro-8-[2-(2,5-difluoro-4-trifluoromethyl-phenyl)-ethyl]-3-ethyl-5,6-dihydro-8H-imidazo[1,5-a]pyrazine-7-carboxylic acid tert-butyl ester (0.700 g; 1.417 mmol) gave after purification by FC (DCM/MeOH/25% aq. NH$_4$OH=250/10/1) the expected product 1-chloro-8-[2-(2,5-difluoro-4-trifluoromethyl-phenyl)-ethyl]-3-ethyl-5,6,7,8-tetrahydro-imidazo[1,5-a]pyrazine as a yellow oil (0.528 g; 95%). LC-MS: t$_R$=0.82 min.; [M+H]$^+$=393.93 g/mol.

1-chloro-3-ethyl-8-[2-(4-trifluoromethoxy-phenyl)-ethyl]-5,6,7,8-tetrahydro-imidazo[1,5-a]pyrazine According to the general procedure (GP13), Boc-deprotection (0° C., 5 min.; rt, 3h30) of 1-chloro-3-ethyl-8-[2-(4-trifluoromethoxy-phenyl)-ethyl]-5,6-dihydro-8H-imidazo[1,5-a]pyrazine-7-carboxylic acid tert-butyl ester (0.288 g; 0.608 mmol) gave the expected product 1-chloro-3-ethyl-8-[2-(4-trifluoromethoxy-phenyl)-ethyl]-5,6,7,8-tetrahydro-imidazo[1,5-a]pyrazine as a yellow oil (0.225 g; 99%). LC-MS: t$_R$=0.82 min.; [M+H]$^+$=374.05 g/mol.

4-[2-(1-chloro-3-ethyl-5,6,7,8-tetrahydro-imidazo[1,5-a]pyrazin-8-yl)-ethyl]-benzonitrile According to the general procedure (GP13), Boc-deprotection (0° C., 10 min.; rt, 1h30) of 1-chloro-8-[2-(4-cyano-phenyl)-ethyl]-3-ethyl-5,6-dihydro-8H-imidazo[1,5-a]pyrazine-7-carboxylic acid tert-butyl ester (0.506 g; 1.219 mmol) gave after purification by FC (DCM/MeOH/25% aq. NH$_4$OH=150/10/1) the expected product 4-[2-(1-chloro-3-ethyl-5,6,7,8-tetrahydro-imidazo[1,5-a]pyrazin-8-yl)-ethyl]-benzonitrile as a yellow oil (0.383 g; 100%). LC-MS: t$_R$=0.73 min.; [M+H]$^+$=315.08 g/mol.

3-ethyl-8-[2-(3-fluoro-4-trifluoromethyl-phenyl)-ethyl]-5,6,7,8-tetrahydro-imidazo[1,5-a]pyrazine-1-carbonitrile According to the general procedure (GP13), Boc-deprotection (0° C., 10 min.; rt, 2 h) of 1-cyano-3-ethyl-8-[2-(3-fluoro-4-trifluoromethyl-phenyl)-ethyl]-5,6-dihydro-8H-imidazo[1,5-a]pyrazine-7-carboxylic acid tert-butyl ester (0.186 g; 0.399 mmol) gave after purification by FC (DCM/MeOH/25% aq. NH$_4$OH=150/10/1) the expected product 3-ethyl-8-[2-(3-fluoro-4-trifluoromethyl-phenyl)-ethyl]-5,6,7,8-tetrahydro-imidazo[1,5-a]pyrazine-1-carbonitrile as a yellow oil (0.141 g; 98%).

8-[2-(3-fluoro-4-trifluoromethyl-phenyl)-ethyl]-3-methyl-5,6,7,8-tetrahydro-imidazo[1,5-a]pyrazine-1-carbonitrile According to the general procedure (GP13), Boc-deprotection (0° C., 10 min.; rt, 2 h) of 1-cyano-8-[2-(3-fluoro-4- trifluoromethyl-phenyl)-ethyl]-3-methyl-5,6-dihydro-8H-imidazo[1,5-a]pyrazine-7-carboxylic acid tert-butyl ester (0.271 g; 0.599 mmol) gave after purification by FC (DCM/MeOH/25% aq. NH$_4$OH=150/10/1) the expected product 8-[2-(3-fluoro-4-trifluoromethyl-phenyl)-ethyl]-3-methyl-5,6,7,8-tetrahydro-imidazo[1,5-a]pyrazine-1-carbonitrile as a pale yellow solid (0.195 g; 92%). LC-MS: $t_R$=0.81 min.; [M+H]$^+$=353.35 g/mol.

1-chloro-3-propyl-8-[2-(4-trifluoromethyl-phenyl)-ethyl]-5,6,7,8-tetrahydro-imidazo[1,5-a]pyrazine According to the general procedure (GP13), Boc-deprotection (0° C., 10 min.; rt, 2 h) of 1-chloro-3-propyl-8-[2-(4-trifluoromethyl-phenyl)-ethyl]-5,6-dihydro-8H-imidazo[1,5-a]pyrazine-7-carboxylic acid tert-butyl ester (1.550 g; 3.284 mmol) gave after purification by FC (DCM/MeOH/25% aq. NH$_4$OH=150/10/1) the expected product 1-chloro-3-propyl-8-[2-(4-trifluoromethyl-phenyl)-ethyl]-5,6,7,8-tetrahydro-imidazo[1,5-a]pyrazine as a yellow oil (1.220 g; 100%). LC-MS: $t_R$=0.84 min.; [M+H]$^+$=372.00 g/mol.

1-chloro-8-[2-(3-fluoro-4-trifluoromethyl-phenyl)-ethyl]-3-propyl-5,6,7,8-tetrahydro-imidazo[1,5-a]pyrazine According to the general procedure (GP13), Boc-deprotection (0° C., 10 min.; rt, 2 h) of 1-chloro-8-[2-(3-fluoro-4-trifluoromethyl-phenyl)-ethyl]-3-propyl-5,6-dihydro-8H-imidazo[1,5-a]pyrazine-7-carboxylic acid tert-butyl ester (1.130 g; 2.306 mmol) gave after purification by FC (DCM/MeOH/25% aq. NH$_4$OH=150/10/1) the expected product 1-chloro-8-[2-(3-fluoro-4-trifluoromethyl-phenyl)-ethyl]-3-propyl-5,6,7,8-tetrahydro-imidazo[1,5-a]pyrazine as a yellow oil (0.899 g; 100%). LC-MS: $t_R$=0.85 min.; [M+H]$^+$=390.01 g/mol.

1-chloro-3-ethyl-8-[2-(2,3,5-trifluoro-phenyl)-ethyl]-5,6,7,8-tetrahydro-imidazo[1,5-a]pyrazine According to the general procedure (GP13), Boc-deprotection (0° C., 10 min.; rt, 2 h) of 1-chloro-3-ethyl-8-[2-(2,3,5-trifluoro-phenyl)-ethyl]-5,6-dihydro-8H-imidazo[1,5-a]pyrazine-7-carboxylic acid tert-butyl ester (0.373 g; 0.840 mmol) gave after purification by FC (DCM/MeOH/25% aq. NH$_4$OH=150/10/1) the expected product 1-chloro-3-ethyl-8-[2-(2,3,5-trifluoro-phenyl)-ethyl]-5,6,7,8-tetrahydro-imidazo[1,5-a]pyrazine as a pale yellow oil (0.277 g; 96%). LC-MS: $t_R$=0.83 min.; [M+H]$^+$=344.41 g/mol.

1-chloro-3-ethyl-8-[2-(3-fluoro-4-methoxy-phenyl)-ethyl]-5,6,7,8-tetrahydro-imidazo[1,5-a]pyrazine According to the general procedure (GP13), Boc-deprotection (0° C., 10 min.; rt, 2 h) of 1-chloro-3-ethyl-8-[2-(3-fluoro-4-methoxy-phenyl)-ethyl]-5,6-dihydro-8H-imidazo[1,5-a]pyrazine-7-carboxylic acid tert-butyl ester (1.790 g; 4.087 mmol) gave after purification by FC (DCM/MeOH/25% aq. NH$_4$OH=150/10/1) the expected product 1-chloro-3-ethyl-8-[2-(3-fluoro-4-methoxy-phenyl)-ethyl]-5,6,7,8-tetrahydro-imidazo[1,5-a]pyrazine as a yellow oil (1.380 g; 100%). LC-MS: $t_R$=0.75 min.; [M+H]$^+$=338.06 g/mol.

1-chloro-8-[2-(2,5-difluoro-4-methoxy-phenyl)-ethyl]-3-ethyl-5,6,7,8-tetrahydro-imidazo[1,5-a]pyrazine According to the general procedure (GP13), Boc-deprotection (0° C., 10 min.; rt, 2 h) of 1-chloro-8-[2-(2,5-difluoro-4-methoxy-phenyl)-ethyl]-3-ethyl-5,6-dihydro-8H-imidazo[1,5-a]pyrazine-7-carboxylic acid tert-butyl ester (1.601 g; 3.511 mmol) gave after purification by FC (DCM/MeOH/25% aq. NH$_4$OH=250/10/1) the expected product 1-chloro-8-[2-(2,5-difluoro-4-methoxy-phenyl)-ethyl]-3-ethyl-5,6,7,8-tetrahydro-imidazo[1,5-a]pyrazine as a yellow oil (1.240 g; 99%). LC-MS: $t_R$=0.80 min.; [M+H]$^+$=356.06 g/mol.

1-chloro-3-ethyl-8-(4-fluoro-3-trifluoromethyl-phenoxymethyl)-5,6,7,8-tetrahydro-imidazo[1,5-a]pyrazine According to the general procedure (GP13), Boc-deprotection (0° C., 10 min.; rt, 8 h) of 1-chloro-3-ethyl-8-(4-fluoro-3-trifluoromethyl-phenoxymethyl)-5,6-dihydro-8H-imidazo[1,5-a]pyrazine-7-carboxylic acid tert-butyl ester (0.245 g; 0.513 mmol) gave after purification by FC (DCM/MeOH/25% aq. NH$_4$OH=600/10/1) the expected product 1-chloro-3-ethyl-8-(4-fluoro-3-trifluoromethyl-phenoxymethyl)-5,6,7,8-tetrahydro-imidazo[1,5-a]pyrazine as a yellow oil (0.117 g; 60%). LC-MS: $t_R$=0.76 min.; [M+H]$^+$=378.32 g/mol.

1-chloro-3-ethyl-8-(4-trifluoromethyl-phenoxymethyl)-5,6,7,8-tetrahydro-imidazo[1,5-a]pyrazine According to the general procedure (GP13), Boc-deprotection (0° C., 10 min.; rt, 2h30) of 1-chloro-3-ethyl-8-(4-trifluoromethyl-phenoxymethyl)-5,6-dihydro-8H-imidazo[1,5-a]pyrazine-7-carboxylic acid tert-butyl ester (0.381 g; 0.828 mmol) gave after purification by FC (DCM/MeOH/25% aq. NH$_4$OH=500/10/1) the expected product 1-chloro-3-ethyl-8-(4-trifluoromethyl-phenoxymethyl)-5,6,7,8-tetrahydro-imidazo[1,5-a]pyrazine as a yellow oil (0.257 g; 86%). LC-MS: $t_R$=0.75 min.; [M+H]$^+$=360.17 g/mol.

1-chloro-8-(3,4-dimethyl-phenoxymethyl)-3-ethyl-5,6,7,8-tetrahydro-imidazo[1,5-a]pyrazine According to the general procedure (GP13), Boc-deprotection (0° C., 10 min.; rt, 2 h) of 1-chloro-8-(3,4-dimethyl-phenoxymethyl)-3-ethyl-5,6-dihydro-8H-imidazo[1,5-a]pyrazine-7-carboxylic acid tert-butyl ester (0.328 g; 0.781 mmol) gave after purification by FC (DCM/MeOH/25% aq. NH$_4$OH=150/10/1) the expected product 1-chloro-8-(3,4-dimethyl-phenoxymethyl)-3-ethyl-5,6,7,8-tetrahydro-imidazo[1,5-a]pyrazine as a pale yellow solid (0.240 g; 96%). LC-MS: $t_R$=0.73 min.; [M+H]$^+$=320.18 g/mol.

1-chloro-3-ethyl-8-(3-trifluoromethyl-phenoxymethyl)-5,6,7,8-tetrahydro-imidazo[1,5-a]pyrazine According to the general procedure (GP13), Boc-deprotection (0° C., 10 min.; rt, 2h30) of 1-chloro-3-ethyl-8-(3-trifluoromethyl-phenoxymethyl)-5,6-dihydro-8H-imidazo[1,5-a]pyrazine-7-carboxylic acid tert-butyl ester (0.403 g; 0.876 mmol) gave after purification by FC (DCM/MeOH/25% aq. NH$_4$OH=600/10/1) the expected product 1-chloro-3-ethyl-8-(3-trifluoromethyl-phenoxymethyl)-5,6,7,8-tetrahydro-imidazo[1,5-a]pyrazine as a yellow oil (0.182 g; 58%). LC-MS: $t_R$=0.74 min.; [M+H]$^+$=360.33 g/mol.

F Synthesis of electrophiles Z—CHPh-C(O)NHR$^4$

F.1 Synthesis of toluene-4-sulfonic acid (S)-methyl carbamoyl-phenyl-methyl ester (S)-2-hydroxy-N-methyl-2-phenyl-acetamide Methyl (S)-(+)-mandelate (17.000 g; 102.304 mmol) was dissolved in a 2.0 M solution of methylamine in MeOH (230 ml; 460 mmol) and kept at rt for 1 day. Another portion of methylamine in MeOH (10 ml; 20 mmol) was added. A third portion of methylamine in MeOH (10 ml; 20 mmol) was added one day later. After additional 24 h the reaction mixture was concentrated to dryness under reduced pressure to give the desired amide (S)-2-hydroxy-N-methyl-2-phenyl-acetamide as pale yellow crystals which were used without further purification.

LC-MS: $t_R$=0.52 min.; [M+H]$^+$=166 g/mol.

toluene-4-sulfonic acid
(S)-methylcarbamoyl-phenyl-methyl ester

DIPEA (2.74 ml; 16.005 mmol) and DMAP (145 mg; 1.186 mmol) were successively added at rt to a solution of (S)-2-hydroxy-N-methyl-2-phenyl-acetamide (2.400 g; 14.528 mmol) in DCM (50 ml). The mixture was treated portionwise with p-toluenesulfonyl chloride (2.770 g; 14.529 mmol) and stirred at rt for 2 h. The solvent was removed in vacuo and the residue was dissolved in EA. The organic solution was then washed twice with an aq. sat. NaHCO$_3$ solution and once with brine. The solvents were removed in vacuo and the residue was recrystallized from EA/tert.-butylmethylether to give the expected tosylate derivative toluene-4-sulfonic acid (S)-methylcarbamoyl-phenyl-methyl ester as colorless crystals. LC-MS: $t_R$=0.93 min.; [M+H]$^+$=320 g/mol.

G Synthesis of Compounds of Formula (I)

N-alkylation of
5,6,7,8-tetrahydro-imidazo[1,5-a]pyrazine
derivatives with tosylates [general procedure for
N-alkylation with electrophiles (GP14)]

To a solution of the respective 5,6,7,8-tetrahydro-imidazo[1,5-a]pyrazine derivative (1 mmol) in 2-butanone (6 ml) was added successively N-ethyldiisopropylamine (2 mmol), and the respective tosylate (1.1 mmol). The resulting mixture was heated at the indicated temperature for the given reaction time.

Example 1

(R)-2'-{1-chloro-3-ethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;

Prepared by reaction (80° C.; 48 h) of 1-chloro-3-ethyl-8-[2-(4-trifluoromethyl-phenyl)-ethyl]-5,6,7,8-tetrahydro-imidazo[1,5-a]pyrazine (89.6 mg; 0.250 mmol) with toluene-4-sulfonic acid (S)-methylcarbamoyl-phenyl-methyl ester (87.9 mg; 0.275 mmol) and subsequent separation of diastereoisomers by preparative HPLC. Yellow solid. LC-MS: $t_R$=0.91 min.; [M+H]$^+$=505.40 g/mol.

Example 2

(R)-2'-{1-chloro-(S)-8-[2-(3,5-difluoro-4-trifluoromethyl-phenyl)-ethyl]-3-ethyl-5,6-dihydro-8H-imidazo[1,5-a]pyrazin-7-yl}-N-methyl-2'-phenyl-acetamide Prepared by reaction (80° C.; 3 days) of 1-chloro-8-[2-(3,5-difluoro-4-trifluoromethyl-phenyl)-ethyl]-3-ethyl-5,6,7,8-tetrahydro-imidazo[1,5-a]pyrazine (70 mg; 0.178 mmol) with toluene-4-sulfonic acid (S)-methylcarbamoyl-phenyl-methyl ester (62.4 mg; 0.196 mmol) and subsequent separation of diastereoisomers by preparative HPLC. Pale yellow solid. LC-MS: $t_R$=0.95 min.; [M+H]$^+$=541.35 g/mol.

Example 3

(R)-2'-{1-chloro-(S)-8-[2-(2,4-difluoro-3-methyl-phenyl)-ethyl]-3-ethyl-5,6-dihydro-8H-imidazo[1,5-a]pyrazin-7-yl}-N-methyl-2'-phenyl-acetamide Prepared by reaction (70° C.; 3 days) of 1-chloro-8-[2-(2,4-difluoro-3-methyl-phenyl)-ethyl]-3-ethyl-5,6,7,8-tetrahydro-imidazo[1,5-a]pyrazine (90.1 mg; 0.265 mmol) with toluene-4-sulfonic acid (S)-methylcarbamoyl-phenyl-methyl ester (93 mg; 0.291 mmol) and subsequent separation of diastereoisomers by preparative HPLC. Colorless solid. LC-MS: $t_R$=0.90 min.; [M+H]$^+$=487.54 g/mol.

Example 4

(R)-2'-{1-chloro-(S)-8-[2-(3,5-difluoro-4-methyl-phenyl)-ethyl]-3-ethyl-5,6-dihydro-8H-imidazo[1,5-a]pyrazin-7-yl}-N-methyl-2'-phenyl-acetamide and
(R)-2'-{1-chloro-(R)-8-[2-(3,5-difluoro-4-methyl-phenyl)-ethyl]-3-ethyl-5,6-dihydro-8H-imidazo[1,5-a]pyrazin-7-yl}-N-methyl-2'-phenyl-acetamide Prepared by reaction (70° C.; 3 days) of 1-chloro-8-[2-(3,5-difluoro-4-methyl-phenyl)-ethyl]-3-ethyl-5,6,7,8-tetrahydro-imidazo[1,5-a]pyrazine (45.9 mg; 0.135 mmol) with toluene-4-sulfonic acid (S)-methylcarbamoyl-phenyl-methyl ester (47.4 mg; 0.148 mmol) and subsequent separation of diastereoisomers by preparative HPLC.

(R)-2'-{1-chloro-(S)-8-[2-(3,5-difluoro-4-methyl-phenyl)-ethyl]-3-ethyl-5,6-dihydro-8H-imidazo[1,5-a]pyrazin-7-yl}-N-methyl-2'-phenyl-acetamide: colorless solid. LC-MS: $t_R$=0.90 min.; [M+H]$^+$=487.54 g/mol.

(R)-2'-{1-chloro-(R)-8-[2-(3,5-difluoro-4-methyl-phenyl)-ethyl]-3-ethyl-5,6-dihydro-8H-imidazo[1,5-a]pyrazin-7-yl}-N-methyl-2'-phenyl-acetamide: colorless solid. LC-MS: $t_R$=0.92 min.; [M+H]$^+$=487.55 g/mol.

Example 5

(R)-2'-{1-chloro-3-ethyl-(S)-8-[2-(3-fluoro-4-trifluoromethyl-phenyl)-ethyl]-5,6-dihydro-8H-imidazo[1,5-a]pyrazin-7-yl}-N-methyl-2'-phenyl-acetamide and
(R)-2'-{1-chloro-3-ethyl-(R)-8-[2-(3-fluoro-4-trifluoromethyl-phenyl)-ethyl]-5,6-dihydro-8H-imidazo[1,5-a]pyrazin-7-yl}-N-methyl-2'-phenyl-acetamide Prepared by reaction (70° C.; 3 days) of 1-chloro-3-ethyl-8-[2-(3-fluoro-4-trifluoromethyl-phenyl)-ethyl]-5,6,7,8-tetrahydro-imidazo[1,5-a]pyrazine (71.1 mg; 0.189 mmol) with toluene-4-sulfonic acid (S)-methylcarbamoyl-phenyl-methyl ester (66.4 mg; 0.207 mmol) and subsequent separation of diastereoisomers by preparative HPLC.

(R)-2'-{1-chloro-3-ethyl-(S)-8-[2-(3-fluoro-4-trifluoromethyl-phenyl)-ethyl]-5,6-dihydro-8H-imidazo[1,5-a]pyrazin-7-yl}-N-methyl-2'-phenyl-acetamide: colorless solid. LC-MS: $t_R$=0.92 min.; [M+H]$^+$=523.52 g/mol.

(R)-2'-{1-chloro-3-ethyl-(R)-8-[2-(3-fluoro-4-trifluoromethyl-phenyl)-ethyl]-5,6-dihydro-8H-imidazo[1,5-a]

pyrazin-7-yl}-N-methyl-2'-phenyl-acetamide: colorless solid. LC-MS: $t_R$=0.94 min.; [M+H]$^+$=523.52 g/mol.

Example 6

(R)-2'-{1-chloro-8-[2-(3,4-dimethyl-phenyl)-ethyl]-3-ethyl-5,6-dihydro-8H-imidazo[1,5-a]pyrazin-7-yl}-N-methyl-2'-phenyl-acetamide Prepared by reaction (70° C.; 3 days) of 1-chloro-8-[2-(3,4-dimethyl-phenyl)-ethyl]-3-ethyl-5,6,7,8-tetrahydro-imidazo[1,5-a]pyrazine (88 mg; 0.276 mmol) with toluene-4-sulfonic acid (S)-methylcarbamoyl-phenyl-methyl ester (97 mg; 0.303 mmol). Purification by preparative HPLC afforded the mixture of 2 diastereoisomers. Colorless solid. LC-MS: $t_R$=0.89 min. and $t_R$=0.91 min.; [M+H]$^+$=465.59 g/mol.

Example 7

(R)-2'-{1-chloro-3-ethyl-(R)-8-[2-(3-fluoro-4-methyl-phenyl)-ethyl]-5,6-dihydro-8H-imidazo[1,5-a]pyrazin-7-yl}-N-methyl-2'-phenyl-acetamide and (R)-2'-{1-chloro-3-ethyl-8-[2-(3-fluoro-4-methyl-phenyl)-ethyl]-5,6-dihydro-8H-imidazo[1,5-a]pyrazin-7-yl}-N-methyl-2'-phenyl-acetamide Prepared by reaction (70° C.; 3 days) of 1-chloro-3-ethyl-8-[2-(3-fluoro-4-methyl-phenyl)-ethyl]-5,6,7,8-tetrahydro-imidazo[1,5-a]pyrazine (68.2 mg; 0.212 mmol) with toluene-4-sulfonic acid (S)-methylcarbamoyl-phenyl-methyl ester (74.4 mg; 0.232 mmol) and subsequent separation of diastereoisomers by preparative HPLC.

(R)-2'-{1-chloro-3-ethyl-(R)-8-[2-(3-fluoro-4-methyl-phenyl)-ethyl]-5,6-dihydro-8H-imidazo[1,5-a]pyrazin-7-yl}-N-methyl-2'-phenyl-acetamide: colorless solid. LC-MS: $t_R$=0.90 min.; [M+H]$^+$=469.53 g/mol.

Mixture of 2 diastereoisomers (R)-2'-{1-chloro-3-ethyl-8-[2-(3-fluoro-4-methyl-phenyl)-ethyl]-5,6-dihydro-8H-imidazo[1,5-a]pyrazin-7-yl}-N-methyl-2'-phenyl-acetamide: colorless solid. LC-MS: $t_R$=0.88 min. and $t_R$=0.90 min.; [M+H]$^+$=469.53 g/mol.

Example 8

(R)-2'-{1-chloro-3-ethyl-(S)-8-[2-(2-fluoro-4-trifluoromethyl-phenyl)-ethyl]-5,6-dihydro-8H-imidazo[1,5-a]pyrazin-7-yl}-N-methyl-2'-phenyl-acetamide and (R)-2'-{1-chloro-3-ethyl-(R)-8-[2-(2-fluoro-4-trifluoromethyl-phenyl)-ethyl]-5,6-dihydro-8H-imidazo[1,5-a]pyrazin-7-yl}-N-methyl-2'-phenyl-acetamide Prepared by reaction (70° C.; 3 days) of 1-chloro-3-ethyl-8-[2-(2-fluoro-4-trifluoromethyl-phenyl)-ethyl]-5,6,7,8-tetrahydro-imidazo[1,5-a]pyrazine (77.8 mg; 0.207 mmol) with toluene-4-sulfonic acid (S)-methylcarbamoyl-phenyl-methyl ester (72.7 mg; 0.227 mmol) and subsequent separation of diastereoisomers by preparative HPLC.

(R)-2'-{1-chloro-3-ethyl-(S)-8-[2-(2-fluoro-4-trifluoromethyl-phenyl)-ethyl]-5,6-dihydro-8H-imidazo[1,5-a]pyrazin-7-yl}-N-methyl-2'-phenyl-acetamide: colorless solid. LC-MS: $t_R$=0.92 min.; [M+H]$^+$=523.52 g/mol.

(R)-2'-{1-chloro-3-ethyl-(R)-8-[2-(2-fluoro-4-trifluoromethyl-phenyl)-ethyl]-5,6-dihydro-8H-imidazo[1,5-a]pyrazin-7-yl}-N-methyl-2'-phenyl-acetamide: colorless solid. LC-MS: $t_R$=0.94 min.; [M+H]$^+$=523.52 g/mol.

Example 9

(R)-2'-{1-chloro-8-[2-(3,4-difluoro-phenyl)-ethyl]-3-ethyl-5,6-dihydro-8H-imidazo[1,5-a]pyrazin-7-yl}-N-methyl-2'-phenyl-acetamide Prepared by reaction (70° C.; 3 days) of 1-chloro-8-[2-(3,4-difluoro-phenyl)-ethyl]-3-ethyl-5,6,7,8-tetrahydro-imidazo[1,5-a]pyrazine (44 mg; 0.135 mmol) with toluene-4-sulfonic acid (S)-methylcarbamoyl-phenyl-methyl ester (47.4 mg; 0.148 mmol). Purification by preparative HPLC afforded the mixture of 2 diastereoisomers: colorless solid. LC-MS: $t_R$=0.87 min. and $t_R$=0.89 min.; [M+H]$^+$=473.54 g/mol.

Example 10

(R)-2'-{1-chloro-(S)-8-[2-(3,5-difluoro-4-methyl-phenyl)-ethyl]-3-methyl-5,6-dihydro-8H-imidazo[1,5-a]pyrazin-7-yl}-N-methyl-2'-phenyl-acetamide and (R)-2'-{1-chloro-(R)-8-[2-(3,5-difluoro-4-methyl-phenyl)-ethyl]-3-methyl-5,6-dihydro-8H-imidazo[1,5-a]pyrazin-7-yl}-N-methyl-2'-phenyl-acetamide Prepared by reaction (80° C.; 3 days) of 1-chloro-8-[2-(3,5-difluoro-4-methyl-phenyl)-ethyl]-3-methyl-5,6,7,8-tetrahydro-imidazo[1,5-a]pyrazine (68 mg; 0.209 mmol) with toluene-4-sulfonic acid (S)-methylcarbamoyl-phenyl-methyl ester (73.3 mg; 0.230 mmol) and subsequent separation of diastereoisomers by preparative HPLC.

(R)-2'-{1-chloro-(S)-8-[2-(3,5-difluoro-4-methyl-phenyl)-ethyl]-3-methyl-5,6-dihydro-8H-imidazo[1,5-a]pyrazin-7-yl}-N-methyl-2'-phenyl-acetamide: colorless solid. LC-MS: $t_R$=0.88 min.; [M+H]$^+$=473.53 g/mol.

(R)-2'-{1-chloro-(R)-8-[2-(3,5-difluoro-4-methyl-phenyl)-ethyl]-3-methyl-5,6-dihydro-8H-imidazo[1,5-a]pyrazin-7-yl}-N-methyl-2'-phenyl-acetamide: colorless solid. LC-MS: $t_R$=0.90 min.; [M+H]$^+$=473.54 g/mol.

Example 11

(R)-2'-{1-chloro-8-[2-(3,4-dimethyl-phenyl)-ethyl]-3-methyl-5,6-dihydro-8H-imidazo[1,5-a]pyrazin-7-yl}-N-methyl-2'-phenyl-acetamide Prepared by reaction (80° C.; 3 days) of 1-chloro-8-[2-(3,4-dimethyl-phenyl)-ethyl]-3-methyl-5,6,7,8-tetrahydro-imidazo[1,5-a]pyrazine (61 mg; 0.201 mmol) with toluene-4-sulfonic acid (S)-methylcarbamoyl-phenyl-methyl ester (70.5 mg; 0.221 mmol). Purification by preparative HPLC afforded the mixture of 2 diastereoisomers: slightly beige solid. LC-MS: $t_R$=0.88 min. and $t_R$=0.89 min.; [M+H]$^+$=451.60 g/mol.

Example 12

(R)-2'-{1-chloro-3-methyl-8-[2-(4-trifluoromethyl-phenyl)-ethyl]-5,6-dihydro-8H-imidazo[1,5-a]pyrazin-7-yl}-N-methyl-2'-phenyl-acetamide Prepared by reaction (80° C.; 3 days) of 1-chloro-3-methyl-8-[2-(4-trifluoromethyl-phenyl)-ethyl]-5,6,7,8-tetrahydro-imidazo[1,5-a]pyrazine (15 mg; 0.044 mmol) with toluene-4-sulfonic acid (S)-methylcarbamoyl-phenyl-methyl ester (15.3 mg; 0.048 mmol). Purification by preparative HPLC afforded the mixture of 2 diastereoisomers: slightly beige solid. LC-MS: $t_R$=0.88 min. and $t_R$=0.89 min.; [M+H]$^+$=491.16 g/mol.

Example 13

(R)-2'-{1-chloro-3-isopropyl-(S)-8-[2-(4-trifluoromethyl-phenyl)-ethyl]-5,6-dihydro-8H-imidazo[1,5-a]pyrazin-7-yl}-N-methyl-2'-phenyl-acetamide and (R)-2'-{1-chloro-3-isopropyl-(R)-8-[2-(4-trifluoromethyl-phenyl)-ethyl]-5,6-dihydro-8H-imidazo[1,5-a]pyrazin-7-yl}-N-methyl-2'-phenyl-acetamide Prepared by reaction (70° C.; 3 days) of 1-chloro-3-isopropyl-8-[2-(4-trifluoromethyl-phenyl)-ethyl]-5,6,7,8-tetrahydro-imidazo[1,5-a]pyrazine (39.6 mg; 0.106 mmol) with toluene-4-sulfonic acid (S)-methylcarbamoyl-phenyl-methyl ester (37.4 mg; 0.117 mmol) and subsequent separation of diastereoisomers by preparative HPLC.

(R)-2'-{1-chloro-3-isopropyl-(S)-8-[2-(4-trifluoromethyl-phenyl)-ethyl]-5,6-dihydro-8H-imidazo[1,5-a]pyrazin-7-yl}-N-methyl-2'-phenyl-acetamide: colorless solid. LC-MS: $t_R$=0.93 min.; [M+H]$^+$=519.55 g/mol.

(R)-2'-{1-chloro-3-isopropyl-(R)-8-[2-(4-trifluoromethyl-phenyl)-ethyl]-5,6-dihydro-8H-imidazo[1,5-a]pyrazin-7-yl}-N-methyl-2'-phenyl-acetamide: colorless solid. LC-MS: $t_R$=0.95 min.; [M+H]$^+$=519.55 g/mol.

Example 14

(R)-2'-{3-isopropyl-1-methoxy-(S)-8-[2-(4-trifluoromethyl-phenyl)-ethyl]-5,6-dihydro-8H-imidazo[1,5-a]pyrazin-7-yl}-N-methyl-2'-phenyl-acetamide Prepared by reaction (70° C.; 3 days) of 3-isopropyl-1-methoxy-8-[2-(4-trifluoromethyl-phenyl)-ethyl]-5,6,7,8-tetrahydro-imidazo[1,5-a]pyrazine (45.6 mg; 0.124 mmol) with toluene-4-sulfonic acid (S)-methylcarbamoyl-phenyl-methyl ester (43.6 mg; 0.136 mmol) and subsequent separation of diastereoisomers by preparative HPLC. Colorless solid. LC-MS: $t_R$=0.87 min.; [M+H]$^+$=515.58 g/mol.

Example 15

(R)-2'-{3-ethyl-1-trifluoromethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide and (R)-2'-{3-ethyl-1-trifluoromethyl-(R)-8-[2-(4-trifluoromethyl-phenyl)-ethyl]-5,6-dihydro-8H-imidazo[1,5-a]pyrazin-7-yl}-N-methyl-2'-phenyl-acetamide Prepared by reaction (70° C.; 4 days) of 3-ethyl-1-trifluoromethyl-8-[2-(4-trifluoromethyl-phenyl)-ethyl]-5,6,7,8-tetrahydro-imidazo[1,5-a]pyrazine (121.6 mg; 0.311 mmol) with toluene-4-sulfonic acid (S)-methylcarbamoyl-phenyl-methyl ester (109.2 mg; 0.342 mmol) and subsequent separation of diastereoisomers by preparative HPLC.

(R)-2'-{3-ethyl-1-trifluoromethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide: slightly beige solid. LC-MS: $t_R$=1.00 min.; [M+H]$^+$=539.44 g/mol.

(R)-2'-{3-ethyl-1-trifluoromethyl-(R)-8-[2-(4-trifluoromethyl-phenyl)-ethyl]-5,6-dihydro-8H-imidazo[1,5-a]pyrazin-7-yl}-N-methyl-2'-phenyl-acetamide: slightly beige solid. LC-MS: $t_R$=1.02 min.; [M+H]$^+$=539.47 g/mol.

Example 16

(R)-2'-{1-chloro-3-methoxymethyl-8-[2-(4-trifluoromethyl-phenyl)-ethyl]-5,6-dihydro-8H-imidazo[1,5-a]pyrazin-7-yl}-N-methyl-2'-phenyl-acetamide Prepared by reaction (70° C.; 4 days) of 1-chloro-3-methoxymethyl-8-[2-(4-trifluoromethyl-phenyl)-ethyl]-5,6,7,8-tetrahydro-imidazo[1,5-a]pyrazine (190 mg; 0.508 mmol) with toluene-4-sulfonic acid (S)-methylcarbamoyl-phenyl-methyl ester (178.5 mg; 0.559 mmol). Purification by preparative HPLC afforded the mixture of 2 diastereoisomers: slightly beige solid. LC-MS: $t_R$=0.98 min., [M+H]$^+$=521.31 g/mol. and $t_R$=1.00 min., [M+H]$^+$=521.29 g/mol.

Example 17

(R)-2'-[1,3-dimethyl-8-(2-p-tolyl-ethyl)-5,6-dihydro-8H-imidazo[1,5-a]pyrazin-7-yl]-N-methyl-2'-phenyl-acetamide Prepared by reaction (80° C.; 16 h) of 1,3-dimethyl-8-(2-p-tolyl-ethyl)-5,6,7,8-tetrahydro-imidazo[1,5-a]pyrazine with toluene-4-sulfonic acid (S)-methylcarbamoyl-phenyl-methyl ester. Purification by preparative HPLC afforded the mixture of 2 diastereoisomers. LC-MS: $t_R$=0.83 min., [M+H]$^+$=417 g/mol.

Example 18

(R)-2'-{1,3-dimethyl-8-[2-(4-trifluoromethyl-phenyl)-ethyl]-5,6-dihydro-8H-imidazo[1,5-a]pyrazin-7-yl}-N-methyl-2'-phenyl-acetamide Prepared by reaction (80° C.; 16 h) of 1,3-dimethyl-8-[2-(4-trifluoromethyl-phenyl)-ethyl]-5,6,7,8-tetrahydro-imidazo[1,5-a]pyrazine with toluene-4-sulfonic acid (S)-methylcarbamoyl-phenyl-methyl ester. Purification by preparative HPLC afforded the mixture of 2 diastereoisomers. LC-MS: $t_R$=0.85 min., [M+H]$^+$=471 g/mol.

Example 19

(R)-2'-{8-[2-(3-chloro-phenyl)-ethyl]-1,3-dimethyl-5,6-dihydro-8H-imidazo[1,5-a]pyrazin-7-yl}-N-methyl-2'-phenyl-acetamide Prepared by reaction (80° C.; 16 h) of 8-[2-(3-chloro-phenyl)-ethyl]-1,3-dimethyl-5,6,7,8-tetrahydro-imidazo[1,5-a]pyrazine with toluene-4-sulfonic acid (S)-methylcarbamoyl-phenyl-methyl ester. Purification by preparative HPLC afforded the mixture of 2 diastereoisomers. LC-MS: $t_R$=0.84 min., [M+H]$^+$=437 g/mol.

Example 20

(R)-2'-{8-[2-(2,3-dimethyl-phenyl)-ethyl]-1,3-dimethyl-5,6-dihydro-8H-imidazo[1,5-a]pyrazin-7-yl}-N-methyl-2'-phenyl-acetamide Prepared by reaction (80° C.; 16 h) of 8-[2-(2,3-dimethyl-phenyl)-ethyl]-1,3-dimethyl-5,6,7,8-tetrahydro-imidazo[1,5-a]pyrazine with toluene-4-sulfonic acid (S)-methylcarbamoyl-phenyl-methyl ester. Purification by preparative HPLC afforded the mixture of 2 diastereoisomers. LC-MS: $t_R$=0.85 min., [M+H]$^+$=431 g/mol.

Example 21

(R)-2'-{8-[2-(2,4-dimethyl-phenyl)-ethyl]-1,3-dimethyl-5,6-dihydro-8H-imidazo[1,5-a]pyrazin-7-yl}-N-methyl-2'-phenyl-acetamide Prepared by reaction (80° C.; 16 h) of 8-[2-(2,4-dimethyl-phenyl)-ethyl]-1,3-dimethyl-5,6,7,8-tetrahydro-imidazo[1,5-a]pyrazine with toluene-4-sulfonic acid (S)-methylcarbamoyl-phenyl-methyl ester. Purification by preparative HPLC afforded the mixture of 2 diastereoisomers. LC-MS: $t_R$=0.85 min., [M+H]$^+$=431 g/mol.

Example 22

(R)-2'-{(S)-8-[2-(3,4-difluoro-phenyl)-ethyl]-1,3-dimethyl-5,6-dihydro-8H-imidazo[1,5-a]pyrazin-7-yl}-N-methyl-2'-phenyl-acetamide Prepared by reaction (80° C.; 16 h) of 8-[2-(3,4-difluoro-phenyl)-ethyl]-1,3-dimethyl-5,6,7,8-tetrahydro-imidazo[1,5-a]pyrazine with toluene-4-sulfonic acid (S)-methylcarbamoyl-phenyl-methyl ester. Purification by preparative HPLC afforded the pure stereoisomer. LC-MS: $t_R$=0.82 min., [M+H]$^+$=439 g/mol.

Example 23

(R)-2'-{8-[2-(2,4-dichloro-phenyl)-ethyl]-1,3-dimethyl-5,6-dihydro-8H-imidazo[1,5-a]pyrazin-7-yl}-N-methyl-2'-phenyl-acetamide Prepared by reaction (80° C.; 16 h) of 8-[2-(2,4-dichloro-phenyl)-ethyl]-1,3-dimethyl-5,6,7,8-tetrahydro-imidazo[1,5-a]pyrazine with toluene-4-sulfonic acid (S)-methylcarbamoyl-phenyl-methyl ester. Purification by preparative HPLC afforded the mixture of 2 diastereoisomers. LC-MS: $t_R$=0.86 min., [M+H]$^+$=471 g/mol.

Example 24

(R)-2'-{8-[2-(3-fluoro-4-methoxy-phenyl)-ethyl]-1,3-dimethyl-5,6-dihydro-8H-imidazo[1,5-a]pyrazin-7-yl}-N-methyl-2'-phenyl-acetamide Prepared by reaction (80° C.; 16 h) of 8-[2-(3-fluoro-4-methoxy-phenyl)-ethyl]-1,3-dimethyl-5,6,7,8-tetrahydro-imidazo[1,5-a]pyrazine with toluene-4-sulfonic acid (S)-methylcarbamoyl-phenyl-methyl ester. Purification by preparative HPLC afforded the mixture of 2 diastereoisomers. LC-MS: $t_R$=0.81 min., [M+H]$^+$=451 g/mol.

Example 25

(R)-2'-{8-[2-(2,4-dimethoxy-phenyl)-ethyl]-1,3-dimethyl-5,6-dihydro-8H-imidazo[1,5-a]pyrazin-7-yl}-N-methyl-2'-phenyl-acetamide Prepared by reaction (80° C.; 16 h) of 8-[2-(2,4-dimethoxy-phenyl)-ethyl]-1,3-dimethyl-5,6,7,8-tetrahydro-imidazo[1,5-a]pyrazine with toluene-4-sulfonic acid (S)-methylcarbamoyl-phenyl-methyl ester. Purification by preparative HPLC afforded the mixture of 2 diastereoisomers. LC-MS: $t_R$=0.81 min., [M+H]$^+$=463 g/mol.

Example 26

(R)-2'-{3-ethyl-1-methyl-(S)-8-[2-(4-trifluoromethyl-phenyl)-ethyl]-5,6-dihydro-8H-imidazo[1,5-a]pyrazin-7-yl}-N-methyl-2'-phenyl-acetamide Prepared by reaction (80° C.; 16 h) of 3-ethyl-1-methyl-8-[2-(4-trifluoromethyl-phenyl)-ethyl]-5,6,7,8-tetrahydro-imidazo[1,5-a]pyrazine with toluene-4-sulfonic acid (S)-methylcarbamoyl-phenyl-methyl ester. Separation of diastereoisomers by preparative HPLC. LC-MS: $t_R$=0.85 min., [M+H]$^+$=485 g/mol.

Example 27

(R)-2'-{(S)-8-[2-(3,4-dimethyl-phenyl)-ethyl]-3-ethyl-1-methoxy-5,6-dihydro-8H-imidazo[1,5-a]pyrazin-7-yl}-N-methyl-2'-phenyl-acetamide and (R)-2'-{(R)-8-[2-(3,4-dimethyl-phenyl)-ethyl]-3-ethyl-1-methoxy-5,6-dihydro-8H-imidazo[1,5-a]pyrazin-7-yl}-N-methyl-2'-phenyl-acetamide Prepared by reaction (80° C.; 4 days) of 8-[2-(3,4-dimethyl-phenyl)-ethyl]-3-ethyl-1-methoxy-5,6,7,8-tetrahydro-imidazo[1,5-a]pyrazine (189.2 mg; 0.604 mmol) with toluene-4-sulfonic acid (S)-methylcarbamoyl-phenyl-methyl ester (212 mg; 0.664 mmol) and subsequent separation of diastereoisomers by preparative HPLC.

(R)-2'-{(S)-8-[2-(3,4-dimethyl-phenyl)-ethyl]-3-ethyl-1-methoxy-5,6-dihydro-8H-imidazo[1,5-a]pyrazin-7-yl}-N-methyl-2'-phenyl-acetamide: colorless solid. LC-MS: $t_R$=0.85 min.; [M+H]$^+$=461.33 g/mol.

(R)-2'-{(R)-8-[2-(3,4-dimethyl-phenyl)-ethyl]-3-ethyl-1-methoxy-5,6-dihydro-8H-imidazo[1,5-a]pyrazin-7-yl}-N-methyl-2'-phenyl-acetamide: colorless solid. LC-MS: $t_R$=0.86 min.; [M+H]$^+$=461.35 g/mol.

Example 28

(R)-2'-{3-ethyl-(S)-8-[2-(4-trifluoromethyl-phenyl)-ethyl]-1-vinyl-5,6-dihydro-8H-imidazo[1,5-a]pyrazin-7-yl}-N-methyl-2'-phenyl-acetamide Prepared by reaction of 3-ethyl-8-[2-(4-trifluoromethyl-phenyl)-ethyl]-1-vinyl-5,6,7,8-tetrahydro-imidazo[1,5-a]pyrazine with toluene-4-sulfonic acid (S)-methylcarbamoyl-phenyl-methyl ester and subsequent separation of diastereoisomers by preparative HPLC. LC-MS: $t_R$=0.88 min., [M+H]$^+$=497.47 g/mol.

Example 29

(R)-2'-{3-ethyl-1-iodo-8-[2-(4-trifluoromethyl-phenyl)-ethyl]-5,6-dihydro-8H-imidazo[1,5-a]pyrazin-7-yl}-N-methyl-2'-phenyl-acetamide Prepared by Boc-deprotection of 3-ethyl-1-iodo-8-[2-(4-trifluoromethyl-phenyl)-ethyl]-5,6-dihydro-8H-imidazo[1,5-a]pyrazine-7-carboxylic acid tert-butyl ester and subsequent reaction of 3-ethyl-1-iodo-8-[2-(4-trifluoromethyl-phenyl)-ethyl]-5,6,7,8-tetrahydro-imidazo[1,5-a]pyrazine with toluene-4-sulfonic acid (S)-methylcarbamoyl-phenylmethyl ester. Purification by preparative HPLC afforded the mixture of 2 diastereoisomers. LC-MS: $t_R$=0.87 min., [M+H]$^+$=597 g/mol.

Example 30

(R)-2'-{1-cyano-3-ethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide and (R)-2'-{1-cyano-3-ethyl-(R)-8-[2-(4-trifluoromethyl-phenyl)-ethyl]-5,6-dihydro-8H-imidazo[1,5-a]pyrazin-7-yl}-N-methyl-2'-phenyl-acetamide Prepared by reaction (80° C.; 16 h) of 3-ethyl-8-[2-(4-trifluoromethyl-phenyl)-ethyl]-5,6,7,8-tetrahydro-imidazo[1,5-a]pyrazine-1-carbonitrile (2.000 g; 5.741 mmol) with toluene-4-sulfonic acid (S)-methylcarbamoyl-phenyl-methyl ester (1.833 g; 5.741 mmol) and subsequent separation of diastereoisomers by preparative HPLC.

(R)-2'-{1-cyano-3-ethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide: colorless solid. LC-MS: $t_R$=0.99 min.; [M+H]$^+$=496.43 g/mol.

(R)-2'-{1-cyano-3-ethyl-(R)-8-[2-(4-trifluoromethyl-phenyl)-ethyl]-5,6-dihydro-8H-imidazo[1,5-a]pyrazin-7-yl}-N-methyl-2'-phenyl-acetamide: colorless solid. LC-MS: $t_R$=1.01 min.; [M+H]$^+$=496.49 g/mol.

Example 31

(R)-2'-{3-ethyl-1-hydroxymethyl-8-[2-(4-trifluoromethyl-phenyl)-ethyl]-5,6-dihydro-8H-imidazo[1,5-a]pyrazin-7-yl}-N-methyl-2'-phenyl-acetamide Prepared by reaction of {3-ethyl-8-[2-(4-trifluoromethyl-phenyl)-ethyl]-5,6,7,8-tetrahydro-imidazo[1,5-a]pyrazin-1-yl}-methanol with toluene-4-sulfonic acid (S)-methylcarbamoyl-phenyl-methyl ester. Purification by preparative HPLC afforded the mixture of 2 diastereoisomers. LC-MS: $t_R$=0.84 min., [M+H]$^+$=501.52 g/mol.

Example 32

3-ethyl-7-(methylcarbamoyl-phenyl-methyl)-8-[2-(4-trifluoromethyl-phenyl)-ethyl]-5,6,7,8-tetrahydro-imidazo[1,5-a]pyrazine-1-carboxylic acid methylamide Prepared by reaction of 3-ethyl-8-[2-(4-trifluoromethyl-phenyl)-ethyl]-5,6,7,8-tetrahydro-imidazo[1,5-a]pyrazine-1-carboxylic acid methylamide (22 mg; 0.057 mmol) with toluene-4-sulfonic acid (S)-methylcarbamoyl-phenyl-methyl ester. Purification by preparative HPLC afforded the mixture of 2 diastereoisomers. LC-MS: $t_R$=0.86 min., [M+H]$^+$=528.45 g/mol.

Example 33

(R)-2'-{1,3-dichloro-8-[2-(4-trifluoromethyl-phenyl)-ethyl]-5,6-dihydro-8H-imidazo[1,5-a]pyrazin-7-yl}-N-methyl-2'-phenyl-acetamide Prepared by reaction (80° C.; 4 days) of 1,3-dichloro-8-[2-(4-trifluoromethyl-phenyl)-ethyl]-5,6,7,8-tetrahydro-imidazo[1,5-a]pyrazine (122 mg; 0.335 mmol) with toluene-4-sulfonic acid (S)-methylcarbamoyl-phenyl-methyl ester (117 mg; 0.368 mmol). Purification by preparative HPLC afforded the mixture of 2 diastereoisomers.

(R)-2'-{1,3-dichloro-8-[2-(4-trifluoromethyl-phenyl)-ethyl]-5,6-dihydro-8H-imidazo[1,5-a]pyrazin-7-yl}-N-methyl-2'-phenyl-acetamide: yellow solid. LC-MS: $t_R$=1.04 min. and $t_R$=1.06 min.; [M+H]$^+$=511.19 g/mol.

Example 34

(R)-2'-{1-chloro-3-ethyl-(S)-8-[2-(3,4,5-trifluoro-phenyl)-ethyl]-5,6-dihydro-8H-imidazo[1,5-a]pyrazin-7-yl}-N-methyl-2'-phenyl-acetamide Prepared by reaction (80° C.; 4 days) of 1-chloro-3-ethyl-8-[2-(3,4,5-trifluoro-phenyl)-ethyl]-5,6,7,8-tetrahydro-imidazo[1,5-a]pyrazine (939 mg; 2.731 mmol) with toluene-4-sulfonic acid (S)-methylcarbamoyl-phenyl-methyl ester. Purification by FC (DCM/MeOH, 25/1) afforded the target compound.

(R)-2'-{1-chloro-3-ethyl-(S)-8-[2-(3,4,5-trifluoro-phenyl)-ethyl]-5,6-dihydro-8H-imidazo[1,5-a]pyrazin-7-yl}-N-methyl-2'-phenyl-acetamide: yellow solid. LC-MS: $t_R$=0.94 min.; [M+H]$^+$=491.05 g/mol.

Example 35

(R)-2'-{1-chloro-(S)-8-[2-(3-fluoro-4-trifluoromethyl-phenyl)-ethyl]-3-methyl-5,6-dihydro-8H-imidazo[1,5-a]pyrazin-7-yl}-N-methyl-2'-phenyl-acetamide Prepared by reaction (80° C.; 2 days) of 1-chloro-8-[2-(3-fluoro-4-trifluoromethyl-phenyl)-ethyl]-3-methyl-5,6,7,8-tetrahydro-imidazo[1,5-a]pyrazine (5.450 g; 15.065 mmol) with toluene-4-sulfonic acid (S)-methylcarbamoyl-phenyl-methyl ester (5.292 g; 16.571 mmol). Purification by FC (DCM/MeOH, 50/1) afforded the target compound.

(R)-2'-{1-chloro-(S)-8-[2-(3-fluoro-4-trifluoromethyl-phenyl)-ethyl]-3-methyl-5,6-dihydro-8H-imidazo[1,5-a]pyrazin-7-yl}-N-methyl-2'-phenyl-acetamide: beige solid. LC-MS: $t_R$=0.95 min.; [M+H]$^+$=508.96 g/mol.

Example 36

(R)-2'-{1-chloro-(S)-8-[2-(3,5-difluoro-4-methoxy-phenyl)-ethyl]-3-ethyl-5,6-dihydro-8H-imidazo[1,5-a]pyrazin-7-yl}-N-methyl-2'-phenyl-acetamide Prepared by reaction (80° C.; 4 days) of 1-chloro-8-[2-(3,5-difluoro-4-methoxy-phenyl)-ethyl]-3-ethyl-5,6,7,8-tetrahydro-imidazo[1,5-a]pyrazine (0.569 g; 1.599 mmol) with toluene-4-sulfonic acid (S)-methylcarbamoyl-phenyl-methyl ester. Purification by FC (DCM/MeOH, 25/1) afforded the target compound.

(R)-2'-{1-chloro-(S)-8-[2-(3,5-difluoro-4-methoxy-phenyl)-ethyl]-3-ethyl-5,6-dihydro-8H-imidazo[1,5-a]pyrazin-7-yl}-N-methyl-2'-phenyl-acetamide: yellow solid. LC-MS: $t_R$=0.92 min.; [M+H]$^+$=503.00 g/mol.

Example 37

(R)-2'-{1-chloro-(S)-8-[2-(4-chloro-3,5-difluoro-phenyl)-ethyl]-3-ethyl-5,6-dihydro-8H-imidazo[1,5-a]pyrazin-7-yl}-N-methyl-2'-phenyl-acetamide Prepared by reaction (80° C.; 3 days) of 1-chloro-8-[2-(4-chloro-3,5-difluoro-phenyl)-ethyl]-3-ethyl-5,6,7,8-tetrahydro-imidazo[1,5-a]pyrazine (0.567 g; 1.574 mmol) with toluene-4-sulfonic acid (S)-methylcarbamoyl-phenyl-methyl ester. Purification by FC (DCM/MeOH, 25/1) afforded the target compound.

(R)-2'-{1-chloro-(S)-8-[2-(4-chloro-3,5-difluoro-phenyl)-ethyl]-3-ethyl-5,6-dihydro-8H-imidazo[1,5-a]pyrazin-7-yl}-N-methyl-2'-phenyl-acetamide: yellow solid. LC-MS: $t_R$=0.96 min.; $[M+H]^+$=506.97 g/mol.

Example 38

(R)-2'-{1-chloro-(S)-8-[2-(3-chloro-4-trifluoromethyl-phenyl)-ethyl]-3-ethyl-5,6-dihydro-8H-imidazo[1,5-a]pyrazin-7-yl}-N-methyl-2'-phenyl-acetamide Prepared by reaction (70° C.; 3 days) of 1-chloro-8-[2-(3-chloro-4-trifluoromethyl-phenyl)-ethyl]-3-ethyl-5,6,7,8-tetrahydro-imidazo[1,5-a]pyrazine (0.508 g; 1.295 mmol) with toluene-4-sulfonic acid (S)-methylcarbamoyl-phenyl-methyl ester. Purification by FC (DCM/MeOH, 50/1) afforded the target compound.

(R)-2'-{1-chloro-(S)-8-[2-(3-chloro-4-trifluoromethyl-phenyl)-ethyl]-3-ethyl-5,6-dihydro-8H-imidazo[1,5-a]pyrazin-7-yl}-N-methyl-2'-phenyl-acetamide: slightly beige solid. LC-MS: $t_R$=0.98 min.; $[M+H]^+$=538.96 g/mol.

Example 39

(R)-2'-{1-chloro-(S)-8-[2-(2,5-difluoro-4-trifluoromethyl-phenyl)-ethyl]-3-ethyl-5,6-dihydro-8H-imidazo[1,5-a]pyrazin-7-yl}-N-methyl-2'-phenyl-acetamide Prepared by reaction (75° C.; 91h30) of 1-chloro-8-[2-(2,5-difluoro-4-trifluoromethyl-phenyl)-ethyl]-3-ethyl-5,6,7,8-tetrahydro-imidazo[1,5-a]pyrazine (0.518 g; 1.315 mmol) with toluene-4-sulfonic acid (S)-methylcarbamoyl-phenyl-methyl ester (0.462 g; 1.447 mmol). Purification by FC (DCM/MeOH, 50/1) afforded the target compound.

(R)-2'-{1-chloro-(S)-8-[2-(2,5-difluoro-4-trifluoromethyl-phenyl)-ethyl]-3-ethyl-5,6-dihydro-8H-imidazo[1,5-a]pyrazin-7-yl}-N-methyl-2'-phenyl-acetamide: slightly beige solid. LC-MS: $t_R$=0.98 min.; $[M+H]^+$=540.91 g/mol.

Example 40

(R)-2'-{1-chloro-3-ethyl-(S)-8-[2-(4-trifluoromethoxy-phenyl)-ethyl]-5,6-dihydro-8H-imidazo[1,5-a]pyrazin-7-yl}-N-methyl-2'-phenyl-acetamide Prepared by reaction (75° C.; 70h30) of 1-chloro-3-ethyl-8-[2-(4-trifluoromethoxy-phenyl)-ethyl]-5,6,7,8-tetrahydro-imidazo[1,5-a]pyrazine (0.215 g; 0.575 mmol) with toluene-4-sulfonic acid (S)-methylcarbamoyl-phenyl-methyl ester (0.202 g; 0.633 mmol). Purification by FC (DCM/MeOH, 50/1) afforded the target compound.

(R)-2'-{1-chloro-3-ethyl-(S)-8-[2-(4-trifluoromethoxy-phenyl)-ethyl]-5,6-dihydro-8H-imidazo[1,5-a]pyrazin-7-yl}-N-methyl-2'-phenyl-acetamide: slightly beige solid. LC-MS: $t_R$=0.96 min.; $[M+H]^+$=520.94 g/mol.

Example 41

(R)-2'-{1-chloro-(S)-8-[2-(4-cyano-phenyl)-ethyl]-3-ethyl-5,6-dihydro-8H-imidazo[1,5-a]pyrazin-7-yl}-N-methyl-2'-phenyl-acetamide Prepared by reaction (80° C.; 4 days) of 4-[2-(1-chloro-3-ethyl-5,6,7,8-tetrahydro-imidazo[1,5-a]pyrazin-8-yl)-ethyl] benzonitrile (0.383 g; 1.217 mmol) with toluene-4-sulfonic acid (S)-methylcarbamoyl-phenyl-methyl ester. Purification by FC (DCM/MeOH, 50/1) afforded the target compound.

(R)-2'-{1-chloro-(S)-8-[2-(4-cyano-phenyl)-ethyl]-3-ethyl-5,6-dihydro-8H-imidazo[1,5-a]pyrazin-7-yl}-N-methyl-2'-phenyl-acetamide: slightly beige solid. LC-MS: $t_R$=0.84 min.; $[M+H]^+$=462.16 g/mol.

Example 42

(R)-2'-{1-cyano-3-ethyl-(S)-8-[2-(3-fluoro-4-trifluoromethyl-phenyl)-ethyl]-5,6-dihydro-8H-imidazo[1,5-a]pyrazin-7-yl}-N-methyl-2'-phenyl-acetamide Prepared by reaction (80° C.; 6 days) of 3-ethyl-8-[2-(3-fluoro-4-trifluoromethyl-phenyl)-ethyl]-5,6,7,8-tetrahydro-imidazo[1,5-a]pyrazine-1-carbonitrile (0.141 g; 0.387 mmol) with toluene-4-sulfonic acid (S)-methylcarbamoyl-phenyl-methyl ester (0.135 g; 0.426 mmol. Purification by preparative HPLC afforded the target compound.

(R)-2'-{1-cyano-3-ethyl-(S)-8-[2-(3-fluoro-4-trifluoromethyl-phenyl)-ethyl]-5,6-dihydro-8H-imidazo[1,5-a]pyrazin-7-yl}-N-methyl-2'-phenyl-acetamide: beige solid. LC-MS: $t_R$=1.04 min.; $[M+H]^+$=514.19 g/mol.

Example 43

(R)-2'-{1-cyano-(S)-8-[2-(3-fluoro-4-trifluoromethyl-phenyl)-ethyl]-3-methyl-5,6-dihydro-8H-imidazo[1,5-a]pyrazin-7-yl}-N-methyl-2'-phenyl-acetamide Prepared by reaction (80° C.; 6 days) of 8-[2-(3-fluoro-4-trifluoromethyl-phenyl)-ethyl]-3-methyl-5,6,7,8-tetrahydro-imidazo[1,5-a]pyrazine-1-carbonitrile (0.195 g; 0.553 mmol) with toluene-4-sulfonic acid (S)-methylcarbamoyl-phenyl-methyl ester (0.194 g; 0.609 mmol). Purification by preparative HPLC afforded the target compound.

(R)-2'-{1-cyano-(S)-8-[2-(3-fluoro-4-trifluoromethyl-phenyl)-ethyl]-3-methyl-5,6-dihydro-8H-imidazo[1,5-a]pyrazin-7-yl}-N-methyl-2'-phenyl-acetamide: yellow solid. LC-MS: $t_R$=0.85 min.; $[M+H]^+$=500.39 g/mol.

Example 44

(R)-2'-{1-chloro-3-propyl-(S)-8-[2-(4-trifluoromethyl-phenyl)-ethyl]-5,6-dihydro-8H-imidazo[1,5-a]pyrazin-7-yl}-N-methyl-2'-phenyl-acetamide Prepared by reaction (70° C.; 3 days) of 1-chloro-3-propyl-8-[2-(4-trifluoromethyl-phenyl)-ethyl]-5,6,7,8-tetrahydro-imidazo[1,5-a]pyrazine (1.220 g; 3.281 mmol) with toluene-4-sulfonic acid (S)-methylcarbamoyl-phenyl-methyl ester. Purification by FC (DCM/MeOH, 50/1) afforded the target compound.

(R)-2'-{1-chloro-3-propyl-(S)-8-[2-(4-trifluoromethyl-phenyl)-ethyl]-5,6-dihydro-8H-imidazo[1,5-a]pyrazin-7-yl}-N-methyl-2'-phenyl-acetamide: yellow solid. LC-MS: $t_R$=0.98 min.; $[M+H]^+$=518.91 g/mol.

Example 45

(R)-2'-{1-chloro-(S)-8-[2-(3-fluoro-4-trifluoromethyl-phenyl)-ethyl]-3-propyl-5,6-dihydro-8H-imidazo[1,5-a]pyrazin-7-yl}-N-methyl-2'-phenyl-acetamide Prepared by reaction (70° C.; 3 days) of 1-chloro-8-[2-(3-fluoro-4-trifluoromethyl-phenyl)-ethyl]-3-propyl-5,6,7,8- tetrahydro-imidazo[1,5-a]pyrazine (0.899 g; 2.306 mmol) with toluene-4-sulfonic acid (S)-methylcarbamoyl-phenyl-methyl ester. Purification by FC (DCM/MeOH, 50/1) afforded the target compound.

(R)-2'-{1-chloro-(S)-8-[2-(3-fluoro-4-trifluoromethyl-phenyl)-ethyl]-3-propyl-5,6-dihydro-8H-imidazo[1,5-a]pyrazin-7-yl}-N-methyl-2'-phenyl-acetamide: yellow solid. LC-MS: $t_R$=0.99 min.; [M+H]$^+$=536.93 g/mol.

Example 46

(R)-2'-{1-cyclopropyl-3-methyl-(S)-8-[2-(4-trifluoromethyl-phenyl)-ethyl]-5,6-dihydro-8H-imidazo[1,5-a]pyrazin-7-yl}-N-methyl-2'-phenyl-acetamide Prepared by reaction (70° C.; 4 days) of 1-cyclopropyl-3-methyl-8-[2-(4-trifluoromethyl-phenyl)-ethyl]-5,6,7,8-tetrahydro-imidazo[1,5-a]pyrazine (0.186 g; 0.532 mmol) with toluene-4-sulfonic acid (S)-methylcarbamoyl-phenyl-methyl ester (0.187 g; 0.586 mmol). Purification by preparative HPLC afforded the target compound.

(R)-2'-{1-cyclopropyl-3-methyl-(S)-8-[2-(4-trifluoromethyl-phenyl)-ethyl]-5,6-dihydro-8H-imidazo[1,5-a]pyrazin-7-yl}-N-methyl-2'-phenyl-acetamide: slightly beige solid. LC-MS: $t_R$=0.88 min.; [M+H]$^+$=497.45 g/mol.

Example 47

(R)-2'-{1-chloro-3-ethyl-8-[2-(2,3,5-trifluoro-phenyl)-ethyl]-5,6-dihydro-8H-imidazo[1,5-a]pyrazin-7-yl}-N-methyl-2'-phenyl-acetamide Prepared by reaction (80° C.; 4 days) of 1-chloro-3-ethyl-8-[2-(2,3,5-trifluoro-phenyl)-ethyl]-5,6,7,8-tetrahydro-imidazo[1,5-a]pyrazine (0.277 g; 0.806 mmol) with toluene-4-sulfonic acid (S)-methylcarbamoyl-phenyl-methyl ester (0.283 g; 0.886 mmol). Purification by preparative HPLC afforded the mixture of epimers.

(R)-2'-{1-chloro-3-ethyl-8-[2-(2,3,5-trifluoro-phenyl)-ethyl]-5,6-dihydro-8H-imidazo[1,5-a]pyrazin-7-yl}-N-methyl-2'-phenyl-acetamide: pale yellow solid. LC-MS: $t_R$=0.87 min., and $t_R$=0.90 min.; [M+H]$^+$=491.27 g/mol.

Example 48

(R)-2'-{1-chloro-3-ethyl-(S)-8-[2-(3-fluoro-4-methoxy-phenyl)-ethyl]-5,6-dihydro-8H-imidazo[1,5-a]pyrazin-7-yl}-N-methyl-2'-phenyl-acetamide Prepared by reaction (80° C.; 3 days) of 1-chloro-3-ethyl-8-[2-(3-fluoro-4-methoxy-phenyl)-ethyl]-5,6,7,8-tetrahydro-imidazo[1,5-a]pyrazine (1.380 g; 4.085 mmol) with toluene-4-sulfonic acid (S)-methylcarbamoyl-phenyl-methyl ester. Purification by FC (DCM/MeOH, 25/1) afforded the target compound.

(R)-2'-{1-chloro-3-ethyl-(S)-8-[2-(3-fluoro-4-methoxy-phenyl)-ethyl]-5,6-dihydro-8H-imidazo[1,5-a]pyrazin-7-yl}-N-methyl-2'-phenyl-acetamide: yellow solid. LC-MS: $t_R$=0.89 min.; [M+H]$^+$=485.02 g/mol.

Example 49

(R)-2'-{1-chloro-(S)-8-[2-(2,5-difluoro-4-methoxy-phenyl)-ethyl]-3-ethyl-5,6-dihydro-8H-imidazo[1,5-a]pyrazin-7-yl}-N-methyl-2'-phenyl-acetamide Prepared by reaction (80° C.; 3 days) of 1-chloro-8-[2-(2,5-difluoro-4-methoxy-phenyl)-ethyl]-3-ethyl-5,6,7,8-tetrahydro-imidazo[1,5-a]pyrazine (1.240 g; 3.485 mmol) with toluene-4-sulfonic acid (S)-methylcarbamoyl-phenyl-methyl ester. Purification by FC (DCM/MeOH, 100/1) afforded the target compound.

(R)-2'-{1-chloro-(S)-8-[2-(2,5-difluoro-4-methoxy-phenyl)-ethyl]-3-ethyl-5,6-dihydro-8H-imidazo[1,5-a]pyrazin-7-yl}-N-methyl-2'-phenyl-acetamide: yellow solid. LC-MS: $t_R$=0.91 min.; [M+H]$^+$=502.94 g/mol.

Example 50

(R)-2'-[1-chloro-3-ethyl-(R)-8-(4-fluoro-3-trifluoromethyl-phenoxymethyl)-5,6-dihydro-8H-imidazo[1,5-a]pyrazin-7-yl]-N-methyl-2'-phenyl-acetamide Prepared by reaction (70° C.; 4 days) of 1-chloro-3-ethyl-8-(4-fluoro-3-trifluoromethyl-phenoxymethyl)-5,6,7,8-tetrahydro-imidazo[1,5-a]pyrazine (0.117 g; 0.310 mmol) with toluene-4-sulfonic acid (S)-methylcarbamoyl-phenyl-methyl ester (0.108 g; 0.341 mmol). Purification by FC (DCM/MeOH, 50/1) afforded the target compound.

(R)-2'-[1-chloro-3-ethyl-(R)-8-(4-fluoro-3-trifluoromethyl-phenoxymethyl)-5,6-dihydro-8H-imidazo[1,5-a]pyrazin-7-yl]-N-methyl-2'-phenyl-acetamide: slightly beige solid. LC-MS: $t_R$=0.92 min.; [M+H]$^+$=525.22 g/mol.

Example 51

(R)-2'-[1-chloro-3-ethyl-(R)-8-(4-trifluoromethyl-phenoxymethyl)-5,6-dihydro-8H-imidazo[1,5-a]pyrazin-7-yl]-N-methyl-2'-phenyl-acetamide Prepared by reaction (70° C.; 4 days) of 1-chloro-3-ethyl-8-(4-trifluoromethyl-phenoxymethyl)-5,6,7,8-tetrahydro-imidazo[1,5-a]pyrazine (0.257 g; 0.714 mmol) with toluene-4-sulfonic acid (S)-methylcarbamoyl-phenyl-methyl ester (0.250 g; 0.786 mmol). Purification by preparative HPLC afforded the target compound.

(R)-2'-[1-chloro-3-ethyl-(R)-8-(4-trifluoromethyl-phenoxymethyl)-5,6-dihydro-8H-imidazo[1,5-a]pyrazin-7-yl]-N-methyl-2'-phenyl-acetamide: slightly beige solid. LC-MS: $t_R$=0.90 min.; [M+H]$^+$=507.25 g/mol.

Example 52

(R)-2'-[1-chloro-(R)-8-(3,4-dimethyl-phenoxymethyl)-3-ethyl-5,6-dihydro-8H-imidazo[1,5-a]pyrazin-7-yl]-N-methyl-2'-phenyl-acetamide Prepared by reaction (80° C.; 4.5 days) of 1-chloro-8-(3,4-dimethyl-phenoxymethyl)-3-ethyl-5,6,7,8-tetrahydro-imidazo[1,5-a]pyrazine (0.240 g; 0.750 mmol) with toluene-4-sulfonic acid (S)-methylcarbamoyl-phenyl-methyl ester (0.263 g; 0.825 mmol). Purification by preparative HPLC afforded the target compound.

(R)-2'-[1-chloro-(R)-8-(3,4-dimethyl-phenoxymethyl)-3-ethyl-5,6-dihydro-8H-imidazo[1,5-a]pyrazin-7-yl]-N-methyl-2'-phenyl-acetamide: pale yellow solid. LC-MS: $t_R$=0.88 min.; [M+H]$^+$=467.41 g/mol.

Example 53

(R)-2'-[1-chloro-3-ethyl-(R)-8-(3-trifluoromethyl-phenoxymethyl)-5,6-dihydro-8H-imidazo[1,5-a]pyrazin-7-yl]-N-methyl-2'-phenyl-acetamide Prepared by reaction (70° C.; 4 days) of 1-chloro-3-ethyl-8-(3-trifluoromethyl-phenoxymethyl)-5,6,7,8-tetrahydroimidazo[1,5-a]pyrazine (0.182 g; 0.506 mmol) with toluene-4-sulfonic acid (S)-methylcarbamoyl-phenyl-methyl ester (0.177 g; 0.556 mmol). Purification by preparative HPLC afforded the target compound.

(R)-2'-[1-chloro-3-ethyl-(R)-8-(3-trifluoromethyl-phenoxymethyl)-5,6-dihydro-8H-imidazo[1,5-a]pyrazin-7-yl]-N-methyl-2'-phenyl-acetamide: slightly beige solid. LC-MS: $t_R$=0.91 min.; [M+H]$^+$=507.25 g/mol.

II. BIOLOGICAL ASSAYS

In Vitro Assay

The orexin receptor antagonistic activity of the compounds of formula (I) and formula (II) is determined in accordance with the following experimental method.

Experimental Method

Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 μg/ml G418, 100 U/ml penicillin, 100 μg/ml streptomycin and 10% inactivated fetal calf serum (FCS). The cells are seeded at 80,000 cells/well into 96-well black clear bottom sterile plates (Costar) which have been precoated with 1% gelatine in Hanks' Balanced Salt Solution (HBSS). All reagents are from Gibco BRL. The seeded plates are incubated overnight at 37° C. in 5% $CO_2$.

Human orexin-A as an agonist is prepared as 1 mM stock solution in MeOH:water (1:1), diluted in HBSS containing 0.1% bovine serum albumin (BSA) and 2 mM HEPES for use in the assay at a final concentration of 10 nM.

Antagonists are prepared as 10 mM stock solution in DMSO, then diluted in 96-well plates, first in DMSO, then in HBSS containing 0.1% bovine serum albumin (BSA) and 2 mM HEPES.

On the day of the assay, 100 μl of loading medium (HBSS containing 1% FCS, 2 mM HEPES, 5 mM probenecid (Sigma) and 3 μM of the fluorescent calcium indicator fluo-3 AM (1 mM stock solution in DMSO with 10% pluronic acid) (Molecular Probes) is added to each well.

The 96-well plates are incubated for 60 min at 37° C. in 5% $CO_2$. The loading solution is then aspirated and cells are washed 3 times with 200 μl HBSS containing 2.5 mM probenecid, 0.1% BSA, 2 mM HEPES. 100 μl of that same buffer is left in each well.

Within the Fluorescent Imaging Plate Reader (FLIPR, Molecular Devices), antagonists are added to the plate in a volume of 50 μl, incubated for 20 min and finally 100 μl of agonist is added. Fluorescence is measured for each well at 1 second intervals, and the height of each fluorescence peak is compared to the height of the fluorescence peak induced by 10 nM orexin-A with buffer in place of antagonist. For each antagonist, $IC_{50}$ value (the concentration of compound needed to inhibit 50% of the agonistic response) is determined. Antagonistic activities ($IC_{50}$ values) of all exemplified compounds are below 1000 nM with respect to the $OX_1$ and/or the $OX_2$ receptor. $IC_{50}$ values of 51 exemplified compounds are in the range of 5-8671 nM with an average of 691 nM with respect to the $OX_1$ receptor. $IC_{50}$ values of all exemplified compounds are in the range of 2-396 nM with an average of 42 nM with respect to the $OX_2$ receptor. Antagonistic activities of selected compounds are displayed in Table 1.

TABLE 1

Antagonistic activities of compounds with respect to $OX_1$ and $OX_2$ receptors.

| Compound of Example (absolute configuration) | $OX_1$ $IC_{50}$ (in nM) | $OX_2$ $IC_{50}$ (in nM) |
|---|---|---|
| 10 (8R; 2'R) | 72 | 14 |
| 11 (8S; 2'R)/(8R; 2'R) | 36 | 11 |
| 15 (8S; 2'R) | 807 | 15 |
| 16 (8S; 2'R)/(8R; 2'R) | 2064 | 33 |
| 25 (8S; 2'R)/(8R; 2'R) | 10000 | 115 |
| 27 (8S; 2'R) | 5 | 4 |
| 28 (8S; 2'R) | 176 | 29 |
| 33 (8S; 2'R)/(8R; 2'R) | 279 | 11 |
| 36 (8S; 2'R) | 17 | 14 |
| 43 (8S; 2'R) | 538 | 14 |
| 46 (8S; 2'R) | 762 | 21 |
| 53 (8R; 2'R) | 412 | 2 |

The invention claimed is:

1. A compound of formula (II):

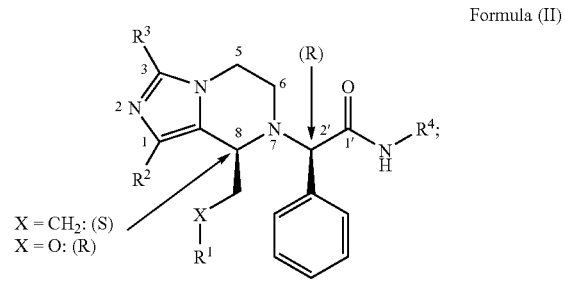

wherein
X represents $CH_2$ or O;
$R^1$ represents a phenyl group, which group is independently mono-, di-, or tri-substituted wherein the substituents are independently selected from the group consisting of ($C_{1-4}$)alkyl, ($C_{1-4}$)alkoxy, halogen, cyano, trifluoromethoxy and trifluoromethyl;
$R^2$ represents ($C_{1-4}$)alkyl, ($C_{1-4}$)alkoxy, ($C_{2-4}$)alkenyl, halogen, cyano, hydroxymethyl, trifluoromethyl, C(O)NR$^5$R$^6$ or cyclopropyl;
$R^3$ represents ($C_{1-4}$)alkyl, ($C_{1-4}$)alkoxy-methyl or halogen;
$R^4$ represents ($C_{1-4}$)alkyl;
$R^5$ represents hydrogen or ($C_{1-4}$)alkyl; and
$R^6$ represents hydrogen or ($C_{1-4}$)alkyl;
wherein, when X represents $CH_2$, the absolute configuration is [(R)-2'; (S)-8]; or, when X represents O, the absolute configuration is [(R)-2'; (R)-8];
or a pharmaceutical acceptable salt thereof.

2. A compound according to claim 1, wherein X represents $CH_2$;
or a pharmaceutical acceptable salt thereof.

3. A compound according to claim 2, wherein
$R^1$ represents a phenyl group, which is independently mono-, di-, or trisubstituted wherein the substituents are independently selected from the group consisting of ($C_{1-4}$)alkyl, halogen and trifluoromethyl;
$R^2$ represents ($C_{1-4}$)alkoxy, halogen, cyano or trifluoromethyl;
$R^3$ represents ($C_{1-4}$)alkyl or halogen;
or a pharmaceutical acceptable salt thereof.

4. A compound according to claim 2, wherein
$R^1$ represents a phenyl group, which is independently mono-, di-, or tri-substituted wherein the substituents are independently selected from the group consisting of methyl, fluorine and trifluoromethyl;

$R^2$ represents methoxy, chlorine, cyano or trifluoromethyl;

$R^3$ represents methyl, ethyl, isopropyl or chlorine; and $R^4$ represents methyl;

or a pharmaceutical acceptable salt thereof.

5. A compound according to claim 1, wherein
$R^1$ represents a phenyl group, which is independently mono-, di-, or tri-substituted wherein the substituents are independently selected from the group consisting of $(C_{1-4})$alkyl, $(C_{1-4})$alkoxy, halogen, trifluoromethoxy and trifluoromethyl;

$R^2$ represents $(C_{1-4})$alkoxy, halogen, cyano or trifluoromethyl; and $R^3$ represents $(C_{1-4})$alkyl or halogen;

or a pharmaceutical acceptable salt thereof.

6. A compound according to claim 1, wherein
$R^1$ represents a phenyl group, which is independently mono-, di-, or tri-substituted wherein the substituents are independently selected from the group consisting of methyl, fluorine and trifluoromethyl;

$R^2$ represents methoxy, chlorine, cyano or trifluoromethyl;

$R^3$ represents methyl, ethyl, isopropyl or chlorine; and $R^4$ represents methyl;

or a pharmaceutical acceptable salt thereof.

7. A compound according to claim 1, wherein $R^2$ represents chlorine;

or a pharmaceutical acceptable salt thereof.

8. A compound according to claim 1, wherein $R^3$ represents methyl or ethyl;

or a pharmaceutical acceptable salt thereof.

9. A compound according to claim 1 selected from the group consisting of:

- (R)-2'-{1-chloro-3-ethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
- (R)-2'-{1-chloro-3-ethyl-(S)-8-[2-(3,5-difluoro-4-trifluoromethyl-phenyl)-ethyl]-5,6-dihydro-8H-imidazo[1,5-a]pyrazin-7-yl}-N-methyl-2'-phenyl-acetamide;
- (R)-2'-{1-chloro-(S)-8-[2-(2,4-difluoro-3-methyl-phenyl)-ethyl]-3-ethyl-5,6-dihydro-8H-imidazo[1,5-a]pyrazin-7-yl}-N-methyl-2'-phenyl-acetamide;
- (R)-2'-{1-chloro-(S)-8-[2-(3,5-difluoro-4-methyl-phenyl)-ethyl]-3-ethyl-5,6-dihydro-8H-imidazo[1,5-a]pyrazin-7-yl}-N-methyl-2'-phenyl-acetamide;
- (R)-2'-{1-chloro-(R)-8-[2-(3,5-difluoro-4-methyl-phenyl)-ethyl]-3-ethyl-5,6-dihydro-8H-imidazo[1,5-a]pyrazin-7-yl}-N-methyl-2'-phenyl-acetamide;
- (R)-2'-{1-chloro-3-ethyl-(S)-8-[2-(3-fluoro-4-trifluoromethyl-phenyl)-ethyl]-5,6-dihydro-8H-imidazo[1,5-a]pyrazin-7-yl}-N-methyl-2'-phenyl-acetamide;
- (R)-2'-{1-chloro-8-[2-(3,4-dimethyl-phenyl)-ethyl]-3-ethyl-5,6-dihydro-8H-imidazo[1,5-a]pyrazin-7-yl}-N-methyl-2'-phenyl-acetamide;
- (R)-2'-{1-chloro-3-ethyl-8-[2-(3-fluoro-4-methyl-phenyl)-ethyl]-5,6-dihydro-8H-imidazo[1,5-a]pyrazin-7-yl}-N-methyl-2'-phenyl-acetamide;
- (R)-2'-{1-chloro-3-ethyl-(R)-8-[2-(3-fluoro-4-methyl-phenyl)-ethyl]-5,6-dihydro-8H-imidazo[1,5-a]pyrazin-7-yl}-N-methyl-2'-phenyl-acetamide;
- (R)-2'-{1-chloro-3-ethyl-(S)-8-[2-(2-fluoro-4-trifluoromethyl-phenyl)-ethyl]-5,6-dihydro-8H-imidazo[1,5-a]pyrazin-7-yl}-N-methyl-2'-phenyl-acetamide;
- (R)-2'-{1-chloro-(S)-8-[2-(3,5-difluoro-4-methyl-phenyl)-ethyl]-3-methyl-5,6-dihydro-8H-imidazo[1,5-a]pyrazin-7-yl}-N-methyl-2'-phenyl-acetamide;
- (R)-2'-{1-chloro-(R)-8-[2-(3,5-difluoro-4-methyl-phenyl)-ethyl]-3-methyl-5,6-dihydro-8H-imidazo[1,5-a]pyrazin-7-yl}-N-methyl-2'-phenyl-acetamide;
- (R)-2'-{1-chloro-8-[2-(3,4-dimethyl-phenyl)-ethyl]-3-methyl-5,6-dihydro-8H-imidazo[1,5-a]pyrazin-7-yl}-N-methyl-2'-phenyl-acetamide;
- (R)-2'-{1-chloro-3-methyl-8-[2-(4-trifluoromethyl-phenyl)-ethyl]-5,6-dihydro-8H-imidazo[1,5-a]pyrazin-7-yl}-N-methyl-2'-phenyl-acetamide;
- (R)-2'-{3-isopropyl-1-methoxy-(S)-8-[2-(4-trifluoromethyl-phenyl)-ethyl]-5,6-dihydro-8H-imidazo[1,5-a]pyrazin-7-yl}-N-methyl-2'-phenyl-acetamide;
- (R)-2'-{(S)-8-[2-(3,4-dimethyl-phenyl)-ethyl]-3-ethyl-1-methoxy-5,6-dihydro-8H-imidazo[1,5-a]pyrazin-7-yl}-N-methyl-2'-phenyl-acetamide;
- (R)-2'-{3-ethyl-(S)-8-[2-(4-trifluoromethyl-phenyl)-ethyl]-1-vinyl-5,6-dihydro-8H-imidazo[1,5-a]pyrazin-7-yl}-N-methyl-2'-phenyl-acetamide;
- (R)-2'-{1-cyano-3-ethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
- (R)-2'-{3-ethyl-1-trifluoromethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
- (R)-2'-{1-chloro-3-methoxymethyl-8-[2-(4-trifluoromethyl-phenyl)-ethyl]-5,6-dihydro-8H-imidazo[1,5-a]pyrazin-7-yl}-N-methyl-2'-phenyl-acetamide;
- (R)-2'-{1-chloro-3-ethyl-(R)-8-[2-(2-fluoro-4-trifluoromethyl-phenyl)-ethyl]-5,6-dihydro-8H-imidazo[1,5-a]pyrazin-7-yl}-N-methyl-2'-phenyl-acetamide;
- (R)-2'-{1-chloro-8-[2-(3,4-difluoro-phenyl)-ethyl]-3-ethyl-5,6-dihydro-8H-imidazo[1,5-a]pyrazin-7-yl}-N-methyl-2'-phenyl-acetamide;
- (R)-2'-{1-chloro-3-isopropyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
- (R)-2'-{1-chloro-3-isopropyl-(R)-8-[2-(4-trifluoromethyl-phenyl)-ethyl]-5,6-dihydro-8H-imidazo[1,5-a]pyrazin-7-yl}-N-methyl-2'-phenyl-acetamide;
- (R)-2'-{3-ethyl-1-iodo-8-[2-(4-trifluoromethyl-phenyl)-ethyl]-5,6-dihydro-8H-imidazo[1,5-a]pyrazin-7-yl}-N-methyl-2'-phenyl-acetamide;
- (R)-2'-{3-ethyl-1-methyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
- (R)-2'-{8-[2-(3-chloro-phenyl)-ethyl]-1,3-dimethyl-5,6-dihydro-8H-imidazo[1,5-a]pyrazin-7-yl}-N-methyl-2'-phenyl-acetamide;
- (R)-2'-[1,3-dimethyl-8-(2-p-tolyl-ethyl)-5,6-dihydro-8H-imidazo[1,5-a]pyrazin-7-yl]-N-methyl-2'-phenyl-acetamide;
- (R)-2'-{8-[2-(2,4-dimethyl-phenyl)-ethyl]-1,3-dimethyl-5,6-dihydro-8H-imidazo[1,5-a]pyrazin-7-yl}-N-methyl-2'-phenyl-acetamide;
- (R)-2'-{8-[2-(3-fluoro-4-methoxy-phenyl)-ethyl]-1,3-dimethyl-5,6-dihydro-8H-imidazo[1,5-a]pyrazin-7-yl}-N-methyl-2'-phenyl-acetamide;
- (R)-2'-{(R)-8-[2-(3,4-dimethyl-phenyl)-ethyl]-3-ethyl-1-methoxy-5,6-dihydro-8H-imidazo[1,5-a]pyrazin-7-yl}-N-methyl-2'-phenyl-acetamide;
- 3-ethyl-7-(methylcarbamoyl-phenyl-methyl)-8-[2-(4-trifluoromethyl-phenyl)-ethyl]-5,6,7,8-tetrahydro-imidazo[1,5-a]pyrazine-1-carboxylic acid methylamide;
- (R)-2'-{(S)-8-[2-(3,4-difluoro-phenyl)-ethyl]-1,3-dimethyl-5,6-dihydro-8H-imidazo[1,5-a]pyrazin-7-yl}-N-methyl-2'-phenyl-acetamide;

(R)-2'-{1,3-dichloro-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{1-chloro-3-ethyl-(S)-8-[2-(3,4,5-trifluoro-phenyl)-ethyl]-5,6-dihydro-8H-imidazo[1,5-a]pyrazin-7-yl}-N-methyl-2'-phenyl-acetamide;
(R)-2'-{1-chloro-(S)-8-[2-(3-fluoro-4-trifluoromethyl-phenyl)-ethyl]-3-methyl-5,6-dihydro-8H-imidazo[1,5-a]pyrazin-7-yl}-N-methyl-2'-phenyl-acetamide;
(R)-2'-{1-chloro-(S)-8-[2-(3,5-difluoro-4-methoxy-phenyl)-ethyl]-3-ethyl-5,6-dihydro-8H-imidazo[1,5-a]pyrazin-7-yl}-N-methyl-2'-phenyl-acetamide;
(R)-2'-{1-chloro-(S)-8-[2-(4-chloro-3,5-difluoro-phenyl)-ethyl]-3-ethyl-5,6-dihydro-8H-imidazo[1,5-a]pyrazin-7-yl}-N-methyl-2'-phenyl-acetamide;
(R)-2'-{1-chloro-(S)-8-[2-(3-chloro-4-trifluoromethyl-phenyl)-ethyl]-3-ethyl-5,6-dihydro-8H-imidazo[1,5-a]pyrazin-7-yl}-N-methyl-2'-phenyl-acetamide;
(R)-2'-{1-chloro-(S)-8-[2-(2,5-difluoro-4-trifluoromethyl-phenyl)-ethyl]-3-ethyl-5,6-dihydro-8H-imidazo[1,5-a]pyrazin-7-yl}-N-methyl-2'-phenyl-acetamide;
(R)-2'-{1-chloro-3-ethyl-(S)-8-[2-(4-trifluoromethoxy-phenyl)-ethyl]-5,6-dihydro-8H-imidazo[1,5-a]pyrazin-7-yl}-N-methyl-2'-phenyl-acetamide;
(R)-2'-{1-chloro-(S)-8-[2-(4-cyano-phenyl)-ethyl]-3-ethyl-5,6-dihydro-8H-imidazo[1,5-a]pyrazin-7-yl}-N-methyl-2'-phenyl-acetamide;
(R)-2'-{1-cyano-3-ethyl-(S)-8-[2-(3-fluoro-4-trifluoromethyl-phenyl)-ethyl]-5,6-dihydro-8H-imidazo[1,5-a]pyrazin-7-yl}-N-methyl-2'-phenyl-acetamide;
(R)-2'-{1-cyano-(S)-8-[2-(3-fluoro-4-trifluoromethyl-phenyl)-ethyl]-3-methyl-5,6-dihydro-8H-imidazo[1,5-a]pyrazin-7-yl}-N-methyl-2'-phenyl-acetamide;
(R)-2'-{1-chloro-3-propyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{1-chloro-(S)-8-[2-(3-fluoro-4-trifluoromethyl-phenyl)-ethyl]-3-propyl-5,6-dihydro-8H-imidazo[1,5-a]pyrazin-7-yl}-N-methyl-2'-phenyl-acetamide;
(R)-2'-{1-cyclopropyl-3-methyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{1-chloro-3-ethyl-8-[2-(2,3,5-trifluoro-phenyl)-ethyl]-5,6-dihydro-8H-imidazo[1,5-a]pyrazin-7-yl}-N-methyl-2'-phenyl-acetamide;
(R)-2'-{1-chloro-3-ethyl-(S)-8-[2-(3-fluoro-4-methoxy-phenyl)-ethyl]-5,6-dihydro-8H-imidazo[1,5-a]pyrazin-7-yl}-N-methyl-2'-phenyl-acetamide;
(R)-2'-{1-chloro-(S)-8-[2-(2,5-difluoro-4-methoxy-phenyl)-ethyl]-3-ethyl-5,6-dihydro-8H-imidazo[1,5-a]pyrazin-7-yl}-N-methyl-2'-phenyl-acetamide;
(R)-2'-[1-chloro-3-ethyl-(R)-8-(4-fluoro-3-trifluoromethyl-phenoxymethyl)-5,6-dihydro-8H-imidazo[1,5-a]pyrazin-7-yl]-N-methyl-2'-phenyl-acetamide;
(R)-2'-[1-chloro-3-ethyl-(R)-8-(4-trifluoromethyl-phenoxymethyl)-5,6-dihydro-8H-imidazo[1,5-a]pyrazin-7-yl]-N-methyl-2'-phenyl-acetamide;
(R)-2'-[1-chloro-(R)-8-(3,4-dimethyl-phenoxymethyl)-3-ethyl-5,6-dihydro-8H-imidazo[1,5-a]pyrazin-7-yl]-N-methyl-2'-phenyl-acetamide; and
(R)-2'-[1-chloro-3-ethyl-(R)-8-(3-trifluoromethyl-phenoxymethyl)-5,6-dihydro-8H-imidazo[1,5-a]pyrazin-7-yl]-N-methyl-2'-phenyl-acetamide;
or a pharmaceutically acceptable salt thereof.

10. A compound according to claim 1 selected from the group consisting of:

(R)-2'-{1-chloro-3-ethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{1-chloro-3-ethyl-(S)-8-[2-(3,5-difluoro-4-trifluoromethyl-phenyl)-ethyl]-5,6-dihydro-8H-imidazo[1,5-a]pyrazin-7-yl}-N-methyl-2'-phenyl-acetamide;
(R)-2'-{1-chloro-(S)-8-[2-(2,4-difluoro-3-methyl-phenyl)-ethyl]-3-ethyl-5,6-dihydro-8H-imidazo[1,5-a]pyrazin-7-yl}-N-methyl-2'-phenyl-acetamide;
(R)-2'-{1-chloro-(S)-8-[2-(3,5-difluoro-4-methyl-phenyl)-ethyl]-3-ethyl-5,6-dihydro-8H-imidazo[1,5-a]pyrazin-7-yl}-N-methyl-2'-phenyl-acetamide;
(R)-2'-{1-chloro-(R)-8-[2-(3,5-difluoro-4-methyl-phenyl)-ethyl]-3-ethyl-5,6-dihydro-8H-imidazo[1,5-a]pyrazin-7-yl}-N-methyl-2'-phenyl-acetamide;
(R)-2'-{1-chloro-3-ethyl-(S)-8-[2-(3-fluoro-4-trifluoromethyl-ethyl-phenyl)-ethyl]-5,6-dihydro-8H-imidazo[1,5-a]pyrazin-7-yl}-N-methyl-2'-phenyl-acetamide;
(R)-2'-{1-chloro-8-[2-(3,4-dimethyl-phenyl)-ethyl]-3-ethyl-5,6-dihydro-8H-imidazo[1,5-a]pyrazin-7-yl}-N-methyl-2'-phenyl-acetamide;
(R)-2'-{1-chloro-3-ethyl-8-[2-(3-fluoro-4-methyl-phenyl)-ethyl]-5,6-dihydro-8H-imidazo[1,5-a]pyrazin-7-yl}-N-methyl-2'-phenyl-acetamide;
(R)-2'-{1-chloro-3-ethyl-(R)-8-[2-(3-fluoro-4-methyl-phenyl)-ethyl]-5,6-dihydro-8H-imidazo[1,5-a]pyrazin-7-yl}-N-methyl-2'-phenyl-acetamide;
(R)-2'-{1-chloro-3-ethyl-(S)-8-[2-(2-fluoro-4-trifluoromethyl-phenyl)-ethyl]-5,6-dihydro-8H-imidazo[1,5-a]pyrazin-7-yl}-N-methyl-2'-phenyl-acetamide;
(R)-2'-{1-chloro-(S)-8-[2-(3,5-difluoro-4-methyl-phenyl)-ethyl]-3-methyl-5,6-dihydro-8H-imidazo[1,5-a]pyrazin-7-yl}-N-methyl-2'-phenyl-acetamide;
(R)-2'-{1-chloro-(R)-8-[2-(3,5-difluoro-4-methyl-phenyl)-ethyl]-3-methyl-5,6-dihydro-8H-imidazo[1,5-a]pyrazin-7-yl}-N-methyl-2'-phenyl-acetamide;
(R)-2'-{1-chloro-8-[2-(3,4-dimethyl-phenyl)-ethyl]-3-methyl-5,6-dihydro-8H-imidazo[1,5-a]pyrazin-7-yl}-N-methyl-2'-phenyl-acetamide;
(R)-2'-{1-chloro-3-methyl-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{3-isopropyl-1-methoxy-(S)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{(S)-8-[2-(3,4-dimethyl-phenyl)-ethyl]-3-ethyl-1-methoxy-5,6-dihydro-8H-imidazo[1,5-a]pyrazin-7-yl}-N-methyl-2'-phenyl-acetamide;
(R)-2'-{3-ethyl-(S)-8-[2-(4-trifluoromethyl-phenyl)-ethyl]-1-vinyl-5,6-dihydro-8H-imidazo[1,5-a]pyrazin-7-yl}-N-methyl-2'-phenyl-acetamide;
(R)-2'-{1-cyano-3-ethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{3-ethyl-1-trifluoromethyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{1-chloro-3-methoxymethyl-8-[2-(4-trifluoromethyl-phenyl)-ethyl]-5,6-dihydro-8H-imidazo[1,5-a]pyrazin-7-yl}-N-methyl-2'-phenyl-acetamide;
(R)-2'-{1-chloro-3-ethyl-(R)-8-[2-(2-fluoro-4-trifluoromethyl-phenyl)-ethyl]-5,6-dihydro-8H-imidazo[1,5-a]pyrazin-7-yl}-N-methyl-2'-phenyl-acetamide;
(R)-2'-{1-chloro-8-[2-(3,4-difluoro-phenyl)-ethyl]-3-ethyl-5,6-dihydro-8H-imidazo[1,5-a]pyrazin-7-yl}-N-methyl-2'-phenyl-acetamide;

(R)-2'-{1-chloro-3-isopropyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{1-chloro-3-isopropyl-(R)-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{3-ethyl-1-iodo-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{3-ethyl-1-methyl-(S)-8-[2-(4-trifluoromethyl-phenyl)-ethyl]-5,6-dihydro-8H-imidazo[1,5-a]pyrazin-7-yl}-N-methyl-2'-phenyl-acetamide;

(R)-2'-{8-[2-(3-chloro-phenyl)-ethyl]-1,3-dimethyl-5,6-dihydro-8H-imidazo[1,5-a]pyrazin-7-yl}-N-methyl-2'-phenyl-acetamide;

(R)-2'-[1,3-dimethyl-8-(2-p-tolyl-ethyl)-5,6-dihydro-8H-imidazo[1,5-a]pyrazin-7-yl]-N-methyl-2'-phenyl-acetamide;

(R)-2'-{8-[2-(2,4-dimethyl-phenyl)-ethyl]-1,3-dimethyl-5,6-dihydro-8H-imidazo[1,5-a]pyrazin-7-yl}-N-methyl-2'-phenyl-acetamide;

(R)-2'-{8-[2-(3-fluoro-4-methoxy-phenyl)-ethyl]-1,3-dimethyl-5,6-dihydro-8H-imidazo[1,5-a]pyrazin-7-yl}-N-methyl-2'-phenyl-acetamide;

(R)-2'-{(R)-8-[2-(3,4-dimethyl-phenyl)-ethyl]-3-ethyl-1-methoxy-5,6-dihydro-8H-imidazo[1,5-a]pyrazin-7-yl}-N-methyl-2'-phenyl-acetamide;

3-ethyl-7-(methylcarbamoyl-phenyl-methyl)-8-[2-(4-trifluoromethyl-phenyl)-ethyl]-5,6,7,8-tetrahydro-imidazo[1,5-a]pyrazine-1-carboxylic acid methylamide;

(R)-2'-{(S)-8-[2-(3,4-difluoro-phenyl)-ethyl]-1,3-dimethyl-5,6-dihydro-8H-imidazo[1,5-a]pyrazin-7-yl}-N-methyl-2'-phenyl-acetamide;

(R)-2'-{1,3-dichloro-8-[2-(4-trifluoromethyl-phenyl)-ethyl]-5,6-dihydro-8H-imidazo[1,5-a]pyrazin-7-yl}-N-methyl-2'-phenyl-acetamide; and or a pharmaceutically acceptable salt thereof.

11. A pharmaceutical composition comprising the compound of claim 1 in free base form, or of a pharmaceutically acceptable salt thereof and a pharmaceutically acceptable carrier material.

* * * * *